(12) United States Patent
Tracewell et al.

(10) Patent No.: US 10,662,415 B2
(45) Date of Patent: May 26, 2020

(54) ENGINEERED BIOSYNTHETIC PATHWAYS FOR PRODUCTION OF (6E)-8-HYDROXYGERANIOL BY FERMENTATION

(71) Applicant: Zymergen Inc., Emeryville, CA (US)

(72) Inventors: Cara Ann Tracewell, Walnut Creek, CA (US); Steven M. Edgar, Albany, CA (US); Stepan Tymoshenko, Emeryville, CA (US); Alexander Glennon Shearer, San Francisco, CA (US)

(73) Assignee: Zymergen Inc., Emeryville, CA (US)

( * ) Notice: Subject to any disclaimer, the term of this patent is extended or adjusted under 35 U.S.C. 154(b) by 0 days.

(21) Appl. No.: 16/450,780

(22) Filed: Jun. 24, 2019

(65) Prior Publication Data

US 2019/0338259 A1  Nov. 7, 2019

Related U.S. Application Data

(63) Continuation of application No. PCT/US2018/064351, filed on Dec. 6, 2018.

(60) Provisional application No. 62/596,013, filed on Dec. 7, 2017.

(51) Int. Cl.
| | | |
|---|---|---|
| *C12N 1/20* | (2006.01) | |
| *C12N 9/16* | (2006.01) | |
| *C12N 1/18* | (2006.01) | |
| *C12N 9/04* | (2006.01) | |
| *C12N 9/02* | (2006.01) | |
| *C12N 9/10* | (2006.01) | |
| *C12N 9/90* | (2006.01) | |
| *C12P 7/18* | (2006.01) | |

(52) U.S. Cl.
CPC ............. *C12N 9/16* (2013.01); *C12N 1/18* (2013.01); *C12N 9/0006* (2013.01); *C12N 9/0073* (2013.01); *C12N 9/1085* (2013.01); *C12N 9/90* (2013.01); *C12P 7/18* (2013.01); *C12Y 101/01034* (2013.01); *C12Y 114/13152* (2015.07); *C12Y 205/01001* (2013.01); *C12Y 205/0101* (2013.01); *C12Y 301/07011* (2015.07); *C12Y 503/03002* (2013.01)

(58) Field of Classification Search
CPC .................................. C12N 9/16; C12N 9/90
USPC ........................................................ 435/158
See application file for complete search history.

(56) References Cited

U.S. PATENT DOCUMENTS

| | | | |
|---|---|---|---|
| 5,753,507 A | 5/1998 | Ohta et al. | |
| 6,242,227 B1 | 6/2001 | Millis et al. | |
| 6,284,506 B1 | 9/2001 | Hoshino et al. | |
| 6,524,811 B1 | 2/2003 | Cunningham et al. | |
| 6,531,303 B1 | 3/2003 | Millis et al. | |
| 6,558,915 B1 | 5/2003 | Tao | |
| 6,586,202 B2 | 7/2003 | Hoshino et al. | |
| 6,806,076 B1 | 10/2004 | Miyake et al. | |
| 6,916,972 B2 | 7/2005 | Falco et al. | |
| 6,989,257 B2 | 1/2006 | Berry et al. | |
| 7,067,677 B2 | 6/2006 | Manzer | |
| 7,067,678 B2 | 6/2006 | Scialdone | |
| 7,122,341 B1 | 10/2006 | Liao | |
| 7,129,392 B2 | 10/2006 | Hahn et al. | |
| 7,132,250 B2 | 11/2006 | Tao | |
| 7,132,268 B2 | 11/2006 | Miyake et al. | |
| 7,135,622 B2 | 11/2006 | Falco et al. | |
| 7,172,886 B2 | 2/2007 | Keasling et al. | |
| 7,183,089 B2 | 2/2007 | Keasling et al. | |
| 7,192,751 B2 | 3/2007 | Keasling et al. | |
| 7,195,887 B2 | 3/2007 | Cahoon et al. | |
| 7,208,298 B2 | 4/2007 | Miyake et al. | |
| 7,217,863 B2 | 5/2007 | Famodu et al. | |
| 7,232,679 B2 | 6/2007 | Berry et al. | |
| 7,282,359 B2 | 10/2007 | Cahoon et al. | |
| 7,364,885 B2 | 4/2008 | Miyake et al. | |
| 7,375,239 B2 | 5/2008 | Chauhan et al. | |
| 7,422,884 B2 | 9/2008 | Bai et al. | |
| 7,531,333 B2 | 5/2009 | Miyake et al. | |
| 7,547,793 B2 | 6/2009 | Hallahan et al. | |
| 7,572,609 B2 | 8/2009 | Berry et al. | |
| 7,618,819 B2 | 11/2009 | Kuehnle | |
| 7,622,282 B2 | 11/2009 | Keasling et al. | |
| 7,622,283 B2 | 11/2009 | Keasling et al. | |
| 7,659,097 B2 | 2/2010 | Renninger et al. | |
| 7,667,017 B2 | 2/2010 | Keasling et al. | |
| 7,670,825 B2 | 3/2010 | Keasling et al. | |
| 7,704,716 B2 | 4/2010 | Pichersky et al. | |
| 7,718,417 B2 | 5/2010 | Millis et al. | |
| 7,732,161 B2 | 6/2010 | Millis et al. | |
| 7,736,881 B2 | 6/2010 | Poulter et al. | |
| 7,736,882 B2 | 6/2010 | Keasling et al. | |

(Continued)

FOREIGN PATENT DOCUMENTS

| | | |
|---|---|---|
| EP | 1115849 B1 | 2/2006 |
| EP | 1392824 B1 | 8/2008 |

(Continued)

OTHER PUBLICATIONS

PCT International Search Report and Written Opinion dated Feb. 26, 2019 issued in PCT/US2018/067333.
PCT International Search Report and Written Opinion dated Mar. 1, 2019 issued in PCT/US2O18/064351.
Alagna, et al. (2012) "Olive phenolic compounds: metabolic and transcriptional profiling during fruit development" *BMC PlantBiology* 12(1): 162 (19 pages).

(Continued)

*Primary Examiner* — Tekchand Saidha
(74) *Attorney, Agent, or Firm* — Emily M. Haliday; Weaver Austin Villeneuve & Sampson LLP

(57) ABSTRACT

The present disclosure describes the engineering of microbial cells for fermentative production of (6E)-8-hydroxygeraniol and provides novel engineered microbial cells and cultures, as well as related (6E)-8-hydroxygeraniol production method.

27 Claims, 7 Drawing Sheets

Specification includes a Sequence Listing.

(56) References Cited

U.S. PATENT DOCUMENTS

| | | |
|---|---|---|
| 7,741,070 B2 | 6/2010 | Stephanopoulos et al. |
| 7,838,279 B2 | 11/2010 | Millis et al. |
| 7,842,497 B2 | 11/2010 | Millis et al. |
| 7,842,855 B2 | 11/2010 | Cahoon et al. |
| 7,915,026 B2 | 3/2011 | Keasling et al. |
| 7,927,861 B2 | 4/2011 | Millis et al. |
| 7,927,862 B2 | 4/2011 | Millis et al. |
| 8,048,658 B2 | 11/2011 | Clark et al. |
| 8,097,438 B2 | 1/2012 | Chang et al. |
| 8,114,645 B2 | 2/2012 | Pitera et al. |
| 8,124,375 B2 | 2/2012 | Pichersky et al. |
| 8,158,383 B2 | 4/2012 | Keasling et al. |
| 8,173,410 B2 | 5/2012 | Bott et al. |
| 8,206,957 B2 | 6/2012 | Schädler et al. |
| 8,236,552 B2 | 8/2012 | Millis et al. |
| 8,241,888 B2 | 8/2012 | Millis et al. |
| 8,257,957 B2 | 9/2012 | Keasling et al. |
| 8,288,147 B2 | 10/2012 | Keasling et al. |
| 8,288,148 B2 | 10/2012 | Cervin et al. |
| 8,309,323 B2 | 11/2012 | Martin et al. |
| 8,338,155 B2 | 12/2012 | Bai et al. |
| 8,361,762 B2 | 1/2013 | Beck et al. |
| 8,415,136 B1 | 4/2013 | Gardner et al. |
| 8,461,322 B2 | 6/2013 | Cahoon et al. |
| 8,476,049 B2 | 7/2013 | McAuliffe et al. |
| 8,512,988 B2 | 8/2013 | Ajikumar et al. |
| 8,552,210 B2 | 10/2013 | Jackson et al. |
| 8,558,015 B2 | 10/2013 | Fisher et al. |
| 8,603,800 B2 | 12/2013 | Gardner et al. |
| 8,709,785 B2 | 4/2014 | Cervin et al. |
| 8,765,403 B2 | 7/2014 | Dueber et al. |
| 8,765,975 B2 | 7/2014 | Hutchenson et al. |
| 8,771,718 B2 | 7/2014 | Scialdone et al. |
| 8,815,548 B2 | 8/2014 | Beck et al. |
| 8,828,684 B2 | 9/2014 | Keasling et al. |
| 8,841,114 B2 | 9/2014 | Lang et al. |
| 8,859,261 B2 | 10/2014 | Gardner et al. |
| 8,951,764 B2 | 2/2015 | Bergsma et al. |
| 8,956,833 B2 | 2/2015 | Swartz et al. |
| 8,986,965 B2 | 3/2015 | McDaniel et al. |
| 8,987,433 B2 | 3/2015 | Mendez et al. |
| 8,993,305 B2 | 3/2015 | Beck et al. |
| 8,999,682 B2 | 4/2015 | Hahn et al. |
| 9,051,587 B2 | 6/2015 | Raab et al. |
| 9,102,954 B2 | 8/2015 | Millis et al. |
| 9,200,296 B2 | 12/2015 | Renninger et al. |
| 9,260,727 B2 | 2/2016 | Cervin et al. |
| 9,382,553 B2 | 7/2016 | Kirby et al. |
| 9,382,554 B2 | 7/2016 | Kallas et al. |
| 9,518,282 B2 | 12/2016 | Ono et al. |
| 9,521,844 B2 | 12/2016 | Fisher et al. |
| 9,670,518 B2 | 6/2017 | Meadows |
| 9,688,652 B2 | 6/2017 | Jackson et al. |
| 9,765,363 B1 | 9/2017 | Renninger |
| 9,809,829 B2 | 11/2017 | Keasling et al. |
| 9,834,800 B2 | 12/2017 | Tange et al. |
| 9,909,146 B2 | 3/2018 | Marliere |
| 10,106,822 B2 | 10/2018 | Renninger et al. |
| 2002/0035058 A1 | 3/2002 | Brown et al. |
| 2002/0119546 A1 | 8/2002 | Falco et al. |
| 2002/0197696 A1 | 12/2002 | Levin et al. |
| 2003/0115634 A1 | 6/2003 | Jomaa et al. |
| 2004/0010815 A1 | 1/2004 | Lange et al. |
| 2005/0287655 A1 | 12/2005 | Tabata et al. |
| 2006/0068393 A1 | 3/2006 | Lacour et al. |
| 2008/0233623 A1 | 9/2008 | Chang et al. |
| 2008/0261280 A1 | 10/2008 | Hahn et al. |
| 2009/0004724 A1 | 1/2009 | Keasling et al. |
| 2009/0053797 A1 | 2/2009 | Shiba et al. |
| 2009/0253174 A1 | 10/2009 | Serber et al. |
| 2010/0178679 A1 | 7/2010 | Anthony et al. |
| 2010/0184178 A1 | 7/2010 | Beck et al. |
| 2010/0311065 A1 | 12/2010 | Udersax et al. |
| 2010/0311136 A1 | 12/2010 | Yoneda et al. |
| 2011/0129883 A1 | 6/2011 | Jomaa et al. |
| 2011/0195470 A1 | 8/2011 | Millis et al. |
| 2011/0287476 A1 | 11/2011 | Renninger et al. |
| 2012/0083020 A1 | 4/2012 | Hahn et al. |
| 2012/0288891 A1 | 11/2012 | Meadows |
| 2013/0137138 A1 | 5/2013 | Hansen |
| 2013/0203132 A1 | 8/2013 | Hahn et al. |
| 2013/0273625 A1 | 10/2013 | Chotani et al. |
| 2013/0276166 A1 | 10/2013 | Hugueney et al. |
| 2013/0323820 A1 | 12/2013 | Chen et al. |
| 2014/0273144 A1 | 9/2014 | Hawkins et al. |
| 2014/0335576 A1 | 11/2014 | Chotani et al. |
| 2014/0370595 A1 | 12/2014 | Dueber et al. |
| 2015/0024009 A1 | 1/2015 | Lang et al. |
| 2015/0087042 A1 | 3/2015 | Keasling et al. |
| 2015/0093797 A1 | 4/2015 | Gardner et al. |
| 2015/0191747 A1 | 7/2015 | Chen et al. |
| 2015/0203873 A1 | 7/2015 | Beck et al. |
| 2015/0203880 A1 | 7/2015 | Stephanopoulos et al. |
| 2015/0225743 A1 | 8/2015 | Donaldson et al. |
| 2015/0225744 A1 | 8/2015 | Beck et al. |
| 2015/0259705 A1 | 9/2015 | Huembelin et al. |
| 2015/0275233 A1 | 10/2015 | Mihara et al. |
| 2015/0299713 A1 | 10/2015 | Jiang et al. |
| 2015/0299732 A1 | 10/2015 | Millis et al. |
| 2015/0315599 A1 | 11/2015 | Shetty et al. |
| 2016/0032323 A1 | 2/2016 | Beck et al. |
| 2016/0040190 A1 | 2/2016 | Renninger et al. |
| 2016/0068831 A1 | 3/2016 | Beck et al. |
| 2016/0177341 A1 | 6/2016 | Chua et al. |
| 2016/0186168 A1 | 6/2016 | Konieczka et al. |
| 2016/0194674 A1 | 7/2016 | Bromann et al. |
| 2018/0030481 A1 | 2/2018 | Keasling et al. |
| 2018/0080054 A1 | 3/2018 | Ostergaard et al. |
| 2018/0171341 A1 | 6/2018 | Chua et al. |
| 2018/0186841 A1 | 7/2018 | Chua et al. |

FOREIGN PATENT DOCUMENTS

| | | |
|---|---|---|
| EP | 1641931 B1 | 11/2008 |
| EP | 1631664 B1 | 3/2009 |
| EP | 0769551 B1 | 5/2009 |
| EP | 1135471 B1 | 5/2009 |
| EP | 1987147 B1 | 7/2010 |
| EP | 1824969 B1 | 3/2011 |
| EP | 1765418 B1 | 12/2011 |
| EP | 2100963 B1 | 12/2011 |
| EP | 2182072 B1 | 12/2012 |
| EP | 1072683 B1 | 8/2013 |
| EP | 2707475 B1 | 9/2015 |
| EP | 2066778 B1 | 1/2016 |
| EP | 2024504 B1 | 2/2016 |
| EP | 2681313 B1 | 4/2016 |
| WO | WO/1999/058649 A1 | 11/1999 |
| WO | WO/2000/044912 A1 | 8/2000 |
| WO | WO/2000/078935 A1 | 12/2000 |
| WO | WO/2008/008256 A2 | 1/2008 |
| WO | WO/2009/005704 A1 | 1/2009 |
| WO | WO/2009/126623 A2 | 10/2009 |
| WO | WO/2010/141452 A1 | 12/2010 |
| WO | WO/2012/016172 A2 | 2/2012 |
| WO | WO/2012/016177 A2 | 2/2012 |
| WO | WO/2012/135591 A2 | 10/2012 |
| WO | WO/2013/096863 A1 | 6/2013 |
| WO | WO/2014/052054 A1 | 4/2014 |
| WO | WO/2014/066892 A1 | 5/2014 |
| WO | WO/2015/030681 A1 | 3/2015 |
| WO | WO/2015/100180 A1 | 7/2015 |
| WO | WO/2015/127305 A2 | 8/2015 |
| WO | WO/2015/189428 A1 | 12/2015 |
| WO | WO/2016/008883 A1 | 1/2016 |
| WO | WO/2016/008885 A1 | 1/2016 |
| WO | WO/2016/044713 A1 | 3/2016 |
| WO | WO/2016/108236 A1 | 7/2016 |
| WO | WO/2018/005935 A1 | 1/2018 |
| WO | WO/2018/111194 A1 | 6/2018 |

(56) References Cited

FOREIGN PATENT DOCUMENTS

WO     WO/2019/113387 A1     6/2019
WO     WO/2019/126778 A1     6/2019

OTHER PUBLICATIONS

Billingsley, et al. (2017) "Engineering the biocatalytic selectivity of iridoid production in *Saccharomyces cerevisiae*." *Metab Eng* 44: p. 117-125. [HHS Public Access—Author manuscript—21 pages].

Brown, et al. (2015) "De novo production of the plant-derived alkaloid strictosidine in yeast" *PNAS* 112(11): 3205-3210.

Campell, et al. (2016) "Engineering of a Nepetalactol-Producing Platform Strain of *Saccharomyces cerevisiae* for the Production of Plant Seco-Iridoids," *ACS Synth Biol*. 5(5):405-14.

Crowley, et al. (1998) "A mutation in a purported regulatory gene affects control of sterol uptake in *Saccharomyces cerevisiae*." *J Bacteriol* 180(16): 4177-83.

Dewick (2002) "The biosynthesis of C5—C25 terpenoid compounds," *Nat Prod Rep*. 19(2):181-222.

Dimster-Denk, et al. (1994) "Feedback regulation of 3-hydroxy-3-methylglutaryl coenzyme A reductase in *Saccharomyces cerevisiae*." *Mol Biol Cell* 5(6): 655-65.

Geu-Flores, et al. (2012) "An alternative route to cyclic terpenes by reductive cyclization in iridoid biosynthesis" *Nature* 492(7427): 138-142.

GreatBay_China (2018) "Project: Nepetalactol Synthesis" Retrieved from the Internet: URL: http://2018.igem.org/wiki/images/f/fd/T--GreatBay_China--notebook_nepetalactol.pdf [retrieved on Feb. 13, 2019] 67 pages.

Hallahan, et al. (1998) "Nepetalactol oxidoreductase in trichomes of the catmint *Nepeta racemose*," *Phytochemistry* 48(3): 421-427.

Hofer, et al. (2013) "Geraniol hydroxylase and hydroxygeraniol oxidase activities of the CYP76 family of cytochrome P450 enzymes and potential for engineering the early steps of the (seco)iridoid pathway" *Metabolic Engineering* 20: 221-232.

Kanehisa, et al. (2000) "KEGG: kyoto encyclopedia of genes and genomes." *Nucleic Acids Res* 28(1): 27-30.

Krithika, et al. (2015) "Characterization of 10-hydroxygeraniol dehydrogenase from Catharanthus roseus reveals cascaded enzymatic activity in iridoid biosynthesis," *Sci Rep*. 5:8258 (6 pages).

Lee, et al. (2015) "A Highly Characterized Yeast Toolkit for Modular, Multipart Assembly" *ACS Synth. Biol* 4(9): 975-986.

Lichman, et al. (2018) "Uncoupled activation and cyclisation in catmint reductive terpenoid biosynthesis," Nature Chemical Biology 15: 71-79 (12 pages) *bioRxiv* doi: doi.org/10.1101/391953 (Posted Aug. 14, 2018).

Loeschcke, et al. (2012) "A Universal Tool for the Transfer and Expression of Biosynthetic Pathways in Bacteria" *ACS Synth. Biol* 2(1): 22-33.

Oswald, et al. (2007) "Monoterpenoid biosynthesis in *Saccharomyces cerevisiae*." *FEMS Yeast Res* 7(3): 413-21.

Polakowski, et al. (1998) "Overexpression of a cytosolic hydroxymethylglutaryl-CoA reductase leads to squalene accumulation in yeast." *Appl Microbiol Biotechnol* 49(1): 66-71.

Redding-Johanson, et al. (2011) "Targeted proteomics for metabolic pathway optimization: Application to terpene production" *Metabolic Engineering* 13(2): 194-203.

Reiling, et al. (2004) "Mono and diterpene production in *Escherichia coli*." *Biotechnol Bioeng* 87(2): 200-12.

Roth, et al. (2017) "Chemoenzymatic Synthesis of a Novel Borneol-Based Polyester." *ChemSusChem* 10(18): 3574-3580.

Sherden, et al. (2017) "Identification of iridoid synthases fromNepetaspecies: Iridoid cyclization does not determine nepetalactone stereochemistry" *Phytochemistry* 145: 48-56.

Smanski, et al. (2014) "Functional optimization of gene clusters by combinatorial design and assembly" *Nature Biotechnology* 32(12): 1241-1249.

Vasilev, et al. (2014) "Assessment of Cultivation Factors that Affect Biomass and Geraniol Production in Transgenic Tobacco Cell Suspension Cultures" *PLOS One* 9(8): e104620 (7 pages).

Vik, et al. (2001) "Upc2p and Ecm22p, dual regulators of sterol biosynthesis in *Saccharomyces cerevisiae*." *Mol Cell Biol* 21(19): 6395-405.

U.S. Appl. No. 16/534,981, filed Aug. 7, 2019, Wawrzyn, et al.

Billingsley, et al. (2017) "Engineering the biocatalytic selectivity of iridoid production in Saccharomyces cerevisiae." *Metabolic Engineering* 44: 117-125.

Billingsley, et al. (2019) "Production of semi-biosynthetic nepetalactone in yeast." *Journal of Industrial Microbiology & Biotechnology* 46: 1365-1370.

Jiang, et al. (2017) "Manipulation of GES and ERG20 for geraniol overproduction in Saccharomyces cerevisiae" *Metabolic Engineering* 41: 57-66.

Miettinen, et al. (2014) "The seco-iridoid pathway from Catharanthus roseus" *Nature Communications* 5: 3606 (12 pages).

Paddon, et al. (2013) "High-level semi-synthetic production of the potent antimalarial artemisinin" *Nature* 496: 528-532 (9 pages).

Zhao, et al. (2016) "Improving monoterpene geraniol production through geranyl diphosphate synthesis regulation in Saccharomyces cerevisiae" *Appl Microbiol Biotechnol* 100:4561-4571 (11 pages).

Zhao, et al. (2016) "Optimization of a Cytochrome P450 Oxidation System for Enhancing Protopanaxadiol Production in Saccharomyces cerevisiae" *Biotechnology and Bioengineering* 113(8): 1787-1795 (9 pages).

Zhao, et al. (2017) "Dynamic control of ERG20 expression combined with minimized endogenous downstream metabolism contributes to the improvement of geraniol production in Saccharomyces cerevisiae" *Microbial Cell Factories* 16:17 (11 pages).

ENGINEERED BIOSYNTHETIC PATHWAYS FOR PRODUCTION OF (6E)-8-HYDROXYGERANIOL BY FERMENTATION

CROSS-REFERENCE TO RELATED APPLICATIONS

This application is a continuation application of international application no. PCT/US2018/64351, filed Dec. 6, 2018, which claims the benefit of U.S. provisional application No. 62/596,013, filed Dec. 7, 2017, both of which are hereby incorporated by reference in their entireties.

STATEMENT AS TO RIGHTS TO INVENTIONS MADE UNDER FEDERALLY SPONSORED RESEARCH AND DEVELOPMENT

This invention was made with Government support under Agreement No. HR0011-15-9-0014, awarded by DARPA. The Government has certain rights in the invention.

INCORPORATION BY REFERENCE OF THE SEQUENCE LISTING

This application includes a sequence listing which has been submitted electronically in ASCII format and is hereby incorporated by reference in its entirety. This ASCII copy, created on Jun. 23, 2019, is named 2019-06-23_ZMGN-P007US_SeqList_ST25.txt and is 327,680 bytes in size.

FIELD OF THE DISCLOSURE

The present disclosure relates generally to the area of engineering microbes for production of (6E)-8-hydroxygeraniol by fermentation.

BACKGROUND (6E)-8-hydroxygeraniol (8-hydroxygeraniol) is an acyclic monoterpene known to exist in nature. A method for the production of terpene alcohols by chemical synthesis is known (U.S. Pat. No. 4,107,219). (6E)-8-hydroxygeraniol is derived from the mevalonate biosynthesis pathway, based on the core metabolite precursor acetyl-CoA (FIG. 1). HMG-CoA reductase in the mevalonate biosynthesis pathway is subject to feedback inhibition [1, 2]. 8-Hydroxygeraniol is a precursor to monoterpene indole alkaloids [3] and monoterpene glycosides (JP2013158298A [4]; U.S. Pat. No. 9,518,282). Terpenes have been used to prepare novel polyester materials [5]. Heat-sealable terpene polymer films have been prepared (U.S. Pat. No. 3,278,646). Hydrogenated terpenes have been used in polymer blends (U.S. Pat. No. 3,361,849). Terpene resins and terpene-phenol resins have been prepared and used as coating protective films for the automobile industry (U.S. Pat. No. 5,643,676). Terpenes have been incorporated into oriented polypropylene films having high moisture barrier properties for use as packaging film material (U.S. Pat. No. 5,500,282).

SUMMARY

The disclosure provides engineered microbial cells, cultures of the microbial cells, and methods for the production of (6E)-8-hydroxygeraniol, including the following:

Embodiment 1

An engineered microbial cell, wherein the engineered microbial cell expresses: (a) a non-native geranyl diphosphate diphosphatase (geraniol synthase); and (b) a non-native geraniol-8-hydroxylase; wherein the engineered microbial cell produces (6E)-8-hydroxygeraniol.

Embodiment 2

The engineered microbial cell of embodiment 1, wherein the engineered microbial cell includes increased activity of one or more upstream (6E)-8-hydroxygeraniol pathway enzyme(s) or of a regulator of upstream pathway activity, said increased activity being increased relative to a control cell.

Embodiment 3

The engineered microbial cell of embodiment 2, wherein the one or more upstream (6E)-8-hydroxygeraniol pathway enzyme(s) are selected from the group consisting of ATP-citrate synthase, an acetyl-CoA synthetase, a thiolase, a hydroxymethylglutaryl coenzyme A synthase (HMG-CoA synthase), a hydroxymethylglutaryl coenzyme A reductase (HMG-CoA reductase), a mevalonate kinase, a phosphomevalonate kinase, a diphosphomevalonate decarboxylase, an isopentenyl-diphosphate delta-isomerase, and a geranyl diphosphate synthase.

Embodiment 4

The engineered microbial cell of embodiment 3, wherein the one or more upstream (6E)-8-hydroxygeraniol pathway enzyme(s) comprise the isopentenyl-diphosphate delta-isomerase.

Embodiment 5

The engineered microbial cell of any one of embodiments 1-4, wherein the engineered microbial cell includes reduced activity of one or more enzyme(s) that consume one or more (6E)-8-hydroxygeraniol pathway precursors, said reduced activity being reduced relative to a control cell.

Embodiment 6

The engineered microbial cell of embodiment 5, wherein the one or more enzyme(s) that consume one or more (6E)-8-hydroxygeraniol pathway precursors comprise a bifunctional (2E,6E)-farnesyl diphosphate synthase/dimethylallyltranstransferase and/or a geranyl pyrophosphate synthase.

Embodiment 7

The engineered microbial cell of any one of embodiments 1-6, wherein the engineered microbial cell additionally expresses a feedback-deregulated HMG-CoA reductase.

Embodiment 8

The engineered microbial cell of any one of embodiments 1-7, wherein the engineered microbial cell includes increased availability of acetyl-CoA due to a higher rate of acetyl-CoA synthesis and/or a lower rate of acetyl-CoA degradation, relative to a control cell.

Embodiment 9

An engineered microbial cell, wherein the engineered microbial cell includes: (a) means for expressing a non-native native geranyl diphosphate diphosphatase (geraniol synthase); and (b) means for expressing a non-native geraniol-8-hydroxylase; wherein the engineered microbial cell produces (6E)-8-hydroxygeraniol.

Embodiment 10

The engineered microbial cell of embodiment 9, wherein the engineered microbial cell includes means for increasing the activity of one or more upstream (6E)-8-hydroxygeraniol pathway enzyme(s) or of a regulator of upstream pathway activity.

Embodiment 11

The engineered microbial cell of embodiment 10, wherein the one or more upstream (6E)-8-hydroxygeraniol pathway enzyme(s) are selected from the group consisting of ATP-citrate synthase, an acetyl-CoA synthetase, a thiolase, a hydroxymethylglutaryl coenzyme A synthase (HMG-CoA synthase), a hydroxymethylglutaryl coenzyme A reductase (HMG-CoA reductase), a mevalonate kinase, a phosphomevalonate kinase, a diphosphomevalonate decarboxylase, an isopentenyl-diphosphate delta-isomerase, and a geranyl diphosphate synthase.

Embodiment 12

The engineered microbial cell of embodiment 11, wherein the one or more upstream (6E)-8-hydroxygeraniol pathway enzyme(s) comprise the isopentenyl-diphosphate delta-isomerase.

Embodiment 13

The engineered microbial cell of any one of embodiments 9-12, wherein the engineered microbial cell includes means for reducing the activity of one or more enzyme(s) that consume one or more (6E)-8-hydroxygeraniol pathway precursors, said reduced activity being reduced relative to a control cell.

Embodiment 14

The engineered microbial cell of embodiment 13, wherein the one or more enzyme(s) that consume one or more (6E)-8-hydroxygeraniol pathway precursors comprise a bifunctional (2E,6E)-farnesyl diphosphate synthase/dimethylallyltranstransferase and/or a geranyl pyrophosphate synthase.

Embodiment 15

The engineered microbial cell of any one of embodiments 9-14, wherein the engineered microbial cell additionally includes means for expressing a feedback-deregulated HMG-CoA reductase.

Embodiment 16

The engineered microbial cell of any one of embodiments 9-15, wherein the engineered microbial cell includes means for increasing the availability of acetyl-CoA due to a higher rate of acetyl-CoA synthesis and/or a lower rate of acetyl-CoA degradation, relative to a control cell.

Embodiment 17

The engineered microbial cell of any one of embodiments 1-16, wherein the engineered microbial cell includes a fungal cell.

Embodiment 18

The engineered microbial cell of embodiment 17, wherein the engineered microbial cell includes a yeast cell.

Embodiment 19

The engineered microbial cell of embodiment 18, wherein the yeast cell is a cell of the genus *Saccharomyces*.

Embodiment 20

The engineered microbial cell of embodiment 19, wherein the yeast cell is a cell of the species *cerevisiae*.

Embodiment 21

The engineered microbial cell of embodiment 18, wherein the yeast cell is a cell of the genus *Yarrowia*.

Embodiment 22

The engineered microbial cell of embodiment 21, wherein the yeast cell is a cell of the species *lipolytica*.

Embodiment 23

The engineered microbial cell of any one of embodiments 1-22, wherein the non-native geraniol synthase includes a geraniol synthase having at least 70% amino acid sequence identity with a geraniol synthase from *Perilla* setoyensis.

Embodiment 24

The engineered microbial cell of any one of embodiments 1-22, wherein the non-native geraniol synthase includes a geraniol synthase having at least 70% amino acid sequence identity with a geraniol synthase from *Vitis vinifera*.

Embodiment 25

The engineered microbial cell of any one of embodiments 1-23, wherein the non-native geraniol-8-hydroxylase includes a geraniol-8-hydroxylase having at least 70% amino acid sequence identity with a geraniol-8-hydroxylase from *Phaseolus angularis*.

Embodiment 26

The engineered microbial cell of any one of embodiments 4 or 12-25, wherein the increased activity of the isopentenyl-diphosphate delta-isomerase is achieved by heterologously expressing a isopentenyl-diphosphate delta-isomerase.

Embodiment 27

The engineered microbial cell of embodiment 26, wherein the heterologous isopentenyl-diphosphate delta-isomerase includes an isopentenyl-diphosphate delta-isomerase having at least 70% amino acid sequence identity with an isopentenyl-diphosphate delta-isomerase from *Saccharomyces cerevisiae*.

Embodiment 28

The engineered microbial cell of any one of embodiments 6, and 14-27, wherein the one or more enzyme(s) that consume one or more (6E)-8-hydroxygeraniol pathway precursors comprise a bifunctional (2E,6E)-farnesyl diphosphate synthase/dimethylallyltranstransferase.

Embodiment 29

The engineered microbial cell of embodiment 28, wherein a bifunctional (2E,6E)-farnesyl diphosphate synthase/dimethylallyltranstransferase having at least 70% amino acid identity with a bifunctional (2E,6E)-farnesyl diphosphate synthase/dimethylallyltranstransferase from *Escherichia coli* and including amino acid substitution S80F.

Embodiment 30

The engineered microbial cell of any one of embodiments 7, or 15-27, wherein the HMG-CoA reductase is a variant of a *S. cerevisiae* HMG-CoA reductase.

Embodiment 31

The engineered microbial cell of any one of embodiments 1-30, wherein, when cultured, the engineered microbial cell produces (6E)-8-hydroxygeraniol at a level greater than 100 µg/L of culture medium.

Embodiment 32

A culture of engineered microbial cells according to any one of embodiments 1-31.

Embodiment 33

The culture of embodiment 32, wherein the substrate includes a carbon source and a nitrogen source selected from the group consisting of urea, an ammonium salt, ammonia, and any combination thereof.

Embodiment 34

The culture of any one of embodiments 32-33, wherein the engineered microbial cells are present in a concentration such that the culture has an optical density at 600 nm of 10-500.

Embodiment 35

The culture of any one of embodiments 32-34, wherein the culture includes (6E)-8-hydroxygeraniol.

Embodiment 36

The culture of any one of embodiments 32-35, wherein the culture includes (6E)-8-hydroxygeraniol at a level greater than 100 µg/L of culture medium.

Embodiment 37

A method of culturing engineered microbial cells according to any one of embodiments 1-31, the method including culturing the cells under conditions suitable for producing (6E)-8-hydroxygeraniol.

Embodiment 38

The method of embodiment 37, wherein the method includes fed-batch culture, with an initial glucose level in the range of 1-100 g/L, followed controlled sugar feeding.

Embodiment 39

The method of embodiment 37 or embodiment 38, wherein the fermentation substrate includes glucose and a nitrogen source selected from the group consisting of urea, an ammonium salt, ammonia, and any combination thereof.

Embodiment 40

The method of any one of embodiments 37-39, wherein the culture is pH-controlled during culturing.

Embodiment 41

The method of any one of embodiments 37-40, wherein the culture is aerated during culturing.

Embodiment 42

The method of any one of embodiments 37-41, wherein the engineered microbial cells produce (6E)-8-hydroxygeraniol at a level greater than 100 µg/L of culture medium.

Embodiment 43

The method of any one of embodiments 37-42, wherein the method additionally includes recovering (6E)-8-hydroxygeraniol from the culture.

Embodiment 44

A method for preparing (6E)-8-hydroxygeraniol using microbial cells engineered to produce (6E)-8-hydroxygeraniol, the method including: (a) expressing a non-native geranyl diphosphate diphosphatase (geraniol synthase) in microbial cells; (b) expressing a non-native geraniol-8-hydroxylase in the microbial cells; (c) cultivating the microbial cells in a suitable culture medium under conditions that permit the microbial cells to produce (6E)-8-hydroxygeraniol, wherein the (6E)-8-hydroxygeraniol is released into the culture medium; and (d) isolating (6E)-8-hydroxygeraniol from the culture medium.

DETAILED DESCRIPTION

Production of di-alcohol such as (6E)-8-hydroxygeraniol by biological fermentation can make a monomer economically accessible for old, as well as newly identified, materials applications. Di-alcohol containing polymers have attractive properties for novel material applications.

Figure 7:
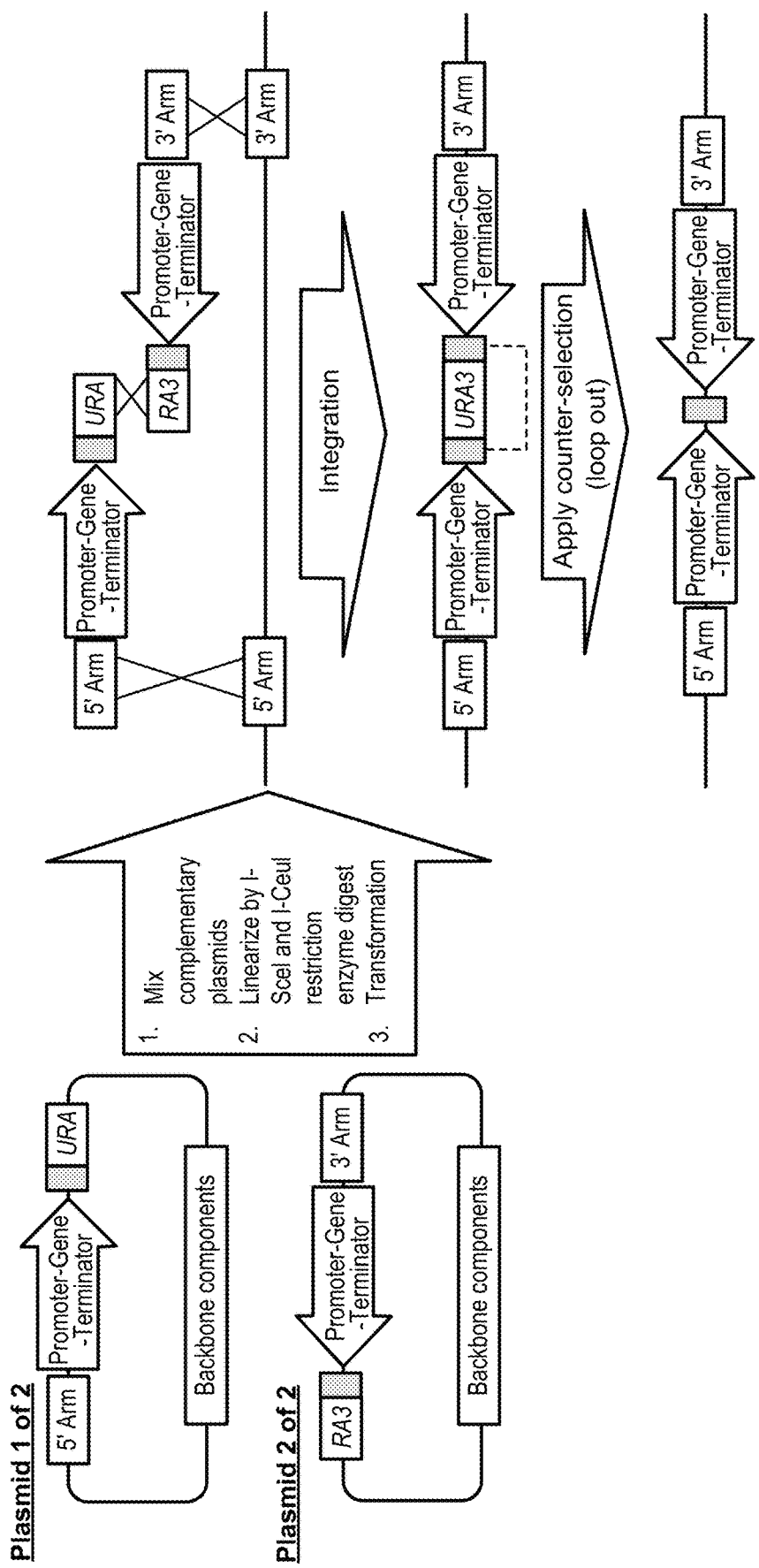
FIG. 7: Integration of Promoter-Gene-Terminator into *S. cerevisiae* and *Yarrowia lipolytica*.
Figure 8:
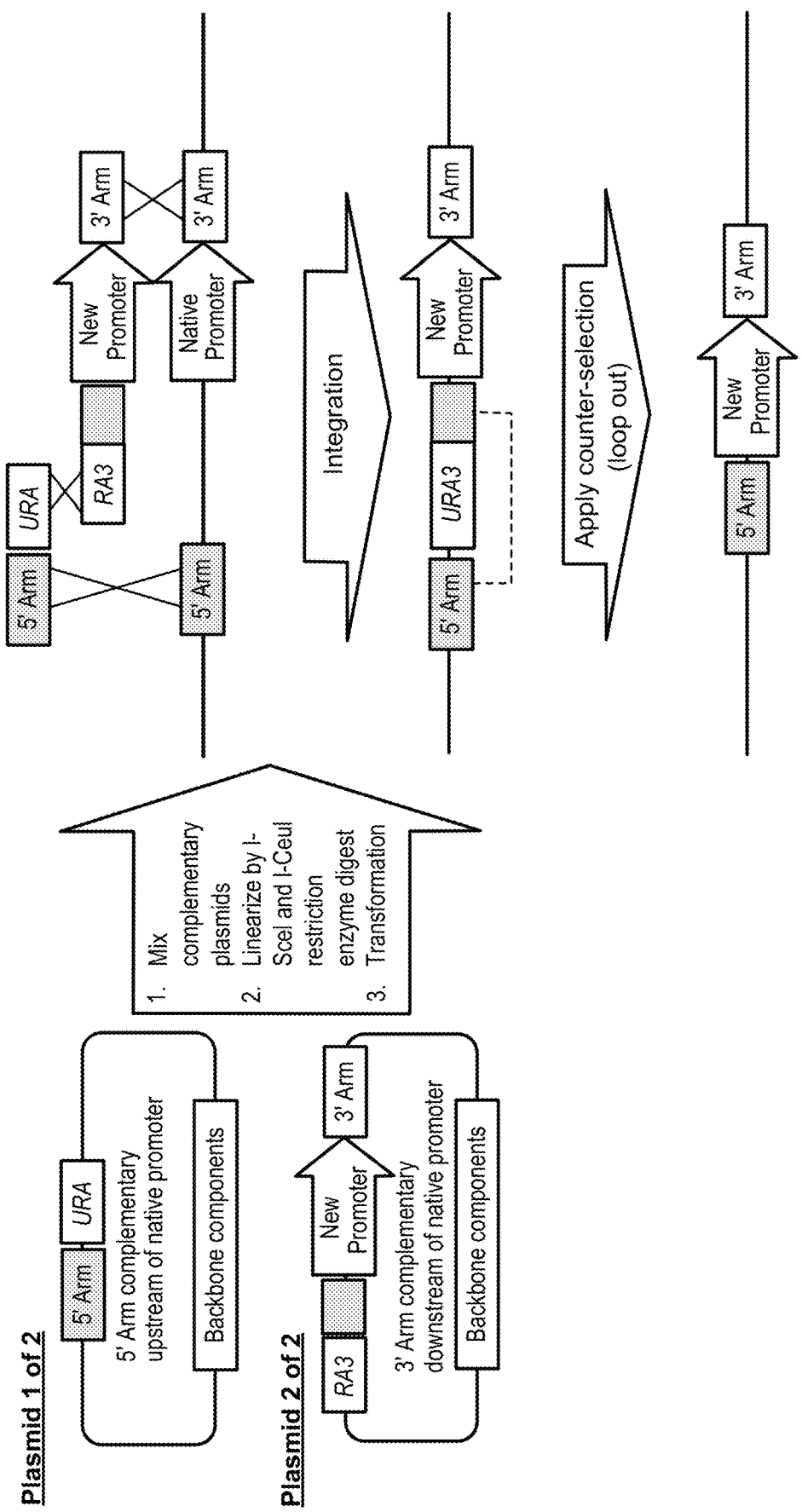
FIG. 8: Promoter replacement in *S. cerevisiae* and *Y. lipolytica*.
Figure 9:
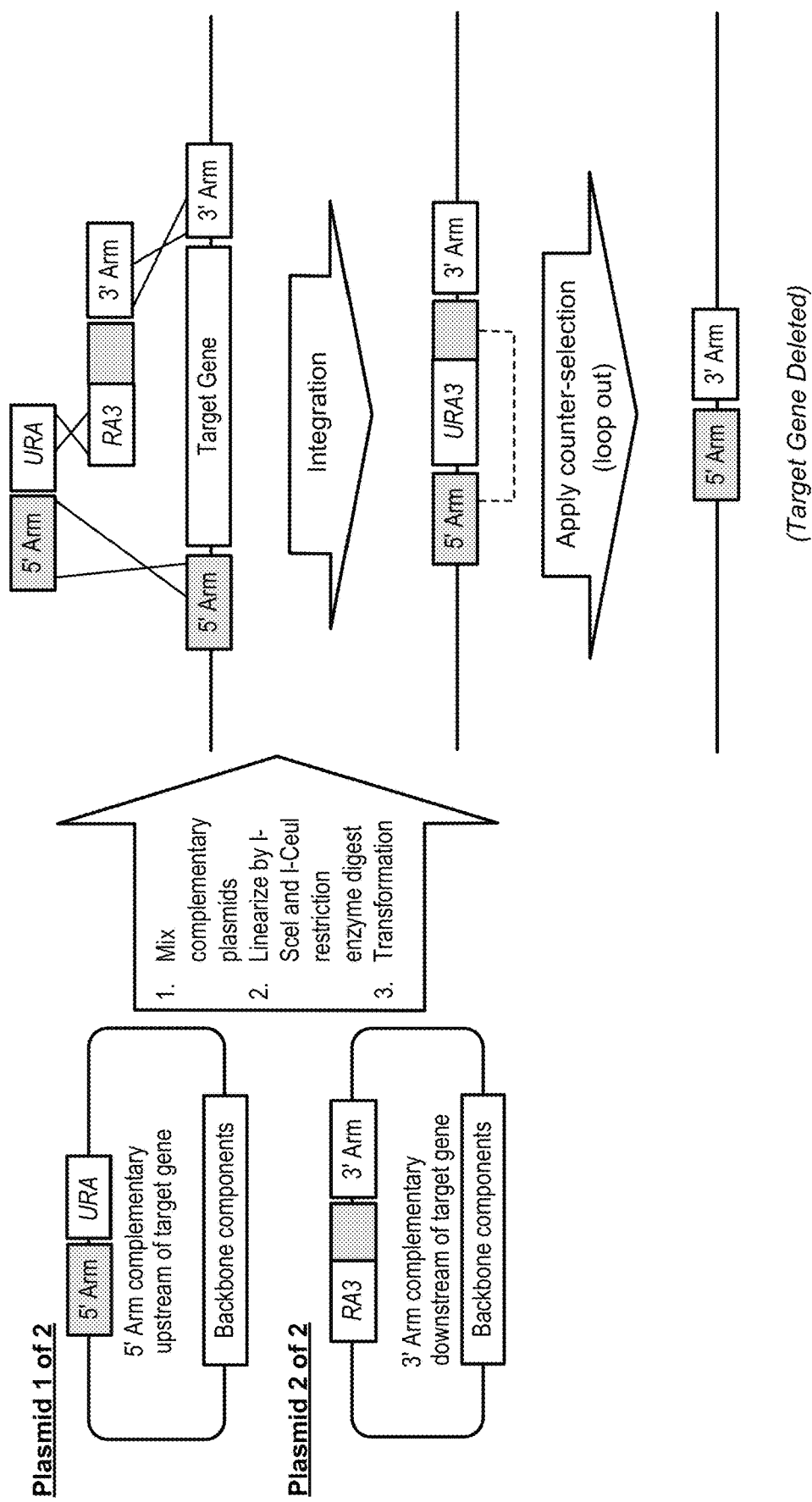
FIG. 9: Targeted gene deletion in *S. cerevisiae* and *Y. lipolytica*.

We conducted a search of metabolism [1] to identify enzymes that enable a metabolic pathway to produce (6E)-8-hydroxygeraniol in industrial host organisms (see Table 1). To engineer production of (6E)-8-hydroxygeraniol an industrial microorganism required genetic engineering tools and methods to manipulate DNA sequences (see FIGS. 7-9). Then, microbial metabolism was systematically reengineered to produce (6E)-8-hydroxygeraniol, including in industrial hosts for which not all biochemical reactions or modes of metabolic regulation have been characterized, by iterative high-throughput (HTP) strain engineering using single-gene and multiple-gene modifications (see, e.g., co-owned and co-pending U.S. Patent Publication No. 20170159045, for methods of HTP strain engineering; see also co-owned U.S. Application No. 62/455,428, which illustrates the engineering of microbes to produce tyramine).

As noted above, (6E)-8-hydroxygeraniol is a monoterpene that is produced metabolically from the terpenoid pathway. There are two terpenoid biosynthesis pathways in microorganisms: the mevalonate pathway and the non-mevalonate pathway. Both *Saccharomyces cerevisiae* and *Yarrowia lipolytica* use the mevalonate pathway for production of terpenes [2].

The present disclosure describes the engineering of microbial cells for fermentative production of (6E)-8-hydroxygeraniol and provides novel engineered microbial cells and cultures, as well as related (6E)-8-hydroxygeraniol production methods.

Definitions

Terms used in the claims and specification are defined as set forth below unless otherwise specified.

The term "fermentation" is used herein to refer to a process whereby a microbial cell converts one or more substrate(s) into a desired product (such as (6E)-8-hydroxygeraniol) by means of one or more biological conversion steps, without the need for any chemical conversion step.

The term "engineered" is used herein, with reference to a cell, to indicate that the cell contains at least one targeted genetic alteration introduced by man that distinguishes the engineered cell from the naturally occurring cell.

The term "native" is used herein to refer to a cellular component, such as a polynucleotide or polypeptide, that is naturally present in a particular cell. A native polynucleotide or polypeptide is endogenous to the cell.

When used with reference to a polynucleotide or polypeptide, the term "non-native" refers to a polynucleotide or polypeptide that is not naturally present in a particular cell.

When used with reference to the context in which a gene is expressed, the term "non-native" refers to a gene expressed in any context other than the genomic and cellular context in which it is naturally expressed. A gene expressed in a non-native manner may have the same nucleotide sequence as the corresponding gene in a host cell, but may be expressed from a vector or from an integration point in the genome that differs from the locus of the native gene.

The term "heterologous" is used herein to describe a polynucleotide or polypeptide introduced into a host cell. This term encompasses a polynucleotide or polypeptide, respectively, derived from a different organism, species, or strain than that of the host cell. In this case, the heterologous polynucleotide or polypeptide has a sequence that is different from any sequence(s) found in the same host cell. However, the term also encompasses a polynucleotide or polypeptide that has a sequence that is the same as a sequence found in the host cell, wherein the polynucleotide or polypeptide is present in a different context than the native sequence (e.g., a heterologous polynucleotide can be linked to a different promotor and inserted into a different genomic location than that of the native sequence). "Heterologous expression" thus encompasses expression of a sequence that is non-native to the host cell, as well as expression of a sequence that is native to the host cell in a non-native context.

As used with reference to polynucleotides or polypeptides, the term "wild-type" refers to any polynucleotide having a nucleotide sequence, or polypeptide having an amino acid, sequence present in a polynucleotide or polypeptide from a naturally occurring organism, regardless of the source of the molecule; i.e., the term "wild-type" refers to sequence characteristics, regardless of whether the molecule is purified from a natural source; expressed recombinantly, followed by purification; or synthesized. The term "wild-type" is also used to denote naturally occurring cells.

A "control cell" is a cell that is otherwise identical to an engineered cell being tested, including being of the same genus and species as the engineered cell, but lacks the specific genetic modification(s) being tested in the engineered cell.

Enzymes are identified herein by the reactions they catalyze and, unless otherwise indicated, refer to any polypeptide capable of catalyzing the identified reaction. Unless otherwise indicated, enzymes may be derived from any organism and may have a native or mutated amino acid sequence. As is well known, enzymes may have multiple functions and/or multiple names, sometimes depending on the source organism from which they derive. The enzyme names used herein encompass orthologs, including enzymes that may have one or more additional functions or a different name.

The term "feedback-deregulated" is used herein with reference to an enzyme that is normally negatively regulated by a downstream product of the enzymatic pathway (i.e., feedback-inhibition) in a particular cell. In this context, a "feedback-deregulated" enzyme is a form of the enzyme that is less sensitive to feedback-inhibition than the native enzyme native to the cell. A feedback-deregulated enzyme may be produced by introducing one or more mutations into a native enzyme. Alternatively, a feedback-deregulated enzyme may simply be a heterologous, native enzyme that, when introduced into a particular microbial cell, is not as sensitive to feedback-inhibition as the native, native enzyme. In some embodiments, the feedback-deregulated enzyme shows no feedback-inhibition in the microbial cell.

The term "(6E)-8-hydroxygeraniol" refers to (2E,6E)-2, 6-Dimethyl-2,6-octadiene-1,8-diol (CAS#26488-97-1).

The term "sequence identity," in the context of two or more amino acid or nucleotide sequences, refers to two or more sequences that are the same or have a specified percentage of amino acid residues or nucleotides that are the same, when compared and aligned for maximum correspondence, as measured using a sequence comparison algorithm or by visual inspection.

For sequence comparison to determine percent nucleotide or amino acid sequence identity, typically one sequence acts as a "reference sequence," to which a "test" sequence is compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence relative to the reference sequence, based on the designated program parameters. Alignment of sequences for comparison can be conducted using BLAST set to default parameters.

The term "titer," as used herein, refers to the mass of a product (e.g., (6E)-8-hydroxygeraniol) produced by a culture of microbial cells divided by the culture volume.

As used herein with respect to recovering (6E)-8-hydroxygeraniol from a cell culture, "recovering" refers to separating the (6E)-8-hydroxygeraniol from at least one other component of the cell culture medium.

Figure 1:
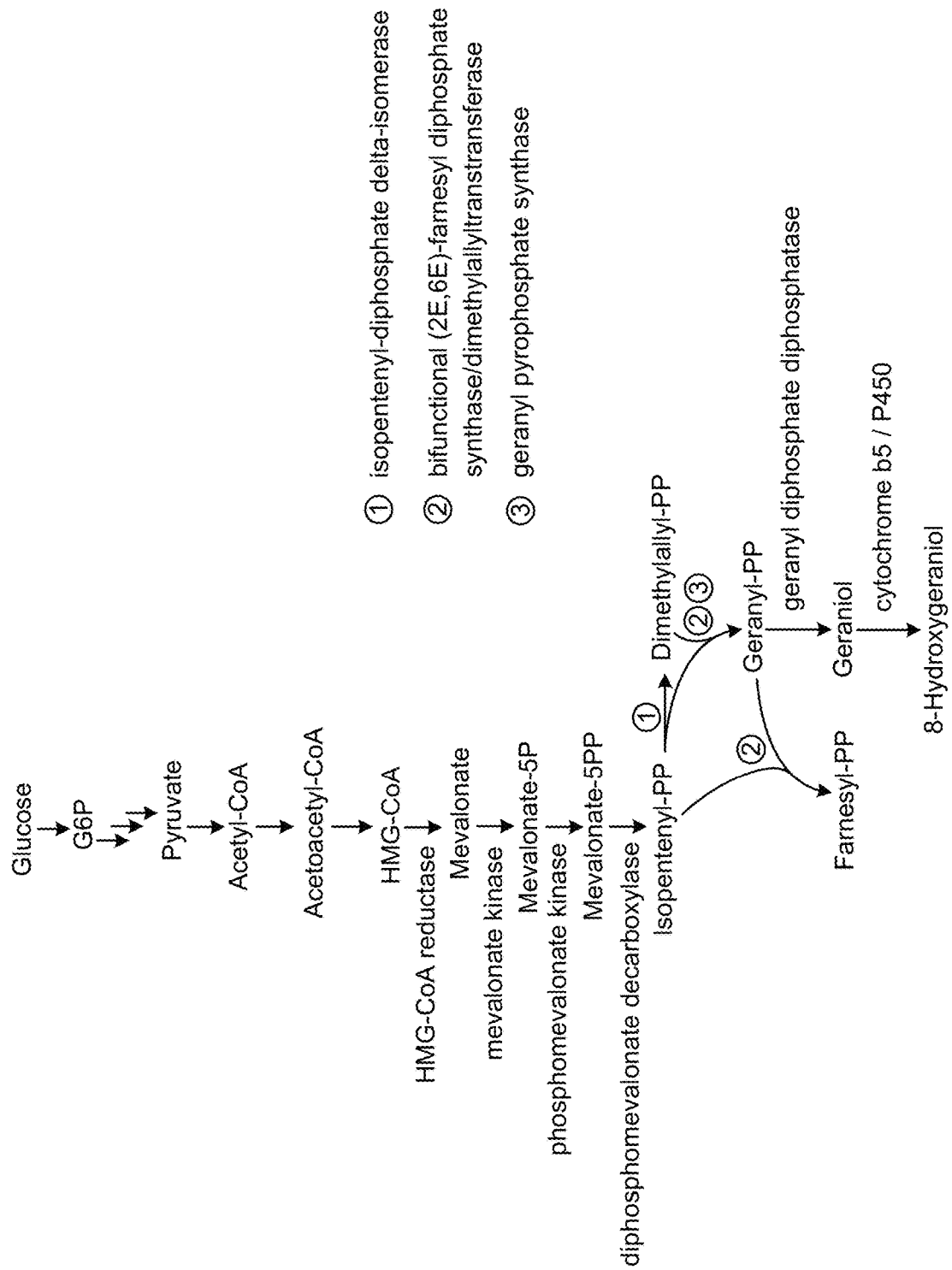
FIG. 1: Pathway for production of (6E)-8-hydroxygeraniol by fermentation.

Engineering Microbes for (6E)-8-Hydroxygeraniol Production (6E)-8-Hydroxygeraniol Biosynthesis Pathway (6E)-8-hydroxygeraniol is derived from the mevalonate biosynthesis pathway, based on the core metabolite precursor acetyl-CoA. This pathway is illustrated in FIG. 1. HMG-CoA reductase in the mevalonate biosynthesis pathway is subject to feedback inhibition. Many microbes, such as *Saccharomyces cerevisiae*, lack the enzymes that catalyze the final two steps in this pathway, namely geranyl diphosphate diphosphatase (geraniol synthase) and geraniol-8-hydroxylase. Production of (6E)-8-hydroxygeraniol in such microbial hosts requires the addition of at least one heterologous geraniol synthase enzyme and at least one heterologous geraniol-8-hydroxylase.

Engineering for Microbial (6E)-8-Hydroxygeraniol Production

Any geraniol synthase and geraniol-8-hydroxylase that are active in the microbial cell being engineered may be introduced into the cell, typically by introducing and expressing the genes encoding the enzymes using standard genetic engineering techniques. Suitable geraniol synthases and geraniol-8-hydroxylases may be derived from any source, including plant, archaeal, fungal, gram-positive bacterial, and gram-negative bacterial sources. Exemplary sources include, but are not limited to: *Perilla setoyensis, Phaseolus angularis, Vitis vinifera* (grape), *Swertia mussotii* (Felwort), *Populus trichocarpa* (Western balsam poplar) (*Populus balsamifera* subsp. *Trichocarpa*), *Papaver somniferum, Petroselinum crispum, Oryza sativa, Methanosphaerula palustris* Methanocaldococcus jannaschii, *Zygosaccharomyces* bailii, *Penicillium marneffei, Talaromyces stipitatus, Trichophyton equinum, Propionibacterium* sp.

oral, *Enterococcus faecium, Streptomyces hygroscopicus, Streptomyces* sviceus, Modestobacter *marinus, Pseudomonas putida, Sinorhizobium fredii*, Cathatanthus roseaus, *Zea mays, Catharanthus roseus* (Madagascar periwinkle) (*Vinca rosea*), *Perilla frutescens* var. *crispa, Perilla frutescens* var. *hirtella, Cinnamomum* tenuipile (Alseodaphne *mollis*), *Ocimum basilicum* (Sweet basil), *Perilla citriodora, Olea europaea* (Common olive), *Phyla dulcis* (Aztec sweet herb) (Lippia *dulcis*), *Rosa rugosa* (*Rugosa* rose), Camptotheca *acuminata* (Happy tree), Citrus jambhiri (Rough lemon), Picrorhiza kurrooa, *Arabidopsis thaliana* (Mouse-ear cress), *Glycine max* (Soybean) (*Glycine hispida*), *Beta vulgaris* (Sugar beet), *Mollugo verticillata* (Green carpetweed), Amborella trichopoda, *Solanum tuberosum* (Potato), *Glycine soja* (Wild soybean), Vanda *coerulea, Oryza barthii, Hypericum* androsaemum (Tutsan), *Solanum lycopersicum* (Tomato) (*Lycopersicon esculentum*), and *Coffea canephora* (*Robusta* coffee).

One or more copies of each of a geraniol synthase and a geraniol-8-hydroxylase gene can be introduced into a selected microbial host cell. If more than one copy of a gene is introduced, the copies can be copies can have the same or different nucleotide sequences. In some embodiments, one or both of the heterologous gene(s) is/are expressed from a strong, constitutive promoter. In some embodiments, the heterologous geraniol synthase and/or the heterologous geraniol-8-hydroxylase genes are expressed from inducible promoters. The heterologous genes can optionally be codon-optimized to enhance expression in the selected microbial host cell.

In Example 1, *S. cerevisiae* was engineered to express geraniol synthase from *Perilla* setoyensis (UniProt ID C0KWV4) (SEQ ID NO:5) and geraniol-8-hydroxylase from *Phaseolus angularis* (UniProt ID C6J436) (SEQ ID NO:11), which yielded a (6E)-8-hydroxygeraniol titer of 37.5 µg/L in a first round of genetic engineering (Table 1, below). This titer was increased in a second round to 122.9 µg/L in a strain that additionally expressed three copies of isopentenyl-diphosphate delta3-delta2-isomerase (UniProt ID P15496) (SEQ ID NO:25).

In Example 2, *Y. lipolytica* was engineered to express geraniol synthase *Perilla* setoyensis (UniProt ID C0KWV4) (SEQ ID NO:99), geraniol 8-hydroxylase from *Phaseolus angularis* (UniProt ID A0A0L9UT99) (SEQ ID NO:115), and isopentenyl-diphosphate delta3-delta2-isomerase from *S. cerevisiae* (UniProt ID P15496) (SEQ ID NO:126), which yielded a (6E)-8-hydroxygeraniol titer of 310 microgram/L.

In Example 3, *S. cerevisiae* was engineered to express geraniol synthase from *Perilla* setoyensis (UniProt ID C0KWV4) (SEQ ID NO:99), geraniol-8-hydroxylase from *Phaseolus angularis* (UniProt ID C6J436), and isopentenyl-diphosphate delta3-delta2-isomerase from *S. cerevisiae* (UniProt ID P15496) (SEQ ID NO:126), which yielded a (6E)-8-hydroxygeraniol titer of 217 microgram/L.

Increasing the Activity of Upstream Enzymes

One approach to increasing (6E)-8-hydroxygeraniol production in a microbial cell that is capable of such production is to increase the activity of one or more upstream enzymes in the (6E)-8-hydroxygeraniol biosynthesis pathway. Upstream pathway enzymes include all enzymes involved in the conversions from a feedstock all the way to into the last native metabolite (i.e., geranyl diphosphate in *S. cerevisiae*). In certain embodiments, the upstream pathway enzymes refer specifically to the enzymes involved in the conversion of key precursors into geranyl diphosphate in the pathway leading to (6E)-8-hydroxygeraniol. Such genes include those encoding an ATP-citrate synthase, an acetyl-CoA synthetase, a thiolase, a hydroxymethylglutaryl coenzyme A synthase (HMG-CoA synthase), a hydroxymethylglutaryl coenzyme A reductase (HMG-CoA reductase), a mevalonate kinase, a phosphomevalonate kinase, a diphosphomevalonate decarboxylase, an isopentenyl-diphosphate delta-isomerase (systematic name: isopentenyl-diphosphate delta2-delta3-isomerase), and a geranyl diphosphate synthase. Suitable upstream pathway genes may be derived from any source, including, for example, those discussed above as sources for a heterologous geraniol synthase or geraniol-8-hydroxylase gene.

In some embodiments, the activity of one or more upstream pathway enzymes is increased by modulating the expression or activity of the native enzyme(s). Examples of this approach include: (1) over-expression of HMG-CoA reductase and/or constitutive over-expression of geranyl diphosphate synthase to increase the level of the (6E)-8-hydroxygeraniol pathway precursor geranyl diphosphate, and/or (2) over-expression of ATP-citrate synthase (P53396) and/or acetyl-CoA synthetase (ACS, Q8ZKF6) improve the availability of acetyl-CoA.

The expression of the native upstream pathway enzymes can be increased by means of one or more natural regulators of upstream pathway activity. For example, to improve expression of the isoprenoid pathway enzymes, one may introduce, and optionally, over-express, a variant of a sterol uptake control protein, UPC2 (UniProt ID Q12151, from Saccharomyces cerevisiae S288c, containing either G888D or G888R [these designations indicate amino acid substitutions, using the standard one-letter code for amino acids, with the first letter referring to the wild-type residue and the last letter referring to the replacement residue; the numbers indicate the position of the amino acid substitution in the translated protein]) [6, 7]. The sterol uptake control protein UPC2 regulates sterol synthesis and the C-terminal amino acid substitutions increase the activity of this transcription factor. For example, UPC2 binding element upstream of ERG8 enables UPC2 transcriptional activation of ERG8 in addition to other sterol biosynthesis pathway genes [7].

Figure 5:
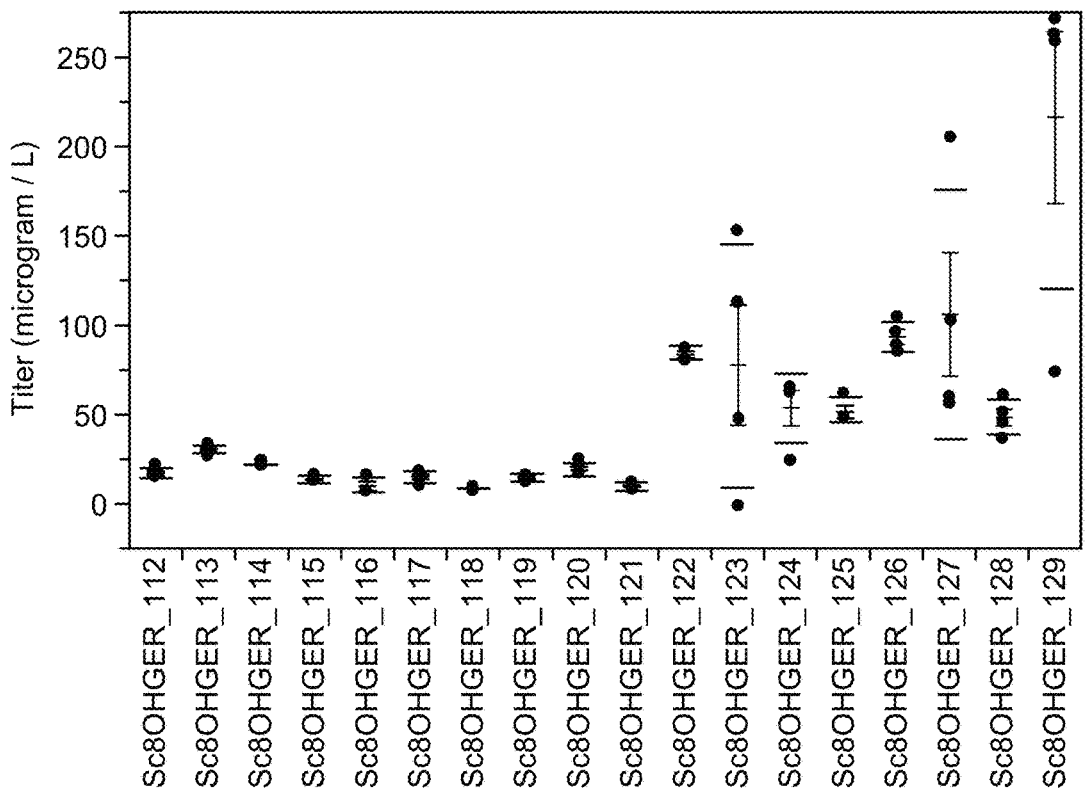
FIG. 5: (6E)-8-Hydroxygeraniol titers measured in the extracellular broth following fermentation in *S. cerevisiae* for host evaluation. (See also Example 3, Table 5.)

Alternatively, or in addition, one or more promoters can be substituted for native promoters using, for example, a technique such as that illustrated in FIG. 5. In certain embodiments, the replacement promoter is stronger than the native promoter and/or is a constitutive promoter.

In some embodiments, the activity of one or more upstream pathway enzymes is supplemented by introducing one or more of the corresponding genes into the geraniol synthase- and geraniol-8-hydroxylase-expressing microbial host cell. Example 1 describes the successful engineering of a microbial host cell to express a heterologous geraniol synthase and a heterologous geraniol-8-hydroxylase, along with an introduced gene encoding an isopentenyl-diphosphate Delta-isomerase.

An introduced upstream pathway gene may be from an organism other than that of the host cell or may simply be an additional copy of a native gene. In some embodiments, one or more such genes are introduced into a microbial host cell capable of (6E)-8-hydroxygeraniol production and expressed from a strong constitutive promoter and/or can optionally be codon-optimized to enhance expression in the selected microbial host cell.

In various embodiments, the engineering of a (6E)-8-hydroxygeraniol-producing microbial cell to increase the activity of one or more upstream pathway enzymes increases the (6E)-8-hydroxygeraniol titer by at least 10, 20, 30, 40, 50, 60, 70, 80, or 90 percent or by at least 2-fold, 2.5-fold, 3-fold, 3.5-fold, 4-fold, 4.5-fold, 5-fold, 5.5-fold, 6-fold, 6.5-fold, 7-fold, 7.5-fold, 8-fold, 8.5-fold, 9-fold, 9.5-fold, 10-fold, 11-fold, 12-fold, 13-fold, 14-fold, 15-fold, 16-fold, 17-fold, 18-fold, 19-fold, 20-fold, 21-fold, 22-fold, 23-fold, 24-fold, 25-fold, 30-fold, 35-fold, 40-fold, 45-fold, 50-fold, 55-fold, 60-fold, 65-fold, 70-fold, 75-fold, 80-fold, 85-fold, 90-fold, 95-fold, or 100-fold. In various embodiments, the increase in (6E)-8-hydroxygeraniol titer is in the range of 10 percent to 100-fold, 2-fold to 50-fold, 5-fold to 40-fold, 10-fold to 30-fold, or any range bounded by any of the values listed above. (Ranges herein include their endpoints.) These increases are determined relative to the (6E)-8-hydroxygeraniol titer observed in a (6E)-8-hydroxygeraniol-producing microbial cell that lacks any increase in activity of upstream pathway enzymes. This reference cell may have one or more other genetic alterations aimed at increasing (6E)-8-hydroxygeraniol production, e.g., the cell may express a feedback-deregulated enzyme.

In various embodiments, the (6E)-8-hydroxygeraniol titers achieved by increasing the activity of one or more upstream pathway genes are at least 100, 200, 300, 400, 500, 600, 700, 800, or 900 µg/L, or at least 1, 10, 50, 75, 100, 200, 300, 400, 500, 600, 700, 800, or 900 mg/L or at least 1, 1.5, 2, 2.5, 3, 3.5, 4, 4.5, 5, or 10 gm/L. In various embodiments, the titer is in the range of 100 µg/L to 10 gm/L, 200 µg/L to 5 gm/L, 500 µg/L to 4 gm/L, 1 mg/L to 3 gm/L, 500 mg/L to 2 gm/L or any range bounded by any of the values listed above.

Introduction of Feedback-Deregulated Enzymes

Since (6E)-8-hydroxygeraniol biosynthesis is subject to feedback inhibition, another approach to increasing (6E)-8-hydroxygeraniol production in a microbial cell engineered to produce (6E)-8-hydroxygeraniol is to introduce feedback-deregulated forms of one or more enzymes that are normally subject to feedback regulation. HMG-CoA reductase is one such enzyme. A feedback-deregulated form can be a heterologous, native enzyme that is less sensitive to feedback inhibition than the native enzyme in the particular microbial host cell. Alternatively, a feedback-deregulated form can be a variant of a native or heterologous enzyme that has one or more mutations or truncations rendering it less sensitive to feedback inhibition than the corresponding native enzyme. Examples of the latter include a variant HMG-CoA reductase (from S. cerevisiae) that has an N-terminal truncation (SEQ ID NO:27). Expression of this feedback-deregulated HMG-CoA reductase in a host cell has been shown to improve mevalonate pathway flux in S. cerevisiae [3] and other organisms (see, e.g., PCT Publication No. WO2001031027A1, describing genetic engineering of plants).

In various embodiments, the engineering of a (6E)-8-hydroxygeraniol-producing microbial cell to express a feedback-deregulated enzymes increases the (6E)-8-hydroxygeraniol titer by at least 10, 20, 30, 40, 50, 60, 70, 80, or 90 percent or by at least 2-fold, 2.5-fold, 3-fold, 3.5-fold, 4-fold, 4.5-fold, 5-fold, 5.5-fold, 6-fold, 6.5-fold, 7-fold, 7.5-fold, 8-fold, 8.5-fold, 9-fold, 9.5-fold, 10-fold, 11-fold, 12-fold, 13-fold, 14-fold, 15-fold, 16-fold, 17-fold, 18-fold, 19-fold, 20-fold, 21-fold, 22-fold, 23-fold, 24-fold, 25-fold, 30-fold, 35-fold, 40-fold, 45-fold, 50-fold, 55-fold, 60-fold, 65-fold, 70-fold, 75-fold, 80-fold, 85-fold, 90-fold, 95-fold, or 100-fold. In various embodiments, the increase in (6E)-8-hydroxygeraniol titer is in the range of 10 percent to 100-fold, 2-fold to 50-fold, 5-fold to 40-fold, 10-fold to 30-fold, or any range bounded by any of the values listed above. These increases are determined relative to the (6E)-8-hydroxygeraniol titer observed in a (6E)-8-hydroxygeraniol-producing microbial cell that does not express a feedback-deregulated enzyme. This reference cell may (but need not) have other genetic alterations aimed at increasing (6E)-8-hydroxygeraniol production, i.e., the cell may have increased activity of an upstream pathway enzyme resulting from some means other than feedback-insensitivity.

In various embodiments, the (6E)-8-hydroxygeraniol titers achieved by using a feedback-deregulated enzyme to increase flux though the (6E)-8-hydroxygeraniol biosynthetic pathway are at least 100, 200, 300, 400, 500, 600, 700, 800, or 900 µg/L, or at least 1, 10, 50, 75, 100, 200, 300, 400, 500, 600, 700, 800, or 900 mg/L or at least 1, 1.5, 2, 2.5, 3, 3.5, 4, 4.5, 5, or 10 g/L. In various embodiments, the titer is in the range of 100 µg/L to 10 g/L, 200 µg/L to 5 g/L, 500 µg/L to 4 g/L, 1 mg/L to 3 g/L, 500 mg/L to 2 g/L or any range bounded by any of the values listed above.

The approaches of supplementing the activity of one or more native enzymes and/or introducing one or more feedback-deregulated enzymes can be combined in geraniol synthase-expressing microbial cells to achieve even higher (6E)-8-hydroxygeraniol production levels.

Reduction of Precursor Consumption

Figure 6:
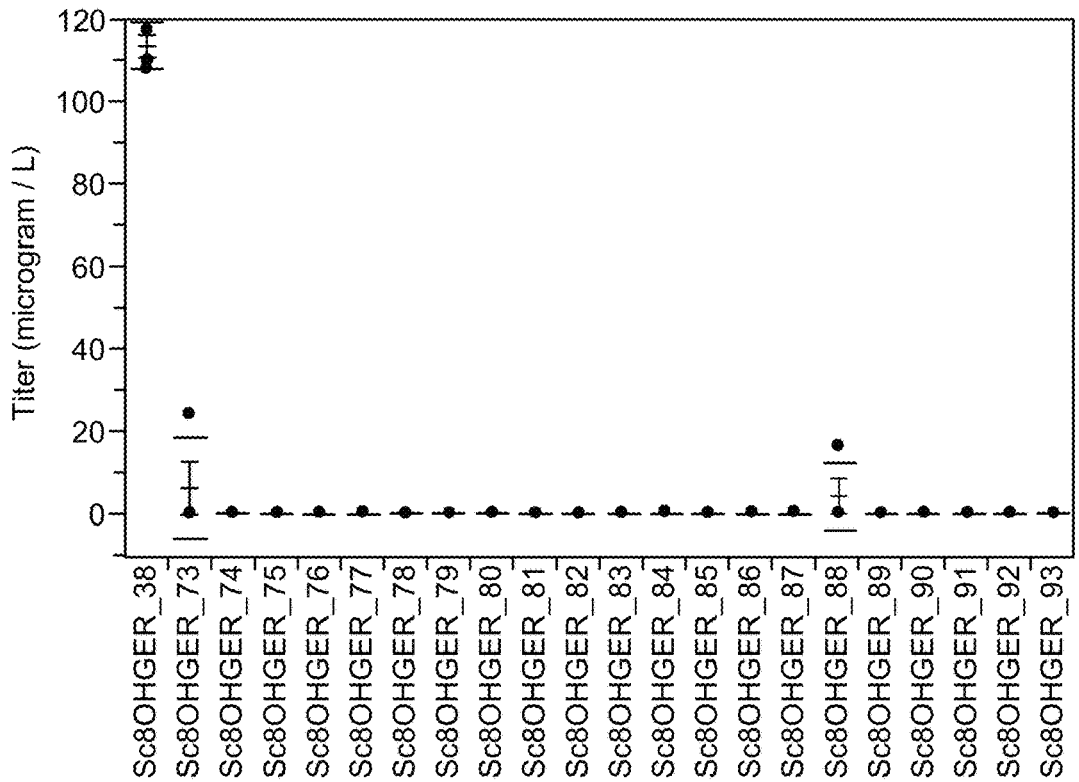
FIG. 6: (6E)-8-Hydroxygeraniol titers measured in the extracellular broth following fermentation in *S. cerevisiae* for fourth (Improvement) round strains. (See also Example 1, Table 3.)

Another approach to increasing (6E)-8-hydroxygeraniol production in a microbial cell that is capable of such production is to decrease the activity of one or more enzymes that shunt one or more precursors of (6E)-8-hydroxygeraniol biosynthesis into one or more side pathways (i.e., pathways leading to other products than (6E)-8-hydroxygeraniol). In some embodiments, the activity of one or more side-pathway enzymes is reduced by modulating the expression or activity of the native enzyme(s). Illustrative side-pathway enzymes include a bifunctional (2E,6E)-farnesyl diphosphate synthase/dimethylallyltranstransferase, a geranylgeranyl pyrophosphate synthase, and any side-pathway enzyme that consumes acetyl Co-A. The activity of such enzymes can be decreased, for example, by substituting the native promoter of the corresponding gene(s) with a less active or inactive promoter or by deleting the corresponding gene(s). See FIGS. 5 and 6 for examples of schemes for promoter replacement and targeted gene deletion, respectively, in S. cervisiae.

The native bifunctional (2E,6E)-farnesyl diphosphate synthase/dimethylallyltranstransferase is bifunctional and can form geranyl diphosphate and subsequently a second reaction can convert geranyl diphosphate to (2E,6E)-farnesyl diphosphate. Because the native enzyme harbors these two activities and the intermediate is a (6E)-8-hydroxygeraniol pathway metabolite, it is beneficial to lower the expression of the native bifunctional (2E,6E)-farnesyl diphosphate synthase/dimethylallyltranstransferase. However, expression of the enzyme harboring the S80F amino acid substitution produces measurable quantities of the monoterpenoid [4] (see also U.S. Pat. No. 8,715,962). For example, to prevent additional flux to sterols, expression or activity of the bifunctional farnesyl-diphosphate farnesyl-transferase (EC 2.5.1.21) encoded by ERG9 in S. cerevisiae, and/or (2E,6E)-farnesyl diphosphate synthase (EC 2.5.1.10) encoded by ERG20 in S. cerevisiae are lowered to maximize geranyl diphosphate pools for (6E)-8-hydroxygeraniol biosynthesis.

In illustrative embodiments in S. cervisiae: (1) the promoter for the bifunctional (2E,6E)-farnesyl diphosphate synthase/dimethylallyltranstransferase (ERG20, YJL167W) can be replaced with the S. cerevisiae pRnr1 promoter to lower expression of this native enzyme which consumes the (6E)-8-hydroxygeneniol pathway metabolite geranyl diphosphate; (2) the promoter for the geranylgeranyl pyrophosphate synthase (Bts1, YPL069C) can be replaced with the S. cerevisiae pPsp2 to lower expression of this native enzyme which also consumes geranyl diphosphate; and/or one or more of the genes Pdc5 (YLR134W), Pdc6 (YGR087C), and Pdc1 (YLR044C) can be deleted to reduce acetyl-CoA consumption.

In various embodiments, the engineering of a (6E)-8-hydroxygeraniol-producing microbial cell to reduce precursor consumption by one or more side pathways increases the (6E)-8-hydroxygeraniol titer by at least 10, 20, 30, 40, 50, 60, 70, 80, or 90 percent or by at least 2-fold, 2.5-fold, 3-fold, 3.5-fold, 4-fold, 4.5-fold, 5-fold, 5.5-fold, 6-fold, 6.5-fold, 7-fold, 7.5-fold, 8-fold, 8.5-fold, 9-fold, 9.5-fold, 10-fold, 11-fold, 12-fold, 13-fold, 14-fold, 15-fold, 16-fold, 17-fold, 18-fold, 19-fold, 20-fold, 21-fold, 22-fold, 23-fold, 24-fold, 25-fold, 30-fold, 35-fold, 40-fold, 45-fold, 50-fold, 55-fold, 60-fold, 65-fold, 70-fold, 75-fold, 80-fold, 85-fold, 90-fold, 95-fold, or 100-fold. In various embodiments, the increase in (6E)-8-hydroxygeraniol titer is in the range of 10 percent to 100-fold, 2-fold to 50-fold, 5-fold to 40-fold, 10-fold to 30-fold, or any range bounded by any of the values listed above. These increases are determined relative to the (6E)-8-hydroxygeraniol-producing microbial cell that does not include genetic alterations to reduce precursor consumption. This reference cell may (but need not) have other genetic alterations aimed at increasing (6E)-8-hydroxygeraniol production, i.e., the cell may have increased activity of an upstream pathway enzyme.

In various embodiments, the (6E)-8-hydroxygeraniol titers achieved by reducing precursor consumption by one or more side pathways are at least 100, 200, 300, 400, 500, 600, 700, 800, or 900 µg/L, or at least 1, 10, 50, 75, 100, 200, 300, 400, 500, 600, 700, 800, or 900 mg/L or at least 1, 1.5, 2, 2.5, 3, 3.5, 4, 4.5, 5, or 10 g/L. In various embodiments, the titer is in the range of 100 µg/L to 10 g/L, 200 µg/L to 5 gm/L, 500 µg/L to 4 g/L, 1 mg/L to 3 g/L, 500 mg/L to 2 g/L or any range bounded by any of the values listed above.

The approaches of increasing the activity of one or more native enzymes and/or introducing one or more feedback-deregulated enzymes and/or reducing precursor consumption by one or more side pathways can be combined to achieve even higher (6E)-8-hydroxygeraniol production levels.

Microbial Host Cells

Any microbe that can be used to express introduced genes can be engineered for fermentative production of (6E)-8-hydroxygeraniol as described above. In certain embodiments, the microbe is one that is naturally incapable of fermentative production of (6E)-8-hydroxygeraniol. In some embodiments, the microbe is one that is readily cultured, such as, for example, a microbe known to be useful as a host cell in fermentative production of compounds of interest. Bacteria cells, including gram positive or gram negative bacteria can be engineered as described above. Examples include, in addition to C. glutamicum cells, Bacillus subtilus, B. licheniformis, B. lentus, B. brevis, B. stearothermophilus, B. alkalophilus, B. amyloliquefaciens, B. clausii, B. halodurans, B. megaterium, B. coagulans, B. circulans, B. lautus, B. thuringiensis, S. albus, S. lividans, S. coelicolor, S. griseus, Pseudomonas sp., P. alcaligenes, P. citrea, Lactobacilis spp. (such as *L. lactis, L. plantarum*), *L. grayi, E. coli, E. faecium, E. gallinarum*, E. casseliflavus, and/or *E. faecalis* cells.

There are numerous types of anaerobic cells that can be used as microbial host cells in the methods described herein. In some embodiments, the microbial cells are obligate anaerobic cells. Obligate anaerobes typically do not grow well, if at all, in conditions where oxygen is present. It is to be understood that a small amount of oxygen may be present, that is, there is some level of tolerance level that obligate anaerobes have for a low level of oxygen. Obligate anaerobes engineered as described above can be grown under substantially oxygen-free conditions, wherein the amount of oxygen present is not harmful to the growth, maintenance, and/or fermentation of the anaerobes.

Alternatively, the microbial host cells used in the methods described herein can be facultative anaerobic cells. Facultative anaerobes can generate cellular ATP by aerobic respiration (e.g., utilization of the TCA cycle) if oxygen is present. However, facultative anaerobes can also grow in the absence of oxygen. Facultative anaerobes engineered as described above can be grown under substantially oxygen-free conditions, wherein the amount of oxygen present is not harmful to the growth, maintenance, and/or fermentation of the anaerobes, or can be alternatively grown in the presence of greater amounts of oxygen.

In some embodiments, the microbial host cells used in the methods described herein are filamentous fungal cells. (See, e.g., Berka & Barnett, Biotechnology Advances, (1989), 7(2):127-154). Examples include *Trichoderma longibrachiatum, T viride, T koningii, T harzianum, Penicillium* sp., *Humicola insolens, H. lanuginose, H. grisea, Chrysosporium* sp., *C. lucknowense, Gliocladium* sp., *Aspergillus* sp. (such as *A. oryzae, A. niger, A. sojae, A. japonicus, A. nidulans*, or *A. awamori*), *Fusarium* sp. (such as *F. roseum, F. graminum F. cerealis, F. oxysporuim*, or *F. venenatum*), *Neurospora* sp. (such as *N. crassa* or Hypocrea sp.), *Mucor* sp. (such as *M. miehei*), *Rhizopus* sp., and Emericella sp. cells. In particular embodiments, the fungal cell engineered as described above is *A. nidulans, A. awamori, A. oryzae, A. aculeatus, A. niger, A. japonicus, T reesei, T viride, F. oxysporum*, or *F. solani*. Illustrative plasmids or plasmid components for use with such hosts include those described in U.S. Patent Pub. No. 2011/0045563.

Yeasts can also be used as the microbial host cell in the methods described herein. Examples include: *Saccharomyces* sp., *Schizosaccharomyces* sp., *Pichia* sp., *Hansenula polymorpha, Pichia stipites, Kluyveromyces marxianus, Kluyveromyces* spp., *Yarrowia lipolytica* and *Candida* sp. In some embodiments, the *Saccharomyces* sp. is *S. cerevisiae* (See, e.g., Romanos et al., Yeast, (1992), 8(6):423-488). Illustrative plasmids or plasmid components for use with such hosts include those described in U.S. Pat. No. 7,659,097 and U.S. Patent Pub. No. 2011/0045563.

In some embodiments, the host cell can be an algal cell derived, e.g., from a green algae, red algae, a glaucophyte, a chlorarachniophyte, a euglenid, a chromista, or a dinoflagellate. (See, e.g., Saunders & Warmbrodt, "Gene Expression in Algae and Fungi, Including Yeast," (1993), National Agricultural Library, Beltsville, Md.). Illustrative plasmids or plasmid components for use in algal cells include those described in U.S. Patent Pub. No. 2011/0045563.

In other embodiments, the host cell is a cyanobacterium, such as cyanobacterium classified into any of the following groups based on morphology: Chlorococcales, Pleurocapsales, Oscillatoriales, Nostocales, Synechosystic or Stigonematales (See, e.g., Lindberg et al., Metab. Eng., (2010) 12(1):70-79). Illustrative plasmids or plasmid components for use in cyanobacterial cells include those described in U.S. Patent Pub. Nos. 2010/0297749 and 2009/0282545 and in Intl. Pat. Pub. No. WO 2011/034863.

Genetic Engineering Methods

Microbial cells can be engineered for fermentative (6E)-8-hydroxygeraniol production using conventional techniques of molecular biology (including recombinant techniques), microbiology, cell biology, and biochemistry, which are within the skill of the art. Such techniques are explained fully in the literature, see e.g., "Molecular Cloning: A Laboratory Manual," fourth edition (Sambrook et al., 2012); "Oligonucleotide Synthesis" (M. J. Gait, ed., 1984); "Culture of Animal Cells: A Manual of Basic Technique and Specialized Applications" (R. I. Freshney, ed., 6th Edition, 2010); "Methods in Enzymology" (Academic Press, Inc.); "Current Protocols in Molecular Biology" (F. M. Ausubel et al., eds., 1987, and periodic updates); "PCR: The Polymerase Chain Reaction," (Mullis et al., eds., 1994); Singleton et al., Dictionary of Microbiology and Molecular Biology 2nd ed., J. Wiley & Sons (New York, N.Y. 1994).

Vectors are polynucleotide vehicles used to introduce genetic material into a cell. Vectors useful in the methods described herein can be linear or circular. Vectors can integrate into a target genome of a host cell or replicate independently in a host cell. For many applications, integrating vectors that produced stable transformants are preferred. Vectors can include, for example, an origin of replication, a multiple cloning site (MCS), and/or a selectable marker. An expression vector typically includes an expression cassette containing regulatory elements that facilitate expression of a polynucleotide sequence (often a coding sequence) in a particular host cell. Vectors include, but are not limited to, integrating vectors, prokaryotic plasmids, episomes, viral vectors, cosmids, and artificial chromosomes.

Illustrative regulatory elements that may be used in expression cassettes include promoters, enhancers, internal ribosomal entry sites (IRES), and other expression control elements (e.g., transcription termination signals, such as polyadenylation signals and poly-U sequences). Such regulatory elements are described, for example, in Goeddel, Gene Expression Technology: Methods In Enzymology 185, Academic Press, San Diego, Calif. (1990).

In some embodiments, vectors may be used to introduce systems that can carry out genome editing, such as CRISPR systems. See U.S. Patent Pub.

No. 2014/0068797, published 6 Mar. 2014; see also Jinek M., et al., "A programmable dual-RNA-guided DNA endonuclease in adaptive bacterial immunity," Science 337:816-21, 2012). In Type II CRISPR-Cas9 systems, Cas9 is a site-directed endonuclease, namely an enzyme that is, or can be, directed to cleave a polynucleotide at a particular target sequence using two distinct endonuclease domains (HNH and RuvC/RNase H-like domains). Cas9 can be engineered to cleave DNA at any desired site because Cas9 is directed to its cleavage site by RNA. Cas9 is therefore also described as an "RNA-guided nuclease." More specifically, Cas9 becomes associated with one or more RNA molecules, which guide Cas9 to a specific polynucleotide target based on hybridization of at least a portion of the RNA molecule(s) to a specific sequence in the target polynucleotide. Ran, F. A., et al., ("In vivo genome editing using *Staphylococcus aureus* Cas9," Nature 520(7546):186-91, 2015, Apr. 9], including all extended data) present the crRNA/tracrRNA sequences and secondary structures of eight Type II CRISPR-Cas9 systems. Cas9-like synthetic proteins are also known in the art (see U.S. Published Patent Application No. 2014-0315985, published 23 Oct. 2014).

Example 1 describes illustrative integration approaches for introducing polynucleotides and other genetic alterations into the genomes of *S. cerevisiae* cells.

Vectors or other polynucleotides can be introduced into microbial cells by any of a variety of standard methods, such as transformation, conjugation, electroporation, nuclear microinjection, transduction, transfection (e.g., lipofection mediated or DEAE-Dextrin mediated transfection or transfection using a recombinant phage virus), incubation with calcium phosphate DNA precipitate, high velocity bombardment with DNA-coated microprojectiles, and protoplast fusion. Transformants can be selected by any method known in the art. Suitable methods for selecting transformants are described in U.S. Patent Pub. Nos. 2009/0203102, 2010/0048964, and 2010/0003716, and International Publication Nos. WO 2009/076676, WO 2010/003007, and WO 2009/132220.

Engineered Microbial Cells

The above-described methods can be used to produce engineered microbial cells that produce, and in certain embodiments, overproduce, (6E)-8-hydroxygeraniol. Engineered microbial cells can have at least 1, 2, 3, 4, 5, 6, 7, 8, 9, 10, or more genetic alterations, such as 30-40 alterations, as compared to a native microbial cell, such as any of the microbial host cells described herein. Engineered microbial cells described in the Example below have one, two, or three genetic alterations, but those of skill in the art can, following the guidance set forth herein, design microbial cells with additional alterations. In some embodiments, the engineered microbial cells have not more than 15, 14, 13, 12, 11, 10, 9, 8, 7, 6, 5, or 4 genetic alterations, as compared to a native microbial cell. In various embodiments, microbial cells engineered for (6E)-8-hydroxygeraniol production can have a number of genetic alterations falling within the any of the following illustrative ranges: 1-10, 1-9, 1-8, 2-7, 2-6, 2-5, 2-4, 2-3, 3-7, 3-6, 3-5, 3-4, etc.

In some embodiments, an engineered microbial cell expresses at least one heterologous geranyl diphosphate diphosphatase (geraniol synthase), such as in the case of a microbial host cell that does not naturally produce (6E)-8-hydroxygeraniol. In various embodiments, the microbial cell can include and express, for example: (1) a single heterologous geraniol synthase gene, (2) two or more heterologous geraniol synthase genes, which can be the same or different (in other words, multiple copies of the same heterologous geraniol synthase genes can be introduced or multiple, different heterologous geraniol synthase genes can be introduced), (3) a single heterologous geraniol synthase gene that is not native to the cell and one or more additional copies of an native geraniol synthase gene, or (4) two or more non-native geraniol synthase genes, which can be the same or different, and one or more additional copies of an native geraniol synthase gene.

In some embodiments, an engineered microbial cell expresses, at least one heterologous geraniol-8-hydroxylase, in addition to at least one heterologous geraniol synthase, such as in the case of a microbial host cell that does not have a geraniol-8-hydroxylase enzyme. In various embodiments, the microbial cell can include and express, for example: (1) a single heterologous geraniol-8-hydroxylase gene, (2) two or more heterologous geraniol-8-hydroxylase genes, which can be the same or different (in other words, multiple copies of the same heterologous geraniol-8-hydroxylase genes can be introduced or multiple, different heterologous geraniol-8-hydroxylase genes can be introduced), (3) a single heterologous geraniol-8-hydroxylase that is not native to the cell and one or more additional copies of an native geraniol-8-hydroxylase gene, or (4) two or more non-native geraniol-8-hydroxylase genes, which can be the same or different, and one or more additional copies of an native geraniol-8-hydroxylase.

This engineered host cell can include at least one additional genetic alteration that increases flux through the pathway leading to the production of geranyl-PP (the immediate precursor of (6E)-8-hydroxygeraniol). These "upstream" enzymes in the pathway include: an ATP-citrate synthase, an acetyl-CoA synthetase, a thiolase, a hydroxymethylglutaryl coenzyme A synthase (HMG-CoA synthase), a hydroxymethylglutaryl coenzyme A reductase (HMG-CoA reductase), a mevalonate kinase, a phosphomevalonate kinase, a diphosphomevalonate decarboxylase, an isopentenyl-diphosphate delta-isomerase, and a geranyl diphosphate synthase, including any isoforms, paralogs, or orthologs having these enzymatic activities (which as those of skill in the art readily appreciate may be known by different names). The at least one additional alteration can increase the activity of the upstream pathway enzyme(s) by any available means, e.g., by: (1) modulating the expression or activity of the native enzyme(s), (2) expressing one or more additional copies of the genes for the native enzymes, or (3) expressing one or more copies of the genes for one or more non-native enzymes.

In some embodiments, increased flux through the pathway can be achieved by expressing one or more genes encoding a feedback-deregulated enzyme, as discussed above. For example, the engineered host cell can include and express one or more feedback-deregulated HMG-CoA reductase genes.

The engineered microbial cells can contain introduced genes that have a native nucleotide sequence or that differ from native. For example, the native nucleotide sequence can be codon-optimized for expression in a particular host cell. The amino acid sequences encoded by any of these introduced genes can be native or can differ from native. In various embodiments, the amino acid sequences have at least 0 percent, 70 percent, 75 percent, 80 percent, 85 percent, 90 percent, 95 percent or 100 percent amino acid sequence identity with a native amino acid sequence.

In some embodiments, increased availability of precursors to (6E)-8-hydroxygeraniol can be achieved by reducing the expression or activity of one or more side-pathway enzymes, such as a bifunctional (2E,6E)-farnesyl diphosphate synthase/dimethylallyltranstransferase, a geranylgeranyl pyrophosphate synthase, and any side-pathway enzyme that consumes acetyl Co-A. For example, the engineered host cell can include one or more promoter swaps to down-regulate expression of any of these enzymes and/or can have their genes deleted to eliminate their expression entirely.

The approach described herein has been carried out in fungal cells, namely the yeast *S. cerevisiae* (a eukaryote), and in bacterial cells, namely *C. glutamicum* (a prokaryote). (See Example 1.)

Illustrative Engineered Fungal Cells

In certain embodiments, the engineered yeast (e.g., *S. cerevisiae*) cell expresses a heterologous geraniol synthase having at least 70 percent, 75 percent, 80 percent, 85 percent, 90 percent, 95 percent or 100 percent amino acid sequence identity to a geraniol synthase from *Perilla setoyensis* (e.g., SEQ ID NO:5). In particular embodiments, the *Perilla setoyensis* geraniol synthase can include SEQ ID NO:5.

The engineered yeast (e.g., *S. cerevisiae*) cell also expresses a heterologous geraniol-8-hydroxylase, which, in certain embodiments, has at least 70 percent, 75 percent, 80 percent, 85 percent, 90 percent, 95 percent or 100 percent amino acid sequence identity to a geraniol-8-hydroxylase from *Phaseolus angularis* (e.g., SEQ ID NO:11). In particular embodiments, the *Phaseolus angularis* geraniol-8-hydroxylase can include SEQ ID NO:11.

These may be the only genetic alterations of the engineered yeast cell, or the yeast cell can include one or more additional genetic alterations, as discussed more generally above.

An illustrative yeast (e.g., *S. cerevisiae*) cell with one or more additional genetic alterations can have increased activity of an upstream pathway enzyme, such as isopentenyl-diphosphate delta-isomerase, relative to the control cell, e.g., produced by introducing an additional copy of a native S. cereviseae isopentenyl-diphosphate delta-isomerase (SEQ ID NO:25) gene into the cell or a gene encoding an isopentenyl-diphosphate delta-isomerase having at least 70 percent, 75 percent, 80 percent, 85 percent, 90 percent, or 95 percent amino acid sequence identity to the native S. cereviseae isopentenyl-diphosphate delta-isomerase.

In particular embodiments, the engineered yeast (e.g., *S. cerevisiae*) cell additionally expresses a variant of a *S. cerevisiae* HMG-CoA reductase, which typically has at least 70 percent, 75 percent, 80 percent, 85 percent, 90 percent, or 95 percent amino acid sequence identity to the native *S. cerevisiae* HMG-CoA reductase or a truncated variant of the *S. cerevisiae* HMG-CoA reductase where amino acid residues 1-529 are deleted. In particular embodiments, the *S. cerevisiae* HMG-CoA reductase variant can include SEQ ID NO:27.

Culturing of Engineered Microbial Cells

Any of the microbial cells described herein can be cultured, e.g., for maintenance, growth, and/or (6E)-8-hydroxygeraniol production.

In some embodiments, the cultures are grown to an optical density at 600 nm of 10-500, such as an optical density of 50-150.

In various embodiments, the cultures include produced (6E)-8-hydroxygeraniol at titers of at least 10, 25, 50, 75, 100, 200, 300, 400, 500, 600, 700, 800, or 900 μg/L, or at least 1, 10, 50, 75, 100, 200, 300, 400, 500, 600, 700, 800, or 900 mg/L or at least 1, 1.5, 2, 2.5, 3, 3.5, 4, 4.5, 5, or 10 gm/L. In various embodiments, the titer is in the range of 10 μg/L to 10 gm/L, 25 μg/L to 10 gm/L, 100 μg/L to 10 gm/L, 200 μg/L to 5 gm/L, 500 μg/L to 4 gm/L, 1 mg/L to 3 gm/L, 500 mg/L to 2 gm/L or any range bounded by any of the values listed above.

Culture Media

Microbial cells can be cultured in any suitable medium including, but not limited to, a minimal medium, i.e., one containing the minimum nutrients possible for cell growth. Minimal medium typically contains: (1) a carbon source for microbial growth; (2) salts, which may depend on the particular microbial cell and growing conditions; and (3) water. Suitable media can also include any combination of the following: a nitrogen source for growth and product formation, a sulfur source for growth, a phosphate source for growth, metal salts for growth, vitamins for growth, and other cofactors for growth.

Any suitable carbon source can be used to cultivate the host cells. The term "carbon source" refers to one or more carbon-containing compounds capable of being metabolized by a microbial cell. In various embodiments, the carbon source is a carbohydrate (such as a monosaccharide, a disaccharide, an oligosaccharide, or a polysaccharide), or an invert sugar (e.g., enzymatically treated sucrose syrup). Illustrative monosaccharides include glucose (dextrose), fructose (levulose), and galactose; illustrative oligosaccharides include dextran or glucan, and illustrative polysaccharides include starch and cellulose. Suitable sugars include C6 sugars (e.g., fructose, mannose, galactose, or glucose) and C5 sugars (e.g., xylose or arabinose). Other, less expensive carbon sources include sugar cane juice, beet juice, sorghum juice, and the like, any of which may, but need not be, fully or partially deionized.

The salts in a culture medium generally provide essential elements, such as magnesium, nitrogen, phosphorus, and sulfur to allow the cells to synthesize proteins and nucleic acids.

Minimal medium can be supplemented with one or more selective agents, such as antibiotics.

To produce (6E)-8-hydroxygeraniol, the culture medium can include, and/or is supplemented during culture with, glucose and/or a nitrogen source such as urea, an ammonium salt, ammonia, or any combination thereof.

Culture Conditions

Materials and methods suitable for the maintenance and growth of microbial cells are well known in the art. See, for example, U.S. Pub. Nos. 2009/0203102, 2010/0003716, and 2010/0048964, and International Pub. Nos. WO 2004/033646, WO 2009/076676, WO 2009/132220, and WO 2010/003007, Manual of Methods for General Bacteriology Gerhardt et al., eds), American Society for Microbiology, Washington, D.C. (1994) or Brock in Biotechnology: A Textbook of Industrial Microbiology, Second Edition (1989) Sinauer Associates, Inc., Sunderland, Mass.

In general, cells are grown and maintained at an appropriate temperature, gas mixture, and pH (such as about 20° C. to about 37° C., about 6% to about 84% $CO_2$, and a pH between about 5 to about 9). In some aspects, cells are grown at 35° C. In certain embodiments, such as where thermophilic bacteria are used as the host cells, higher temperatures (e.g., 50° C.-75° C.) may be used. In some aspects, the pH ranges for fermentation are between about pH 5.0 to about pH 9.0 (such as about pH 6.0 to about pH 8.0 or about 6.5 to about 7.0). Cells can be grown under aerobic, anoxic, or anaerobic conditions based on the requirements of the particular cell.

Standard culture conditions and modes of fermentation, such as batch, fed-batch, or continuous fermentation that can be used are described in U.S. Publ. Nos. 2009/0203102, 2010/0003716, and 2010/0048964, and International Pub. Nos. WO 2009/076676, WO 2009/132220, and WO 2010/003007. Batch and Fed-Batch fermentations are common and well known in the art, and examples can be found in Brock, Biotechnology: A Textbook of Industrial Microbiology, Second Edition (1989) Sinauer Associates, Inc.

In some embodiments, the cells are cultured under limited sugar (e.g., glucose) conditions. In various embodiments, the amount of sugar that is added is less than or about 105% (such as about 100%, 90%, 80%, 70%, 60%, 50%, 40%, 30%, 20%, or 10%) of the amount of sugar that can be consumed by the cells. In particular embodiments, the amount of sugar that is added to the culture medium is approximately the same as the amount of sugar that is consumed by the cells during a specific period of time. In some embodiments, the rate of cell growth is controlled by limiting the amount of added sugar such that the cells grow at the rate that can be supported by the amount of sugar in the cell medium. In some embodiments, sugar does not accumulate during the time the cells are cultured. In various embodiments, the cells are cultured under limited sugar conditions for times greater than or about 1, 2, 3, 5, 10, 15, 20, 25, 30, 35, 40, 50, 60, or 70 hours or even up to about 5-10 days. In various embodiments, the cells are cultured under limited sugar conditions for greater than or about 5, 10, 15, 20, 25, 30, 35, 40, 50, 60, 70, 80, 90, 95, or 100% of the total length of time the cells are cultured. While not intending to be bound by any particular theory, it is believed that limited sugar conditions can allow more favorable regulation of the cells.

In some aspects, the cells are grown in batch culture. The cells can also be grown in fed-batch culture or in continuous culture. Additionally, the cells can be cultured in minimal medium, including, but not limited to, any of the minimal media described above. The minimal medium can be further supplemented with 1.0% (w/v) glucose (or any other six-carbon sugar) or less. Specifically, the minimal medium can be supplemented with 1% (w/v), 0.9% (w/v), 0.8% (w/v), 0.7% (w/v), 0.6% (w/v), 0.5% (w/v), 0.4% (w/v), 0.3% (w/v), 0.2% (w/v), or 0.1% (w/v) glucose. In some cultures, significantly higher levels of sugar (e.g., glucose) are used, e.g., at least 10% (w/v), 20% (w/v), 30% (w/v), 40% (w/v), 50% (w/v), 60% (w/v), 70% (w/v), or up to the solubility limit for the sugar in the medium. In some embodiments, the sugar levels falls within a range of any two of the above values, e.g.: 0.1-10% (w/v), 1.0-20% (w/v), 10-70% (w/v), 20-60% (w/v), or 30-50% (w/v). Furthermore, different sugar levels can be used for different phases of culturing. For fed-batch culture (e.g., of *S. cerevisiae* or *C. glutamicum*), the sugar level can be about 100-200 g/L (10-20% (w/v)) in the batch phase and then up to about 500-700 g/L (50-70% in the feed).

Additionally, the minimal medium can be supplemented 0.1% (w/v) or less yeast extract. Specifically, the minimal medium can be supplemented with 0.1% (w/v), 0.09% (w/v), 0.08% (w/v), 0.07% (w/v), 0.06% (w/v), 0.05% (w/v), 0.04% (w/v), 0.03% (w/v), 0.02% (w/v), or 0.01% (w/v) yeast extract. Alternatively, the minimal medium can be supplemented with 1% (w/v), 0.9% (w/v), 0.8% (w/v), 0.7% (w/v), 0.6% (w/v), 0.5% (w/v), 0.4% (w/v), 0.3% (w/v), 0.2% (w/v), or 0.1% (w/v) glucose and with 0.1% (w/v), 0.09% (w/v), 0.08% (w/v), 0.07% (w/v), 0.06% (w/v), 0.05% (w/v), 0.04% (w/v), 0.03% (w/v), or 0.02% (w/v) yeast extract. In some cultures, significantly higher levels of yeast extract can be used, e.g., at least 1.5% (w/v), 2.0% (w/v), 2.5% (w/v), or 3% (w/v). In some cultures (e.g., of *S. cerevisiae* or *C. glutamicum*), the yeast extract level falls within a range of any two of the above values, e.g.: 0.5-3.0% (w/v), 1.0-2.5% (w/v), or 1.5-2.0% (w/v).

Illustrative materials and methods suitable for the maintenance and growth of the engineered microbial cells described herein can be found below in Example 1.

(6E)-8-hydroxygeraniol Production and Recovery

Any of the methods described herein may further include a step of recovering (6E)-8-hydroxygeraniol. In some embodiments, the produced (6E)-8-hydroxygeraniol contained in a so-called harvest stream is recovered/harvested from the production vessel. The harvest stream may include, for instance, cell-free or cell-containing aqueous solution coming from the production vessel, which contains (6E)-8-hydroxygeraniol as a result of the conversion of production substrate by the resting cells in the production vessel. Cells still present in the harvest stream may be separated from the (6E)-8-hydroxygeraniol by any operations known in the art, such as for instance filtration, centrifugation, decantation, membrane crossflow ultrafiltration or microfiltration, tangential flow ultrafiltration or microfiltration or dead end filtration. After this cell separation operation, the harvest stream is essentially free of cells.

Further steps of separation and/or purification of the produced (6E)-8-hydroxygeraniol from other components contained in the harvest stream, i.e., so-called downstream processing steps may optionally be carried out. These steps may include any means known to a skilled person, such as, for instance, concentration, extraction, crystallization, precipitation, adsorption, ion exchange, and/or chromatography. Any of these procedures can be used alone or in combination to purify (6E)-8-hydroxygeraniol. Further purification steps can include one or more of, e.g., concentration, crystallization, precipitation, washing and drying, treatment with activated carbon, ion exchange, nanofiltration, and/or re-crystallization. The design of a suitable purification protocol may depend on the cells, the culture medium, the size of the culture, the production vessel, etc. and is within the level of skill in the art.

The following example is given for the purpose of illustrating various embodiments of the disclosure and is not meant to limit the present disclosure in any fashion. Changes therein and other uses which are encompassed within the spirit of the disclosure, as defined by the scope of the claims, will be identifiable to those skilled in the art.

Example 1—Construction and Selection of Strains of *Saccharomyces cerevisiae* Engineered to Produce (6E)-8-hydroxygeraniol Plasmid/DNA Design All strains tested for this work were transformed with plasmid DNA designed using proprietary software. Plasmid designs were specific to one of the two host organisms engineered in this work. The plasmid DNA was physically constructed by a standard DNA assembly method. This plasmid DNA was then used to integrate metabolic pathway inserts by one of two host-specific methods, each described below.

*S. cerevisiae* Pathway Integration

Figure 2:
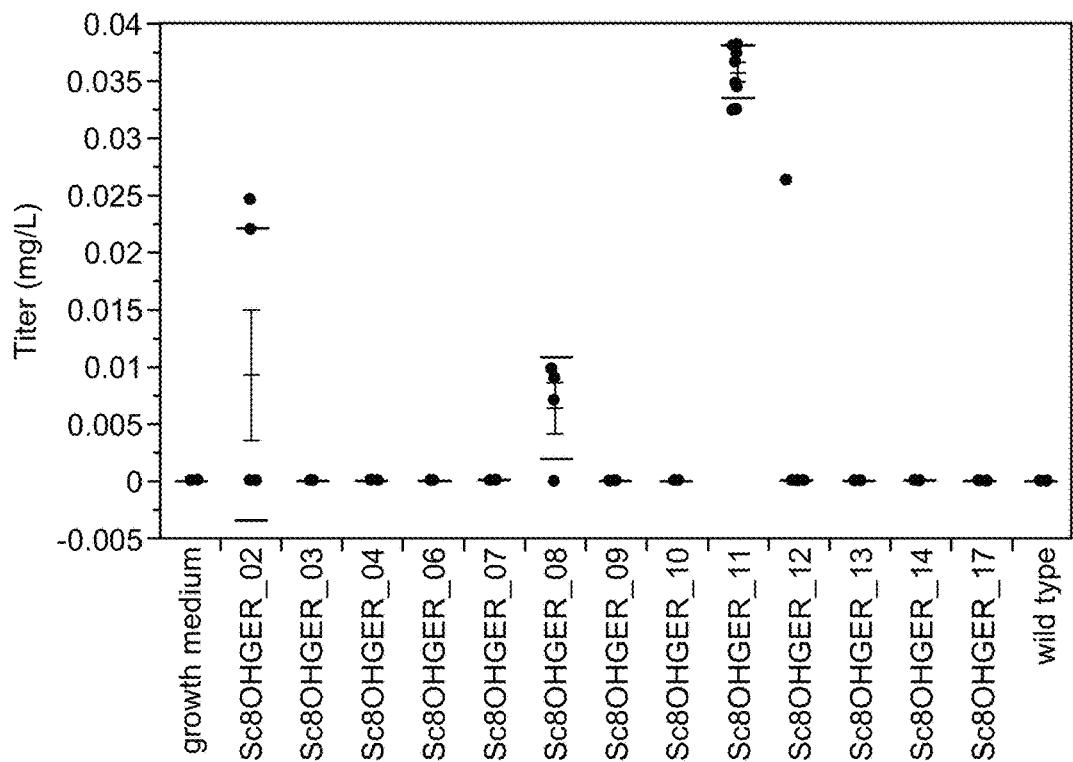
FIG. 2: (6E)-8-Hydroxygeraniol titers measured in the extracellular broth following fermentation by the first round engineered host *Saccharomyces cerevisiae*. (See also Example 1, Table 1.)
Figure 3:
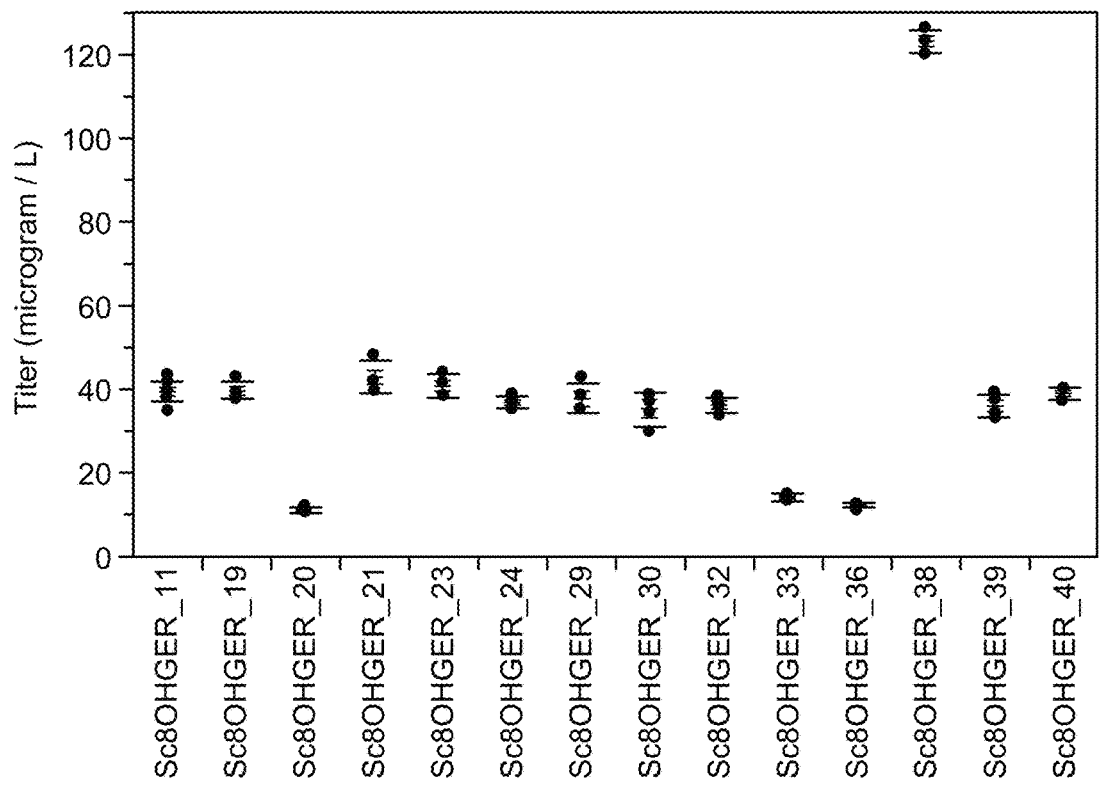
FIG. 3: (6E)-8-Hydroxygeraniol titers measured in the extracellular broth following fermentation by the second round engineered host *S. cerevisiae*. (See also Example 1, Table 2.)
Figure 4:
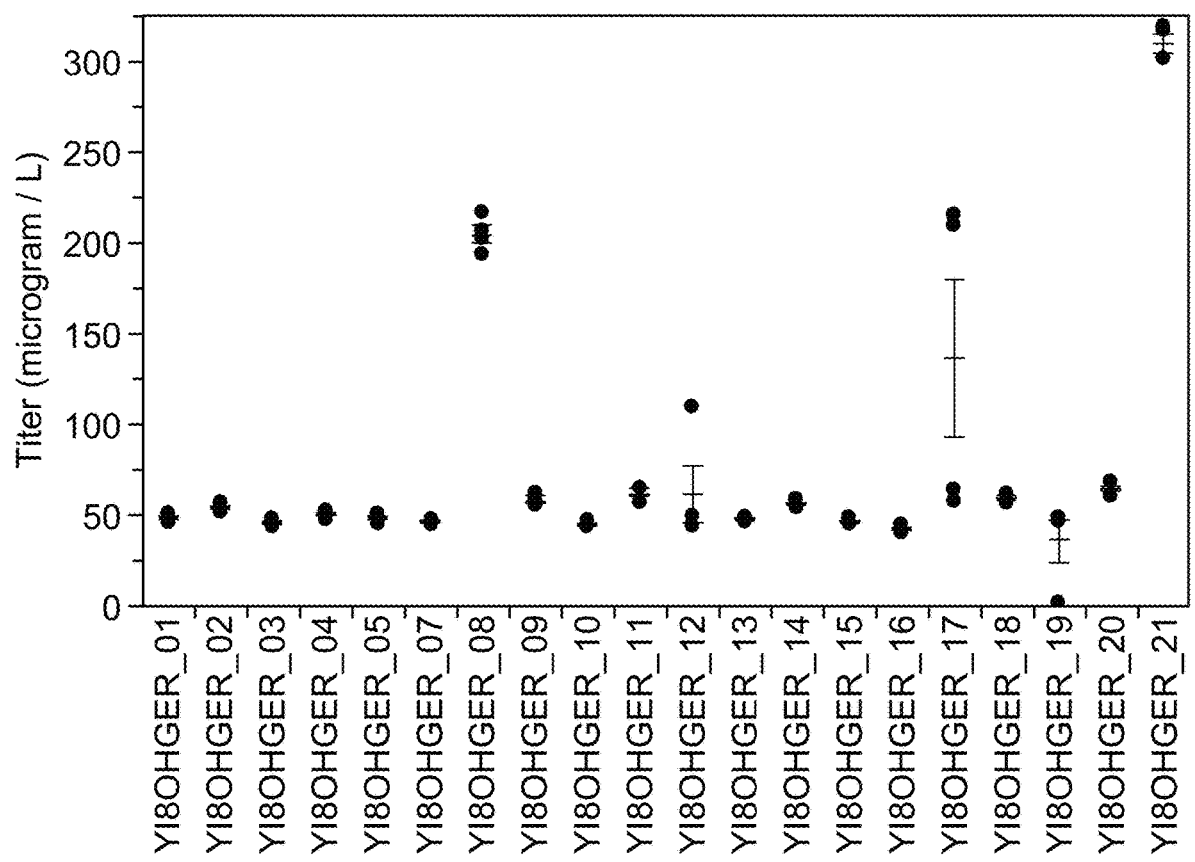
FIG. 4: (6E)-8-Hydroxygeraniol titers measured in the extracellular broth following fermentation by the first round engineered host *Yarrowia lipolytica*. (See also Example 2, Table 4.)

A "split-marker, double-crossover" genomic integration strategy has been developed to engineer *S. cerevisiae* strains. FIG. 2 illustrates genomic integration of complementary, split-marker plasmids and verification of correct genomic integration via colony PCR in *S. cerevisiae*. Two plasmids with complementary 5' and 3' homology arms and overlapping halves of a URA3 selectable marker (direct repeats shown by the hashed bars) were digested with meganucleases and transformed as linear fragments. A triple-crossover event integrated the desired heterologous genes into the targeted locus and re-constituted the full URA3 gene. Colonies derived from this integration event were assayed using two 3-primer reactions to confirm both the 5' and 3' junctions (UF/IF/wt-R and DR/IF/wt-F). For strains in which further engineering is desired, the strains can be plated on 5-FOA plates to select for the removal of URA3, leaving behind a small single copy of the original direct repeat. This genomic integration strategy can be used for gene knock-out, gene knock-in, and promoter titration in the same workflow.

Cell Culture

The workflow established for *S. cerevisiae* involved a hit-picking step that consolidated successfully built strains using an automated workflow that randomized strains across the plate. For each strain that was successfully built, up to four replicates were tested from distinct colonies to test colony-to-colony variation and other process variation. If fewer than four colonies were obtained, the existing colonies were replicated so that at least four wells were tested from each desired genotype.

The colonies were consolidated into 96-well plates with selective medium (SD-ura for *S. cerevisiae*) and cultivated for two days until saturation and then frozen with 16.6% glycerol at −80° C. for storage. The frozen glycerol stocks were then used to inoculate a seed stage in minimal media with a low level of amino acids to help with growth and recovery from freezing. The seed plates were grown at 30° C. for 1-2 days. The seed plates were then used to inoculate a main cultivation plate with minimal medium and grown for 48-88 hours. Plates were removed at the desired time points and tested for cell density (OD600), viability and glucose, supernatant samples stored for LC-MS analysis for product of interest.

Cell Density

Cell density was measured using a spectrophotometric assay detecting absorbance of each well at 600 nm. Robotics were used to transfer fixed amounts of culture from each cultivation plate into an assay plate, followed by mixing with 175 mM sodium phosphate (pH 7.0) to generate a 10-fold dilution. The assay plates were measured using a Tecan M1000 spectrophotometer and assay data uploaded to a LIMS database. A non-inoculated control was used to subtract background absorbance. Cell growth was monitored by inoculating multiple plates at each stage, and then sacrificing an entire plate at each time point.

To minimize settling of cells while handling large number of plates (which could result in a non-representative sample during measurement) each plate was shaken for 10-15 seconds before each read. Wide variations in cell density within a plate may also lead to absorbance measurements outside of the linear range of detection, resulting in underestimate of higher OD cultures. In general, the tested strains so far have not varied significantly enough for this be a concern.

Liquid-Solid Separation

To harvest extracellular samples for analysis by LC-MS, liquid and solid phases were separated via centrifugation. Cultivation plates were centrifuged at 2000 rpm for 4 minutes, and the supernatant was transferred to destination plates using robotics. 75 µL of supernatant was transferred to each plate, with one stored at 4° C., and the second stored at 80° C. for long-term storage.

First Round Genetic Engineering Results

A first round of genetic engineering and screening was carried out using *S. cerevisiae* as host cells. A library approach was taken to identify functional enzymes in the host organism. A broad search of geraniol synthase sequences identified in total 13 orthologous sequences. A heterologous geraniol synthase was expressed in the host cells, in some cases, along with a heterologous geraniol-8-hydroxylase. In some cases, the geraniol synthase and/or geraniol-8-hydroxylase nucleotide sequences were codon-optimized for *S. cerevisiae*. The strains were produced and cultured as described above, and the (6E)-8-hydroxygeraniol titer in the culture media was measured by LC-MS. The strains and results are shown in Table 1 and in FIG. 2. The best-performing first-round strain was a *S. cerevisiae* strain expressing a *Perilla setoyensis* geraniol synthase, along with a *Phaseolus angularis* geraniol-8-hydroxylase, which gave a (6E)-8-hydroxygeraniol titer of 37.5 µg/L of culture medium. This strain was selected for a second round of genetic engineering and screening.

TABLE 1

First round results in *Saccharomyces cerevisiae*

| Strain name | Titer (mg/L) | E1 Uniprot ID | Enzyme 1 - activity name | Enzyme 1 - source organism | E1 Codon Optimization Abbrev. | E2 Uniprot ID | Enzyme 2 - activity name | Enzyme 2 - source organism | E2 Codon Optimization Abbrev. |
|---|---|---|---|---|---|---|---|---|---|
| Sc8OHGER_02 | 9.4 | E5GAH8 | geraniol synthase (SEQ ID NO: 1) (SEQ ID NO: 2) | *Vitis vinifera* (Grape) | modified Cg codon usage | D1MI46 | geraniol 8-hydroxylase (SEQ ID NO: 7) (SEQ ID NO: 8) | *Swertia mussotii* (Felwort) | modified Cg codon usage |
| Sc8OHGER_08 | 6.5 | D7SQP4 | geraniol synthase (SEQ ID NO: 3) (SEQ ID NO: 4) | *Vitis vinifera* (Grape) | modified Cg codon usage | B9GW31 | geraniol 8-hydroxylase (SEQ ID NO: 9) (SEQ ID NO: 10) | *Populus trichocarpa* (Western balsam poplar) (*Populus balsamifera* subsp. *trichocarpa*) | modified Cg codon usage |
| Sc8OHGER_11 | 37.5 | C0KWV4 | geraniol synthase (SEQ ID NO: 5) (SEQ ID NO: 6) | *Perilla setoyensis* | modified Cg codon usage | A0A0L9UT99 | geraniol 8-hydroxylase (SEQ ID NO: 11) (SEQ ID NO: 12) | *Phaseolus angularis* (Azuki bean) (*Vigna angularis*) | modified Cg codon usage |

Second Round Genetic Engineering Results

The best-performing first-round strain was used at the starting host for a second round of genetic engineering using a combinatorial library approach. In this round, an additional copy of 1-3 upstream pathway genes were introduced into separate "daughter" strains, under the control of a strong, constitutive promoters (Table 2). Upstream pathway genes represent all genes involved in the conversion of key precursors (e.g., acetyl-CoA) into the last native metabolite in the pathway leading to (6E)-8-hydroxygeraniol. Enzymes selected to be tested in strains in the combinatorial library approach are shown in the mevalonate pathway diagram (FIG. 1). The best-performing strain from this round overexpressed an isopentenyl-diphosphate delta-isomerase from *S. cerevisiae*, giving a (6E)-8-hydroxygeraniol titer of 123 µg/L of culture medium.

TABLE 2

Second round results in *Saccharomyces cerevisiae*

| Strain name | Titer (mg/L) | E1 Uniprot ID | Enzyme 1 - activity name *Saccharomyces cerevisiae* | Enzyme 1 - source organism | E2 Uniprot ID | Enzyme 2 - activity name | Enzyme 2 - source organism |
|---|---|---|---|---|---|---|---|
| Sc8OHGER_19 | 39.5 | P07277 | ATP: (R)-mevalonate 5-phosphotransferase (SEQ ID NO: 13) (SEQ ID NO: 14) | *Saccharomyces cerevisiae* | | | |
| Sc8OHGER_20 | 10.9 | P08524 | Geranylgeranyl pyrophosphate synthase (SEQ ID NO: 15) (SEQ ID NO: 16) | *Saccharomyces cerevisiae* | | | |
| Sc8OHGER_21 | 42.8 | P54839 | acetyl-CoA: acetoacetyl-CoA C-acetyltransferase (SEQ ID NO: 17) (SEQ ID NO: 18) | *Saccharomyces cerevisiae* | | | |
| Sc8OHGER_23 | 40.5 | P41338 | Acetyl-CoA: acetyl-CoA C-acetyltransferase (SEQ ID NO: 19) (SEQ ID NO: 20) | *Saccharomyces cerevisiae* | | | |
| Sc8OHGER_24 | 36.6 | P12684 | (R)-Mevalonate: NADP+ oxidoreductase (CoA acylating) (SEQ ID NO: 21) (SEQ ID NO: 22) | *Saccharomyces cerevisiae* | P41338 | Acetyl-CoA: acetyl-CoA C-acetyltransferase (SEQ ID NO: 19) (SEQ ID NO: 20) | *Saccharomyces cerevisiae* |
| Sc8OHGER_29 | 37.8 | P12684 | (R)-Mevalonate: NADP+ oxidoreductase (CoA acylating) (SEQ ID NO: 21) (SEQ ID NO: 22) | *Saccharomyces cerevisiae* | P07277 | ATP: (R)-mevalonate 5-phosphotransferase (SEQ ID NO: 13) (SEQ ID NO: 14) | *Saccharomyces cerevisiae* |
| Sc8OHGER_30 | 34.9 | P24521 | ATP: (R)-5-phosphomevalonate phosphotransferase (SEQ ID NO: 23) (SEQ ID NO: 24) | *Saccharomyces cerevisiae* | | | |
| Sc8OHGER_32 | 36.2 | P12684 | (R)-Mevalonate: NADP+ oxidoreductase (CoA acylating) (SEQ ID NO: 21) (SEQ ID NO: 22) | *Saccharomyces cerevisiae* | P08524 | Geranylgeranyl pyrophosphate synthase (SEQ ID NO: 15) (SEQ ID NO: 16) | *Saccharomyces cerevisiae* |
| Sc8OHGER_33 | 13.9 | P12684 | (R)-Mevalonate: NADP+ oxidoreductase (CoA acylating) (SEQ ID NO: 21) (SEQ ID NO: 22) | *Saccharomyces cerevisiae* | P08524 | Geranylgeranyl pyrophosphate synthase (SEQ ID NO: 15) (SEQ ID NO: 16) | *Saccharomyces cerevisiae* |
| Sc8OHGER_36 | 11.7 | P12684 | (R)-Mevalonate: NADP+ oxidoreductase (CoA acylating) (SEQ ID NO: 21) (SEQ ID NO: 22) | *Saccharomyces cerevisiae* | P08524 | Geranylgeranyl pyrophosphate synthase (SEQ ID NO: 15) (SEQ ID NO: 16) | *Saccharomyces cerevisiae* |
| Sc8OHGER_38 | 122.9 | P15496 | Isopentenyl-diphosphate delta3-delta2-isomerase (SEQ ID NO: 25) (SEQ ID NO: 26) | *Saccharomyces cerevisiae* | P15496 | Isopentenyl-diphosphate delta3-delta2-isomerase (SEQ ID NO: 25) (SEQ ID NO: 26) | *Saccharomyces cerevisiae* |
| Sc8OHGER_39 | 35.6 | P12684 | (R)-Mevalonate: NADP+ oxidoreductase (CoA acylating) (SEQ ID NO: 21) (SEQ ID NO: 22) | *Saccharomyces cerevisiae* | | | |
| Sc8OHGER_40 | 38.7 | P15496 | ATP: (R)-5-diphosphomevalonate carboxy-lyase (SEQ ID NO: 25) (SEQ ID NO: 26) | *Saccharomyces cerevisiae* | | | |

| Strain name | Titer (mg/L) | E1 Uniprot ID | Enzyme 1 - activity name *Saccharomyces cerevisiae* | E3 Uniprot ID | Enzyme 3 - activity name | Enzyme 3 - source organism |
|---|---|---|---|---|---|---|
| Sc8OHGER_19 | 39.5 | P07277 | ATP: (R)-mevalonate 5-phosphotransferase (SEQ ID NO: 13) (SEQ ID NO: 14) | | | |

TABLE 2-continued

Second round results in *Saccharomyces cerevisiae*

| | | | | | | | |
|---|---|---|---|---|---|---|---|
| Sc8OHGER_20 | 10.9 | P08524 | Geranylgeranyl pyrophosphate synthase (SEQ ID NO: 15) (SEQ ID NO: 16) | | | | |
| Sc8OHGER_21 | 42.8 | P54839 | acetyl-CoA: acetoacetyl-CoA C-acetyltransferase (SEQ ID NO: 17) (SEQ ID NO: 18) | | | | |
| Sc8OHGER_23 | 40.5 | P41338 | Acetyl-CoA: acetyl-CoA C-acetyltransferase (SEQ ID NO: 19) (SEQ ID NO: 20) | | | | |
| Sc8OHGER_24 | 36.6 | P12684 | (R)-Mevalonate: NADP+ oxidoreductase (CoA acylating) (SEQ ID NO: 21) (SEQ ID NO: 22) | P24521 | ATP: (R)-5-phosphomevalonate phosphotransferase (SEQ ID NO: 23) (SEQ ID NO: 24) | *Saccharomyces cerevisiae* | |
| Sc8OHGER_29 | 37.8 | P12684 | (R)-Mevalonate: NADP+ oxidoreductase (CoA acylating) (SEQ ID NO: 21) (SEQ ID NO: 22) | P54839 | acetyl-CoA: acetoacetyl-CoA C-acetyltransferase (SEQ ID NO: 17) (SEQ ID NO: 18) | *Saccharomyces cerevisiae* | |
| Sc8OHGER_30 | 34.9 | P24521 | ATP: (R)-5-phosphomevalonate phosphotransferase (SEQ ID NO: 23) (SEQ ID NO: 24) | | | | |
| Sc8OHGER_32 | 36.2 | P12684 | (R)-Mevalonate: NADP+ oxidoreductase (CoA acylating) (SEQ ID NO: 21) (SEQ ID NO: 22) | P15496 | Isopentenyl-diphosphate delta3-delta2-isomerase (SEQ ID NO: 25) (SEQ ID NO: 26) | *Saccharomyces cerevisiae* | |
| Sc8OHGER_33 | 13.9 | P12684 | (R)-Mevalonate: NADP+ oxidoreductase (CoA acylating) (SEQ ID NO: 21) (SEQ ID NO: 22) | P24521 | ATP: (R)-5-phosphomevalonate phosphotransferase (SEQ ID NO: 23) (SEQ ID NO: 24) | *Saccharomyces cerevisiae* | |
| Sc8OHGER_36 | 11.7 | P12684 | (R)-Mevalonate: NADP+ oxidoreductase (CoA acylating) (SEQ ID NO: 21) (SEQ ID NO: 22) | P07277 | ATP: (R)-mevalonate 5-phosphotransferase (SEQ ID NO: 13) (SEQ ID NO: 14) | *Saccharomyces cerevisiae* | |
| Sc8OHGER_38 | 122.9 | P15496 | Isopentenyl-diphosphate delta3-delta2-isomerase (SEQ ID NO: 25) (SEQ ID NO: 26) | P15496 | Isopentenyl-diphosphate delta3-delta2-isomerase (SEQ ID NO: 25) (SEQ ID NO: 26) | *Saccharomyces cerevisiae* | |
| Sc8OHGER_39 | 35.6 | P12684 | (R)-Mevalonate: NADP+ oxidoreductase (CoA acylating) (SEQ ID NO: 21) (SEQ ID NO: 22) | | | | |
| Sc8OHGER_40 | 38.7 | P15496 | ATP: (R)-5-diphosphomevalonate carboxy-lyase (SEQ ID NO: 25) (SEQ ID NO: 26) | | | | |

Third and Fourth Round Genetic Engineering Results

A third round of genetic engineering produced no improved strains, most likely due to an error in strain construction. Fourth (Improvement) round strain designs and results are shown in Table 3.

TABLE 3

Fourth (Improvement) round strain designs for testing 1-3 heterologous enzymes to improve (6E)-8-hydroxygeraniol production in *Saccharomyces cerevisiae* (Improvement round)

| Strain name *S. cerevisiae* | Titer (microgram/L) | E1 Uniprot ID | Enzyme 1 - activity name | E1 Modifications | Enzyme 1 - source organism | E2 Uniprot ID | Enzyme 2 - activity name | Enzyme 2 - source organism | E3 Uniprot ID | Enzyme 3 - activity name | E3 Modifications | Enzyme 3 - source organism |
|---|---|---|---|---|---|---|---|---|---|---|---|---|
| Sc8OHGER_38 | 113.597 | P15496 | Isopentenyl-diphosphate delta3-delta2-isomerase (SEQ ID NO: 25) (SEQ ID NO: 26) | | *S. cerevisiae* (strain ATCC 204508/ S288c) (Baker's yeast) | | | | | | | |
| Sc8OHGER_73 | 6.043 | P12683 | 3-hydroxy-3-methylglutaryl-coenzyme A reductase 1 (HMG-CoA reductase 1) (EC 1.1.1.34) (SEQ ID NO: 27) (SEQ ID NO: 28) | truncated | *S. cerevisiae* S288c | | | | | | | |
| Sc8OHGER_74 | 0 | P12684 | (R)-Mevalonate: NADP+ oxidoreductase (CoA acylating) (SEQ ID NO: 21) (SEQ ID NO: 22) | | *S. cerevisiae* S288c | P12684 | (R)-Mevalonate: NADP+ oxidoreductase (CoA acylating) (SEQ ID NO: 21) (SEQ ID NO: 22) | *S. cerevisiae* S288c | | | | |
| Sc8OHGER_75 | 0 | Q9FD86 | 3-hydroxy-3-methylglutaryl coenzyme A reductase (HMG-CoA reductase) (EC 1.1.1.88) (SEQ ID NO: 29) (SEQ ID NO: 30) | | *Staphylococcus aureus* | | | | | | | |
| Sc8OHGER_76 | 0 | V4HIU8 | 3-hydroxy-3-methylglutaryl-CoA reductase (SEQ ID NO: 31) (SEQ ID NO: 32) | | *Candidatus Halobonum tyrrellensis* G22 | | | | | | | |
| Sc8OHGER_77 | 0 | A0A0A0KA96 | 3-hydroxy-3-methylglutaryl coenzyme A reductase (HMG-CoA reductase) (EC 1.1.1.34) (SEQ ID NO: 33) (SEQ ID NO: 34) | | *Cucumis sativus* (Cucumber) | | | | | | | |
| Sc8OHGER_78 | 0 | A0A0F8XPA3 | 3-hydroxy-3-methylglutaryl coenzyme A reductase (HMG-CoA reductase) (SEQ ID NO: 35) (SEQ ID NO: 36) | | *Loktiarchaeum* sp. GC14_75 | | | | | | | |

TABLE 3-continued

Fourth (Improvement) round strain designs for testing 1-3 heterologous enzymes to improve (6E)-8-hydroxygeraniol production in *Saccharomyces cerevisiae* (Improvement round)

| Strain name S. cerevisiae | Titer (microgram/L) | E1 Uniprot ID | Enzyme 1 - activity name | E1 Modifications | Enzyme 1 - source organism | E2 Uniprot ID | Enzyme 2 - activity name | Enzyme 2 - source organism | E3 Uniprot ID | Enzyme 3 - activity name | E3 Modifications | Enzyme 3 - source organism |
|---|---|---|---|---|---|---|---|---|---|---|---|---|
| Sc8OHGER_79 | 0 | G3HXP6 | 3-hydroxy-3-methylglutaryl-coenzyme A reductase (SEQ ID NO: 37) (SEQ ID NO: 38) | | *Cricetulus griseus* | | | | | | | |
| Sc8OHGER_80 | 0 | A0A0V8RU49 | 3-hydroxy-3-methylglutaryl coenzyme A reductase (HMG-CoA reductase) (EC 1.1.1.34) A reductase (SEQ ID NO: 39) (SEQ ID NO: 40) | | *Pyrodictium occultum* | | | | | | | |
| Sc8OHGER_82 | 0 | P08524 | Farnesyl pyrophosphate synthase (FPP synthase) (FPS) (EC 2.5.1.10) ((2E,6E)-farnesyl diphosphate synthase) (Dimethylallyltransferase) (EC 2.5.1.1) (Farnesyl diphosphate synthase) (Geranyltransferase) (SEQ ID NO: 41) (SEQ ID NO: 42) | K197G | *S. cerevisiae* S288c | | | | | | | |
| Sc8OHGER_83 | 0 | Q8LKJ2 | Geranyl diphosphate synthase (SEQ ID NO: 43) (SEQ ID NO: 44) | | *Abies grandis* | | | | | | | |
| Sc8OHGER_84 | 0 | B1A9K6 | Geranyl diphosphate synthase 2 (SEQ ID NO: 45) (SEQ ID NO: 46) | | *Picea abies* | | | | | | | |
| Sc8OHGER_85 | 0 | BAP82233.1 | No Activity Name Found (SEQ ID NO: 47) (SEQ ID NO: 48) | | 0 | | | | | | | |

TABLE 3-continued

Fourth (Improvement) round strain designs for testing 1-3 heterologous enzymes to improve (6E)-8-hydroxygeraniol production in *Saccharomyces cerevisiae* (Improvement round)

| Strain name *S. cerevisiae* | Titer (micro-gram/L) | E1 Uniprot ID | Enzyme 1 - activity name | E1 Modi-fications | Enzyme 1 - source organism | E2 Uniprot ID | Enzyme 2 - activity name | Enzyme 2 - source organism | E3 Uniprot ID | Enzyme 3 - activity name | E3 Modi-fications | Enzyme 3 - source organism |
|---|---|---|---|---|---|---|---|---|---|---|---|---|
| Sc8OHGER_86 | 0 | Q1A746 | Geranyl pyrophosphate synthase (SEQ ID NO: 49) (SEQ ID NO: 50) | | *Solanum lycopersicum* | | | | | | | |
| Sc8OHGER_87 | 0 | B2MV87 | Geranyl pyrophosphate synthase (EC 2.5.1.1) (SEQ ID NO: 51) (SEQ ID NO: 52) | | *Catharanthus roseus* | | | | | | | |
| Sc8OHGER_88 | 4.109 | A0A160PQU3 | Polyprenyl synthetase (SEQ ID NO: 53) (SEQ ID NO: 54) | | *C. glutamicum* | | | | | | | |
| Sc8OHGER_89 | 0 | P54383 | Farnesyl diphosphate synthase (FPP synthase) (EC 2.5.1.10) ((2E,6E)-farnesyl diphosphate synthase) (Geranyltrans-transferase) (SEQ ID NO: 55) (SEQ ID NO: 56) | S81F | *Bacillus subtilis* (strain 168) | | | | | | | |
| Sc8OHGER_90 | 0 | P07277 | ATP: (R)-mevalonate 5-phospho-transferase (SEQ ID NO: 13) (SEQ ID NO: 14) | | *S. cerevisiae* S288c | | | | | | | |
| Sc8OHGER_91 | 0 | P24521 | ATP: (R)-5-phospho-mevalonate phospho-transferase (SEQ ID NO: 23) (SEQ ID NO: 24) | | *S. cerevisiae* S288c | | | | | | | |
| Sc8OHGER_92 | 0 | P41338 | Acetyl-CoA: acetyl-CoA C-acetyltransferase (SEQ ID NO: 29) (SEQ ID NO: 20) | | *S. cerevisiae* S288c | | | | | | | |

TABLE 3-continued

Fourth (Improvement) round strain designs for testing 1-3 heterologous enzymes to improve (6E)-8-hydroxygeraniol production in *Saccharomyces cerevisiae* (Improvement round)

| Strain name *S. cerevisiae* | Titer (microgram/L) | E1 Uniprot ID | Enzyme 1 - activity name | E1 Modifications | Enzyme 1 - source organism | E2 Uniprot ID | Enzyme 2 - activity name | Enzyme 2 - source organism | E3 Uniprot ID | Enzyme 3 - activity name | E3 Modifications | Enzyme 3 - source organism |
|---|---|---|---|---|---|---|---|---|---|---|---|---|
| Sc8OHGER_93 | 0 | P32377 | ATP: (R)-5-diphosphomevalonate carboxylyase (adding ATP; isopentenyl-diphosphate-forming) (SEQ ID NO: 57) (SEQ ID NO: 58) | | *S. cerevisiae* S288c | | | | | | | |
| Sc8OHGER_94 | | P54839 | acetyl-CoA: acetoacetyl-CoA C-acetyltransferase (thioester-hydrolysing, carboxymethyl-forming) (SEQ ID NO: 17) (SEQ ID NO: 18) | | *S. cerevisiae* S288c | | | | | | | |
| Sc8OHGER_95 | | P07277 | ATP: (R)-mevalonate 5-phosphotransferase (SEQ ID NO: 13) (SEQ ID NO: 14) | | *S. cerevisiae* S288c | P12684 | (R)-Mevalonate: NADP+ oxidoreductase (CoA acylating) (SEQ ID NO: 21) (SEQ ID NO: 22) | *S. cerevisiae* S288c | P08524 | Farnesyl pyrophosphate synthase (EC 2.5.1.10), Dimethylallyl-transtransferase (EC 2.5.1.1) (SEQ ID NO: 77) (SEQ ID NO: 78) | F96W, N127W | *S. cerevisiae* S288c |
| Sc8OHGER_96 | | P24521 | ATP: (R)-5-phosphomevalonate phosphotransferase (SEQ ID NO: 23) (SEQ ID NO: 24) | | *S. cerevisiae* S288c | P12684 | (R)-Mevalonate: NADP+ oxidoreductase (CoA acylating) (SEQ ID NO: 21) (SEQ ID NO: 22) | *S. cerevisiae* S288c | P08524 | Farnesyl pyrophosphate synthase (EC 2.5.1.10), Dimethylallyl-transtransferase (EC 2.5.1.1) (SEQ ID NO: 77) (SEQ ID NO: 78) | F96W, N127W | *S. cerevisiae* S288c |
| Sc8OHGER_97 | | P41338 | Acetyl-CoA: acetyl-CoA C-acetyltransferase (SEQ ID NO: 19) (SEQ ID NO: 20) | | *S. cerevisiae* S288c | P12684 | (R)-Mevalonate: NADP+ oxidoreductase (CoA acylating) (SEQ ID NO: 21) (SEQ ID NO: 22) | *S. cerevisiae* S288c | P08524 | Farnesyl pyrophosphate synthase (EC 2.5.1.10), Dimethylallyl-transtransferase (EC 2.5.1.1) (SEQ ID NO: 77) (SEQ ID NO: 78) | F96W, N127W | *S. cerevisiae* S288c |
| Sc8OHGER_98 | | P32377 | ATP: (R)-5-diphosphomevalonate carboxylyase (adding ATP; isopentenyl-diphosphate-forming); (SEQ ID NO: 57) (SEQ ID NO: 58) | | *S. cerevisiae* S288c | P12684 | (R)-Mevalonate: NADP+ oxidoreductase (CoA acylating) (SEQ ID NO: 21) (SEQ ID NO: 22) | *S. cerevisiae* S288c | P08524 | Farnesyl pyrophosphate synthase (EC 2.5.1.10), Dimethylallyl-transtransferase (EC 2.5.1.1) (SEQ ID NO: 77) (SEQ ID NO: 78) | F96W, N127W | *S. cerevisiae* S288c |

TABLE 3-continued

Fourth (Improvement) round strain designs for testing 1-3 heterologous enzymes to improve (6E)-8-hydroxygeraniol production in *Saccharomyces cerevisiae* (Improvement round)

| Strain name *S. cerevisiae* | Titer (microgram/L) | E1 Uniprot ID | Enzyme 1 - activity name | E1 Modifications | Enzyme 1 - source organism | E2 Uniprot ID | Enzyme 2 - activity name | Enzyme 2 - source organism | E3 Uniprot ID | Enzyme 3 - activity name | E3 Modifications | Enzyme 3 - source organism |
|---|---|---|---|---|---|---|---|---|---|---|---|---|
| Sc8OHGER_99 | | P54839 | acetyl-CoA: acetoacetyl-CoA C-acetyltransferase (thioester-hydrolysing, carboxymethyl-forming) (SEQ ID NO: 17) (SEQ ID NO: 18) | | *S. cerevisiae* S288c | P12684 | (R)-Mevalonate: NADP+ oxidoreductase (CoA acylating) (SEQ ID NO: 21) (SEQ ID NO: 22) | *S. cerevisiae* S288c | P08524 | Farnesyl pyrophosphate synthase (EC 2.5.1.10), Dimethylallyl-transtransferase (EC 2.5.1.1) (SEQ ID NO: 77) (SEQ ID NO: 78) (SEQ ID NO: 78) | F96W, N127W | *S. cerevisiae* S288c |
| Sc8OHGER_100 | | Q6C3H5 | YALI0E34793p (SEQ ID NO: 59) (SEQ ID NO: 60) | | *Yarrowia lipolytica* CLIB 122/E 150 | | | | | | | |
| Sc8OHGER_101 | | Q8ZKF6 | Acetyl-coenzyme A synthetase (Acs) (AcCoA synthetase) (EC 6.2.1.1) (Acetate-CoA ligase) (Acyl-activating enzyme) (SEQ ID NO: 61) (SEQ ID NO: 62) | L641P | *Salmonella typhimurium* LT2 | | | | | | | |
| Sc8OHGER_102 | | P54115 | Magnesium-activated aldehyde dehydrogenase, cytosolic (EC 1.2.1.4) (Mg(2+)-activated acetaldehyde dehydrogenase) (Mg(2+)-ACDH) (SEQ ID NO: 63) (SEQ ID NO: 64) | | *S. cerevisiae* S288c | | | | | | | |
| Sc8OHGER_103 | | Q8ZKF6 | Acetyl-coenzyme A synthetase (Acs) (AcCoA synthetase) (EC 6.2.1.1) (Acetate-CoA ligase) (Acyl-activating enzyme) (SEQ ID NO: 61) (SEQ ID NO: 62) | L641P | *Salmonella typhimurium* LT2 | P00331 | Alcohol dehydrogenase 2 (EC 1.1.1.1) (Alcohol dehydrogenase II) (YADH-2) (SEQ ID NO: 65) (SEQ ID NO: 66) | *S. cerevisiae* S288c | | | | |
| Sc8OHGER_104 | | Q8ZKF6 | Acetyl-coenzyme A synthetase (Acs) (AcCoA synthetase) (EC 6.2.1.1) (Acetate-CoA ligase) (Acyl- | L641P | *Salmonella typhimurium* LT2 | P54115 | Magnesium-activated aldehyde dehydrogenase, cytosolic (EC 1.2.1.4) (Mg(2+)-activated acetaldehyde | *S. cerevisiae* S288c | | | | |

TABLE 3-continued

Fourth (Improvement) round strain designs for testing 1-3 heterologous enzymes to improve (6E)-8-hydroxygeraniol production in Saccharomyces cerevisiae (Improvement round)

| Strain name S. cerevisiae | Titer (microgram/L) | E1 Uniprot ID | Enzyme 1 - activity name | E1 Modifications | Enzyme 1 - source organism | E2 Uniprot ID | Enzyme 2 - activity name | Enzyme 2 - source organism | E3 Uniprot ID | Enzyme 3 - activity name | E3 Modifications | Enzyme 3 - source organism |
|---|---|---|---|---|---|---|---|---|---|---|---|---|
| | | | activating enzyme) (SEQ ID NO: 61) (SEQ ID NO: 62) | | | | dehydrogenase) (Mg(2+)-ACDH) (SEQ ID NO: 63) (SEQ ID NO: 64) | | | | | |
| Sc8OHGER_105 | | P00331 | Alcohol dehydrogenase 2 (EC 1.1.1.1) (Alcohol dehydrogenase II) (YADH-2) (SEQ ID NO: 65) (SEQ ID NO: 66) | | S. cerevisiae S288c | P54115 | Magnesium-activated aldehyde dehydrogenase, cytosolic (EC 1.2.1.4) (Mg(2+)-activated acetaldehyde dehydrogenase) (Mg(2+)-ACDH) (SEQ ID NO: 63) (SEQ ID NO: 64) | S. cerevisiae S288c | | | | |
| Sc8OHGER_106 | | P00331 | Alcohol dehydrogenase 2 (EC 1.1.1.1) (Alcohol dehydrogenase II) (YADH-2) (SEQ ID NO: 65) (SEQ ID NO: 66) | | S. cerevisiae S288c | P54115 | Magnesium-activated aldehyde dehydrogenase, cytosolic (EC 1.2.1.4) (Mg(2+)-activated acetaldehyde dehydrogenase) (Mg(2+)-ACDH) (SEQ ID NO: 63) (SEQ ID NO: 64) | S. cerevisiae S288c | P41338 | Acetyl-CoA: acetyl-CoA C-acetyltransferase (SEQ ID NO: 19) (SEQ ID NO: 20) | | S. cerevisiae S288c |
| Sc8OHGER_107 | | P12684 | (R)-Mevalonate: NADP+ oxidoreductase (CoA acylating) (SEQ ID NO: 21) (SEQ ID NO: 22) | | S. cerevisiae S288c | P40312 | Cytochrome b5 (SEQ ID NO: 71) (SEQ ID NO: 72) | S. cerevisiae S288c | P22939 | Farnesyl pyrophosphate synthase (EC 2.5.1.10), Dimethylallyl-transtransferase (EC 2.5.1.1) (SEQ ID NO: 79) (SEQ ID NO: 80) | S80F | E. coli (strain K12) |
| Sc8OHGER_108 | | Q6C7Y1 | YALI0D24431p (SEQ ID NO: 67) (SEQ ID NO: 68) | | Yarrowia lipolytica CLIB 122/E 150 | Q5BAJ5 | Citrate lyase subunit (Eurofung) (SEQ ID NO: 73) (SEQ ID NO: 74) | Emericella nidulans ATCC 38163 | | | | |
| Sc8OHGER_109 | | P0AFG8 | Pyruvate dehydrogenase E1 component (PDH E1 component) (EC 1.2.4.1) (SEQ ID NO: 69) (SEQ ID NO: 70) | | E. coli (strain K12) | P06959 | Dihydrolipoyllysine-residue acetyltransferase component of pyruvate dehydrogenase complex (EC 2.3.1.12) | E. coli (strain K12) | E0IYR5 | Dihydrolipoyl dehydrogenase (EC 1.8.1.4) (SEQ ID NO: 81) (SEQ ID NO: 82) | G187A, G191A, E205V, M206R, F207K, D208H, P212R | E. coli ATCC 9637 |

TABLE 3-continued

Fourth (Improvement) round strain designs for testing 1-3 heterologous enzymes to improve (6E)-8-hydroxygeraniol production in *Saccharomyces cerevisiae* (Improvement round)

| Strain name *S. cerevisiae* | Titer (microgram/L) | E1 Uniprot ID | Enzyme 1 - activity name | E1 Modifications | Enzyme 1 - source organism | E2 Uniprot ID | Enzyme 2 - activity name | Enzyme 2 - source organism | E3 Uniprot ID | Enzyme 3 - activity name | E3 Modifications | Enzyme 3 - source organism |
|---|---|---|---|---|---|---|---|---|---|---|---|---|
| Sc8OHGER_110 | | P0AFG8 | Pyruvate dehydrogenase E1 component (PDH E1) (EC 1.2.4.1) (SEQ ID NO: 69) (SEQ ID NO: 70) | | *E. coli* (strain K12) | P06959 | Dihydrolipoyllysine-residue acetyltransferase component of pyruvate dehydrogenase complex (EC 2.3.1.12) (Dihydrolipoamide acetyltransferase component of pyruvate dehydrogenase complex) (E2) (SEQ ID NO: 75) (SEQ ID NO: 76) | *E. coli* (strain K12) | E0IYR5 | Dihydrolipoyl dehydrogenase (EC 1.8.1.4) (SEQ ID NO: 83) (SEQ ID NO: 84) | | *E. coli* ATCC 9637 |

Note:
There is evidence that these strains do not have the genes from the first two rounds as intended. Also, all enzyme genes had modified codon usage for Cg and Sc.

Example 2—Construction and Selection of Strains of *Yarrowia lipolytica* Engineered to Produce (6E)-8-Hydroxygeraniol

*Yarrowia lipolytica* was engineered using the approached described above for *S. cerevisiae*. The strains constructed in the first round of genetic engineering and their (6E)-8-hydroxygeranial titers are shown in Table 4.

TABLE 4

First round results for (6E)-8-hydroxygeraniol production in *Yarrowia lipolytica*

| *Y. lipolytica* | Titer (μg/L) | E1 Uni-prot ID | Enzyme 1 - activity name | E1 Modifications | Enzyme 1 - source organism | E1 Codon Optimization Abbrev. | E2 Uni-prot ID | Enzyme 2 - activity name |
|---|---|---|---|---|---|---|---|---|
| Yl8OHGER_01 | 48.4 | P22939 | Farnesyl diphosphate synthase (SEQ ID NO: 85) (SEQ ID NO: 86) | S80F | *E. coli* K12 | *B. subtillus* | C0KWV4 | Geraniol synthase (SEQ ID NO: 92) (SEQ ID NO: 94) |
| Yl8OHGER_02 | 53.8 | P22939 | Farnesyl diphosphate synthase (SEQ ID NO: 85) (SEQ ID NO: 87) | S80F | *E. coli* K12 | modified codon usage for Cg and Sc | C0KWV4 | Geraniol synthase (SEQ ID NO: 92) (SEQ ID NO: 93) |
| Yl8OHGER_03 | 45.9 | P22939 | Farnesyl diphosphate synthase (SEQ ID NO: 85) (SEQ ID NO: 88) | S80F | *E. coli* K12 | *S. cerevisiae* | C0KWV4 | Geraniol synthase (SEQ ID NO: 92) (SEQ ID NO: 95) |
| Yl8OHGER_04 | 50.7 | P22939 | Farnesyl diphosphate synthase (SEQ ID NO: 85) (SEQ ID NO: 89) | S80F | *E. coli* K12 | *Y. lipolytica* | C0KWV4 | Geraniol synthase (SEQ ID NO: 92) (SEQ ID NO: 96) |
| Yl8OHGER_05 | 48.2 | P22939 | Farnesyl diphosphate synthase (SEQ ID NO: 85) (SEQ ID NO: 86) | S80F | *E. coli* K12 | *B. subtillus* | E5GAH8 | Geraniol synthase (SEQ ID NO: 97) (SEQ ID NO: 98) |
| Yl8OHGER_06 |  | P22939 | Farnesyl diphosphate synthase (SEQ ID NO: 85) (SEQ ID NO: 87) | S80F | *E. coli* K12 | modified codon usage for Cg and Sc | E5GAH8 | Geraniol synthase (SEQ ID NO: 97) (SEQ ID NO: 99) |
| Yl8OHGER_07 | 46.2 | P22939 | Farnesyl diphosphate synthase (SEQ ID NO: 85) (SEQ ID NO: 88) | S80F | *E. coli* K12 | *S. cerevisiae* | E5GAH8 | Geraniol synthase (SEQ ID NO: 97) (SEQ ID NO: 100) |
| Yl8OHGER_08 | 204.9 | P22939 | Farnesyl diphosphate synthase (SEQ ID NO: 85) (SEQ ID NO: 89) | S80F | *E. coli* K12 | *Y. lipolytica* | E5GAH8 | Geraniol synthase (SEQ ID NO: 97) (SEQ ID NO: 101) |
| Yl8OHGER_09 | 58.6 | P22939 | Farnesyl diphosphate synthase (SEQ ID NO: 85) (SEQ ID NO: 86) | S80F | *E. coli* K12 | *B. subtillus* | C0KWV4 | Geraniol synthase (SEQ ID NO: 92) (SEQ ID NO: 94) |

TABLE 4-continued

First round results for (6E)-8-hydroxygeraniol production in *Yarrowia lipolytica*

| | | | | | | | | |
|---|---|---|---|---|---|---|---|---|
| YI8OHGER_10 | 45.2 | P22939 | Farnesyl diphosphate synthase (SEQ ID NO: 85) (SEQ ID NO: 88) | S80F | *E. coli* K12 | *S. cerevisiae* | C0KWV4 | Geraniol synthase (SEQ ID NO: 92) (SEQ ID NO: 95) |
| YI8OHGER_11 | 62.9 | P22939 | Farnesyl diphosphate synthase (SEQ ID NO: 85) (SEQ ID NO: 89) | S80F | *E. coli* K12 | *Y. lipolytica* | C0KWV4 | Geraniol synthase (SEQ ID NO: 92) (SEQ ID NO: 96) |
| YI8OHGER_12 | 61.7 | P08524 | Farnesyl pyrophosphate synthase (SEQ ID NO: 77) (SEQ ID NO: 90) | F96W, N127W | *S. cerevisiae* S288c | *B. subtillus* | C0KWV4 | Geraniol synthase (SEQ ID NO: 92) (SEQ ID NO: 94) |
| YI8OHGER_13 | 47.6 | P08524 | Farnesyl pyrophosphate synthase (SEQ ID NO: 77) (SEQ ID NO: 78) | F96W, N127W | *S. cerevisiae* S288c | *S. cerevisiae* | C0KWV4 | Geraniol synthase (SEQ ID NO: 92) (SEQ ID NO: 95) |
| YI8OHGER_14 | 56.4 | P08524 | Farnesyl pyrophosphate synthase (SEQ ID NO: 77) (SEQ ID NO: 91) | F96W, N127W | *S. cerevisiae* S288c | *Y. lipolytica* | C0KWV4 | Geraniol synthase (SEQ ID NO: 92) (SEQ ID NO: 96) |
| YI8OHGER_15 | 46.5 | P08524 | Farnesyl pyrophosphate synthase (SEQ ID NO: 77) (SEQ ID NO: 90) | F96W, N127W | *S. cerevisiae* S288c | *B. subtillus* | E5GAH8 | Geraniol synthase (SEQ ID NO: 97) (SEQ ID NO: 98) |
| YI8OHGER_16 | 42.9 | P08524 | Farnesyl pyrophosphate synthase (SEQ ID NO: 77) (SEQ ID NO: 78) | F96W, N127W | *S. cerevisiae* S288c | *S. cerevisiae* | E5GAH8 | Geraniol synthase (SEQ ID NO: 97) (SEQ ID NO: 100) |
| YI8OHGER_17 | 136.8 | P08524 | Farnesyl pyrophosphate synthase (SEQ ID NO: 77) (SEQ ID NO: 91) | F96W, N127W | *S. cerevisiae* S288c | *Y. lipolytica* | E5GAH8 | Geraniol synthase (SEQ ID NO: 97) (SEQ ID NO: 101) |
| YI8OHGER_18 | 59.8 | P08524 | Farnesyl pyrophosphate synthase (SEQ ID NO: 77) (SEQ ID NO: 90) | F96W, N127W | *S. cerevisiae* S288c | *B. subtillus* | C0KWV4 | Geraniol synthase (SEQ ID NO: 92) (SEQ ID NO: 94) |
| YI8OHGER_19 | 36.4 | P08524 | Farnesyl pyrophosphate synthase (SEQ ID NO: 77) (SEQ ID NO: 78) | F96W, N127W | *S. cerevisiae* S288c | *S. cerevisiae* | C0KWV4 | Geraniol synthase (SEQ ID NO: 92) (SEQ ID NO: 95) |
| YI8OHGER_20 | 65.0 | P08524 | Farnesyl pyrophosphate synthase (SEQ ID NO: 77) (SEQ ID NO: 91) | F96W, N127W | *S. cerevisiae* S288c | *Y. lipolytica* | C0KWV4 | Geraniol synthase (SEQ ID NO: 92) (SEQ ID NO: 96) |

TABLE 4-continued

First round results for (6E)-8-hydroxygeraniol production in *Yarrowia lipolytica*

| | | | | | | | | |
|---|---|---|---|---|---|---|---|---|
| YI8OHGER_21 | 310.1 | C0KVW4 | geraniol synthase (SEQ ID NO: 92) (SEQ ID NO: 93) | *Perilla setoyensis* | modified codon usage for Cg and Sc | A0A0L9UT99 | geraniol 8-hydroxylase (SEQ ID NO: 102) (SEQ ID NO: 103) | |

| *Y. lipolytica* | Enzyme 2 - source organism | E2 Codon Optimization Abbrev. | E3 Uniprot ID | Enzyme 3 - activity name | Enzyme 3 - source organism | E3 Codon Optimization Abbrev. |
|---|---|---|---|---|---|---|
| YI8OHGER_01 | *Perilla setoyensis* | *B. subtillus* | A0A0L9UT99 | Uncharacterized protein (SEQ ID NO: 102) (SEQ ID NO: 104) | *Phaseolus angularis* | *B. subtillus* |
| YI8OHGER_02 | *Perilla setoyensis* | modified codon usage for Cg and Sc | A0A0L9UT99 | Uncharacterized protein (SEQ ID NO: 102) (SEQ ID NO: 103) | *Phaseolus angularis* | modified codon usage for Cg and Sc |
| YI8OHGER_03 | *Perilla setoyensis* | *S. cerevisiae* | A0A0L9UT99 | Uncharacterized protein (SEQ ID NO: 102) (SEQ ID NO: 105) | *Phaseolus angularis* | *S. cerevisiae* |
| YI8OHGER_04 | *Perilla setoyensis* | *Y. lipolytica* | A0A0L9UT99 | Uncharacterized protein (SEQ ID NO: 102) (SEQ ID NO: 106) | *Phaseolus angularis* | *Y. lipolytica* |
| YI8OHGER_05 | *Vitis vinifera* | *B. subtillus* | A0A0L9UT99 | Uncharacterized protein (SEQ ID NO: 102) (SEQ ID NO: 104) | *Phaseolus angularis* | *B. subtillus* |
| YI8OHGER_06 | *Vitis vinifera* | modified codon usage for Cg and Sc | A0A0L9UT99 | Uncharacterized protein (SEQ ID NO: 102) (SEQ ID NO: 103) | *Phaseolus angularis* | modified codon usage for Cg and Sc |
| YI8OHGER_07 | *Vitis vinifera* | *S. cerevisiae* | A0A0L9UT99 | Uncharacterized protein (SEQ ID NO: 102) (SEQ ID NO: 105) | *Phaseolus angularis* | *S. cerevisiae* |
| YI8OHGER_08 | *Vitis vinifera* | *Y. lipolytica* | A0A0L9UT99 | Uncharacterized protein (SEQ ID NO: 102) (SEQ ID NO: 106) | *Phaseolus angularis* | *Y. lipolytica* |
| YI8OHGER_09 | *Perilla setoyensis* | *B. subtillus* | D1MI46 | Geraniol 8-hydroxylase (SEQ ID NO: 107) (SEQ ID NO: 108) | *Swertia mussotii* | *B. subtillus* |
| YI8OHGER_10 | *Perilla setoyensis* | *S. cerevisiae* | D1MI46 | Geraniol 8-hydroxylase (SEQ ID NO: 107) (SEQ ID NO: 109) | *Swertia mussotii* | *S. cerevisiae* |
| YI8OHGER_11 | *Perilla setoyensis* | *Y. lipolytica* | D1MI46 | Geraniol 8-hydroxylase (SEQ ID NO: 107) (SEQ ID NO: 110) | *Swertia mussotii* | *Y. lipolytica* |
| YI8OHGER_12 | *Perilla setoyensis* | *B. subtillus* | A0A0L9UT99 | Uncharacterized protein (SEQ ID NO: 102) (SEQ ID NO: 104) | *Phaseolus angularis* | *B. subtillus* |
| YI8OHGER_13 | *Perilla setoyensis* | *S. cerevisiae* | A0A0L9UT99 | Uncharacterized protein (SEQ ID NO: 102) (SEQ ID NO: 105) | *Phaseolus angularis* | *S. cerevisiae* |
| YI8OHGER_14 | *Perilla setoyensis* | *Y. lipolytica* | A0A0L9UT99 | Uncharacterized protein (SEQ ID NO: 102) (SEQ ID NO: 106) | *Phaseolus angularis* | *Y. lipolytica* |
| YI8OHGER_15 | *Vitis vinifera* | *B. subtillus* | A0A0L9UT99 | Uncharacterized protein (SEQ ID NO: 102) (SEQ ID NO: 104) | *Phaseolus angularis* | *B. subtillus* |
| YI8OHGER_16 | *Vitis vinifera* | *S. cerevisiae* | A0A0L9UT99 | Uncharacterized protein (SEQ ID NO: 102) (SEQ ID NO: 105) | *Phaseolus angularis* | *S. cerevisiae* |

TABLE 4-continued

First round results for (6E)-8-hydroxygeraniol production in Yarrowia lipolytica

| | | | | | | |
|---|---|---|---|---|---|---|
| Yl8OHGER_17 | Vitis vinifera | Y. lipolytica | A0A0L9UT99 | Uncharacterized protein (SEQ ID NO: 102) (SEQ ID NO: 106) | Phaseolus angularis | Y. lipolytica |
| Yl8OHGER_18 | Perilla setoyensis | B. subtillus | D1MI46 | Geraniol 8-hydroxylase (SEQ ID NO: 107) (SEQ ID NO: 108) | Swertia mussotii | B. subtillus |
| Yl8OHGER_19 | Perilla setoyensis | S. cerevisiae | D1MI46 | Geraniol 8-hydroxylase (SEQ ID NO: 107) (SEQ ID NO: 109) | Swertia mussotii | S. cerevisiae |
| Yl8OHGER_20 | Perilla setoyensis | Y. lipolytica | D1MI46 | Geraniol 8-hydroxylase (SEQ ID NO: 107) (SEQ ID NO: 110) | Swertia mussotii | Y. lipolytica |
| Yl8OHGER_21 | Phaseolus angularis | modified codon usage for Cg and Sc | P15496 | Isopentenyl-diphosphate delta3-delta2-isomerase (SEQ ID NO: 25) (SEQ ID NO: 111) | S. cerevisiae S288c | modified codon usage for Cg and Sc |

Example 3—Host Evaluation for (6E)-8-Hydroxygeraniol Production

The best-performing enzymes were tested in four hosts: Yarrowia lipolytica, Bacillus subtillus, Corynebacteria glutamicum, Saccharomyces cerevisiae. The results for S. cerevisiae are shown in Table 5, below.

The best performing strain in Y. lipolytica produced a titer of 310 microgram/L. This Y. lipolytica strain expressed geraniol synthase (UniProt ID COKWV4) from Perilla setoyensis, geraniol 8-hydroxylase (UniProt ID A0A0L9UT99) from Phaseolus angularis and isopentenyl-diphosphate delta3-delta2-isomerase (UniProt ID P15496) from S. cerevisiae. The second-best performing Y. lipolytica strain produced 200 microgram/L, and this strain expressed farnesyl diphosphate synthase (UniProt ID P22939) from Escherichia coli K12 harboring amino acid substitution S80F [4], geraniol synthase (UniProt ID E5GAH8) from Vitis vinifera, and geraniol 8-hydroxylase (UniProt ID A0A0L9UT99) from Phaseolus angularis.

The best performing strain in S. cerevisiae produced a titer of 217 microgram/L. This S. cerevisiae strain expressed geraniol synthase (UniProt ID COKWV4) from Perilla setoyensis, geraniol 8-hydroxylase (UniProt ID A0A0L9UT99) from Phaseolus angularis and isopentenyl-diphosphate delta3-delta2-isomerase (UniProt ID P15496) from S. cerevisiae).

There was no titer produced by either B. subtillus or C. glutamicum strains.

TABLE 5

Host evaluation designs for (6E)-8-hydroxygeraniol production tested in S. cerevisiae

| S. cerevisiae | Titer (µg/L) | E1 Uniprot ID | Enzyme 1 - activity name | E1 Modifications | Enzyme 1 - source organism | E1 Codon Optimization Abbrev. | E2 Uniprot ID | Enzyme 2 - activity name | Enzyme 2 - source organism |
|---|---|---|---|---|---|---|---|---|---|
| Sc8OHGER_112 | 18.1 | P22939 | Farnesyl diphosphate synthase (SEQ ID NO: 85) (SEQ ID NO: 86) | S80F | E. coli K12 | B. subtillus | C0KWV4 | Geraniol synthase (SEQ ID NO: 92) (SEQ ID NO: 94) | Perilla setoyensis SEQ ID NO: 99SEQ ID NO: 101 |
| Sc8OHGER_113 | 31.1 | P22939 | Farnesyl diphosphate synthase (SEQ ID NO: 85) (SEQ ID NO: 88) | S80F | E. coli K12 | S. cerevisiae | C0KWV4 | Geraniol synthase (SEQ ID NO: 92) (SEQ ID NO: 95) | Perilla setoyensis SEQ ID NO: 99SEQ ID NO: 102 |
| Sc8OHGER_114 | 23.4 | P22939 | Farnesyl diphosphate synthase (SEQ ID NO: 85) (SEQ ID NO: 89) | S80F | E. coli K12 | Y. lipolytica | C0KWV4 | Geraniol synthase (SEQ ID NO: 92) (SEQ ID NO: 96) | Perilla setoyensis |

TABLE 5-continued

Host evaluation designs for (6E)-8-hydroxygeraniol production tested in *S. cerevisiae*

| Name | Value | ID | Enzyme | Mutation | Source 1 | Source 2 | Code | Enzyme 2 | Species |
|---|---|---|---|---|---|---|---|---|---|
| Sc8OHGER_115 | 14.7 | P22939 | Farnesyl diphosphate synthase (SEQ ID NO: 85) (SEQ ID NO: 86) | S80F | *E. coli* K12 | *B. subtillus* | E5GAH8 | Geraniol synthase (SEQ ID NO: 97) (SEQ ID NO: 98) | *Vitis vinifera* |
| Sc8OHGER_116 | 11.3 | P22939 | Farnesyl diphosphate synthase (SEQ ID NO: 85) (SEQ ID NO: 88) | S80F | *E. coli* K12 | *S. cerevisiae* | E5GAH8 | Geraniol synthase (SEQ ID NO: 97) (SEQ ID NO: 100) | *Vitis vinifera* |
| Sc8OHGER_117 | 15.5 | P22939 | Farnesyl diphosphate synthase (SEQ ID NO: 85) (SEQ ID NO: 89) | S80F | *E. coli* K12 | *Y. lipolytica* | E5GAH8 | Geraniol synthase (SEQ ID NO: 97) (SEQ ID NO: 101) | *Vitis vinifera* |
| Sc8OHGER_118 | 9.2 | P22939 | Farnesyl diphosphate synthase (SEQ ID NO: 85) (SEQ ID NO: 86) | S80F | *E. coli* K12 | *B. subtillus* | C0KWV4 | Geraniol synthase (SEQ ID NO: 92) (SEQ ID NO: 94) | *Perilla setoyensis* |
| Sc8OHGER_119 | 15.3 | P22939 | Farnesyl diphosphate synthase (SEQ ID NO: 85) (SEQ ID NO: 87) | S80F | *E. coli* K12 | modified codon usage for Cg and Sc | C0KWV4 | Geraniol synthase (SEQ ID NO: 92) (SEQ ID NO: 93 | *Perilla setoyensis* |
| Sc8OHGER_120 | 20.5 | P22939 | Farnesyl diphosphate synthase (SEQ ID NO: 85) (SEQ ID NO: 88) | S80F | *E. coli* K12 | *S. cerevisiae* | C0KWV4 | Geraniol synthase (SEQ ID NO: 92) (SEQ ID NO: 95) | *Perilla setoyensis* |
| Sc8OHGER_121 | 10.6 | P22939 | Farnesyl diphosphate synthase (SEQ ID NO: 85) (SEQ ID NO: 89) | S80F | *E. coli* K12 | *Y. lipolytica* | C0KWV4 | Geraniol synthase (SEQ ID NO: 92) (SEQ ID NO: 96) | *Perilla setoyensis* |
| Sc8OHGER_122 | 85.4 | P08524 | Farnesyl pyrophosphate synthase (SEQ ID NO: 77) (SEQ ID NO: 90) | F96W, N127W | *S. cerevisiae* 8288c | *B. subtillus* | C0KWV4 | Geraniol synthase (SEQ ID NO: 92) (SEQ ID NO: 94) | *Perilla setoyensis* |
| Sc8OHGER_123 | 78.6 | P08524 | Farnesyl pyrophosphate synthase (SEQ ID NO: 77) (SEQ ID NO: 91) | F96W, N127W | *S. cerevisiae* 8288c | *Y. lipolytica* | C0KWV4 | Geraniol synthase (SEQ ID NO: 92) (SEQ ID NO: 96) | *Perilla setoyensis* |
| Sc8OHGER_124 | 54.4 | P08524 | Farnesyl pyrophosphate synthase (SEQ ID NO: 77) (SEQ ID NO: 90) | F96W, N127W | *S. cerevisiae* 8288c | *B. subtillus* | E5GAH8 | Geraniol synthase (SEQ ID NO: 97) (SEQ ID NO: 98) | *Vitis vinifera* |
| Sc8OHGER_125 | 52.7 | P08524 | Farnesyl pyrophosphate synthase (SEQ ID NO: 77) (SEQ ID NO: 78) | F96W, N127W | *S. cerevisiae* 8288c | *S. cerevisiae* | E5GAH8 | Geraniol synthase (SEQ ID NO: 97) (SEQ ID NO: 100) | *Vitis vinifera* |

TABLE 5-continued

Host evaluation designs for (6E)-8-hydroxygeraniol production tested in *S. cerevisiae*

| | | | | | | | | |
|---|---|---|---|---|---|---|---|---|
| Sc8OHGER_126 | 94.4 | P08524 | Farnesyl pyrophosphate synthase (SEQ ID NO: 77) (SEQ ID NO: 91) | F96W, N127W | *S. cerevisiae* 8288c | *Y. lipolytica* | E5GAH8 | Geraniol synthase (SEQ ID NO: 97) (SEQ ID NO: 101) | *Vitis vinifera* |
| Sc8OHGER_127 | 106.6 | P08524 | Farnesyl pyrophosphate synthase (SEQ ID NO: 77) (SEQ ID NO: 78) | F96W, N127W | *S. cerevisiae* 8288c | *S. cerevisiae* | C0KWV4 | Geraniol synthase (SEQ ID NO: 92) (SEQ ID NO: 95) | *Perilla setoyensis* |
| Sc8OHGER_128 | 49.4 | P08524 | Farnesyl pyrophosphate synthase (SEQ ID NO: 77) (SEQ ID NO: 91) | F96W, N127W | *S. cerevisiae* 8288c | *Y. lipolytica* | C0KWV4 | Geraniol synthase (SEQ ID NO: 92) (SEQ ID NO: 96) | *Perilla setoyensis* |
| Sc8OHGER_129 | 217.0 | C0KWV4 | geraniol synthase (SEQ ID NO: 92) (SEQ ID NO: 93) | | *Perilla setoyensis* | modified codon usage for Cg and Sc | A0A0L9UT99 | geraniol 8-hydroxylase (SEQ ID NO: 102) (SEQ ID NO: 103) | *Phaseolus angularis* |

| | | Titer (µg/L) *S. cerevisiae* | E1 Uniprot ID | E2 Codon Optimization Abbrev. | E3 Uniprot ID | Enzyme 3 - activity name | Enzyme 3 - source organism | E3 Codon Optimization Abbrev. |
|---|---|---|---|---|---|---|---|---|
| | Sc8OHGER_112 | 18.1 | P22939 | *B. subtillus* | A0A0L9UT99 | Uncharacterized protein (SEQ ID NO: 102) (SEQ ID NO: 104) | *Phaseolus angularis* | *B. subtillus* |
| | Sc8OHGER_113 | 31.1 | P22939 | *S. cerevisiae* | A0A0L9UT99 | Uncharacterized protein (SEQ ID NO: 102) (SEQ ID NO: 105) | *Phaseolus angularis* | *S. cerevisiae* |
| | Sc8OHGER_114 | 23.4 | P22939 | *Y. lipolytica* | A0A0L9UT99 | Uncharacterized protein (SEQ ID NO: 102) (SEQ ID NO: 106) | *Phaseolus angularis* | *Y. lipolytica* |
| | Sc8OHGER_115 | 14.7 | P22939 | *B. subtillus* | A0A0L9UT99 | Uncharacterized protein (SEQ ID NO: 102) (SEQ ID NO: 104) | *Phaseolus angularis* | *B. subtillus* |
| | Sc8OHGER_116 | 11.3 | P22939 | *S. cerevisiae* | A0A0L9UT99 | Uncharacterized protein (SEQ ID NO: 102) (SEQ ID NO: 105) | *Phaseolus angularis* | *S. cerevisiae* |
| | Sc8OHGER_117 | 15.5 | P22939 | *Y. lipolytica* | A0A0L9UT99 | Uncharacterized protein (SEQ ID NO: 102) (SEQ ID NO: 106) | *Phaseolus angularis* | *Y. lipolytica* |
| | Sc8OHGER_118 | 9.2 | P22939 | *B. subtillus* | D1MI46 | Geraniol 8-hydroxylase (SEQ ID NO: 107) (SEQ ID NO: 108) | *Swertia mussotii* | *B. subtillus* |
| | Sc8OHGER_119 | 15.3 | P22939 | modified codon usage for Cg and Sc | D1MI46 | Geraniol 8-hydroxylase (SEQ ID NO: 107) (SEQ ID NO: 112) | *Swertia mussotii* | modified codon usage for Cg and Sc |
| | Sc8OHGER_120 | 20.5 | P22939 | *S. cerevisiae* | D1MI46 | Geraniol 8-hydroxylase | *Swertia mussotii* | *S. cerevisiae* |
| | Sc8OHGER_121 | 10.6 | P22939 | *Y. lipolytica* | D1MI46 | Geraniol 8-hydroxylase (SEQ ID NO: 107) (SEQ ID NO: 109) | *Swertia mussotii* | *Y. lipolytica* |
| | Sc8OHGER_122 | 85.4 | P08524 | *B. subtillus* | A0A0L9UT99 | Uncharacterized protein (SEQ ID NO: 102) (SEQ ID NO: 104) | *Phaseolus angularis* | *B. subtillus* |
| | Sc8OHGER_123 | 78.6 | P08524 | *Y. lipolytica* | A0A0L9UT99 | Uncharacterized protein (SEQ ID NO: 102) (SEQ ID NO: 106) | *Phaseolus angularis* | *Y. lipolytica* |

TABLE 5-continued

Host evaluation designs for (6E)-8-hydroxygeraniol production tested in S. cerevisiae

| | | | | | | | |
|---|---|---|---|---|---|---|---|
| Sc8OHGER_124 | 54.4 | P08524 | B. subtillus | A0A0L9UT99 | Uncharacterized protein (SEQ ID NO: 102) (SEQ ID NO: 104) | Phaseolus angularis | B. subtillus |
| Sc8OHGER_125 | 52.7 | P08524 | S. cerevisiae | A0A0L9UT99 | Uncharacterized protein (SEQ ID NO: 102) (SEQ ID NO: 105) | Phaseolus angularis | S. cerevisiae |
| Sc8OHGER_126 | 94.4 | P08524 | Y. lipolytica | A0A0L9UT99 | Uncharacterized protein (SEQ ID NO: 102) (SEQ ID NO: 106) | Phaseolus angularis | Y. lipolytica |
| Sc8OHGER_127 | 106.6 | P08524 | S. cerevisiae | D1MI46 | Geraniol 8-hydroxylase (SEQ ID NO: 107) (SEQ ID NO: 109) | Swertia mussotii | S. cerevisiae |
| Sc8OHGER_128 | 49.4 | P08524 | Y. lipolytica | D1MI46 | Geraniol 8-hydroxylase (SEQ ID NO: 107) (SEQ ID NO: 110) | Swertia mussotii | Y. lipolytica |
| Sc8OHGER_129 | 217.0 | C0KWV4 | modified codon usage for Cg and Sc | P15496 | Isopentenyl-diphosphate delta3-delta2-isomerase (SEQ ID NO: 25) (SEQ ID NO: 111) | S. cerevisiae 8288c | modified codon usage for Cg and Sc |

REFERENCES

1. Polakowski, T., U. Stahl, and C. Lang, *Overexpression of a cytosolic hydroxymethylglutaryl-CoA reductase leads to squalene accumulation in yeast*. Appl Microbiol Biotechnol, 1998. 49(1): p. 66-71.
2. Dimster-Denk, D., M. K. Thorsness, and J. Rine, Feedback regulation of 3-hydroxy-3-methylglutaryl coenzyme A reductase in *Saccharomyces cerevisiae*. Mol Biol Cell, 1994. 5(6): p. 655-65.
3. Billingsley, J. M., et al., Engineering the biocatalytic selectivity of iridoid production in *Saccharomyces cerevisiae*. Metab Eng, 2017. 44: p. 117-125.
4. Eiichiro Ono, N. T., Method for utilizing monoterpene glycosidation enzyme. 2015.
5. Roth, S., et al., Chemoenzymatic *Synthesis of a Novel Borneol-Based Polyester*. ChemSusChem, 2017. 10(18): p. 3574-3580.
6. Crowley, J. H., et al., A mutation in a purported regulatory gene affects control of sterol uptake in *Saccharomyces cerevisiae*. J Bacteriol, 1998. 180(16): p. 4177-83.
7. Vik, A. and J. Rine, Upc2p and Ecm22p, dual regulators of sterol biosynthesis in *Saccharomyces cerevisiae*. Mol Cell Biol, 2001. 21(19): p. 6395-405.
1. Kanehisa, M. and S. Goto, KEGG: kyoto encyclopedia of genes and genomes. Nucleic Acids Res, 2000. 28(1): p. 27-30.
2. Oswald, M., et al., Monoterpenoid biosynthesis in *Saccharomyces cerevisiae*. FEMS Yeast Res, 2007. 7(3): p. 413-21.
3. Polakowski, T., U. Stahl, and C. Lang, Overexpression of a cytosolic hydroxymethylglutaryl-CoA reductase leads to squalene accumulation in yeast. Appl Microbiol Biotechnol, 1998. 49(1): p. 66-71.
4. Reiling, K. K., et al., Mono and diterpene production in *Escherichia coli*. Biotechnol Bioeng, 2004. 87(2): p. 200-12.

What is claimed is:

1. An engineered microbial cell, wherein the engineered microbial cell expresses:
   (a) a non-native geranyl diphosphate diphosphatase (geraniol synthase); and
   (b) a non-native geraniol-8-hydroxylase;
   wherein the engineered microbial cell comprises increased activity of one or more upstream (6E)-8-hydroxygeraniol pathway enzyme(s), said increased activity being increased relative to a control cell, the one or more upstream pathway enzymes being selected from the group consisting of ATP-citrate synthase, an acetyl-CoA synthetase, a thiolase, a hydroxymethylglutaryl coenzyme A synthase (HMG-CoA synthase), a hydroxymethylglutaryl coenzyme A reductase (HMG-CoA reductase), a mevalonate kinase, a phosphomevalonate kinase, a diphosphomevalonate decarboxylase, an isopentenyl-diphosphate delta-isomerase, and a geranyl diphosphate synthase; and
   wherein, when cultured, the engineered microbial cell produces (6E)-8-hydroxygeraniol at a level greater than 10 mg/L of culture medium.

2. The engineered microbial cell of claim 1, wherein the one or more upstream (6E)-8-hydroxygeraniol pathway enzyme(s) comprise the isopentenyl-diphosphate delta-isomerase.

3. The engineered microbial cell of claim 1, wherein the engineered microbial cell comprises reduced activity of one or more enzyme(s) that consume one or more (6E)-8-hydroxygeraniol pathway precursors, said reduced activity being reduced relative to a control cell, the one or more enzyme(s) that consume one or more (6E)-8-hydroxygeraniol pathway precursors comprising a bifunctional (2E,6E)-farnesyl diphosphate synthase/dimethylallyltranstransferase and/or a geranyl pyrophosphate synthase.

4. The engineered microbial cell of claim 1, wherein the engineered microbial cell additionally expresses a feedback-deregulated HMG-CoA reductase.

5. The engineered microbial cell of claim 1, wherein the engineered microbial cell over-expresses an ATP-citrate synthase and/or an acetyl-CoA synthetase to increase availability of acetyl-CoA, relative to a control cell, and/or comprises an inactivated or deleted gene selected from the group consisting of Pdc5, Pdc6, and Pdc1 to reduce the rate of acetyl-CoA consumption, relative to a control cell.

6. The engineered microbial cell of claim 1, wherein the engineered microbial cell comprises a fungal cell.

7. The engineered microbial cell of claim 1, wherein the non-native geraniol synthase comprises a geraniol synthase having at least 70% amino acid sequence identity with a geraniol synthase from *Perilla* setoyensis comprising SEQ ID NO:5.

8. The engineered microbial cell of claim 1, wherein the non-native geraniol synthase comprises a geraniol synthase having at least 70% amino acid sequence identity with a geraniol synthase from *Vitis vinifera* comprising SEQ ID NO:97.

9. The engineered microbial cell of claim 1, wherein the non-native geraniol-8-hydroxylase comprises a geraniol-8-hydroxylase having at least 70% amino acid sequence identity with a geraniol-8-hydroxylase from *Phaseolus angularis* comprising SEQ ID NO:11.

10. The engineered microbial cell of claim 2, wherein the increased activity of the isopentenyl-diphosphate delta-isomerase is achieved by heterologously expressing an isopentenyl-diphosphate delta-isomerase.

11. The engineered microbial cell of claim 10, wherein the heterologous isopentenyl-diphosphate delta-isomerase comprises an isopentenyl-diphosphate delta-isomerase having at least 70% amino acid sequence identity with an isopentenyl-diphosphate delta-isomerase from *Saccharomyces cerevisiae* comprising SEQ ID NO:25.

12. The engineered microbial cell of claim 3, wherein the one or more enzyme(s) that consume one or more (6E)-8-hydroxygeraniol pathway precursors comprise a bifunctional (2E,6E)-farnesyl diphosphate synthase/dimethylallyltranstransferase.

13. The engineered microbial cell of claim 12, wherein the bifunctional (2E,6E)-farnesyl diphosphate synthase/dimethylallyltranstransferase dimethylallyltranstransferase comprises amino acid substitution S80F and has at least 70% amino acid sequence identity with a bifunctional (2E,6E)-farnesyl diphosphate synthase/dimethylallyltranstransferase from *Escherichia coli* comprising SEQ ID NO:85.

14. The engineered microbial cell of claim 1, wherein, when cultured, the engineered microbial cell produces (6E)-8-hydroxygeraniol at a level greater than 50 mg/L of culture medium.

15. A culture of engineered microbial cells according to claim 1.

16. The culture of claim 15, wherein the culture comprises (6E)-8-hydroxygeraniol at a level greater than 10 mg/L of culture medium.

17. A method of culturing engineered microbial cells according to claim 1, the method comprising culturing the cells under conditions suitable for producing (6E)-8-hydroxygeraniol.

18. The method of claim 17, wherein the method additionally comprises recovering (6E)-8-hydroxygeraniol from the culture.

19. The engineered microbial cell of claim 1, wherein the one or more upstream pathway enzymes comprises ATP-citrate synthase.

20. The engineered microbial cell of claim 1, wherein the one or more upstream pathway enzymes comprises an acetyl-CoA synthetase.

21. The engineered microbial cell of claim 1, wherein the one or more upstream pathway enzymes comprises a thiolase.

22. The engineered microbial cell of claim 1, wherein the one or more upstream pathway enzymes comprises a hydroxymethylglutaryl coenzyme A synthase (HMG-CoA synthase).

23. The engineered microbial cell of claim 1, wherein the one or more upstream pathway enzymes comprises a hydroxymethylglutaryl coenzyme A reductase (HMG-CoA reductase).

24. The engineered microbial cell of claim 1, wherein the one or more upstream pathway enzymes comprises a mevalonate kinase.

25. The engineered microbial cell of claim 1, wherein the one or more upstream pathway enzymes comprises a phosphomevalonate kinase.

26. The engineered microbial cell of claim 1, wherein the one or more upstream pathway enzymes comprises a diphosphomevalonate decarboxylase.

27. The engineered microbial cell of claim 1, wherein the one or more upstream pathway enzymes comprises a geranyl diphosphate synthase.

\* \* \* \* \*

```
SEQUENCE LISTING

<160> NUMBER OF SEQ ID NOS: 112

<210> SEQ ID NO 1
<211> LENGTH: 591
<212> TYPE: PRT
<213> ORGANISM: Vitis vinifera (Grape)

<400> SEQUENCE: 1

Met Ser Arg Phe Val Thr Met Pro Ser His Val Leu Pro Ser Ser Phe
1               5                   10                  15

Val Ala Pro Ser Leu Gln Val Ser Ser Pro Cys Ser Trp Arg Thr
            20                  25                  30

Arg Pro Ser Pro Cys Thr Ser Cys His Leu Ser Pro Ser Ser Ser
        35                  40                  45

Lys Pro Leu Leu Gly Ser His Asp Tyr Ser Leu Leu Lys Ser Leu Thr
    50                  55                  60
```

```
Leu Ser Pro His Ala Val Asn Ser Glu Ala Asp Ser Ser Thr Arg Arg
 65                  70                  75                  80

Met Lys Glu Val Lys Glu Arg Thr Trp Glu Ala Phe Tyr Arg Ala Trp
                 85                  90                  95

Asp Ser Arg Ala Ala Met Glu Met Val Asp Thr Val Glu Arg Leu Gly
            100                 105                 110

Leu Ser Tyr His Phe Glu Asp Glu Ile Asn Ala Leu Leu Gln Arg Phe
        115                 120                 125

Cys Asp Trp Asn Ala Ser Glu Asp Leu Phe Thr Thr Ala Leu Arg Phe
    130                 135                 140

Arg Leu Leu Arg Gln Asn Gly Phe Pro Thr His Ser Asp Val Phe Gly
145                 150                 155                 160

Lys Phe Met Asp Lys Asn Gly Lys Phe Lys Glu Ser Leu Thr Glu Asp
                165                 170                 175

Ile Trp Gly Met Leu Ser Leu His Glu Ala Ser His Leu Gly Ala Lys
            180                 185                 190

Asn Glu Glu Val Leu Ala Glu Ala Lys Glu Phe Thr Arg Ile His Leu
        195                 200                 205

Ile Gln Ser Met Pro His Met Glu Pro His Phe Ser Ser His Val Gly
    210                 215                 220

Arg Ala Leu Glu Leu Pro Arg His Leu Arg Met Val Arg Leu Glu Ala
225                 230                 235                 240

Arg Asn Tyr Ile Gly Glu Tyr Ser Arg Glu Ser Asn Pro Asn Leu Ala
                245                 250                 255

Phe Leu Glu Leu Ala Lys Leu Asp Phe Asp Met Val Gln Ser Leu His
            260                 265                 270

Gln Lys Glu Leu Ala Glu Ile Val Arg Trp Trp Lys Gln Leu Gly Leu
        275                 280                 285

Val Asp Lys Leu Asp Phe Ala Arg Asp Arg Pro Met Glu Cys Phe Leu
    290                 295                 300

Trp Thr Val Gly Ile Phe Pro Asp Pro Arg His Ser Ser Cys Arg Ile
305                 310                 315                 320

Glu Leu Thr Lys Ala Ile Ala Ile Leu Leu Val Ile Asp Asp Ile Tyr
                325                 330                 335

Asp Ser Tyr Gly Ser Leu Asp Glu Leu Ala Leu Phe Thr Asp Ala Val
            340                 345                 350

Lys Arg Trp Asp Leu Gly Ala Met Asp Gln Leu Pro Glu Tyr Met Lys
        355                 360                 365

Ile Cys Tyr Met Ala Leu Tyr Asn Thr Thr Asn Asp Ile Ala Tyr Arg
    370                 375                 380

Ile Leu Lys Glu His Gly Trp Ser Val Ile Glu Asp Leu Lys Arg Thr
385                 390                 395                 400

Trp Met Asp Ile Phe Gly Ala Phe Leu Ala Glu Ala Tyr Cys Phe Lys
                405                 410                 415

Gly Gly His Val Pro Ser Leu Glu Glu Tyr Leu Thr Asn Ala Val Thr
            420                 425                 430

Thr Gly Gly Thr Tyr Met Ala Leu Val His Ala Phe Phe Leu Met Gly
        435                 440                 445

Gln Gly Val Thr Arg Glu Asn Met Ala Met Leu Lys Pro Tyr Pro Asn
    450                 455                 460

Ile Phe Ser Cys Ser Gly Lys Ile Leu Arg Leu Trp Asp Asp Leu Gly
465                 470                 475                 480
```

```
Thr Ala Arg Glu Glu Gln Glu Arg Gly Asp Asn Ala Ser Ser Ile Glu
            485                 490                 495

Cys Tyr Lys Arg Glu Arg Glu Met Asp Thr Val Leu Glu Asp Glu Ala
        500                 505                 510

Cys Arg Lys His Ile Arg Gln Met Ile Gln Ser Leu Trp Val Glu Leu
    515                 520                 525

Asn Gly Glu Leu Val Ala Ser Ser Ala Leu Pro Leu Ser Ile Ile Lys
530                 535                 540

Ala Ala Phe Asn Leu Ser Arg Thr Ala Gln Val Ile Tyr Gln His Gly
545                 550                 555                 560

Asp Asp Asn Lys Thr Ser Ser Val Glu Asp His Val Gln Ala Leu Leu
                565                 570                 575

Phe Arg Pro Val Ser Ser Asn Gly His Ala Gln Ile Thr Met His
            580                 585                 590

<210> SEQ ID NO 2
<211> LENGTH: 1773
<212> TYPE: DNA
<213> ORGANISM: Artificial
<220> FEATURE:
<223> OTHER INFORMATION: mutated and/or codon-optimized sequence

<400> SEQUENCE: 2
atgtcgcgtt tttgtcaccat gccctctcac gtcctgcctt catcatttgt cgccccatcc        60
cttcaagttt ccagctcgcc ctgcagctgg cgtacccgac cgtcgccctg caccagctgc       120 caccttttcgc catcgtcgag ctctaaaccg ttgttgggta gccacgatta cagcctgttg       180
aagagcctga ccctttcgcc acacgcggtg aattccgaag cagactcttc gactcgccgt       240
atgaaagaag tgaaagaacg aacctgggag gcattctacc gcgcttggga ttcgcgcgca       300
gcaatggaaa tggtagatac tgttgaacga ctgggacttt cttaccactt cgaagacgaa       360
atcaacgcac tcctccaacg cttttgtgac tggaacgcta gcgaggattt gttcacaact       420
gcgctgcgct ttcgcctgct tcgccaaaac ggtttcccga cccacagcga cgtcttcggc       480
aaatttatgg ataaaaatgg caaattcaaa gaatcactga ccgaagacat ttggggtatg       540
ttgtcccctt acgaggcgtc tcaccttggt gctaaaaacg aagaagtcct tgcggaggct       600
aaagaattta ctcgcatcca tctgattcag tcgatgccac acatggagcc tcatttttcg       660
tcgcacgtgg gccgagctct ggagctgccg cgccacctgc gtatggtccg tttgaagcca       720
cgtaactata tcggcgagta ttcgcgcgag tccaatccaa accttgcatt cctggagttg       780
gccaagttgg atttcgatat ggtgcagtct ttgcaccaga agaattggcc gaaatcgtg       840 cgctggtgga aacagctggg cctcgtggac aagttggatt tcgcacgtga ccgcccaatg       900
gaatgttttc ctctggaccgt tggcatcttt ccggatcccc gacactcctc gtgccgcatc       960
gaacttacca agctattgc aattctgttg gtgatcgacg acatctatga ttcctacggc      1020
tcgctggatg aactcgctct ctttaccgat gccgtcaagc gctgggatct gggagccatg      1080
gatcaactcc cagaatacat gaagatttgt tacatggcgc tgtacaacac caccaatgat      1140
atcgcttatc gcatcctcaa agagcatggt tggtccgtca tcgaggactt gaaacgaacg      1200
tggatggata tctttggcgc attccttgct gaggcatatt gcttcaaagg aggccatgtg      1260
ccttcgcttg aggaatattt gaccaacgca gttacgactg gcggtaccta tatggcactg      1320
gtgcacgcct tctttcttat gggacagggc gtgacccgcg agaatatggc aatgctgaag      1380
ccctatccta atatctttag ctgctcagga agatcctcc gtctttggga tgatcttggc      1440
```

```
acagcgcgtg aggagcagga gcgtggcgac aacgccagct ccatcgaatg ctacaagcgt   1500
gaacgtgaga tggacaccgt cctcgaagat gaggcatgcc gcaaacacat ccgtcaaatg   1560
attcagtcct tgtgggttga attgaatggc gagcttgtgg cttcatctgc attgccgctg   1620
tccatcatca aggcagcgtt caatctctcc cgcaccgcac aagtgattta tcagcacggt   1680
gacgataaca aaacgtcctc tgttgaggat catgttcaag ccttgctttt ccgtcctgtt   1740
tcctccaatg gtcacgcaca aattaccatg cac                                1773

<210> SEQ ID NO 3
<211> LENGTH: 292
<212> TYPE: PRT
<213> ORGANISM: Vitis vinifera (Grape)

<400> SEQUENCE: 3
```

Met Glu Cys Phe Leu Trp Thr Val Gly Ile Phe Pro Asp Pro Arg His
1               5                   10                  15

Ser Ser Cys Arg Ile Glu Leu Thr Lys Ala Ile Ala Ile Leu Leu Val
            20                  25                  30

Ile Asp Asp Ile Tyr Asp Ser Tyr Gly Ser Leu Asp Glu Leu Ala Leu
        35                  40                  45

Phe Thr Asp Ala Val Lys Arg Trp Asp Leu Gly Ala Met Asp Gln Leu
    50                  55                  60

Pro Glu Tyr Met Lys Ile Cys Tyr Met Ala Leu Tyr Asn Thr Thr Asn
65                  70                  75                  80

Asp Ile Ala Tyr Arg Ile Leu Lys Glu His Gly Trp Ser Val Ile Glu
                85                  90                  95

Asp Leu Lys Arg Thr Trp Met Asp Ile Phe Gly Ala Phe Leu Ala Glu
            100                 105                 110

Ala Tyr Cys Phe Lys Gly His Val Pro Ser Leu Glu Glu Tyr Leu
        115                 120                 125

Thr Asn Ala Val Thr Thr Gly Gly Thr Tyr Met Ala Leu Val His Ala
    130                 135                 140

Phe Phe Leu Met Gly Gln Gly Val Thr Arg Glu Asn Met Ala Met Leu
145                 150                 155                 160

Lys Pro Tyr Pro Asn Ile Phe Ser Cys Ser Gly Lys Ile Leu Arg Leu
                165                 170                 175

Trp Asp Asp Leu Gly Thr Ala Arg Glu Glu Gln Glu Arg Gly Asp Asn
            180                 185                 190

Ala Ser Ser Ile Glu Cys Tyr Lys Arg Glu Arg Glu Met Asp Thr Val
        195                 200                 205

Leu Glu Asp Glu Ala Cys Arg Lys His Ile Arg Gln Met Ile Gln Ser
    210                 215                 220

Leu Trp Val Glu Leu Asn Gly Glu Leu Val Ala Ser Ser Ala Leu Pro
225                 230                 235                 240

Leu Ser Ile Ile Lys Ala Ala Phe Asn Leu Ser Arg Thr Ala Gln Val
                245                 250                 255

Ile Tyr Gln His Gly Asp Asp Asn Lys Thr Ser Ser Val Glu Asp His
            260                 265                 270

Val Gln Ala Leu Leu Phe Arg Pro Val Ser Ser Asn Gly His Ala Gln
        275                 280                 285

Ile Thr Met His
    290

```
<210> SEQ ID NO 4
```

<211> LENGTH: 876
<212> TYPE: DNA
<213> ORGANISM: Artificial
<220> FEATURE:
<223> OTHER INFORMATION: mutated and/or codon-optimized sequence

<400> SEQUENCE: 4

```
atggaatgtt ttctgtggac cgttggtatt tcccagacc cgcgacactc ttcctgtcgt      60
atcgaactta cgaaagcgat tgcaatcctt tggtgattg atgatatcta cgactcgtac     120
ggctcattgg acgaacttgc gctcttcacc gatgcagtaa aacgctggga tttgggcgcc    180
atggatcaat tgccggaata catgaagatc tgctatatgg cattgtacaa caccacgaac    240
gacatcgcat atcgtatcct caaagagcac ggttggtctg taatcgaaga cctcaagcgc    300
acctggatgg atatcttcgg agcgttcctc gcagaagcgt attgcttcaa gggtggacac    360
gttccttccc tcgaagaata cctgacaaac gcggttacta ccggaggtac atacatggct    420
ctcgtgcatg ctttctttct tatgggtcag ggtgttaccc gcgaaaacat ggcgatgctt    480
aaaccgtatc caaacatctt ctcgtgttca ggcaagatcc tgcgcttgtg ggatgatttg    540
ggaacagctc gcgaagagca ggagcgtggt gataacgcaa gctctatcga atgttacaaa    600
cgtgaacgcg aaatggacac agtcctggag atgaagcct gccgcaagca cattcgccag     660
atgatccaat ccctctgggt tgaactgaac ggcgaactcg ttgcaagctc cgcgctgccg    720
ctttcgatca ttaaggcggc cttcaatctc tcgcgcactg cacaggttat ttaccagcat    780
ggcgatgaca ataaaacgtc ctccgtagaa gatcatgtgc aggctctgtt gtttcgccca    840
gtgagcagca acggacacgc acagatcacg atgcac                              876
```

<210> SEQ ID NO 5
<211> LENGTH: 603
<212> TYPE: PRT
<213> ORGANISM: Perilla setoyensis

<400> SEQUENCE: 5

```
Met Cys Ser Ile Ser Gln Lys Val Val Ile Gly Leu Asn Lys Ala Ala
 1               5                  10                  15
Ala Asn Asn Cys Leu Gln Asn Leu Asp Arg Arg Gly Phe Lys Thr Arg
                20                  25                  30
Arg Val Ser Ser Ser Glu Ala Ala Ser Cys Leu Arg Ala Ser Ser Ser
            35                  40                  45
Leu Gln Leu Asp Val Lys Pro Val Glu Glu Gly Arg Arg Ser Gly Asn
        50                  55                  60
Tyr Gln Pro Ser Ile Trp Asp Phe Asn Tyr Val Gln Ser Leu Asn Thr
 65                  70                  75                  80
Pro Tyr Lys Glu Glu Arg Tyr Leu Thr Arg His Ala Glu Leu Ile Val
                 85                  90                  95
Gln Val Lys Pro Leu Leu Glu Lys Lys Met Glu Ala Thr Gln Gln Leu
            100                 105                 110
Glu Leu Ile Asp Asp Leu Asn Asn Leu Gly Leu Ser Tyr Phe Phe Gln
        115                 120                 125
Asp Arg Ile Lys Gln Ile Leu Ser Phe Ile Tyr Asp Glu Asn Gln Cys
    130                 135                 140
Phe His Ser Asn Ile Asn Asp Gln Ala Glu Lys Arg Asp Leu Tyr Phe
145                 150                 155                 160
Thr Ala Leu Gly Phe Arg Leu Leu Arg Gln His Gly Phe Asn Val Ser
                165                 170                 175
```

```
Gln Glu Val Phe Asp Cys Phe Lys Asn Asp Lys Gly Ser Asp Phe Lys
            180                 185                 190
Ala Ser Leu Ser Gly Asn Thr Lys Gly Leu Leu Gln Leu Tyr Glu Ala
            195                 200                 205
Ser Phe Leu Val Arg Glu Gly Glu Asp Thr Leu Glu Leu Ala Arg Gln
            210                 215                 220
Phe Ala Thr Lys Phe Leu Arg Arg Lys Leu Asp Glu Ile Asp Asp Asn
225                 230                 235                 240
His Leu Leu Ser Arg Ile His His Ser Leu Glu Ile Pro Leu His Trp
                245                 250                 255
Arg Ile Gln Arg Leu Glu Ala Arg Trp Phe Leu Asp Ala Tyr Ala Thr
                260                 265                 270
Arg His Asp Met Asn Pro Ile Ile Leu Glu Leu Ala Lys Leu Asp Phe
                275                 280                 285
Asn Ile Ile Gln Ala Thr His Gln Glu Glu Leu Lys Asp Val Ser Arg
            290                 295                 300
Trp Trp Gln Asn Thr Arg Leu Ala Glu Lys Leu Pro Phe Val Arg Asp
305                 310                 315                 320
Arg Leu Val Glu Ser Tyr Phe Trp Ala Ile Ala Leu Phe Glu Pro His
                325                 330                 335
Gln Tyr Gly Tyr Gln Arg Arg Val Ala Ala Lys Ile Ile Thr Leu Ala
                340                 345                 350
Thr Ser Ile Asp Asp Val Tyr Asp Ile Tyr Gly Thr Leu Asp Glu Leu
            355                 360                 365
Gln Leu Phe Thr Asp Asn Phe Arg Arg Trp Asp Thr Glu Ser Leu Gly
            370                 375                 380
Gly Leu Pro Tyr Ser Met Gln Leu Phe Tyr Met Val Ile His Asn Phe
385                 390                 395                 400
Val Ser Glu Leu Ala Tyr Glu Ile Leu Lys Glu Lys Gly Phe Ile Ala
                405                 410                 415
Ile Pro Tyr Leu Gln Arg Ser Trp Val Asp Leu Ala Glu Ser Phe Leu
                420                 425                 430
Lys Glu Ala Asn Trp Tyr Tyr Ser Gly Tyr Thr Pro Ser Leu Glu Glu
                435                 440                 445
Tyr Ile Asp Asn Gly Ser Ile Ser Ile Gly Ala Val Ala Val Leu Ser
            450                 455                 460
Gln Val Tyr Phe Thr Leu Ala Asn Ser Ile Glu Lys Pro Lys Ile Glu
465                 470                 475                 480
Ser Met Tyr Lys Tyr His His Ile Leu Arg Leu Ser Gly Leu Leu Val
                485                 490                 495
Arg Leu His Asp Asp Leu Gly Thr Ser Leu Phe Glu Lys Lys Arg Gly
                500                 505                 510
Asp Val Pro Lys Ala Val Glu Ile Cys Met Lys Glu Arg Asn Asp Thr
            515                 520                 525
Glu Glu Glu Ala Glu Glu His Val Lys Tyr Leu Ile Arg Glu Ala Trp
            530                 535                 540
Lys Glu Met Asn Thr Ala Thr Ala Ala Gly Cys Pro Phe Met Asp
545                 550                 555                 560
Glu Leu Asn Val Ala Ala Ala Asn Leu Gly Arg Ala Ala Gln Phe Val
                565                 570                 575
Tyr Leu Asp Gly Asp Gly His Gly Val Gln His Ser Lys Ile His Gln
            580                 585                 590
Gln Met Gly Gly Leu Met Phe Lys Pro Tyr Val
```

<210> SEQ ID NO 6
<211> LENGTH: 1809
<212> TYPE: DNA
<213> ORGANISM: Artificial
<220> FEATURE:
<223> OTHER INFORMATION: mutated and/or codon-optimized sequence

<400> SEQUENCE: 6

| | |
|---|---|
| atgtgcagca tctctcaaaa ggtcgttatt ggattgaata aggcagcggc caataactgc | 60 |
| ctccaaaacc ttgatcgccg aggttttaaa cacgccgtg tttcatcctc cgaagcggct | 120 |
| tcttgcctcc gagcctcaag ctcgctgcag cttgatgtca gccggtgga ggaaggccga | 180 |
| cgttccggta actatcagcc atcaatctgg gattttaatt atgtccagtc cctcaacacc | 240 |
| ccctacaaag aggaacgtta ccttacccga cacgcggaac tcatcgttca ggtcaagccg | 300 |
| cttctcgaaa aaagatgga ggctactcag cagttggagc tcatcgatga ccttaacaac | 360 |
| ctcggtctga gctacttttt ccaagaccgc atcaagcaga ttctctcatt catctatgat | 420 |
| gaaaatcagt gtttccactc caatatcaat gatcaagctg aaaagcgaga cctgtacttt | 480 |
| accgcccttg atttcgtct ccttcgccag cacggcttta acgtgtctca ggaggtgttc | 540 |
| gattgcttca aaacgataa aggctccgat tttaaagcgt ccctgtctgg aaacaccaag | 600 |
| ggcctcctcc agctctacga agcctccttc ttggtccgtg agggtgaaga caccctcgaa | 660 |
| ctggcccgtc agttcgcgac caagttcctg cgccgcaagc ttgacgaaat cgacgacaac | 720 |
| catctgctct cacgaattca ccactcactc gaaatcccgt gcactggcg catccagcgt | 780 |
| ctggaggcgc gctggtttct ggacgcgtac gctacacgcc acgatatgaa tcccattatc | 840 |
| ttggagctcg caaaactgga ctttaatatt attcaagcaa cccaccaaga gagctcaag | 900 |
| gacgtgagcc gttggtggca gaatacgcgc ctggccgaaa agctcccgtt tgtgcgcgat | 960 |
| cgacttgtcg agtcatactt tgggccatc gcactctttg agccacatca atatggatac | 1020 |
| cagcgccgtg ttgctgccaa gattatcacc ctcgcgacat ccatcgatga cgtgtacgac | 1080 |
| atctacggca ctctcgacga gctccaactt tttaccgata acttccgtcg ctgggacacg | 1140 |
| gaatccttgg gcggtcttcc ttactcgatg cagttgttct acatggtgat tcacaacttt | 1200 |
| gtctctgagt tggcctatga aatcctgaaa gaaaaaggtt tatcgccat ccccactcc | 1260 |
| caacgctcct gggttgattt ggcagaatcc tttttgaaag aggcaaactg gtactactct | 1320 |
| ggttatacac cctcccctcga agaatacatc gacaacggct ccatctcaat ggcgcagta | 1380 |
| gctgtgttgt cccaagttta tttcactttg gcaaattcta tcgaaaagcc aaagattgaa | 1440 |
| tctatgtaca agtaccacca tattttgcgt ctgtcgggtt tgttggtgcg cctgcacgat | 1500 |
| gacttgggaa cttccttgtt cgagaagaag cgcggcgatg ttcctaaggc ggtcgaaatt | 1560 |
| tgcatgaaag aacgcaacga tacggaggag gaagcagaag aacacgttaa gtacttgatt | 1620 |
| cgcgaagcct ggaaggagat gaacactgct acggcagctg caggatgtcc ttttatggat | 1680 |
| gagctcaacg tggctgctgc caatctgggt cgcgcagccc agttcgtgta cctcgacgga | 1740 |
| gacggtcatg gcgtgcagca ctccaaaatc catcaacaga tgggtggcct tatgtttaaa | 1800 |
| ccgtatgtg | 1809 |

<210> SEQ ID NO 7
<211> LENGTH: 495
<212> TYPE: PRT
<213> ORGANISM: Swertia mussotii (Felwort)

<400> SEQUENCE: 7

Met Asp Phe Asp Phe Leu Thr Ile Ala Ile Gly Phe Leu Phe Thr Ile
1               5                   10                  15

Thr Leu Tyr Gln Ala Leu Asn Phe Phe Ser Arg Lys Ser Lys Asn Leu
            20                  25                  30

Pro Pro Gly Pro Ser Pro Leu Pro Leu Ile Gly Asn Leu His Leu Leu
        35                  40                  45

Gly Asp Gln Pro His Lys Ser Leu Ala Lys Leu Ala Lys Lys His Gly
    50                  55                  60

Pro Ile Met Gly Leu Gln Leu Gly Gln Val Thr Thr Ile Val Val Thr
65                  70                  75                  80

Ser Ser Gly Met Ala Lys Glu Val Leu Gln Lys Gln Asp Leu Ala Phe
                85                  90                  95

Ser Ser Arg Ser Ile Pro Asn Ala Ile His Ala His Asp Gln Tyr Lys
            100                 105                 110

Tyr Ser Val Ile Trp Leu Pro Val Ala Ser Arg Trp Arg Gly Leu Arg
            115                 120                 125

Lys Ala Leu Asn Ser Asn Met Phe Ser Gly Asn Arg Leu Asp Ala Asn
130                 135                 140

Gln His Leu Arg Ser Arg Lys Val Gln Glu Leu Ile Ala Tyr Cys Arg
145                 150                 155                 160

Lys Ser Ser Gln Thr Gly Asp Ala Ile Asp Val Gly Arg Ala Ala Phe
                165                 170                 175

Arg Thr Ser Leu Asn Leu Leu Ser Asn Thr Met Phe Ser Lys Asp Leu
            180                 185                 190

Thr Asp Pro Tyr Ser Asp Ser Ala Lys Glu Phe Lys Asp Leu Val Trp
        195                 200                 205

Asn Val Met Val Glu Ala Gly Lys Pro Asn Leu Val Asp Tyr Phe Pro
    210                 215                 220

Leu Leu Asp Lys Val Asp Pro Gln Gly Ile Arg Lys Arg Met Thr Ile
225                 230                 235                 240

His Phe Gly Lys Ile Leu Glu Leu Phe Gly Gly Leu Ile Asp Glu Arg
                245                 250                 255

Leu Gln Gln Lys Lys Ala Lys Gly Val Asn Asp Asp Val Leu Asp Val
            260                 265                 270

Leu Leu Thr Thr Ser Glu Glu Ser Pro Glu Glu Ile Asp Arg Thr His
        275                 280                 285

Ile Gln Arg Met Cys Leu Asp Leu Phe Val Ala Gly Thr Asp Thr Thr
    290                 295                 300

Ser Ser Thr Leu Glu Trp Ala Met Ser Glu Met Leu Lys Asn Pro Glu
305                 310                 315                 320

Lys Met Lys Ala Ala Gln Ala Glu Leu Ala Gln Val Ile Gly Lys Gly
                325                 330                 335

Lys Ala Val Glu Glu Ala Asp Leu Ala Arg Leu Pro Tyr Leu Arg Cys
            340                 345                 350

Ala Ile Lys Glu Thr Leu Arg Ile His Pro Pro Val Pro Leu Leu Ile
        355                 360                 365

Pro Arg Arg Thr Glu Gln Glu Val Glu Val Cys Gly Tyr Thr Val Pro
    370                 375                 380

Lys Asn Ser Gln Val Leu Val Asn Val Trp Ala Ile Ser Arg Asp Asp
385                 390                 395                 400

Ala Ile Trp Lys Asp Pro Leu Ser Phe Lys Pro Glu Arg Phe Leu Glu 405                 410                 415
Ser Glu Leu Glu Met Arg Gly Lys Asp Phe Glu Leu Ile Pro Phe Gly
            420                 425                 430

Ala Gly Arg Arg Ile Cys Pro Gly Leu Pro Leu Ala Val Arg Met Val
        435                 440                 445

Pro Val Met Leu Gly Ser Leu Leu Asn Ser Phe Asp Trp Lys Leu Glu
    450                 455                 460

Gly Gly Ile Ala Pro Lys Asp Leu Asp Met Glu Glu Lys Phe Gly Ile
465                 470                 475                 480

Thr Leu Gln Lys Ala His Pro Leu Arg Ala Val Ala Thr Pro Leu
                485                 490                 495

<210> SEQ ID NO 8
<211> LENGTH: 1486
<212> TYPE: DNA
<213> ORGANISM: Artificial
<220> FEATURE:
<223> OTHER INFORMATION: mutated and/or codon-optimized sequence

<400> SEQUENCE: 8

```
atggatttcg acttccttac tatcgcgatt ggttttctgt ttactatcac tttgtaccaa      60
gcgcttaact tcttttcccg taaatcaaag aatctcccac caggtccgtc cccattgcca     120
ctcattggta acttgcatct gctcggtgac caaccccata gtcactggc caaactcgca     180
aagaaacatg gtcctatcat gggactgcaa ctgggtcaag tcaccaccat cgttgtaacg     240
tcttctggta tggcgaagga ggttctccag aagcaggacc tggccttttc aagccgttcc     300
atcccaaacg caatccacgc ccatgaccaa tataagtata gcgtgatttg ctcccggtg      360
gcgtcccgat ggcgaggtct gcgtaaggcg ctcaactcca atatgttctc tggaaatcgc     420
ctggatgcaa atcagcactt gcgttcacga aaggtccagg aactgatcgc ctattgccgc     480
aagtcatctc aaactggcga tgctattgat gttggtcgcg cagcattccg cacttcattg     540
aacctgctta gcaacaccat gttcagcaag gaccttacag acccttattc tgactccgca     600
aaagaattta aggatctcgt tttggaacgtg atggtggagg caggcaaacc caatttggtt     660
gactacttcc ctctgttgga taaagttgac ccccaaggca ttcgaaagcg catgaccatt     720
catttcggta aaatcctcga attgtttggc ggacttatcg acgaacgatt gcagcaaaaa     780
aaagcaaagg gagtgaacga cgacgtgctg acgtgctcc ttaccacttc agaggaaagc     840
ccggaggaaa tcgaccgtac ccatatccag cgcatgtgcc tggacttgtt cgtcgcgggc     900
acggacacta cgtcgtcgac gctcgaatgg gccatgtctg aaatgcttaa gaaccccgaa     960
aaaatgaagg cggcccaggc agaactggcc caggttattg aaaaggcaa ggctgttgaa    1020
gaagcagact ggcgcgcct gccataccctg cgctgcgcta ttaaagagac ccttcgaatc    1080
catcctccgg ttccactgct gattcctcga cgcacggaac aagaggtcga ggtgtgcggt    1140
tatacggttc cgaagaactc acaggtttg gtgaacgttt gggccatctc tcgagacgat    1200
gcaatttgga aggatccact ctcctttaag cctgaacgtt ttctggagtc tgaattggag    1260
atgcgtggta aggatttcga gcttatccca ttcggtgcgg gccgacgcat ttgcccgggc    1320
cttcctctgg cggtgcgcat ggtcccagtg atgcttggat ctctttttgaa ctcattcgat    1380
tggaagctgg agggcggcat cgcgcctaag gacttggaca tggaagaaaa gttcggcatc    1440
acgctgcaga agcccaccc tctccgcgct gtcgccactc cactgt                   1486
```

<210> SEQ ID NO 9

<211> LENGTH: 505
<212> TYPE: PRT
<213> ORGANISM: Populus trichocarpa (Western balsam poplar) (Populus balsamifera subsp. trichocarpa)

<400> SEQUENCE: 9

```
Met Asn Phe Phe Ile Ser Val Leu Leu Tyr Phe Leu Leu Thr Phe Ala
1               5                  10                  15

Val Ile Gln Ser Leu Asp Tyr Ile Leu Arg Arg Ser Lys Arg Lys Ser
            20                  25                  30

Gly Lys Leu Pro Pro Gly Pro Ser Arg Leu Pro Ile Val Gly Asn Leu
        35                  40                  45

Leu Asp Leu Gly Asp Lys Pro His Lys Ser Leu Ala Lys Leu Ala Lys
50                  55                  60

Thr His Gly Gln Leu Met Ser Leu Lys Leu Gly Gln Val Thr Thr Ile
65                  70                  75                  80

Val Val Ser Ser Ala Thr Met Ala Lys Glu Val Leu Gln Lys His Asp
                85                  90                  95

Leu Thr Phe Cys Asn Arg Thr Val Val Asp Ala Val Arg Ala Leu Asp
            100                 105                 110

His His Glu Ala Gly Ile Ala Trp Leu Pro Val Ala Thr Arg Trp Arg
        115                 120                 125

Asn Leu Arg Lys Ile Cys Asn Ser His Ile Phe Thr Ser Gln Lys Leu
130                 135                 140

Asp Ala Asn Gln Asp Leu Arg Arg Lys Val Gln Asp Leu Leu Ala
145                 150                 155                 160

Glu Val Gln Glu Arg Cys Leu Val Gly Glu Ala Val Asp Leu Arg Gln
                165                 170                 175

Ala Ala Phe Thr Ala Thr Leu Asn Ala Leu Ser Asn Thr Val Leu Ser
            180                 185                 190

Leu Asp Leu Thr Asp Leu Ser Ser Asp Ile Ala Arg Glu Phe Lys Glu
        195                 200                 205

His Ile Ser Cys Ile Met Asp Glu Ala Gly Lys Pro Asn Leu Val Asp
210                 215                 220

Tyr Phe Pro Leu Leu Arg Arg Ile Asp Pro Gln Gly Ile Arg Arg Arg
225                 230                 235                 240

Thr Ala Ile His Phe Gly Lys Val Phe Asp Leu Phe Asp Arg Leu Ile
                245                 250                 255

Ile Glu Arg Leu Gln Leu Arg Lys Val Lys Gly Tyr Ile Pro Leu Asp
            260                 265                 270

Asp Met Leu Asp Thr Leu Leu Thr Ile Ser Glu Val Asn Asn Glu Glu
        275                 280                 285

Met Asp Ala Thr Arg Ile Lys His Phe Phe Leu Asp Leu Phe Gly Ala
290                 295                 300

Gly Thr Asp Thr Thr Ser Ser Thr Leu Glu Trp Ala Met Ala Glu Leu
305                 310                 315                 320

Leu His Ser Pro Lys Thr Leu Leu Lys Ala Arg Ala Glu Leu Glu Arg
                325                 330                 335

Thr Ile Gly Glu Gly Asn Leu Leu Glu Glu Ser Asp Ile Thr Arg Leu
            340                 345                 350

Pro Tyr Leu Gln Ala Val Ile Lys Glu Thr Leu Arg Leu His Pro Ala
        355                 360                 365

Val Pro Phe Leu Leu Pro His Lys Ala Gly Ala Asp Ala Glu Ile Gly
370                 375                 380
```

```
Gly Phe Thr Val Pro Lys Asn Ala Gln Val Leu Val Asn Val Trp Ala
385                 390                 395                 400

Ile Gly Arg Asp Pro Ser Met Trp Glu Asp Pro Asn Ser Phe Val Pro
            405                 410                 415

Glu Arg Phe Leu Glu Ser Gly Ile Asp His Arg Gly Gln Asn Phe Glu
        420                 425                 430

Phe Ile Pro Phe Gly Ser Gly Arg Arg Ile Cys Pro Gly Leu Pro Leu
    435                 440                 445

Ala Met Arg Met Leu Pro Leu Met Leu Gly Ser Leu Ile Leu Ser Phe
    450                 455                 460

Asp Trp Lys Leu Ala Asp Gly Val Thr Pro Glu Asn Leu Asn Met Asp
465                 470                 475                 480

Asp Lys Phe Gly Leu Thr Leu Leu Lys Ala Gln Pro Leu Arg Ala Ile
                485                 490                 495

Pro Ile Thr Arg Glu Leu Lys His Gly
                500                 505

<210> SEQ ID NO 10
<211> LENGTH: 1515
<212> TYPE: DNA
<213> ORGANISM: Artificial
<220> FEATURE:
<223> OTHER INFORMATION: mutated and/or codon-optimized sequence

<400> SEQUENCE: 10
```

| | | | | | |
|---|---|---|---|---|---|
| atgaactttt | tcatctctgt | gctgttgtat | ttccttctga | cattcgcggt | gattcaatcc | 60 |
| ctggactaca | tccttcgccg | ctccaagcgt | aagtccggca | aactgccgcc | aggcccttca | 120 |
| cgacttccga | ttgttggaaa | cctgctggac | ctgggagaca | gccccacaa | tccctcgca | 180 |
| aagctggcga | aaaccacgg | ccaattgatg | tcacttaagc | tcggacaagt | gaccacgatc | 240 |
| gtggtttcaa | gcgctaccat | ggccaaggag | gtgttgcaga | gcatgatct | gactttctgt | 300 |
| aaccgcactg | ttgttgacgc | tgttcgcgcg | ctggaccacc | atgaggccgg | cattgcgtgg | 360 |
| ctgccagtgg | ctacccgttg | gcgcaacctg | cgtaaaattt | gcaatagcca | tatctttaca | 420 |
| tcccagaaac | tcgacgctaa | tcaagacctg | cgacgcaaaa | aagtccagga | tctgctggca | 480 |
| gaagtgcaag | agcgctgcct | ggtaggtgag | gctgttgact | tgcgtcaagc | agcatttacc | 540 |
| gcgactctta | tgccctgag | caacactgtt | ttgtcgctcg | acctcaccga | tctgtcatca | 600 |
| gatatcgctc | gcgagtttaa | agagcacatc | tcctgcatta | tggatgaagc | gggcaagcca | 660 |
| aacctggttg | attactttcc | tttgcttcgc | gcatcgacc | cgcagggcat | tcgtcgccgc | 720 |
| actgcaattc | acttcggcaa | ggtgttcgat | ctcttcgatc | gcttgattat | cgaacgtttg | 780 |
| cagctccgca | agtcaaggg | ttacattccc | ctggacgaca | tgctggacac | tttgctcacg | 840 |
| atctcagaag | tcaacaacga | agagatggac | gctacacgta | tcaagcactt | ttttttggat | 900 |
| tgttcggcg | caggcaccga | tacgacttca | tcgactcttg | agtgggccat | ggcagagctc | 960 |
| ttgcactcgc | cgaaaaccct | cctcaaagcc | cgcgctgaac | tggaacgcac | catcggcgag | 1020 |
| ggcaatcttt | tggaggaatc | cgacatcacc | cgtctccct | acctgcaggc | tgtcatcaag | 1080 |
| gagactctcc | gactccatcc | agccgtgccc | ttcctccttc | cacacaaggc | aggcgctgat | 1140 |
| gctgaaatcg | gcggttttac | tgtgccaaaa | aacgcgcagg | tcttggtgaa | tgtctgggcg | 1200 |
| attggccgtg | atccctcaat | gtgggaagac | cccaattcct | tcgtccctga | acgcttcttg | 1260 |
| gaatcaggta | tcgatcaccg | aggacaaaac | tttgaattta | tcccctttcgg | cagcggacgt | 1320 |
| cgaatttgcc | caggtcttcc | gctggcgatg | cgtatgctcc | ctctcatgct | cggttctctc | 1380 |

```
atcttgtcct tcgactggaa gttggcagat ggtgtgacgc cagaaaactt gaacatggac    1440
gataagttcg gtttgactct cctgaaagct cagccccttc gtgcgatccc catcacccga    1500
gaattgaaac acggt                                                     1515
```

<210> SEQ ID NO 11
<211> LENGTH: 501
<212> TYPE: PRT
<213> ORGANISM: Phaseolus angularis (Azuki bean) (Vigna angularis)

<400> SEQUENCE: 11

```
Met Glu Thr Asn Ser Thr Leu Phe Phe Thr Phe Thr Val Leu Leu Ile
1               5                   10                  15

Thr Ile Ile Thr Phe Leu Lys Ala Leu Lys Ser Leu Phe Thr Pro Asn
            20                  25                  30

Lys Ser Lys Ser Asn Leu Pro Pro Gly Pro Lys Gly Leu Pro Leu Val
        35                  40                  45

Gly Asn Leu Leu Gln Leu Gly Ala Lys Pro His Gln Thr Leu Ala Thr
    50                  55                  60

Leu Ala Asn Ile His Gly Ser Ile Met Ser Leu Lys Leu Gly Gln Glu
65                  70                  75                  80

Thr Thr Ile Val Met Ser Ser Ala Glu Ala Lys Gly Val Leu Gln
                85                  90                  95

Ile His Asp His Phe Leu Ser Asn Arg Lys Ile Pro Asp Ala Met Arg
            100                 105                 110

Gly Ser Ser His Asp His Phe Ser Leu Pro Phe Met Pro Val Ser Gln
        115                 120                 125

Gln Trp Arg Glu Leu Arg Lys Leu Cys Asn Glu Leu Leu Phe Ser Asn
    130                 135                 140

Lys Asn Leu Asp Ala Thr Gln Gly Leu Arg Ser Lys Lys Val Arg Glu
145                 150                 155                 160

Leu Tyr Ser Asp Ile His Arg Ser Ser Leu Lys Gly Glu Pro Val Asn
                165                 170                 175

Ile Gly Arg Leu Ala Phe Lys Thr Thr Ile Asn Gln Leu Ser Asn Thr
            180                 185                 190

Ile Tyr Ser Glu Asp Phe Leu Gln Ser Ala Glu Lys Ala Gly Glu Met
        195                 200                 205

Lys Glu Leu Val Thr Asn Ile Met Lys Glu Val Gly Arg Pro Asn Leu
    210                 215                 220

Ala Asp Cys Phe Pro Val Leu Lys Met Ile Asp Pro His Gly Ile Arg
225                 230                 235                 240

Arg Arg Thr Gly Ser Tyr Phe Ser Lys Leu Leu Asn Ile Phe Lys Ser
                245                 250                 255

Leu Ile His Lys Arg Leu Glu Leu Arg Lys Asp Ala Ala Gly Tyr Cys
            260                 265                 270

Thr Lys Lys Asp Met Leu Asp Ala Met Leu Asn Asp Ala Gln His Lys
        275                 280                 285

Met Asp Ile Val Lys Ile Gln Arg Leu Ser Leu Asp Leu Phe Val Ala
    290                 295                 300

Gly Thr Asp Thr Val Thr Ser Thr Val Glu Trp Ala Met Ala Glu Leu
305                 310                 315                 320

Leu His Asn Pro His Val Met Ser Lys Ala Lys Glu Glu Leu Glu Arg
                325                 330                 335

Ile Ile Gly Lys Asp Asn Leu Val Glu Glu Ser Asp Ile Ala Lys Leu
```

```
           340                 345                 350
Pro Tyr Leu Gln Ala Ile Val Lys Glu Thr Phe Arg Leu His Pro Ala
            355                 360                 365

Val Pro Leu Leu Leu Pro Arg Lys Ala Glu Val Glu Phe Glu Met His
        370                 375                 380

Gly Tyr Thr Ile Pro Lys Gly Ala Gln Val Leu Ile Asn Val Trp Ala
385                 390                 395                 400

Ile Gly Arg Asp Pro Asn Leu Trp Glu Lys Pro Arg Leu Phe Trp Pro
                405                 410                 415

Glu Arg Phe Leu Glu Ser Glu Ile Asp Phe Lys Gly Arg Ser Phe Glu
            420                 425                 430

Leu Thr Pro Phe Gly Gly Arg Arg Ile Cys Pro Gly Leu Pro Leu
        435                 440                 445

Ala Ile Arg Leu Val Phe Leu Met Leu Gly Leu Phe Ile Asn Ser Phe
        450                 455                 460

Asp Trp Glu Leu Gln Asp Ile Gln Pro Glu Asp Met Asn Met Asp Glu
465                 470                 475                 480

Asn Phe Gly Leu Thr Leu Glu Lys Ala Gln Pro Val Leu Ala Ile Pro
                485                 490                 495

Ile Ile Pro Lys His
            500

<210> SEQ ID NO 12
<211> LENGTH: 1503
<212> TYPE: DNA
<213> ORGANISM: Artificial
<220> FEATURE:
<223> OTHER INFORMATION: mutated and/or codon-optimized sequence

<400> SEQUENCE: 12
atggagacta actctaccct tttctttaca ttcaccgtcc tcctgatcac aatcattacg      60
ttcctgaagg cgttgaaatc tttgtttacc cctaacaagt caaaatctaa cctcccaccc     120
ggtcccaagg ccttcctttt ggttggcaac ctgcttcagt gggcgcgaa gccgcaccag      180 accctcgcaa ccctcgcaaa catccacgga tccatcatgt ccctcaaatt gggtcaagag     240
acaaccatcg tgatgtcttc cgctgaggcc gcaaagggag ttctgcagat tcatgatcat     300
ttcctctcaa accgcaaaat ccccgacgca atgcgcggct cctcccacga ccacttctcc     360
cttcctttca tgcctgtttc ccaacagtgg cgagaattgc gaaagctttg caacgaactc     420
ctgttctcca caagaaacct ggacgctaca caaggcctgc gctccaaaaa ggttcgagaa     480
ctgtacagcg atattcaccg cagctcgctg aagggcgagc ccgtgaacat cggtcgtctg     540
gcttttaaaa cgaccatcaa ccaactttct aacaccatct actcggaaga cttcttgcaa     600
tccgccgaga agcgggcga atgaaggaa ctcgttacca atattatgaa ggaggttggc      660
cgcccgaacc ttgccgactg cttccccgtt ctgaaaatga tcgaccccca cggcatccgc     720
cgtcgaaccg gctcttactt cagcaagctg cttaatatct caaatccct gatccacaag      780 cgtctggaac ttcgtaaaga tgctgcgggc tactgtacta aaaaggatat gcttgacgcg     840
atgctgaacg acgcccaaca caaatggac atcgttaaga tccagcgtct ctctcttgat      900
ttgttcgttg caggaacgga taccgtcacc tccactgtcg agtgggctat ggctgaactg     960
cttcacaacc cccacgttat gtcaaaggct aaagaggaac tcgaacgcat tatcggtaag    1020
gataatctgg tggaggagtc agacatcgcc aagttgcctt acttgcaggc tatcgtgaag    1080
gagaccttcc gtctccaccc agcagtcccc cttttgctgc cacgcaaagc cgaggttgaa    1140
```

```
tttgaaatgc acggttacac aatccccaaa ggcgcccagg tcctgatcaa tgtctgggcc    1200
attggtcgcg acccgaactt gtgggaaaag ccacgcctgt tttggcccga gcgatttctt    1260
gaatccgaga tcgacttcaa gggccgatcg ttcgagctca ccccgttcgg cggcggccgt    1320
cgcatctgcc ctggactccc attggcgatc cgacttgttt ttctgatgct cggcctgttt    1380
attaactctt tcgattggga acttcaggac attcagccgg aagacatgaa tatggacgaa    1440
aacttcggtc tgactcttga aaaggcccag ccagttctcg caattccaat cattccaaaa    1500
cac                                                                  1503
```

<210> SEQ ID NO 13
<211> LENGTH: 443
<212> TYPE: PRT
<213> ORGANISM: Saccharomyces cerevisiae

<400> SEQUENCE: 13

```
Met Ser Leu Pro Phe Leu Thr Ser Ala Pro Gly Lys Val Ile Ile Phe
1               5                   10                  15

Gly Glu His Ser Ala Val Tyr Asn Lys Pro Ala Val Ala Ala Ser Val
            20                  25                  30

Ser Ala Leu Arg Thr Tyr Leu Leu Ile Ser Glu Ser Ser Ala Pro Asp
        35                  40                  45

Thr Ile Glu Leu Asp Phe Pro Asp Ile Ser Phe Asn His Lys Trp Ser
    50                  55                  60

Ile Asn Asp Phe Asn Ala Ile Thr Glu Asp Gln Val Asn Ser Gln Lys
65                  70                  75                  80

Leu Ala Lys Ala Gln Gln Ala Thr Asp Gly Leu Ser Gln Glu Leu Val
                85                  90                  95

Ser Leu Leu Asp Pro Leu Leu Ala Gln Leu Ser Glu Ser Phe His Tyr
            100                 105                 110

His Ala Ala Phe Cys Phe Leu Tyr Met Phe Val Cys Leu Cys Pro His
        115                 120                 125

Ala Lys Asn Ile Lys Phe Ser Leu Lys Ser Thr Leu Pro Ile Gly Ala
    130                 135                 140

Gly Leu Gly Ser Ser Ala Ser Ile Ser Val Ser Leu Ala Leu Ala Met
145                 150                 155                 160

Ala Tyr Leu Gly Gly Leu Ile Gly Ser Asn Asp Leu Glu Lys Leu Ser
                165                 170                 175

Glu Asn Asp Lys His Ile Val Asn Gln Trp Ala Phe Ile Gly Glu Lys
            180                 185                 190

Cys Ile His Gly Thr Pro Ser Gly Ile Asp Asn Ala Val Ala Thr Tyr
        195                 200                 205

Gly Asn Ala Leu Leu Phe Glu Lys Asp Ser His Asn Gly Thr Ile Asn
    210                 215                 220

Thr Asn Asn Phe Lys Phe Leu Asp Asp Phe Pro Ala Ile Pro Met Ile
225                 230                 235                 240

Leu Thr Tyr Thr Arg Ile Pro Arg Ser Thr Lys Asp Leu Val Ala Arg
                245                 250                 255

Val Arg Val Leu Val Thr Glu Lys Phe Pro Glu Val Met Lys Pro Ile
            260                 265                 270

Leu Asp Ala Met Gly Glu Cys Ala Leu Gln Gly Leu Glu Ile Met Thr
        275                 280                 285

Lys Leu Ser Lys Cys Lys Gly Thr Asp Asp Glu Ala Val Glu Thr Asn
    290                 295                 300
```

```
Asn Glu Leu Tyr Glu Gln Leu Leu Glu Leu Ile Arg Ile Asn His Gly
305                 310                 315                 320

Leu Leu Val Ser Ile Gly Val Ser His Pro Gly Leu Glu Leu Ile Lys
            325                 330                 335

Asn Leu Ser Asp Asp Leu Arg Ile Gly Ser Thr Lys Leu Thr Gly Ala
        340                 345                 350

Gly Gly Gly Gly Cys Ser Leu Thr Leu Leu Arg Arg Asp Ile Thr Gln
    355                 360                 365

Glu Gln Ile Asp Ser Phe Lys Lys Lys Leu Gln Asp Asp Phe Ser Tyr
370                 375                 380

Glu Thr Phe Glu Thr Asp Leu Gly Gly Thr Gly Cys Cys Leu Leu Ser
385                 390                 395                 400

Ala Lys Asn Leu Asn Lys Asp Leu Lys Ile Lys Ser Leu Val Phe Gln
            405                 410                 415

Leu Phe Glu Asn Lys Thr Thr Thr Lys Gln Gln Ile Asp Asp Leu Leu
        420                 425                 430

Leu Pro Gly Asn Thr Asn Leu Pro Trp Thr Ser
            435                 440
```

<210> SEQ ID NO 14
<211> LENGTH: 1329
<212> TYPE: DNA
<213> ORGANISM: Artificial
<220> FEATURE:
<223> OTHER INFORMATION: mutated and/or codon-optimized sequence

<400> SEQUENCE: 14

```
atgtccctgc cattcctcac gtccgcacca ggaaaagtca ttatctttgg cgaacattcc      60
gcagtgtaca acaagcctgc cgtggctgcc tccgtgagcg ccctccgcac ctacttgctg     120
attagcgaga gctctgcccc agataccatc gagctggatt tccagacat ctcctttaac      180
cataaatggt ccattaacga ttttaacgcg attaccgaag atcaagtcaa cagccagaag     240
ctcgcaaagg cacaacaggc aacagatggc ctctcccagg agcttgtttc cctcctggat     300
ccactgcttg cacagctctc agaatccttt cactaccatg ccgctttctg tttcctgtac     360
atgttcgtgt gtctctgccc ccacgcgaag aacatcaagt tcagcctgaa gtcgacactc     420
cctatcggtg ctggtctcgg atcgtccgcg agcatctcgg tctcgttggc acttgcaatg     480
gcatacctcg gtggtcttat tggttcaaac gatctggaaa agttgtcgga aaacgataaa     540
catattgtga accagtgggc attcatcggc gaaaaatgta ccacggcac cccagcgga      600
atcgataacg cggttgcaac ctacggaaat gctttgctgt cgagaagga ttcccacaat     660
ggaacgatta acacgaataa ctttaagttc ctcgacgatt tccccgcaat tcccatgatc    720
ctcacctaca cccgtatccc tcgttcgacc aaagacttgg tcgctcgcgt acgcgtgttg    780
gtcacggaaa agtttccaga ggtcatgaaa cctattcttg atgccatggg tgagtgcgcc    840
cttcagggcc tggagattat gactaagctg tccaagtgca agggtacgga cgacgaggca    900
gtcgaaacta acaatgaact ctacgagcag cttctggaat tgatccgcat caaccacggt    960
ctgctcgtgt ccatcggcgt gtctcaccca ggactggaac tgattaaaaa cctctcggat   1020
gacctccgta tcggctctac caagctgacc ggcgccggag cggtggatg ctctctcacc    1080
ttgctccgac gcgatatcac ccaggagcag atcgattctt tcaaaaagaa actccaagat   1140
gacttctctt acgagacttt tgagactgac ctcggtggca ccggctgctg cttgcttttcc  1200
gcgaagaact tgaataaaga tctcaaaatc aaatctctcg tcttccagct cttcgaaaac   1260
```

```
aagaccacca ccaagcaaca gatcgatgac ttgctccttc caggcaacac taaccttcct    1320
tggacaagc                                                            1329
```

<210> SEQ ID NO 15
<211> LENGTH: 352
<212> TYPE: PRT
<213> ORGANISM: Saccharomyces cerevisiae

<400> SEQUENCE: 15

```
Met Ala Ser Glu Lys Glu Ile Arg Arg Glu Arg Phe Leu Asn Val Phe
1               5                   10                  15

Pro Lys Leu Val Glu Glu Leu Asn Ala Ser Leu Leu Ala Tyr Gly Met
            20                  25                  30

Pro Lys Glu Ala Cys Asp Trp Tyr Ala His Ser Leu Asn Tyr Asn Thr
        35                  40                  45

Pro Gly Gly Lys Leu Asn Arg Gly Leu Ser Val Val Asp Thr Tyr Ala
    50                  55                  60

Ile Leu Ser Asn Lys Thr Val Glu Gln Leu Gly Gln Glu Glu Tyr Glu
65                  70                  75                  80

Lys Val Ala Ile Leu Gly Trp Cys Ile Glu Leu Leu Gln Ala Tyr Trp
                85                  90                  95

Leu Val Ala Asp Asp Met Met Asp Lys Ser Ile Thr Arg Arg Gly Gln
            100                 105                 110

Pro Cys Trp Tyr Lys Val Pro Glu Val Gly Glu Ile Ala Ile Trp Asp
        115                 120                 125

Ala Phe Met Leu Glu Ala Ala Ile Tyr Lys Leu Leu Lys Ser His Phe
    130                 135                 140

Arg Asn Glu Lys Tyr Tyr Ile Asp Ile Thr Glu Leu Phe His Glu Val
145                 150                 155                 160

Thr Phe Gln Thr Glu Leu Gly Gln Leu Met Asp Leu Ile Thr Ala Pro
                165                 170                 175

Glu Asp Lys Val Asp Leu Ser Lys Phe Ser Leu Lys Lys His Ser Phe
            180                 185                 190

Ile Val Thr Phe Lys Thr Ala Tyr Tyr Ser Phe Tyr Leu Pro Val Ala
        195                 200                 205

Leu Ala Met Tyr Val Ala Gly Ile Thr Asp Glu Lys Asp Leu Lys Gln
    210                 215                 220

Ala Arg Asp Val Leu Ile Pro Leu Gly Glu Tyr Phe Gln Ile Gln Asp
225                 230                 235                 240

Asp Tyr Leu Asp Cys Phe Gly Thr Pro Glu Gln Ile Gly Lys Ile Gly
                245                 250                 255

Thr Asp Ile Gln Asp Asn Lys Cys Ser Trp Val Ile Asn Lys Ala Leu
            260                 265                 270

Glu Leu Ala Ser Ala Glu Gln Arg Lys Thr Leu Asp Glu Asn Tyr Gly
        275                 280                 285

Lys Lys Asp Ser Val Ala Glu Ala Lys Cys Lys Lys Ile Phe Asn Asp
    290                 295                 300

Leu Lys Ile Glu Gln Leu Tyr His Glu Tyr Glu Glu Ser Ile Ala Lys
305                 310                 315                 320

Asp Leu Lys Ala Lys Ile Ser Gln Val Asp Glu Ser Arg Gly Phe Lys
                325                 330                 335

Ala Asp Val Leu Thr Ala Phe Leu Asn Lys Val Tyr Lys Arg Ser Lys
            340                 345                 350
```

<210> SEQ ID NO 16
<211> LENGTH: 1056
<212> TYPE: DNA
<213> ORGANISM: Artificial
<220> FEATURE:
<223> OTHER INFORMATION: mutated and/or codon-optimized sequence

<400> SEQUENCE: 16

| | | | | | |
|---|---|---|---|---|---|
| atggcatccg | agaaggaaat | ccgtcgtgaa | cgattcctga | cgtattccc | aaagctcgtc | 60 |
| gaagagctta | atgcttcctt | gcttgcgtac | ggaatgccga | aggaagcgtg | cgactggtat | 120 |
| gcgcattctc | tcaactataa | acacctggc | ggtaagctga | atcgcggtct | cagcgtggtg | 180 |
| gacacgtacg | caatcctcag | caataagacc | gtggaacagc | tgggacagga | ggagtacgag | 240 |
| aaagttgcta | tccttggatg | gtgtatcgaa | ctgctgcaag | cctattggtt | ggtagctgat | 300 |
| gacatgatgg | ataagagcat | cactcgacgt | ggtcaaccat | gctggtacaa | ggtgccggag | 360 |
| gttggcgaaa | tcgcgatctg | ggatgcgttc | atgttggagg | ccgcaattta | taagcttctc | 420 |
| aagtcccact | ttcgtaacga | aaagtactat | attgacatca | cagaactctt | tcatgaagtg | 480 |
| accttccaaa | ccgagctcgg | ccaactcatg | gatttgatca | ccgcccccga | agataaggtg | 540 |
| gaccttcga | agttctccct | caagaagcac | tcgttcattg | ttaccttcaa | gacagcatac | 600 |
| tactcatttt | acctgccagt | cgccctcgca | atgtacgtgg | cgggcatcac | tgatgaaaag | 660 |
| gatctgaagc | aggcccgcga | cgtccttatc | cctcttggag | agtacttcca | gatccaggac | 720 |
| gattacttgg | attgttttgg | caccccagag | cagattggta | aaatcggtac | tgatatccaa | 780 |
| gacaacaaat | gttcctgggt | aattaacaag | gctctcgagt | tggcttccgc | ggaacaacgc | 840 |
| aagactcttg | acgaaaatta | cggtaagaaa | gattcagtcg | ctgaagccaa | gtgcaagaaa | 900 |
| atctttaacg | atcttaaaat | cgaacagttg | taccacgagt | atgaagagtc | tatcgctaaa | 960 |
| gacctgaaag | ctaaaatttc | ccaggtcgat | gagtcacgcg | gcttcaaagc | ggatgtgctc | 1020 |
| accgccttcc | ttaacaaggt | gtataagcgc | tccaaa | | | 1056 |

<210> SEQ ID NO 17
<211> LENGTH: 491
<212> TYPE: PRT
<213> ORGANISM: Saccharomyces cerevisiae

<400> SEQUENCE: 17

Met Lys Leu Ser Thr Lys Leu Cys Trp Cys Gly Ile Lys Gly Arg Leu
1               5                   10                  15

Arg Pro Gln Lys Gln Gln Leu His Asn Thr Asn Leu Gln Met Thr
            20                  25                  30

Glu Leu Lys Lys Gln Lys Thr Ala Glu Gln Lys Thr Arg Pro Gln Asn
        35                  40                  45

Val Gly Ile Lys Gly Ile Gln Ile Tyr Ile Pro Thr Gln Cys Val Asn
    50                  55                  60

Gln Ser Glu Leu Glu Lys Phe Asp Gly Val Ser Gln Gly Lys Tyr Thr
65                  70                  75                  80

Ile Gly Leu Gly Gln Thr Asn Met Ser Phe Val Asn Asp Arg Glu Asp
                85                  90                  95

Ile Tyr Ser Met Ser Leu Thr Val Leu Ser Lys Leu Ile Lys Ser Tyr
            100                 105                 110

Asn Ile Asp Thr Asn Lys Ile Gly Arg Leu Glu Val Gly Thr Glu Thr
        115                 120                 125

Leu Ile Asp Lys Ser Lys Ser Val Lys Ser Val Leu Met Gln Leu Phe

```
            130                 135                 140
Gly Glu Asn Thr Asp Val Glu Gly Ile Asp Thr Leu Asn Ala Cys Tyr
145                 150                 155                 160

Gly Gly Thr Asn Ala Leu Phe Asn Ser Leu Asn Trp Ile Glu Ser Asn
                165                 170                 175

Ala Trp Asp Gly Arg Asp Ala Ile Val Val Cys Gly Asp Ile Ala Ile
            180                 185                 190

Tyr Asp Lys Gly Ala Ala Arg Pro Thr Gly Gly Ala Gly Thr Val Ala
        195                 200                 205

Met Trp Ile Gly Pro Asp Ala Pro Ile Val Phe Asp Ser Val Arg Ala
    210                 215                 220

Ser Tyr Met Glu His Ala Tyr Asp Phe Tyr Lys Pro Asp Phe Thr Ser
225                 230                 235                 240

Glu Tyr Pro Tyr Val Asp Gly His Phe Ser Leu Thr Cys Tyr Val Lys
                245                 250                 255

Ala Leu Asp Gln Val Tyr Lys Ser Tyr Ser Lys Lys Ala Ile Ser Lys
            260                 265                 270

Gly Leu Val Ser Asp Pro Ala Gly Ser Asp Ala Leu Asn Val Leu Lys
        275                 280                 285

Tyr Phe Asp Tyr Asn Val Phe His Val Pro Thr Cys Lys Leu Val Thr
    290                 295                 300

Lys Ser Tyr Gly Arg Leu Leu Tyr Asn Asp Phe Arg Ala Asn Pro Gln
305                 310                 315                 320

Leu Phe Pro Glu Val Asp Ala Glu Leu Ala Thr Arg Asp Tyr Asp Glu
                325                 330                 335

Ser Leu Thr Asp Lys Asn Ile Glu Lys Thr Phe Val Asn Val Ala Lys
            340                 345                 350

Pro Phe His Lys Glu Arg Val Ala Gln Ser Leu Ile Val Pro Thr Asn
        355                 360                 365

Thr Gly Asn Met Tyr Thr Ala Ser Val Tyr Ala Ala Phe Ala Ser Leu
    370                 375                 380

Leu Asn Tyr Val Gly Ser Asp Asp Leu Gln Gly Lys Arg Val Gly Leu
385                 390                 395                 400

Phe Ser Tyr Gly Ser Gly Leu Ala Ala Ser Leu Tyr Ser Cys Lys Ile
                405                 410                 415

Val Gly Asp Val Gln His Ile Ile Lys Glu Leu Asp Ile Thr Asn Lys
            420                 425                 430

Leu Ala Lys Arg Ile Thr Glu Thr Pro Lys Asp Tyr Glu Ala Ala Ile
        435                 440                 445

Glu Leu Arg Glu Asn Ala His Leu Lys Lys Asn Phe Lys Pro Gln Gly
    450                 455                 460

Ser Ile Glu His Leu Gln Ser Gly Val Tyr Tyr Leu Thr Asn Ile Asp
465                 470                 475                 480

Asp Lys Phe Arg Arg Ser Tyr Asp Val Lys Lys
                485                 490

<210> SEQ ID NO 18
<211> LENGTH: 1473
<212> TYPE: DNA
<213> ORGANISM: Artificial
<220> FEATURE:
<223> OTHER INFORMATION: mutated and/or codon-optimized sequence

<400> SEQUENCE: 18
atgaaattgt ctaccaagct ctgttggtgt ggcatcaaag gccgtcttcg cccacagaaa      60
```

```
cagcaacagc tgcacaatac caacctccag atgaccgagc ttaaaaagca aaagacggca      120
gagcagaaga ctcgccctca gaatgtcggc attaagggca ttcaaatcta catcccaacc      180
cagtgcgtaa atcagagcga gcttgaaaag ttcgatggag tatcccaggg aaagtataca      240
attggactgg ccagaccaa catgtcgttc gtgaacgacc gcgaagacat ttattcgatg       300
tcgcttactg tgttgagcaa attgatcaaa tcctacaaca ttgatactaa taaaattggt      360
cgcctcgagg tcggcaccga aaccctgatc gataagtcga agagcgtgaa aagcgtgctg      420
atgcaacttt tcggtgagaa caccgatgtg gaaggaatcg ataccettaa cgcatgttac      480 ggtggaacca acgccttgtt taattcgctt aactggatcg aatcgaacgc atgggatggc      540
cgcgatgcaa tcgtggtttg cggagatatc gccatttacg acaagggcgc cgcgcgcccc      600
acgggcggcg cgggcacagt ggcaatgtgg atcggtcctg atgcaccaat tgtgttcgat      660
tcggtccgag caagctatat ggagcatgcc tatgatttct acaaaccaga ttttaccagc      720
gaatacccct acgtcgatgg tcacttctcc ttgacatgct acgtcaaggc gcttgaccag      780
gtgtacaaga gctactccaa aaaggcgatc tccaaaggcc tggtgtccga tcctgcaggt      840
tcagatgctc ttaatgttct taagtatttc gattacaacg ttttccacgt gcccacgtgc      900
aaactcgtga cgaagtcata tggtcgcctc ttgtataacg attttcgagc taatccacag      960 cttttttccgg aagtggacgc agagctggcc acccgcgact acgacgagtc tctcacggat     1020
aagaatatcg aaaaaacttt cgtgaatgtg gctaaaccat tccataagga acgcgtcgca      1080
caatctctca ttgttcccac gaacaccgga aacatgtaca cggcctcagt gtatgctgca      1140
ttcgcgtcac tgcttaacta tgttggatct gatgacctgc aaggtaaacg cgttggactc      1200
ttctcttacg gttcgggttt ggcagcttcg ctgtactcct gcaagattgt cggagacgtc      1260
cagcatatca ttaaagaact ggacattaca aacaagctcg cgaaacgcat cactgaaacg      1320
cccaaggatt acgaagcggc cattgaattg cgcgagaacg cacatttgaa gaaaaacttt     1380
aaaccgcaag atccatcga acacctgcaa tcgggtgtct attatctcac caacattgac      1440
gataagtttc gacgttccta tgatgttaaa aag                                   1473
```

<210> SEQ ID NO 19
<211> LENGTH: 398
<212> TYPE: PRT
<213> ORGANISM: Saccharomyces cerevisiae

<400> SEQUENCE: 19

```
Met Ser Gln Asn Val Tyr Ile Val Ser Thr Ala Arg Thr Pro Ile Gly
1               5                   10                  15

Ser Phe Gln Gly Ser Leu Ser Ser Lys Thr Ala Val Glu Leu Gly Ala
            20                  25                  30

Val Ala Leu Lys Gly Ala Leu Ala Lys Val Pro Glu Leu Asp Ala Ser
        35                  40                  45

Lys Asp Phe Asp Glu Ile Ile Phe Gly Asn Val Leu Ser Ala Asn Leu
    50                  55                  60

Gly Gln Ala Pro Ala Arg Gln Val Ala Leu Ala Gly Leu Ser Asn
65                  70                  75                  80

His Ile Val Ala Ser Thr Val Asn Lys Val Cys Ala Ser Ala Met Lys
                85                  90                  95

Ala Ile Ile Leu Gly Ala Gln Ser Ile Lys Cys Gly Asn Ala Asp Val
            100                 105                 110

Val Val Ala Gly Gly Cys Glu Ser Met Thr Asn Ala Pro Tyr Tyr Met
```

|   |   | 115 |   |   | 120 |   |   | 125 |   |   |   |
|---|---|---|---|---|---|---|---|---|---|---|---|

Pro Ala Ala Arg Ala Gly Ala Lys Phe Gly Gln Thr Val Leu Val Asp
130                 135                 140

Gly Val Glu Arg Asp Gly Leu Asn Asp Ala Tyr Asp Gly Leu Ala Met
145                 150                 155                 160

Gly Val His Ala Glu Lys Cys Ala Arg Asp Trp Ile Thr Arg Glu
                165                 170                 175

Gln Gln Asp Asn Phe Ala Ile Glu Ser Tyr Gln Lys Ser Gln Lys Ser
            180                 185                 190

Gln Lys Glu Gly Lys Phe Asp Asn Glu Ile Val Pro Val Thr Ile Lys
        195                 200                 205

Gly Phe Arg Gly Lys Pro Asp Thr Gln Val Thr Lys Asp Glu Glu Pro
    210                 215                 220

Ala Arg Leu His Val Glu Lys Leu Arg Ser Ala Arg Thr Val Phe Gln
225                 230                 235                 240

Lys Glu Asn Gly Thr Val Thr Ala Ala Asn Ala Ser Pro Ile Asn Asp
                245                 250                 255

Gly Ala Ala Val Ile Leu Val Ser Glu Lys Val Leu Lys Glu Lys
            260                 265                 270

Asn Leu Lys Pro Leu Ala Ile Ile Lys Gly Trp Gly Glu Ala Ala His
        275                 280                 285

Gln Pro Ala Asp Phe Thr Trp Ala Pro Ser Leu Ala Val Pro Lys Ala
    290                 295                 300

Leu Lys His Ala Gly Ile Glu Asp Ile Asn Ser Val Asp Tyr Phe Glu
305                 310                 315                 320

Phe Asn Glu Ala Phe Ser Val Val Gly Leu Val Asn Thr Lys Ile Leu
                325                 330                 335

Lys Leu Asp Pro Ser Lys Val Asn Val Tyr Gly Gly Ala Val Ala Leu
            340                 345                 350

Gly His Pro Leu Gly Cys Ser Gly Ala Arg Val Val Thr Leu Leu
        355                 360                 365

Ser Ile Leu Gln Gln Glu Gly Gly Lys Ile Gly Val Ala Ala Ile Cys
    370                 375                 380

Asn Gly Gly Gly Gly Ala Ser Ser Ile Val Ile Glu Lys Ile
385                 390                 395

<210> SEQ ID NO 20
<211> LENGTH: 1194
<212> TYPE: DNA
<213> ORGANISM: Artificial
<220> FEATURE:
<223> OTHER INFORMATION: mutated and/or codon-optimized sequence

<400> SEQUENCE: 20
atgtcacaga atgtctacat cgtctctacc gcccgcaccc cgattggttc cttccagggt    60
tctcttagct cgaaaacagc ggttgaactc ggcgccgttg cactgaaagg agccttggct   120
aaagtaccag aattggacgc gtccaaggac ttcgatgaaa ttattttcgg taacgtactg   180
tcagctaatc tcggccaagc tccagctcgc caggtcgcgc tcgctgcggg cctctccaat   240
cacattgtgg ccagcactgt gaataaggtc tgcgcatcgg cgatgaaggc gattatcctg   300
ggcgcccaga gcattaaatg cggtaatgca gatgttgtgg ttgccggtgg ctgtgagtcg   360
atgaccaacg ctccgtacta catgcccgct gcacgcgctg cgctaaatt cggtcaaacc   420 gtcctggtcg atggtgtcga gcgcgatggc ctcaacgatg cgtacgacgg cctcgcgatg   480

-continued

```
ggagtacacg ctgagaagtg tgcccgcgac tgggatatca cccgagagca gcaggacaat      540
tttgccatcg agagctatca gaagtcacaa aagtcacaga aggagggtaa attcgataac      600
gaaatcgttc cagtgacgat caaaggcttc cgcggtaagc cagatactca agtaaccaaa      660
gatgaggaac ctgcccgctt gcacgtagag aagctccgct cggcccgcac tgtcttccag      720
aaagaaaatg gaaccgtgac ggcagctaac gcaagcccta ttaacgacgg tgcggcagcg      780
gtcattctcg tgtcagaaaa ggtgctgaaa gaaaagaacc tcaaacctct ggccatcatc      840
aagggctggg gtgaggccgc tcaccaacct gctgacttca cctgggcacc atccctggct      900
gtaccaaaag cactcaagca cgctggtatt gaagatatca actccgtcga ctacttcgaa      960
tttaatgagg cattctcggt tgtcggcctt gttaacacta agattcttaa gctcgatcca     1020
tccaaggtca atgtatatgg cggtgcggtt gctttgggcc atcctctcgg ttgctcagga     1080
gcccgcgtgg ttgttactct cctcagcatt cttcagcagg agggtggaaa gatcggcgtc     1140
gctgctattt gcaacggcgg tggtggtgcc tcctcaattg ttattgaaaa gatt           1194
```

<210> SEQ ID NO 21
<211> LENGTH: 1045
<212> TYPE: PRT
<213> ORGANISM: Saccharomyces cerevisiae

<400> SEQUENCE: 21

```
Met Ser Leu Pro Leu Lys Thr Ile Val His Leu Val Lys Pro Phe Ala
1               5                   10                  15

Cys Thr Ala Arg Phe Ser Ala Arg Tyr Pro Ile His Val Ile Val Val
                20                  25                  30

Ala Val Leu Leu Ser Ala Ala Tyr Leu Ser Val Thr Gln Ser Tyr
            35                  40                  45

Leu Asn Glu Trp Lys Leu Asp Ser Asn Gln Tyr Ser Thr Tyr Leu Ser
        50                  55                  60

Ile Lys Pro Asp Glu Leu Phe Glu Lys Cys Thr His Tyr Tyr Arg Ser
65                  70                  75                  80

Pro Val Ser Asp Thr Trp Lys Leu Leu Ser Ser Lys Glu Ala Ala Asp
                85                  90                  95

Ile Tyr Thr Pro Phe His Tyr Tyr Leu Ser Thr Ile Ser Phe Gln Ser
            100                 105                 110

Lys Asp Asn Ser Thr Thr Leu Pro Ser Leu Asp Asp Val Ile Tyr Ser
        115                 120                 125

Val Asp His Thr Arg Tyr Leu Leu Ser Glu Glu Pro Lys Ile Pro Thr
    130                 135                 140

Glu Leu Val Ser Glu Asn Gly Thr Lys Trp Arg Leu Arg Asn Asn Ser
145                 150                 155                 160

Asn Phe Ile Leu Asp Leu His Asn Ile Tyr Arg Asn Met Val Lys Gln
                165                 170                 175

Phe Ser Asn Lys Thr Ser Glu Phe Asp Gln Phe Asp Leu Phe Ile Ile
            180                 185                 190

Leu Ala Ala Tyr Leu Thr Leu Phe Tyr Thr Leu Cys Cys Leu Phe Asn
        195                 200                 205

Asp Met Arg Lys Ile Gly Ser Lys Phe Trp Leu Ser Phe Ser Ala Leu
    210                 215                 220

Ser Asn Ser Ala Cys Ala Leu Tyr Leu Ser Leu Tyr Thr Thr His Ser
225                 230                 235                 240

Leu Leu Lys Lys Pro Ala Ser Leu Leu Ser Leu Val Ile Gly Leu Pro
                245                 250                 255
```

```
Phe Ile Val Val Ile Ile Gly Phe Lys His Lys Val Arg Leu Ala Ala
            260                 265                 270

Phe Ser Leu Gln Lys Phe His Arg Ile Ser Ile Asp Lys Lys Ile Thr
        275                 280                 285

Val Ser Asn Ile Ile Tyr Glu Ala Met Phe Gln Glu Gly Ala Tyr Leu
290                 295                 300

Ile Arg Asp Tyr Leu Phe Tyr Ile Ser Ser Phe Ile Gly Cys Ala Ile
305                 310                 315                 320

Tyr Ala Arg His Leu Pro Gly Leu Val Asn Phe Cys Ile Leu Ser Thr
                325                 330                 335

Phe Met Leu Val Phe Asp Leu Leu Ser Ala Thr Phe Tyr Ser Ala
            340                 345                 350

Ile Leu Ser Met Lys Leu Glu Ile Asn Ile Ile His Arg Ser Thr Val
        355                 360                 365

Ile Arg Gln Thr Leu Glu Glu Asp Gly Val Val Pro Thr Thr Ala Asp
370                 375                 380

Ile Ile Tyr Lys Asp Glu Thr Ala Ser Glu Pro His Phe Leu Arg Ser
385                 390                 395                 400

Asn Val Ala Ile Ile Leu Gly Lys Ala Ser Val Ile Gly Leu Leu Leu
                405                 410                 415

Leu Ile Asn Leu Tyr Val Phe Thr Asp Lys Leu Asn Ala Thr Ile Leu
        420                 425                 430

Asn Thr Val Tyr Phe Asp Ser Thr Ile Tyr Ser Leu Pro Asn Phe Ile
        435                 440                 445

Asn Tyr Lys Asp Ile Gly Asn Leu Ser Asn Gln Val Ile Ile Ser Val
450                 455                 460

Leu Pro Lys Gln Tyr Tyr Thr Pro Leu Lys Lys Tyr His Gln Ile Glu
465                 470                 475                 480

Asp Ser Val Leu Leu Ile Ile Asp Ser Val Ser Asn Ala Ile Arg Asp
                485                 490                 495

Gln Phe Ile Ser Lys Leu Leu Phe Phe Ala Phe Ala Val Ser Ile Ser
            500                 505                 510

Ile Asn Val Tyr Leu Leu Asn Ala Ala Lys Ile His Thr Gly Tyr Met
        515                 520                 525

Asn Phe Gln Pro Gln Ser Asn Lys Ile Asp Asp Leu Val Val Gln Gln
530                 535                 540

Lys Ser Ala Thr Ile Glu Phe Ser Glu Thr Arg Ser Met Pro Ala Ser
545                 550                 555                 560

Ser Gly Leu Glu Thr Pro Val Thr Ala Lys Asp Ile Ile Ile Ser Glu
                565                 570                 575

Glu Ile Gln Asn Asn Glu Cys Val Tyr Ala Leu Ser Ser Gln Asp Glu
            580                 585                 590

Pro Ile Arg Pro Leu Ser Asn Leu Val Glu Leu Met Glu Lys Glu Gln
        595                 600                 605

Leu Lys Asn Met Asn Asn Thr Glu Val Ser Asn Leu Val Val Asn Gly
610                 615                 620

Lys Leu Pro Leu Tyr Ser Leu Glu Lys Lys Leu Glu Asp Thr Thr Arg
625                 630                 635                 640

Ala Val Leu Val Arg Arg Lys Ala Leu Ser Thr Leu Ala Glu Ser Pro
                645                 650                 655

Ile Leu Val Ser Glu Lys Leu Pro Phe Arg Asn Tyr Asp Tyr Asp Arg
            660                 665                 670
```

Val Phe Gly Ala Cys Cys Glu Asn Val Ile Gly Tyr Met Pro Ile Pro
                675                 680                 685

Val Gly Val Ile Gly Pro Leu Ile Ile Asp Gly Thr Ser Tyr His Ile
690                 695                 700

Pro Met Ala Thr Thr Glu Gly Cys Leu Val Ala Ser Ala Met Arg Gly
705                 710                 715                 720

Cys Lys Ala Ile Asn Ala Gly Gly Ala Thr Val Leu Thr Lys
                725                 730                 735

Asp Gly Met Thr Arg Gly Pro Val Val Arg Phe Pro Thr Leu Ile Arg
                740                 745                 750

Ser Gly Ala Cys Lys Ile Trp Leu Asp Ser Glu Glu Gly Gln Asn Ser
                755                 760                 765

Ile Lys Lys Ala Phe Asn Ser Thr Ser Arg Phe Ala Arg Leu Gln His
                770                 775                 780

Ile Gln Thr Cys Leu Ala Gly Asp Leu Leu Phe Met Arg Phe Arg Thr
785                 790                 795                 800

Thr Thr Gly Asp Ala Met Gly Met Asn Met Ile Ser Lys Gly Val Glu
                805                 810                 815

Tyr Ser Leu Lys Gln Met Val Glu Glu Tyr Gly Trp Glu Asp Met Glu
                820                 825                 830

Val Val Ser Val Ser Gly Asn Tyr Cys Thr Asp Lys Lys Pro Ala Ala
                835                 840                 845

Ile Asn Trp Ile Glu Gly Arg Gly Lys Ser Val Val Ala Glu Ala Thr
                850                 855                 860

Ile Pro Gly Asp Val Val Lys Ser Val Leu Lys Ser Asp Val Ser Ala
865                 870                 875                 880

Leu Val Glu Leu Asn Ile Ser Lys Asn Leu Val Gly Ser Ala Met Ala
                885                 890                 895

Gly Ser Val Gly Gly Phe Asn Ala His Ala Ala Asn Leu Val Thr Ala
                900                 905                 910

Leu Phe Leu Ala Leu Gly Gln Asp Pro Ala Gln Asn Val Glu Ser Ser
                915                 920                 925

Asn Cys Ile Thr Leu Met Lys Glu Val Asp Gly Asp Leu Arg Ile Ser
                930                 935                 940

Val Ser Met Pro Ser Ile Glu Val Gly Thr Ile Gly Gly Gly Thr Val
945                 950                 955                 960

Leu Glu Pro Gln Gly Ala Met Leu Asp Leu Leu Gly Val Arg Gly Pro
                965                 970                 975

His Pro Thr Glu Pro Gly Ala Asn Ala Arg Gln Leu Ala Arg Ile Ile
                980                 985                 990

Ala Cys Ala Val Leu Ala Gly Glu Leu Ser Leu Cys Ser Ala Leu Ala
                995                 1000                1005

Ala Gly His Leu Val Gln Ser His Met Thr His Asn Arg Lys Thr
                1010                1015                1020

Asn Lys Ala Asn Glu Leu Pro Gln Pro Ser Asn Lys Gly Pro Pro
                1025                1030                1035

Cys Lys Thr Ser Ala Leu Leu
                1040                1045

<210> SEQ ID NO 22
<211> LENGTH: 3135
<212> TYPE: DNA
<213> ORGANISM: Artificial
<220> FEATURE:
<223> OTHER INFORMATION: mutated and/or codon-optimized sequence

<400> SEQUENCE: 22

```
atgtccttgc ctcttaagac catcgtgcac ctggtaaagc ctttcgcctg cactgcccgc      60
ttctccgcgc gctacccccat ccacgttatc gtggtggcgg tgctgctctc ggcggcagct    120
tacttgagcg taacccaatc ctacttgaat gaatggaagc tcgactcgaa ccagtactcc    180
acctacctta gcatcaagcc tgatgaattg ttcgaaaaat gtacccacta ctaccgctct    240
ccagtgtctg atacttggaa actccttagc tctaaggaag ctgcagatat ttacaccccc    300
ttccattatt acctgtccac catttccttc cagtccaagg acaactcgac caccctgccc    360
agcctggatg acgttatcta ctccgtagac catacccgct acttgctcag cgaggaaccg    420
aaaatcccga cggaactcgt atccgaaaac ggaaccaagt ggcgtctgcg taataactct    480
aactttatcc ttgatctcca caacatttat cgcaatatgg ttaagcagtt ctcaaacaaa    540
acctcggaat tgaccaatt cgacttgttc atcattctcg cagcatattt gactttgttt    600
tacaccctct gctgtctctt taatgacatg cgcaaaatcg ctccaagtt ctggcttttcc    660
ttctcagctc tttccaacag cgcctgcgca ctttatttga gcttgtacac tacccactcc    720
ctccttaaga aaccagcttc cctcctctcc ctcgtcatcg gcttgccatt catcgtggtt    780
atcattggtt tcaaacataa ggtgcgcctc gctgcgttct ccctgcagaa gtttcaccga    840
attagcatcg ataaaagat cacggtctct aacattatct acgaagccat gttccaagaa    900
ggcgcgtacc ttatccgaga ttacctgttc tacatttcca gcttcatcgg ttgtgctatc    960
tacgcacgcc accttccagg tctggtgaat ttctgcattc tctccaccctt tatgcttgtg   1020
tttgatctcc ttttgagcgc cactttctat agcgcgatcc tctcaatgaa actggaaatc   1080
aacatcattc accgcagcac cgtcattcgc cagacccttg aagaagatgg cgtggtgccg   1140
accaccgccg atattattta taagatgaa accgcatccg aaccacattt cctgcgttcc   1200
aacgtggcga ttatccttgg taaggcgtcg gtcattggac tgctgctgct gattaatttg   1260
tacgttttca cagataagct caacgcgacg attctgaata ctgtttactt cgattctacc   1320
atctattccc tcccgaactt catcaactat aaggatatcg gaaaccttttc taatcaagtc   1380
attattagcg ttctgccaaa gcagtactac acccctttga aaaagtatca tcagattgag   1440
gactctgtgc tccttatcat cgactccgtg agcaatgcta ttcgcgatca atttatctcc   1500
aagctcttgt ttttcgcgtt cgctgtttca atttccatca acgtgtacct gttgaacgca   1560
gctaagattc acacgggcta catgaatttc cagccccaat ccaacaagat tgatgaccctt   1620
gtcgtgcaac agaagtctgc aaccattgaa ttctccgaga cccgatccat gcctgcatcc   1680
tccggcctcg agaccccagt taccgcgaag gacatcatta tttcagaaga aatccagaat   1740
aatgaatgcg tatacgcgct gtcatctcag gatgaaccca ttcgcccgtt gtcgaacctt   1800
gttgaactga tggagaaaga gcaactgaaa aatatgaaca cacagaagtt ttctaacttg   1860
gtggtgaacg gtaaattgcc gttgtactcc ctggaaaaga actcgaaga taccaccccga   1920
gccgttcttg ttcgacgcaa ggcgctttcc accctggccg aatctccaat ccttgtttcc   1980
gaaaaactcc ctttcgcaa ctacgattac gatcgtgtgt tcggcgcgtg ttgcgagaac   2040
gtaattggct acatgcctat cccagtagga gtgatcggcc ctctcatcat cgatggcacc   2100
agctaccata ttccaatggc aaccacagaa ggttgcttgg tagcaagcgc gatgcgagga   2160
tgcaaagcaa tcaacgctgg aggcggtgct accaccgttc tgaccaagga tggaatgact   2220
cgcggccccg tagtccgctt ccctactctc atccgctctg gtgcgtgcaa gatttggctc   2280
```

```
gattccgagg aaggccagaa ctctatcaaa aaagcgttca acagcacctc ccgcttcgcc    2340
cgtttgcaac acattcagac ttgcctggca ggcgacctcc tcttcatgcg tttccgcacc    2400
actactggcg acgcaatggg tatgaacatg atctccaaag gagttgagta ctcgctcaaa    2460
cagatggtgg aagagtatgg ctgggaagac atggaagttg tgtccgtttc cggtaactac    2520
tgcacggaca agaaaccagc tgcgatcaat tggattgagg acgcggcaa atctgtcgtc     2580 gcggaggcaa ccatcccagg tgacgtcgtc aaatccgttc tcaaatctga cgtctccgca    2640
ctggttgaac tgaacatctc taagaaacctt gtgggttctg ctatggctgg cagcgtcggt    2700
ggctttaacg cgcatgcggc gaaccttgtt accgcgctct cctggcgct cggacaggat     2760 cccgcgcaga atgtggagtc atcaaattgc attacactga tgaaggaggt ggacggcgat    2820
ctgcgtatct ctgtttccat gccgtccatt gaggtgggta ccattggtgg cggcacagtc    2880
ttggagcctc agggtgccat gctggatctg ttgggcgtac gtggccccca tcctaccgaa    2940
ccaggcgcaa acgacgcca gctcgcgcgc attatcgcat cgccgtgct ggcaggtgaa      3000 ttgtccctct gctcagcctt ggccgcgggt catttggtcc aaagccacat gacccataac    3060
cgcaaaacga ataaggccaa cgaacttcct caaccttcaa acaagggtcc accttgcaaa    3120
acctccgcgc tgttg                                                     3135
```

<210> SEQ ID NO 23
<211> LENGTH: 451
<212> TYPE: PRT
<213> ORGANISM: Saccharomyces cerevisiae

<400> SEQUENCE: 23

```
Met Ser Glu Leu Arg Ala Phe Ser Ala Pro Gly Lys Ala Leu Leu Ala
1               5                   10                  15

Gly Gly Tyr Leu Val Leu Asp Thr Lys Tyr Glu Ala Phe Val Val Gly
                20                  25                  30

Leu Ser Ala Arg Met His Ala Val Ala His Pro Tyr Gly Ser Leu Gln
            35                  40                  45

Gly Ser Asp Lys Phe Glu Val Arg Val Lys Ser Lys Gln Phe Lys Asp
        50                  55                  60

Gly Glu Trp Leu Tyr His Ile Ser Pro Lys Ser Gly Phe Ile Pro Val
65                  70                  75                  80

Ser Ile Gly Gly Ser Lys Asn Pro Phe Ile Glu Lys Val Ile Ala Asn
                85                  90                  95

Val Phe Ser Tyr Phe Lys Pro Asn Met Asp Asp Tyr Cys Asn Arg Asn
                100                 105                 110

Leu Phe Val Ile Asp Ile Phe Ser Asp Asp Ala Tyr His Ser Gln Glu
            115                 120                 125

Asp Ser Val Thr Glu His Arg Gly Asn Arg Arg Leu Ser Phe His Ser
        130                 135                 140

His Arg Ile Glu Glu Val Pro Lys Thr Gly Leu Gly Ser Ser Ala Gly
145                 150                 155                 160

Leu Val Thr Val Leu Thr Thr Ala Leu Ala Ser Phe Phe Val Ser Asp
                165                 170                 175

Leu Glu Asn Asn Val Asp Lys Tyr Arg Glu Val Ile His Asn Leu Ala
                180                 185                 190

Gln Val Ala His Cys Gln Ala Gln Gly Lys Ile Gly Ser Gly Phe Asp
            195                 200                 205

Val Ala Ala Ala Ala Tyr Gly Ser Ile Arg Tyr Arg Arg Phe Pro Pro
        210                 215                 220
```

```
Ala Leu Ile Ser Asn Leu Pro Asp Ile Gly Ser Ala Thr Tyr Gly Ser
225                 230                 235                 240

Lys Leu Ala His Leu Val Asp Glu Glu Asp Trp Asn Ile Thr Ile Lys
            245                 250                 255

Ser Asn His Leu Pro Ser Gly Leu Thr Leu Trp Met Gly Asp Ile Lys
        260                 265                 270

Asn Gly Ser Glu Thr Val Lys Leu Val Gln Lys Val Lys Asn Trp Tyr
    275                 280                 285

Asp Ser His Met Pro Glu Ser Leu Lys Ile Tyr Thr Glu Leu Asp His
290                 295                 300

Ala Asn Ser Arg Phe Met Asp Gly Leu Ser Lys Leu Asp Arg Leu His
305                 310                 315                 320

Glu Thr His Asp Asp Tyr Ser Asp Gln Ile Phe Glu Ser Leu Glu Arg
                325                 330                 335

Asn Asp Cys Thr Cys Gln Lys Tyr Pro Glu Ile Thr Glu Val Arg Asp
            340                 345                 350

Ala Val Ala Thr Ile Arg Arg Ser Phe Arg Lys Ile Thr Lys Glu Ser
        355                 360                 365

Gly Ala Asp Ile Glu Pro Pro Val Gln Thr Ser Leu Leu Asp Asp Cys
370                 375                 380

Gln Thr Leu Lys Gly Val Leu Thr Cys Leu Ile Pro Gly Ala Gly Gly
385                 390                 395                 400

Tyr Asp Ala Ile Ala Val Ile Thr Lys Gln Asp Val Asp Leu Arg Ala
                405                 410                 415

Gln Thr Ala Asn Asp Lys Arg Phe Ser Lys Val Gln Trp Leu Asp Val
            420                 425                 430

Thr Gln Ala Asp Trp Gly Val Arg Lys Glu Lys Asp Pro Glu Thr Tyr
        435                 440                 445

Leu Asp Lys
    450

<210> SEQ ID NO 24
<211> LENGTH: 1353
<212> TYPE: DNA
<213> ORGANISM: Artificial
<220> FEATURE:
<223> OTHER INFORMATION: mutated and/or codon-optimized sequence

<400> SEQUENCE: 24
atgtccgaac tgcgcgcatt tccgcgcct ggtaaggcgc tgctcgccgg cggctacctt      60
gtgttggaca ctaaatacga ggccttcgtg gtgggccttt ccgcacgtat gcacgccgtc     120
gctcatcctt atggttcgtt gcaaggttcc gataagtttg aggtgcgcgt gaaatccaaa     180
cagtttaaag atggtgaatg ctgtaccac atcagcccaa agtcaggctt cattccagta     240
tccattggtg gttccaagaa tccatttatc gagaaggtca ttgccaacgt cttttcatac     300
ttcaaaccaa acatggatga ttattgtaat cgcaacttgt tcgtgatcga tatcttctct     360
gacgacgctt atcactcgca ggaagattcc gttacggagc atcgtggaaa ccgacgtctg     420
tcatttcatt cgcaccgcat cgaggaagtt cccaagaccg gctgggctc gtctgccggc     480 cttgtcactg ttttgactac cgccctcgca tctttcttcg tgtctgacct tgaaaacaac     540
gttgataagt accgcgaggt gattcacaac ctggcgcagg tagcgcactg ccaggcgcag     600
ggaaaaattg cagcggcctt tgatgtggct gctgctgcat acggcagcat ccgttaccgc     660
cgcttcccac cagcgcttat tagcaacctg ccggacatcg gctccgcgac ttacggttcc     720
```

```
aaattggccc accttgtcga cgaggaagac tggaacatca caatcaagtc taaccacctc      780
ccttccggcc tgacgctctg gatgggcgat atcaagaatg gctctgaaac cgtgaagctc      840
gtgcagaagg ttaagaactg gtacgactca cacatgcctg aatcgttgaa atctacacc      900 gagcttgatc acgcgaactc ccgtttcatg gacggattgt cgaagttgga ccgtctgcat      960
gaaacgcacg acgattattc cgaccaaatc tttgaatcgc tggaacgtaa cgattgtact     1020
tgtcagaagt atcccgaaat caccgaggtc cgcgacgcgg tcgcgacaat tcgccgctca     1080
ttccgcaaaa tcactaagga atccggtgct gacattgagc ccccggttca gacctccctg     1140
ctcgatgatt gccagactct caagggtgtc ttgacgtgtt tgatccccgg agccggcggc     1200
tacgatgcca tcgcagttat caccaagcag gatgtggatc tccgcgcgca gacagcaaac     1260
gataagcgct tttcaaaggt gcagtggctg acgtgacccc aagctgattg gggcgttcgt     1320
aaagaaaaag atccagagac atatctggat aag                                  1353
```

<210> SEQ ID NO 25
<211> LENGTH: 288
<212> TYPE: PRT
<213> ORGANISM: Saccharomyces cerevisiae

<400> SEQUENCE: 25

```
Met Thr Ala Asp Asn Asn Ser Met Pro His Gly Ala Val Ser Ser Tyr
1               5                   10                  15

Ala Lys Leu Val Gln Asn Gln Thr Pro Glu Asp Ile Leu Glu Glu Phe
            20                  25                  30

Pro Glu Ile Ile Pro Leu Gln Gln Arg Pro Asn Thr Arg Ser Ser Glu
        35                  40                  45

Thr Ser Asn Asp Glu Ser Gly Glu Thr Cys Phe Ser Gly His Asp Glu
    50                  55                  60

Glu Gln Ile Lys Leu Met Asn Glu Asn Cys Ile Val Leu Asp Trp Asp
65                  70                  75                  80

Asp Asn Ala Ile Gly Ala Gly Thr Lys Lys Val Cys His Leu Met Glu
                85                  90                  95

Asn Ile Glu Lys Gly Leu Leu His Arg Ala Phe Ser Val Phe Ile Phe
            100                 105                 110

Asn Glu Gln Gly Glu Leu Leu Leu Gln Gln Arg Ala Thr Glu Lys Ile
        115                 120                 125

Thr Phe Pro Asp Leu Trp Thr Asn Thr Cys Cys Ser His Pro Leu Cys
    130                 135                 140

Ile Asp Asp Glu Leu Gly Leu Lys Gly Lys Leu Asp Asp Lys Ile Lys
145                 150                 155                 160

Gly Ala Ile Thr Ala Ala Val Arg Lys Leu Asp His Glu Leu Gly Ile
                165                 170                 175

Pro Glu Asp Glu Thr Lys Thr Arg Gly Lys Phe His Phe Leu Asn Arg
            180                 185                 190

Ile His Tyr Met Ala Pro Ser Asn Glu Pro Trp Gly Glu His Glu Ile
        195                 200                 205

Asp Tyr Ile Leu Phe Tyr Lys Ile Asn Ala Lys Glu Asn Leu Thr Val
    210                 215                 220

Asn Pro Asn Val Asn Glu Val Arg Asp Phe Lys Trp Val Ser Pro Asn
225                 230                 235                 240

Asp Leu Lys Thr Met Phe Ala Asp Pro Ser Tyr Lys Phe Thr Pro Trp
                245                 250                 255
```

```
Phe Lys Ile Ile Cys Glu Asn Tyr Leu Phe Asn Trp Trp Glu Gln Leu
            260                 265                 270

Asp Asp Leu Ser Glu Val Glu Asn Asp Arg Gln Ile His Arg Met Leu
        275                 280                 285
```

<210> SEQ ID NO 26
<211> LENGTH: 864
<212> TYPE: DNA
<213> ORGANISM: Artificial
<220> FEATURE:
<223> OTHER INFORMATION: mutated and/or codon-optimized sequence

<400> SEQUENCE: 26

```
atgacagcag ataacaattc catgcctcac ggtgctgtgt cttcatacgc gaaactggtg      60
cagaaccaaa cacctgagga tattctcgag gaattccccg aaatcatccc tctccagcag     120
cgcccgaaca cccgctcctc tgaaacctct aatgacgaat ccggcgagac atgtttctcc     180
ggccacgacg aagagcaaat taagctgatg aacgaaaatt gcatcgtgtt ggactgggat     240
gacaacgcca ttggagccgg taccaaaaag gtgtgccatc tgatggagaa cattgaaaag     300
ggactgctcc atcgagcttt ctcagtgttc attttcaatg aacagggtga gctcctgctg     360
caacagcgcg aacggaaaa gattaccttc cccgacctct ggactaacac ctgctgctca     420
cacccattgt gtatcgatga cgaacttggc ttgaagggca agcttgatga taagattaag     480
ggcgcaatca cggccgctgt tcgtaaactc gatcacgaac ttggaattcc tgaagacgaa     540
accaagactc gcggcaaatt tcacttcttg aatcgtatcc actatatggc gccttccaac     600
gagccttggg gcgagcacga gatcgactat attttgttct acaagatcaa tgcaaaggag     660
aacctgactg tgaacccgaa tgtgaatgaa gtgcgtgact tcaagtgggt ctcaccgaac     720
gatctgaaga ccatgtttgc cgatccatcc tacaaattca ccccgtggtt caaaattatc     780
tgtgaaaact atctgttcaa ttggtgggaa caactcgacg atttgtccga ggtcgagaac     840
gatcgtcaaa tccaccgtat gctt                                            864
```

<210> SEQ ID NO 27
<211> LENGTH: 527
<212> TYPE: PRT
<213> ORGANISM: Artificial
<220> FEATURE:
<223> OTHER INFORMATION: mutated and/or codon-optimized sequence

<400> SEQUENCE: 27

```
Met Ala Ala Asp Gln Leu Val Lys Thr Glu Val Thr Lys Lys Ser Phe
1               5                   10                  15

Thr Ala Pro Val Gln Lys Ala Ser Thr Pro Val Leu Thr Asn Lys Thr
            20                  25                  30

Val Ile Ser Gly Ser Lys Val Lys Ser Leu Ser Ser Ala Gln Ser Ser
        35                  40                  45

Ser Ser Gly Pro Ser Ser Ser Glu Glu Asp Asp Ser Arg Asp Ile
    50                  55                  60

Glu Ser Leu Asp Lys Lys Ile Arg Pro Leu Glu Glu Leu Glu Ala Leu
65                  70                  75                  80

Leu Ser Ser Gly Asn Thr Lys Gln Leu Lys Asn Lys Glu Val Ala Ala
                85                  90                  95

Leu Val Ile His Gly Lys Leu Pro Leu Tyr Ala Leu Glu Lys Lys Leu
            100                 105                 110

Gly Asp Thr Thr Arg Ala Val Ala Val Arg Arg Lys Ala Leu Ser Ile
        115                 120                 125
```

```
Leu Ala Glu Ala Pro Val Leu Ala Ser Asp Arg Leu Pro Tyr Lys Asn
            130                 135                 140

Tyr Asp Tyr Asp Arg Val Phe Gly Ala Cys Cys Glu Asn Val Ile Gly
145                 150                 155                 160

Tyr Met Pro Leu Pro Val Gly Val Ile Gly Pro Leu Val Ile Asp Gly
                165                 170                 175

Thr Ser Tyr His Ile Pro Met Ala Thr Thr Glu Gly Cys Leu Val Ala
            180                 185                 190

Ser Ala Met Arg Gly Cys Lys Ala Ile Asn Ala Gly Gly Gly Ala Thr
        195                 200                 205

Thr Val Leu Thr Lys Asp Gly Met Thr Arg Gly Pro Val Val Arg Phe
210                 215                 220

Pro Thr Leu Lys Arg Ser Gly Ala Cys Lys Ile Trp Leu Asp Ser Glu
225                 230                 235                 240

Glu Gly Gln Asn Ala Ile Lys Lys Ala Phe Asn Ser Thr Ser Arg Phe
                245                 250                 255

Ala Arg Leu Gln His Ile Gln Thr Cys Leu Ala Gly Asp Leu Leu Phe
            260                 265                 270

Met Arg Phe Arg Thr Thr Thr Gly Asp Ala Met Gly Met Asn Met Ile
        275                 280                 285

Ser Lys Gly Val Glu Tyr Ser Leu Lys Gln Met Val Glu Glu Tyr Gly
290                 295                 300

Trp Glu Asp Met Glu Val Val Ser Val Ser Gly Asn Tyr Cys Thr Asp
305                 310                 315                 320

Lys Lys Pro Ala Ala Ile Asn Trp Ile Glu Gly Arg Gly Lys Ser Val
                325                 330                 335

Val Ala Glu Ala Thr Ile Pro Gly Asp Val Val Arg Lys Val Leu Lys
            340                 345                 350

Ser Asp Val Ser Ala Leu Val Glu Leu Asn Ile Ala Lys Asn Leu Val
        355                 360                 365

Gly Ser Ala Met Ala Gly Ser Val Gly Gly Phe Asn Ala His Ala Ala
370                 375                 380

Asn Leu Val Thr Ala Val Phe Leu Ala Leu Gly Gln Asp Pro Ala Gln
385                 390                 395                 400

Asn Val Glu Ser Ser Asn Cys Ile Thr Leu Met Lys Glu Val Asp Gly
                405                 410                 415

Asp Leu Arg Ile Ser Val Ser Met Pro Ser Ile Glu Val Gly Thr Ile
            420                 425                 430

Gly Gly Gly Thr Val Leu Glu Pro Gln Gly Ala Met Leu Asp Leu Leu
        435                 440                 445

Gly Val Arg Gly Pro His Ala Thr Ala Pro Gly Thr Asn Ala Arg Gln
450                 455                 460

Leu Ala Arg Ile Val Ala Cys Ala Val Leu Ala Gly Glu Leu Ser Leu
465                 470                 475                 480

Cys Ala Ala Leu Ala Ala Gly His Leu Val Gln Ser His Met Thr His
                485                 490                 495

Asn Arg Lys Pro Ala Glu Pro Thr Lys Pro Asn Asn Leu Asp Ala Thr
            500                 505                 510

Asp Ile Asn Arg Leu Lys Asp Gly Ser Val Thr Cys Ile Lys Ser
        515                 520                 525

<210> SEQ ID NO 28
<211> LENGTH: 1581
```

-continued

<212> TYPE: DNA
<213> ORGANISM: Artificial
<220> FEATURE:
<223> OTHER INFORMATION: mutated and/or codon-optimized sequence

<400> SEQUENCE: 28

| | |
|---|---|
| atggcggctg atcagctcgt taaaacggaa gtaacaaaga atccttcac cgctcccgta | 60 |
| cagaaagctt ctactcctgt cttgaccaac aagaccgtta tctccggctc taaagtgaaa | 120 |
| tcgctctctt ccgcccagag cagctcatcc ggtccgtcgt cttcctccga agaggacgac | 180 |
| tcacgtgata ttgaatcact ggataaaaag attcgaccgc tcgaagagct tgaggcgctt | 240 |
| ttgagctccg caataccaa acagttgaag aacaaggagg ttgccgccct tgtgattcac | 300 |
| ggcaaacttc cgctctatgc cttggagaag aagttgggag acaccacgcg cgcagtggcc | 360 |
| gtgcgccgca aggcactgtc tattctcgcg gaggcacccg tcctggcttc cgaccgcttg | 420 |
| ccctacaaga actacgatta cgaccgtgtc ttcggcgcat gttgcgagaa tgtaatcgga | 480 |
| tatatgcccc ttcccgttgg cgtgatcggc ccacttgtca tcgatggcac atcataccat | 540 |
| attccaatgg cgaccaccga gggttgcctc gtggcgtcgg ccatgcgcgg ttgtaaggcc | 600 |
| atcaacgccg gaggtggagc aactaccgta cttactaagg acggcatgac tcgtggcccc | 660 |
| gtggtgcgtt tcccgactct taaacgctcc ggtgcgtgca agatctggtt ggattccgag | 720 |
| gagggacaga acgcaatcaa aaaagctttc aacagcactt ctcgcttcgc tcgacttcag | 780 |
| cacattcaga cctgtctcgc tggtgacttg ttgttcatgc gttttcgcac caccactgga | 840 |
| gacgcgatgg gcatgaatat gattagcaaa ggagtggaat actccctcaa acaaatggtg | 900 |
| gaagaatatg gctgggaaga catggaagtg gtttccgtgt ctggtaatta tgtaccgac | 960 |
| aagaagccgg cagccatcaa ctggattgag ggccgtggca agtccgtggt ggcggaggcg | 1020 |
| acaattccgg gtgatgtcgt gcgcaaagtt ctcaagtctg acgtgtcagc gttggtagaa | 1080 |
| ctgaacatcg caaaaaacct tgtaggatcg gcaatggctg gttcagtggg cggtttttaat | 1140 |
| gcgcacgcag ccaacctcgt caccgctgtg ttccttgccc tgggtcagga tccagcacag | 1200 |
| aatgtggaaa gctcgaactg catcaccctg atgaaagaag tggatggcga cttgcgtatc | 1260 |
| tccgtctcga tgccatcaat cgaagtgggt accatcggtg gcggaaccgt gttggaacca | 1320 |
| cagggagcaa tgcttgatct cctcggcgtt cgaggtccgc acgccacggc gcccggcacc | 1380 |
| aacgcacgtc agctggcacg catcgtggct tgcgcggttc tcgcgggtga attgagcctc | 1440 |
| tgcgcagccc tggcagcggg tcacctggtg caatctcaca tgacacataa ccgtaaacca | 1500 |
| gccgagccca ccaagccgaa taacctcgac gccactgata ttaaccgctt gaaggatggt | 1560 |
| tccgtcacct gcatcaaatc t | 1581 |

<210> SEQ ID NO 29
<211> LENGTH: 425
<212> TYPE: PRT
<213> ORGANISM: Staphylococcus aureus

<400> SEQUENCE: 29

Met Gln Ser Leu Asp Lys Asn Phe Arg His Leu Ser Arg Gln Gln Lys
1               5                   10                  15

Leu Gln Gln Leu Val Asp Lys Gln Trp Leu Ser Glu Asp Gln Phe Asp
            20                  25                  30

Ile Leu Leu Asn His Pro Leu Ile Asp Glu Glu Val Ala Asn Ser Leu
        35                  40                  45

Ile Glu Asn Val Ile Ala Gln Gly Ala Leu Pro Val Gly Leu Leu Pro

```
                  50                  55                  60
Asn Ile Ile Val Asp Asp Lys Ala Tyr Val Val Pro Met Met Val Glu
 65                  70                  75                  80

Glu Pro Ser Val Ala Ala Ser Tyr Gly Ala Lys Leu Val Asn
                 85                  90                  95

Gln Thr Gly Gly Phe Lys Thr Val Ser Ser Glu Arg Ile Met Ile Gly
                100                 105                 110

Gln Ile Val Phe Asp Gly Val Asp Asp Thr Glu Lys Leu Ser Ala Asp
                115                 120                 125

Ile Lys Ala Leu Glu Lys Gln Ile His Lys Ile Ala Asp Glu Ala Tyr
                130                 135                 140

Pro Ser Ile Lys Ala Arg Gly Gly Tyr Gln Arg Ile Ala Ile Asp
145                 150                 155                 160

Thr Phe Pro Glu Gln Gln Leu Leu Ser Leu Lys Val Phe Val Asp Thr
                165                 170                 175

Lys Asp Ala Met Gly Ala Asn Met Leu Asn Thr Ile Leu Glu Ala Ile
                180                 185                 190

Thr Ala Phe Leu Lys Asn Glu Ser Pro Gln Ser Asp Ile Leu Met Ser
                195                 200                 205

Ile Leu Ser Asn His Ala Thr Ala Ser Val Val Lys Val Gln Gly Glu
                210                 215                 220

Ile Asp Val Lys Asp Leu Ala Arg Gly Glu Arg Thr Gly Glu Val
225                 230                 235                 240

Ala Lys Arg Met Glu Arg Ala Ser Val Leu Ala Gln Val Asp Ile His
                245                 250                 255

Arg Ala Ala Thr His Asn Lys Gly Val Met Asn Gly Ile His Ala Val
                260                 265                 270

Val Leu Ala Thr Gly Asn Asp Thr Arg Gly Ala Glu Ala Ser Ala His
                275                 280                 285

Ala Tyr Ala Ser Arg Asp Gly Gln Tyr Arg Gly Ile Ala Thr Trp Arg
                290                 295                 300

Tyr Asp Gln Lys Arg Gln Arg Leu Ile Gly Thr Ile Glu Val Pro Met
305                 310                 315                 320

Thr Leu Ala Ile Val Gly Gly Gly Thr Lys Val Leu Pro Ile Ala Lys
                325                 330                 335

Ala Ser Leu Glu Leu Leu Asn Val Asp Ser Ala Gln Glu Leu Gly His
                340                 345                 350

Val Val Ala Ala Val Gly Leu Ala Gln Asn Phe Ala Ala Cys Arg Ala
                355                 360                 365

Leu Val Ser Glu Gly Ile Gln Gln Gly His Met Ser Leu Gln Tyr Lys
                370                 375                 380

Ser Leu Ala Ile Val Val Gly Ala Lys Gly Asp Glu Ile Ala Gln Val
385                 390                 395                 400

Ala Glu Ala Leu Lys Gln Glu Pro Arg Ala Asn Thr Gln Val Ala Glu
                405                 410                 415

Arg Ile Leu Gln Glu Ile Arg Gln Gln
                420                 425

<210> SEQ ID NO 30
<211> LENGTH: 1275
<212> TYPE: DNA
<213> ORGANISM: Artificial
<220> FEATURE:
<223> OTHER INFORMATION: mutated and/or codon-optimized sequence
```

<400> SEQUENCE: 30

```
atgcaatccc tcgataaaaa tttccgtcac ctttctcgac agcagaaatt gcagcaactt      60
gttgacaagc aatggctctc ggaggatcaa ttcgatatcc tgctcaatca cccactgatc     120
gatgaggagg tcgccaattc cctgattgag aacgtcatcg cgcagggtgc actgcccgtg     180
ggccttctgc ctaacatcat cgtcgatgac aaggcctacg tagtacctat gatggtcgaa     240
gaaccgtccg tggtggcagc tgcttcctat ggtgccaagc tggtcaacca gaccggcgga     300
ttcaagactg tgtcttctga acgcattatg atcggacaga ttgtcttcga tggtgttgat     360
gatacggaaa agctctctgc agacatcaag gcattggaga aacagatcca taaaatcgcg     420
gatgaggcgt accectccat caaagcgcgc ggcggcggct atcagcgaat cgctattgac     480
accttccctg aacagcagct gctctccctg aaagtcttcg tggatactaa ggacgccatg     540
ggtgcaaata tgttgaacac catcctggag gccatcaccg cgttcctgaa gacgagagc      600
cctcagtcgg atattttgat gtcaatcctg tccaatcacg ccactgcatc tgtggtaaaa     660
gtgcaaggtg aaatcgatgt caagatctc gcccgcggag aacgcacggg cgaagaggtc     720
gcaaaacgaa tggagcgcgc ctctgttctt gcgcaggtgg atatccaccg cgctgcgacc     780
cacaataaag gtgtgatgaa cggcatccat gcagtcgtac ttgccaccgg caacgatact     840
cgcggtgcag aagcgtctgc ccatgcatat gcgtcgcgag atggtcaata ccgtggcatt     900
gctacatggc gttacgatca aaaacgccag cgtctcattg gtacgatcga ggttcctatg     960
accctggcca tcgtcggcgg aggcaccaaa gtcctcccga tcgcaaaggc ctcgctcgaa    1020
cttttgaatg tcgatagcgc acaagaactc ggtcacgtcg tagcagccgt gggtctggcg    1080
cagaacttcg cagcgtgtcg agcacttgtc tccgagggca ttcagcaggg tcacatgtcc    1140
cttcagtaca aaagcttggc aattgttgtg ggtgcaaagg tgatgagat tgcccaggtc     1200
gcagaagcac tcaaacaaga gccacgtgcg aacacgcagg ttgccgagcg tatccttcaa    1260
gaaattcgac aacaa                                                      1275
```

<210> SEQ ID NO 31
<211> LENGTH: 446
<212> TYPE: PRT
<213> ORGANISM: Candidatus Halobonum tyrrellensis G22

<400> SEQUENCE: 31

```
Met Ser Asp Ala Asp Thr Glu Arg Leu Ala Ala Arg Val Arg Glu Gly
1               5                   10                  15

Asp Leu Arg Leu Tyr Glu Leu Glu Glu His Ala Asp Ala Asp Thr Ala
            20                  25                  30

Val Ala Ala Arg Arg Leu Leu Val Glu Glu Ala Ser Gly Ala Glu Leu
        35                  40                  45

Glu Thr Thr Gly Glu Tyr Ala Phe Pro Ala Glu Met Ala Thr Gly Thr
    50                  55                  60

Asn Val Glu Asn Met Val Gly Ala Val Gln Val Pro Val Gly Val Val
65                  70                  75                  80

Gly Pro Val Thr Ile Asp Gly Gly Ala Leu Ser Gly Glu Arg His Val
                85                  90                  95

Pro Met Ala Thr Thr Glu Gly Ala Leu Leu Ala Ser Val Asn Arg Gly
            100                 105                 110

Cys Ser Ala Leu Asn Thr Ala Gly Gly Ala Ser Ala Arg Val Leu Lys
        115                 120                 125

Asn Arg Met Thr Arg Ala Pro Val Phe Arg Val Asp Gly Val Val Glu
```

```
            130                 135                 140
Ala Glu Ala Leu Ala Ser Trp Thr Arg Asp Asn Val Glu Ala Leu Arg
145                 150                 155                 160

Ala Val Ala Glu Ala Thr Thr Asn His Gly Glu Leu Arg Glu Val Arg
                165                 170                 175

Pro Tyr Ala Val Gly Asn Asn Val Tyr Leu Arg Phe Ala Tyr Asp Thr
            180                 185                 190

Lys Asp Ala Met Gly Met Asn Met Ala Thr Ile Ala Thr Glu Ala Ala
                195                 200                 205

Cys Glu Val Val Glu Asp Glu Thr Gly Ala Glu Leu Val Ala Leu Ser
            210                 215                 220

Gly Asn Leu Cys Ser Asp Lys Lys Pro Ala Ala Val Asn Ala Val Glu
225                 230                 235                 240

Gly Arg Gly Arg Thr Val Ala Ala Asp Val Thr Val Pro Arg Glu Thr
                245                 250                 255

Val Arg Glu Thr Leu Lys Thr Thr Pro Glu Ala Val Ala Glu Val Asn
            260                 265                 270

Thr Arg Lys Asn Leu Val Gly Ser Ala Lys Ala Gly Ser Leu Gly Phe
        275                 280                 285

Asn Ala His Val Ala Asn Ala Val Ala Val Phe Leu Ala Thr Gly
    290                 295                 300

Gln Asp Ala Ala Gln Val Val Glu Gly Ala Asn Ala Ile Thr Thr Ala
305                 310                 315                 320

Glu Val Val Ala Gly Asp Ala Pro Ser Arg Thr Val Asp Arg Asn Gly
                325                 330                 335

Ala Ala Glu Ser Gly Val Gly Pro Asp Gly Asp Ala Pro Asp Gly Asp
            340                 345                 350

Ala Pro Asp Gly Asp Gly Ala Ala Gly Arg Gly Gly Asp Leu Tyr
        355                 360                 365

Val Ser Val Thr Leu Ala Ser Leu Glu Val Gly Thr Val Gly Gly Gly
    370                 375                 380

Thr Lys Leu Pro Thr Gln Ala Glu Ala Leu Asp Val Leu Gly Val Arg
385                 390                 395                 400

Gly Gly Gly Asp Pro Ala Gly Ser Asn Ala Asp Ala Leu Ala Glu Ala
                405                 410                 415

Val Ala Val Thr Ala Leu Ala Gly Glu Leu Ser Leu Leu Ser Ala Leu
            420                 425                 430

Ala Ser Arg Asn Leu Ser Ser Ala His Ala Glu Leu Gly Arg
        435                 440                 445

<210> SEQ ID NO 32
<211> LENGTH: 1338
<212> TYPE: DNA
<213> ORGANISM: Artificial
<220> FEATURE:
<223> OTHER INFORMATION: mutated and/or codon-optimized sequence

<400> SEQUENCE: 32
atgtcagacg ctgacaccga gcgtctggct gcgcgcgttc gcgagggtga tctgcgcctg     60
tatgagctgg aggagcacgc ggatgcagat actgctgtcg ccgctcgtcg tctcttggtg    120
gaagaggcct ccggtgcaga acttgagact accggtgaat atgctttccc tgcagaaatg    180
gcaaccggca ccaatgtcga gaacatggtc ggtgctgttc aggttccagt gggcgtagtg    240
ggtcctgtta cgattgatgg cggtgcgctg tctggcgagc gtcacgtccc aatggctaca    300
```

-continued

```
accgaaggtg cgctcctcgc gtccgtcaat cgcggctgct cggccctcaa cacagctggt    360
ggtgcatcag ctcgtgtcct gaagaatcgc atgactcgtg ccccgtcttt cgcgtcgat     420
ggcgtcgtcg aagccgaggc gcttgcttcg tggacccgcg acaacgtgga agcgctccgt    480
gcagtggctg aagctaccac caaccacgga gaactccgcg aagtgcgccc atacgctgtg    540
ggcaacaacg tctaccttcg attcgcttat gataccaagg atgcaatggg catgaatatg    600
gccactatcg ccaccgaggc ggcgtgcgag gtggtggaag atgaaaccgg cgctgagctg    660
gttgcactga gcggtaacct ttgctctgat aagaagccag ccgctgtgaa cgcagtggaa    720
ggtcgcggtc gcacagttgc tgctgatgtg acggttcctc gcgagaccgt tcgcgagacc    780
ctgaagacca cccctgaggc cgtggccgag gttaacacgc gcaagaactt ggtgggaagc    840
gcgaaggccg gctcattggg atttaatgct catgtggcaa acgccgtggc agcagtcttt    900
cttgcaacag tcaggatgc tgcgcaggtc gtggaaggtg ctaacgccat cactacggcg    960
gaagtcgtcg caggcgatgc tccatcccgt accgtggatc gcaatggcgc tgctgaatcc   1020
ggcgtaggtc cggatggtga tgcacctgac ggtgatgcac cggatggtga cggcgcagca   1080
gcaggtcgtg gcggcgacct ctatgttagc gtgaccctgg cctcactgga ggtcggtacc   1140
gtgggcggcg gtacgaaact gcccacccaa gcggaagcat tggacgtgct cggtgtacgt   1200
ggaggaggtg atcctgctgg tagcaacgca gatgctctcg ctgaagccgt tgctgtgacc   1260
gctttggctg tgagttgtc tcttctttcc gctctcgcca ccgtaacct ctcgtcggca   1320
cacgctgaac tgggacgc                                                 1338
```

<210> SEQ ID NO 33
<211> LENGTH: 665
<212> TYPE: PRT
<213> ORGANISM: Cucumis sativus (Cucumber)

<400> SEQUENCE: 33

```
Met Thr His Cys Ser Gln Leu Pro Thr His Lys Ala Thr Thr Glu
1               5                   10                  15

Lys Asn Asp Glu Pro Ile Pro Leu Gly Pro Val Gln Leu Ser Trp Pro
                20                  25                  30

Gly Ser Val Val Glu Lys Gly Glu Lys Ser Ser Phe His Tyr Lys Pro
            35                  40                  45

Pro Phe Ala Ser Arg Ser Gly Ala Gly Val Phe His Phe Leu Phe Phe
        50                  55                  60

Ser Cys Leu Thr Met Asp Ala Arg Arg Arg Ser Ser Thr Leu Val
65                  70                  75                  80

Lys Lys Leu Thr Ala Asp Glu Pro Pro Val Lys Ser Met Asp Lys Asn
                85                  90                  95

Pro Leu Lys Val Lys Met Leu Glu Arg Gln His Val His Asp Asp Ala
            100                 105                 110

Val Lys Ala Ser Asp Val Leu Pro Leu Pro Ile Tyr Leu Thr Asn Ala
        115                 120                 125

Ala Phe Phe Thr Leu Phe Phe Ser Val Val Tyr Phe Leu Leu Thr Arg
    130                 135                 140

Trp Arg Glu Lys Ile Arg Ser Ser Thr Pro Leu His Val Val Thr Leu
145                 150                 155                 160

Ser Glu Met Val Ala Ile Ser Ala Phe Ile Ala Ser Phe Ile Tyr Leu
                165                 170                 175

Leu Gly Phe Phe Gly Ile Asp Phe Val Gln Ser Ile Phe Arg Pro Ser
            180                 185                 190
```

```
His Asp Val Trp Thr Ser Glu Asp Glu Val Val Ile Ile Lys Glu
        195                 200                 205

Asp Thr Arg Lys Val Pro Cys Gly Ala Gly Ile Asp Cys Ser Ile Pro
    210                 215                 220

Ile Leu Ala Pro Pro Met Pro Ser Val Pro Lys Val Val Asp Pro Leu
225                 230                 235                 240

Pro Val Ser Ile Asp Leu Thr Glu Glu Asp Glu Glu Ile Val Lys Ser
                245                 250                 255

Val Val Asp Gly Ser Thr Pro Ser Tyr Ser Leu Glu Ser Lys Leu Gly
            260                 265                 270

Asp Cys Gly Arg Ala Ala Ala Ile Arg Arg Val Ala Leu Gln Arg Val
        275                 280                 285

Thr Gly Lys Ser Leu Ser Gly Leu Pro Leu Glu Gly Phe Asp Tyr Ala
    290                 295                 300

Ser Ile Leu Gly Gln Cys Cys Glu Met Pro Ile Gly Tyr Val Gln Ile
305                 310                 315                 320

Pro Val Gly Ile Ala Gly Pro Leu Leu Leu Asp Gly Lys Glu Tyr Ser
                325                 330                 335

Val Pro Met Ala Thr Thr Glu Gly Cys Leu Val Ala Ser Thr Asn Arg
            340                 345                 350

Gly Cys Lys Ala Ile Met Ile Ser Gly Gly Ala Asn Ser Val Leu Leu
        355                 360                 365

Arg Asp Ala Met Thr Arg Ala Pro Val Met Arg Phe Ala Thr Ala Lys
    370                 375                 380

Arg Ala Ala Glu Leu Lys Phe Tyr Val Glu Asp Pro Ala Asn Phe Asp
385                 390                 395                 400

Thr Leu Ala Ser Val Phe Asn Lys Ser Ser Arg Phe Gly Arg Leu Gln
                405                 410                 415

Ser Ile Lys Cys Ala Ile Ala Gly Lys Asn Leu Tyr Met Arg Phe Ser
            420                 425                 430

Cys Ser Thr Gly Asp Ala Met Gly Met Asn Met Val Ser Lys Gly Val
        435                 440                 445

Gln Asn Val Leu Asp Phe Leu Gln Asn Asp Phe Pro Asp Met Asp Val
    450                 455                 460

Ile Gly Ile Ser Gly Asn Tyr Cys Ser Asp Lys Lys Pro Ala Ala Val
465                 470                 475                 480

Asn Trp Ile Glu Gly Arg Gly Lys Ser Val Val Cys Glu Val Thr Ile
                485                 490                 495

Lys Gly Asp Val Val Arg Lys Val Leu Lys Thr Asp Val Gln Ala Leu
            500                 505                 510

Val Glu Leu Asn Met Leu Lys Asn Leu Thr Gly Ser Ala Met Ala Gly
        515                 520                 525

Ala Leu Gly Gly Phe Asn Ala His Ala Ser Asn Ile Val Ser Ala Ile
    530                 535                 540

Tyr Ile Ala Thr Gly Gln Asp Pro Ala Gln Asn Val Glu Ser Ser His
545                 550                 555                 560

Cys Ile Thr Met Met Glu Ala Val Asn Asp Gly Gln Asp Leu His Val
                565                 570                 575

Ser Val Thr Met Pro Ser Ile Glu Val Gly Thr Val Gly Gly Gly Thr
            580                 585                 590

Gln Leu Ala Ser Gln Ser Ala Cys Leu Asn Leu Leu Gly Val Lys Gly
        595                 600                 605
```

```
Ala Asn Arg Glu Ala Pro Gly Ser Asn Ser Arg Leu Leu Ala Thr Ile
610                 615                 620

Val Ala Ala Ser Val Leu Ala Gly Glu Leu Ser Leu Met Ser Ala Ile
625                 630                 635                 640

Ser Ala Gly Gln Leu Val Arg Ser His Met Lys Tyr Asn Arg Ser Ser
                645                 650                 655

Arg Asp Ile Thr Lys Ala Ser Ser Ser
                660                 665

<210> SEQ ID NO 34
<211> LENGTH: 1995
<212> TYPE: DNA
<213> ORGANISM: Artificial
<220> FEATURE:
<223> OTHER INFORMATION: mutated and/or codon-optimized sequence

<400> SEQUENCE: 34
atgacccatt gctcccagtt gccgacccac aaggcgacga cgactgaaaa aaacgatgag     60
cctattcccc ttggccccgt gcaactgagc tggccgggtt ccgttgttga aaagggagaa    120
aagtcatcgt tccattataa gccccattc gcgtctcgca gcggcgcagg cgtatttcat     180
tttctctttt tctcgtgctt gactatggac gcccgtcgcc gtcgctcttc gactctggtg    240
aagaaactta ctgcggatga gcctccagta aaatctatgg ataaaaatcc tcttaaagtc    300
aagatgcttg aacgacagca tgtccatgac gatgccgtaa aggcgtcgga tgtgctccca    360
ctgccaatct accttactaa cgctgcattc ttcactctgt tctttccgt ggtatatttc     420
cttcttacgc gctggcgtga gaagattcgt agctccacgc ccctgcacgt agtaaccctc    480
tcagaaatgg tggctatctc tgccttcatc gcctcgttca tttacctgct ggcttttttc    540
ggcattgatt tcgtgcagtc catcttccgc ccctcccacg atgtctggac ctcagaggac    600
gacgaagtgg tcatcatcaa agaagacact cgcaaggtcc catgtggcgc cggaattgac    660
tgttccattc caattctggc ccctcctatg ccctcggtgc cgaaggtggt tgatccgctg    720
cctgtgtcca ttgatctcac cgaggaggat gaagagattg tgaagtcagt cgtcgacggc    780
tcgacacctt cttactcatt ggagtctaag ctcggagatt gtggccgagc ggctgctatc    840
cgacgtgttg cacttcagcg cgtgactggc aagtcgctgt ctggcctccc gctggagggc    900
ttcgactatg cttccatcct cggacagtgt tgcgagatgc ccattggcta cgtgcaaatt    960
cccgtgggaa ttgccggccc cattgctttt gatggtaagg aatacagcgt ccccatggcg   1020
acgaccgaag gatgccttgt ggcctccacc aaccgaggct gcaaggcgat catgatctcc   1080
ggaggcgcta actccgtcct ccttcgtgat gccatgacac gtgcgccagt gatgcgcttt   1140
gcgactgcta gcgcgccgc ggaactcaaa ttctacgttg aagacccggc taacttcgat   1200
acccttgcct ccgtatttaa caaatctagc cgctttggac gcctgcagag catcaaatgt   1260
gccatcgccg gcaaaaacct ctatatgcga ttttcgtgct ccactggcga cgctatggga   1320
atgaatatgg tttccaaggg cgtacagaac gttctggact tctccagaa tgattttcca   1380
gacatggatg taatcggaat cagcggaaac tattgttcag ataagaagcc agccgccgtt   1440
aattggatcg aaggacgcgg caagtccgtc gtgtgcgagg ttaccatcaa aggcgatgtt   1500
gtccgcaagg tcctgaagac agatgtccag gcactggtgg aactcaacat gttgaaaaat   1560
cttacgggtt ccgcaatggc tggcgcactt ggtggcttta cgctcatgc atccaacatc   1620
gtttcagcca tctacatcgc gacgggacag gatcccgctc aaaacgtgga aagctcccat   1680
tgcatcacta tgatggaggc cgtaaacgat ggtcaggatc ttcacgtgag cgtgaccatg    1740
```

-continued

```
ccatccatcg aggtgggaac cgtaggcggt ggcacgcaac tggcatccca gtccgcctgc    1800
ctgaacctct tgggtgttaa gggcgcgaat cgcgaagctc caggttcaaa ttctcgcttg    1860
ctcgccacca ttgtggccgc atcagttctt gcaggcgaac ttagcctcat gtcagcgatc    1920
tccgccggcc aactcgtccg cagccacatg aaatacaatc gttcatcacg cgatatcacc    1980
aaggcttcat catcc                                                      1995
```

<210> SEQ ID NO 35
<211> LENGTH: 428
<212> TYPE: PRT
<213> ORGANISM: Lokiarchaeum sp. GC14_75

<400> SEQUENCE: 35

```
Met Ile Met Lys Asp Phe His Ser Asp Ile Ser Gly Phe Tyr Lys Leu
1               5                   10                  15

Ser Ile Asp Glu Arg Gln Lys Leu Leu Ser Lys Leu Val Asn Leu Asn
            20                  25                  30

Pro Glu Asp Leu Glu Ile Leu Lys Glu Leu Gly Tyr Phe Thr Pro Thr
        35                  40                  45

Gln Ile Asp Thr Leu Ile Glu Asn Val Val Gly Ser Tyr Gln Leu Pro
    50                  55                  60

Leu Gly Leu Ala Phe Asn Phe Arg Ile Asn Ser Lys Asp Tyr Ile Ile
65                  70                  75                  80

Pro Met Val Ile Glu Glu Pro Ser Val Val Ala Ala Ala Ser Asn Ala
                85                  90                  95

Ala Lys Met Ala Arg Lys His Gly Gly Phe His Ser Glu Asp Val Pro
            100                 105                 110

Pro Ile Met Ile Ser Gln Ile Gln Ile Thr Lys Leu Lys Asp Ile Glu
        115                 120                 125

Ala Ala Lys Asp Val Leu Glu Ala Lys Lys Gln Asp Leu Leu Lys Ile
    130                 135                 140

Ala Asn Glu Gln Asp Pro Leu Leu Asn Lys Leu Gly Gly Gly Ala Gln
145                 150                 155                 160

Asn Ile Glu Ile His Glu Ile Gln Thr Asn Lys Gly Lys Met Ile Ile
                165                 170                 175

Leu His Leu Leu Val Asn Val Leu Asp Ala Met Gly Ala Asn Ile Val
            180                 185                 190

Asn Thr Met Ala Glu Ala Ile Ser Pro Tyr Ile Glu Glu Ile Cys Gly
        195                 200                 205

Gly Lys Ile Tyr Leu Arg Ile Val Ser Asn Leu Ala Thr His Arg Val
    210                 215                 220

Ala Arg Ser Lys Ala Thr Phe Asp Lys Glu Met Leu Gly Gly Glu Glu
225                 230                 235                 240

Val Val Glu Gly Ile Met Asn Ala Tyr Glu Phe Ala Leu Ala Asp Pro
                245                 250                 255

Tyr Arg Ala Thr Thr His Asn Lys Gly Ile Met Asn Gly Val Val Ala
            260                 265                 270

Leu Thr Leu Ala Thr Gly Asn Asp Thr Arg Ala Ile Glu Ser Gly Ala
        275                 280                 285

His Ser Tyr Ala Ser Leu Ser Gly Arg Tyr Leu Pro Leu Thr Lys Phe
    290                 295                 300

Asp Val Asp Ser Gln Gly Asn Leu Val Gly Glu Ile Glu Ile Pro Leu
305                 310                 315                 320
```

```
Ala Leu Gly Ile Ile Gly Gly Met Thr Lys Ile His Pro Met Ala Arg
                325                 330                 335

Leu Ala Leu Lys Ile Leu Asn Leu Lys Ser Ser Glu Leu Ala Gln
            340                 345                 350

Val Gly Ala Ala Leu Gly Leu Ala Gln Asn Val Ala Ala Leu Arg Ala
        355                 360                 365

Leu Ala Ala Glu Gly Ile Gln Lys Gly His Met Ala Leu His Ser Arg
    370                 375                 380

Asn Ile Ala Lys Val Ala Gly Val Pro Asp Glu Leu Ile Glu Lys Val
385                 390                 395                 400

Ser Lys Lys Met Val Ala Asp Lys Lys Ile Arg Val Asp Tyr Ala Lys
                405                 410                 415

Glu Ile Phe Gln Lys Ile Lys Asp Gly Glu Asn Ile
            420                 425

<210> SEQ ID NO 36
<211> LENGTH: 1284
<212> TYPE: DNA
<213> ORGANISM: Artificial
<220> FEATURE:
<223> OTHER INFORMATION: mutated and/or codon-optimized sequence

<400> SEQUENCE: 36
atgatcatga aagacttcca ctccgatatt tccggtttct acaagctgtc catcgatgag     60
cgccagaagc ttttgagcaa gcttgtaaac ctgaacccgg aagatctgga aattcttaag    120
gaactgggct atttcacccc gactcaaatt gacaccctga tcgagaacgt tgtcggctcc    180
tatcaacttc ccttgggatt ggccttcaac tttcgcatca attctaagga ttacatcatc    240
cctatggtga tcgaagagcc atccgtggta gctgcagcat ccaatgcggc taagatggct    300
cgcaaacacg gcggttttca ctctgaagat gttcctccaa tcatgatctc acagattcaa    360
atcaccaaat tgaaagatat cgaggcagct aaagatgtcc tcgaggcgaa gaagcaggat    420
ttgctcaaga ttgccaacga acaagatccg ctgctgaaca acttggcgg tggcgcccag    480
aacatcgaaa tccacgaaat ccaaactaac aagggcaaga tgatcatcct ccatctgctc    540
gtaaacgttc tcgatgccat gggtgccaac atcgtcaata ccatggcgga ggctatctct    600
ccatacatcg aagagatctg cggtggcaag atctaccttc gcattgtttc caacctggca    660
acccaccgtg tggcgcgttc caaggcaacc ttcgataagg aaatgctggg cggcgaagag    720
gtggtggaag gcatcatgaa tgcatatgaa ttcgcgctgg cggaccccta ccgcgctacc    780
acccataaca agggtatcat gaatggtgtt gtggctttga ctctggcgac gggtaatgac    840
acccgcgcaa tcgagagcgg agcccactct tacgcatccc tttccggccg ttacctgccc    900
ctgaccaagt tgacgtaga ttctcaaggt aaccttgtgg gagaaatcga gattcctctt     960
gccctgggca ttatcggtgg tatgaccaag atccatccaa tggcccgtct ggctttgaag    1020
attcttaacc ttaaatcatc ttcagaactt gcacaggtag gtgcggcgct gggacttgcc    1080
caaaacgttg cagctctgcg cgcgctcgcc gctgaaggta tccagaaagg tcacatggca    1140
ctccactcac gtaatattgc aaaggtcgca ggcgtccctg acgaactgat tgaaaaagtg    1200
tctaaaaaga tggtcgccga taaaaagatt cgtgtggatt atgcaaagga aatcttccag    1260
aagatcaagg acggcgaaaa catt                                           1284

<210> SEQ ID NO 37
<211> LENGTH: 931
<212> TYPE: PRT
```

<213> ORGANISM: Cricetulus griseus

<400> SEQUENCE: 37

Met Thr Pro Asp Met Arg Lys Thr Gly Arg Cys Glu Ala Phe Leu Glu
1               5                   10                  15

Gln Arg Ser Ile Leu Leu Pro Asn Arg Phe Leu Phe Ser Gly His Pro
            20                  25                  30

His Ala Ala Thr Leu Thr Leu Pro Gln Glu Gly Pro Ser Gln Val Arg
        35                  40                  45

Phe Arg Gly Arg Gly Thr Pro Pro Ala Gly Ser Pro Ile Ala Arg Glu
    50                  55                  60

Gly Gly Val Leu Ala Gly Ala Pro His Gly Ser Gly Thr Asn Lys Lys
65                  70                  75                  80

Val Val Met Leu Glu Leu Asp Gln Leu Leu Val Gly Ser Ala Val Val
                85                  90                  95

Arg Asp Gly Ala Val Pro Val Leu Arg Pro Gly Ser Arg Asp Arg Val
            100                 105                 110

Ala Thr Met Leu Ser Arg Leu Phe Arg Met His Gly Leu Phe Val Ala
        115                 120                 125

Ser His Pro Trp Glu Val Ile Val Gly Thr Val Thr Leu Thr Ile Cys
    130                 135                 140

Met Met Ser Met Asn Met Phe Thr Gly Asn Asn Lys Ile Cys Gly Trp
145                 150                 155                 160

Asn Tyr Glu Cys Pro Lys Phe Glu Glu Asp Val Leu Ser Ser Asp Ile
                165                 170                 175

Ile Ile Leu Thr Ile Thr Arg Cys Ile Ala Ile Leu Tyr Ile Tyr Phe
            180                 185                 190

Gln Phe Gln Asn Leu Arg Gln Leu Gly Ser Lys Tyr Ile Leu Gly Ile
        195                 200                 205

Ala Gly Leu Phe Thr Ile Phe Ser Ser Phe Val Phe Ser Thr Val Val
    210                 215                 220

Ile His Phe Leu Asp Lys Glu Leu Thr Gly Leu Asn Glu Ala Leu Pro
225                 230                 235                 240

Phe Phe Leu Leu Leu Ile Asp Leu Ser Arg Ala Ser Ala Leu Ala Lys
                245                 250                 255

Phe Ala Leu Ser Ser Asn Ser Gln Asp Glu Val Arg Glu Asn Ile Ala
            260                 265                 270

Arg Gly Met Ala Ile Leu Gly Pro Thr Phe Thr Leu Asp Ala Leu Val
        275                 280                 285

Glu Cys Leu Val Ile Gly Val Gly Thr Met Ser Gly Val Arg Gln Leu
    290                 295                 300

Glu Ile Met Cys Cys Phe Gly Cys Met Ser Val Leu Ala Asn Tyr Phe
305                 310                 315                 320

Val Phe Met Thr Phe Phe Pro Ala Cys Val Ser Leu Val Leu Glu Leu
                325                 330                 335

Ser Arg Glu Ser Arg Glu Gly Arg Pro Ile Trp Gln Leu Ser His Phe
            340                 345                 350

Ala Arg Val Leu Glu Glu Glu Glu Asn Lys Pro Asn Pro Val Thr Gln
        355                 360                 365

Arg Val Lys Met Ile Met Ser Leu Gly Leu Val Leu Val His Ala His
    370                 375                 380

Ser Arg Trp Ile Ala Asp Pro Ser Pro Gln Asn Ser Thr Thr Glu His
385                 390                 395                 400

```
Ser Lys Val Ser Leu Gly Leu Asp Glu Asp Val Ser Lys Arg Ile Glu
            405                 410                 415

Pro Ser Val Ser Leu Trp Gln Phe Tyr Leu Ser Lys Met Ile Ser Met
        420                 425                 430

Asp Ile Glu Gln Val Val Thr Leu Ser Leu Ala Phe Leu Leu Ala Val
            435                 440                 445

Lys Tyr Ile Phe Phe Glu Gln Ala Glu Thr Glu Ser Thr Leu Ser Leu
        450                 455                 460

Lys Asn Pro Ile Thr Ser Pro Val Val Thr Pro Lys Lys Ala Pro Asp
465                 470                 475                 480

Asn Cys Cys Arg Arg Glu Pro Leu Leu Val Arg Arg Ser Glu Lys Leu
                485                 490                 495

Ser Ser Val Glu Glu Glu Pro Gly Val Ser Gln Asp Arg Lys Val Glu
            500                 505                 510

Val Ile Lys Pro Leu Val Val Glu Thr Glu Ser Ala Ser Arg Ala Thr
        515                 520                 525

Phe Val Leu Gly Ala Ser Gly Thr Ser Pro Pro Val Ala Ala Arg Thr
        530                 535                 540

Gln Glu Leu Glu Ile Glu Leu Pro Ser Glu Pro Arg Pro Asn Glu Glu
545                 550                 555                 560

Cys Leu Gln Ile Leu Glu Ser Ala Glu Lys Gly Ala Lys Phe Leu Ser
                565                 570                 575

Asp Ala Glu Ile Ile Gln Leu Val Asn Ala Lys His Ile Pro Ala Tyr
            580                 585                 590

Lys Leu Glu Thr Leu Met Glu Thr His Glu Arg Gly Val Ser Ile Arg
        595                 600                 605

Arg Gln Leu Leu Ser Thr Lys Leu Pro Glu Pro Ser Ser Leu Gln Tyr
        610                 615                 620

Leu Pro Tyr Arg Asp Tyr Asn Tyr Ser Leu Val Met Gly Ala Cys Cys
625                 630                 635                 640

Glu Asn Val Ile Gly Tyr Met Pro Ile Pro Val Gly Val Ala Gly Pro
                645                 650                 655

Leu Cys Leu Asp Gly Lys Glu Tyr Gln Val Pro Met Ala Thr Thr Glu
            660                 665                 670

Gly Cys Leu Val Ala Ser Thr Asn Arg Gly Cys Arg Ala Ile Gly Leu
        675                 680                 685

Gly Gly Gly Ala Ser Ser Arg Val Leu Ala Asp Gly Met Thr Arg Gly
        690                 695                 700

Pro Val Val Arg Leu Pro Arg Ala Cys Asp Ser Ala Glu Val Lys Ala
705                 710                 715                 720

Trp Leu Glu Thr Pro Glu Gly Phe Ala Val Ile Lys Asp Ala Phe Asp
                725                 730                 735

Ser Thr Ser Arg Phe Ala Arg Leu Gln Lys Leu His Val Thr Met Ala
            740                 745                 750

Gly Arg Asn Leu Tyr Ile Arg Phe Gln Ser Lys Thr Gly Asp Ala Met
        755                 760                 765

Gly Met Asn Met Ile Ser Lys Gly Thr Glu Lys Ala Leu Leu Lys Leu
        770                 775                 780

Gln Glu Phe Phe Pro Glu Met Gln Ile Leu Ala Val Ser Gly Asn Tyr
785                 790                 795                 800

Cys Thr Asp Lys Lys Pro Ala Ala Ile Asn Trp Ile Glu Gly Arg Gly
                805                 810                 815

Lys Thr Val Val Cys Glu Ala Val Ile Pro Ala Lys Val Val Arg Glu
```

```
              820                 825                 830
Val Leu Lys Thr Thr Thr Glu Ala Met Ile Asp Val Asn Ile Asn Lys
            835                 840                 845

Asn Leu Val Gly Ser Ala Met Ala Gly Ser Ile Gly Gly Tyr Asn Ala
        850                 855                 860

His Ala Ala Asn Ile Val Thr Ala Ile Tyr Ile Ala Cys Gly Gln Met
865                 870                 875                 880

Leu Gly Val Gln Gly Ala Cys Lys Asp Asn Pro Gly Glu Asn Ala Arg
                885                 890                 895

Gln Leu Ala Arg Ile Val Cys Gly Thr Val Met Ala Gly Glu Leu Ser
            900                 905                 910

Leu Met Ala Ala Leu Ala Ala Gly His Leu Val Arg Ser His Met Val
        915                 920                 925

His Asn Arg
    930

<210> SEQ ID NO 38
<211> LENGTH: 2793
<212> TYPE: DNA
<213> ORGANISM: Artificial
<220> FEATURE:
<223> OTHER INFORMATION: mutated and/or codon-optimized sequence

<400> SEQUENCE: 38
atgacccctg acatgcgcaa gactggccgc tgcgaggcat tcctggagca acgctccatc      60
ttgctcccta tcgcttcct cttttcagga cacccacacg cagcaacctt gacacttcct     120
caggaaggcc caagccaggt ccgctttcgc ggacgaggca cgccgcccgc cggaagcccc     180
atcgcacgcg aaggcggtgt cctcgcaggt gctcctcacg gctctggcac taataaaaaa     240
gtcgtgatgt tggaattgga ccagttgctg gtgggctctg ccgtcgtgcg tgacggtgct     300
gtacctgtgt tgcgtcctgg ctcacgcgac cgcgtcgcca cgatgctgtc tcgcttgttc     360
cgcatgcatg gacttttttgt ggcttctcac ccgtgggaag tgatcgtggg tacggtaaca     420
ctcaccatct gcatgatgtc catgaatatg ttcaccggta acaataaaat ttgtggctgg     480
aattatgagt gcccaaagtt cgaagaggac gtcttgtcct ctgatatcat catttttgacc     540 atcacccgtt gcatcgctat tctgtacatc tatttccagt ccaaaacct gcgtcaactg     600 ggttcaaagt acatccttgg tatcgcgggt cttttcacaa ttttttcgtc cttcgtgttc     660
agcactgtgg ttatccactt tttggacaag gaattgacag gacttaatga ggcgctccct     720
ttcttcctcc tgctgattga cctttcccga gcgtcagcat ggcgaaaatt tgcattgtcg     780
tctaattctc aagatgaagt ccgagagaac atcgctcgcg gtatggcgat cctgggtccg     840
accttcacgc tcgatgctct ggtagagtgc cttgtcatcg gtgtaggcac catgagcgga     900
gtccgccagt tggagattat gttgctttt ggttgtatgt ctgtgctcgc caattacttc     960
gtattcatga ctttttttcc tgcctgcgtg tctctcgtcc tcgaactctc ccgagagtcc    1020
cgcgagggcc gtccaatttg gcagctgtca cacttcgcac gagtcctcga ggaagaggaa    1080
aataagccaa accccagttac acagcgtgtt aagatgatca tgagcctggg cctggttctc    1140
gttcacgctc acagccgttg gatcgctgat ccgtctcccc aaaactccac gaccgaacac    1200
tccaaggttt ctcttggttt ggatgaagac gttcaaagc gcatcgagcc ctccgtttcc    1260
ctctggcagt tttacctgtc caagatgatt tcgatggata tcgagcaggt cgtgacccttt    1320 agcttggcgt tcctttttggc agttaagtac atcttcttcg agcaggcaga aacggagtct    1380
```

```
acattgtcac tcaagaaccc tatcacgtca ccagtggtga ccccaaaaaa agcacctgat    1440
aattgttgcc gccgtgaacc gctgcttgtt cgccgttccg agaagttgag cagcgtggaa    1500
gaggaaccgg gcgtctccca agaccgcaaa gttgaagtga ttaagccgct cgtcgtcgag    1560
acagaatccg cttcccgcgc tacttttgtc ttgggcgcat ctggaacatc ccctcctgtg    1620
gcggcacgta cacaggagtt ggagattgag ctgccatctg aaccacgtcc caacgaagag    1680
tgcttgcaga tcttggagtc cgccgaaaag ggcgccaagt tcctctctga cgccgaaatc    1740
atccagcttg tgaatgccaa acacattcca gcatacaaat tggaaacgct gatggaaact    1800
catgaacgcg cgtctctat tcgccgacag cttcttagca ctaaactccc ggagccatcg    1860
tcgttgcagt atctcccata tcgagactac aactactcct tggtgatggg agcatgctgt    1920
gaaaacgtca tcggctacat gccgatccca gtaggcgtgg caggtccact ttgccttgat    1980
ggcaaggagt accaggtccc catggctacc acggagggct gccttgttgc atccacaaac    2040
cgtggctgtc gcgcgatcgg tcttggcgga ggagcatcat cgcgtgtact tgctgatggt    2100
atgacccgcg gccctgtagt tcgtctcccc cgcgcgtgcg atagcgctga ggttaaggcc    2160
tggttggaaa cacctgaggg atttgcagtg atcaaggacg cctttgactc tacctcacgc    2220
ttcgcgcgct tgcagaagct ccacgttacc atggcgggtc gcaacttgta tatccgcttc    2280
cagtccaaaa ccggagacgc tatgggaatg aatatgatct ccaaaggtac cgaaaaagct    2340
ctcctgaagc tccaggaatt cttcccagaa atgcaaattc tcgcggttag cggcaactat    2400
tgcaccgaca agaagccagc agccatcaac tggatcgagg gtcgaggtaa gaccgttgtc    2460
tgcgaggccg ttattccggc taaggtggtc cgtgaggtgc tgaagaccac gacggaagcg    2520
atgatcgatg tgaacatcaa caagaacctc gtcggctccg cgatggcggg ttccattggc    2580
ggttacaatg ctcacgctgc taatatcgta actgctattt atattgcttg cggtcagatg    2640
cttggcgttc aaggtgcatg caaggataac ccaggtgaga acgcccgtca gttggcacgt    2700
atcgtatgcg gcaccgtgat ggcaggcgaa cttttccctta tggccgcact ggcggctggt    2760
cacctcgtcc gttcacacat ggttcataac cgc                               2793
```

<210> SEQ ID NO 39  
<211> LENGTH: 428  
<212> TYPE: PRT  
<213> ORGANISM: Pyrodictium occultum

<400> SEQUENCE: 39

```
Met Gly Glu Glu Arg Ser Leu Arg Asp Arg Leu Glu Glu Val Val Gln
1               5                  10                  15

Gly Ile Val Glu Gly Arg Ile Arg Leu His Glu Ala Asp Arg Leu Leu
            20                  25                  30

Gly Asn Ala Asn Ala Ala Ala Leu Ala Arg Arg Leu Ala Leu Glu Arg
        35                  40                  45

Met Leu Gly Val Gly Leu Ser Ser Ile Gly Ser Thr Ile Leu Asp Phe
    50                  55                  60

Glu Glu Leu Val Gly Arg Asn Ile Glu Asn Pro Ile Gly Ala Val Gln
65                  70                  75                  80

Ile Pro Leu Gly Val Ala Gly Pro Leu Arg Val His Gly Glu Tyr Ala
                85                  90                  95

Arg Gly Asp Phe Tyr Ile Pro Leu Ala Thr Thr Glu Gly Ala Leu Val
            100                 105                 110

Ala Ser Val Asn Arg Gly Ala Lys Ala Val Thr Leu Ser Gly Gly Ala
        115                 120                 125
```

```
Arg Ala Arg Val Leu Arg Asp Gly Met Ala Arg Ala Pro Val Phe Trp
    130                 135                 140

Thr Pro Gly Val Glu Glu Ala Ala Arg Leu Ala Glu Trp Val Gln Glu
145                 150                 155                 160

His Met Glu Glu Val Arg Arg Glu Ala Glu Ser Thr Thr Arg His Gly
                165                 170                 175

Arg Leu Leu Glu Ile Gln Pro Phe Ile Ala Gly Asn Ile Val Trp Leu
            180                 185                 190

Arg Phe Val Tyr Ser Thr Gly Asp Ala Met Gly Met Asn Met Ala Thr
            195                 200                 205

Ile Ala Thr Asp Lys Ala Ala Glu Trp Ile Leu Arg Asn Tyr Pro Gly
    210                 215                 220

Glu Ala Lys Leu Ile Ala Ile Ser Gly Asn Leu Cys Thr Asp Lys Lys
225                 230                 235                 240

Pro Ala Leu Leu Asn Ala Ile Leu Gly Arg Gly Lys Thr Val Val Ala
                245                 250                 255

Glu Ala Thr Ile Lys Arg Asp Ile Ala Leu Arg Val Leu Lys Ala Ala
                260                 265                 270

Pro Glu Asp Ile Asp Thr Val Asn Arg Val Lys Asn Leu Leu Gly Ser
            275                 280                 285

Ala Arg Ala Gly Ser Pro Ser Phe Asn Ala His Tyr Ala Asn Ile Ile
    290                 295                 300

Ala Ala Ile Phe Ile Ala Thr Gly Gln Asp Val Ala Gln Val Val Glu
305                 310                 315                 320

Ser Ser Met Gly Tyr Thr Trp Thr Glu Val Arg Asn Gly Asp Leu Tyr
                325                 330                 335

Ile Ser Val Thr Leu Pro Ser Leu Glu Leu Gly Thr Val Gly Gly Gly
            340                 345                 350

Thr Arg Leu Pro Thr Gln Arg Glu Ala Leu Ala Leu Leu Gly Ala Ala
    355                 360                 365

Gly Gly Gly Asn Pro Pro Gly Ala Asn Ala Lys Lys Leu Ala Glu Val
370                 375                 380

Thr Ala Ala Ala Val Leu Ala Gly Glu Leu Asn Leu Leu Ala Ala Leu
385                 390                 395                 400

Ala Ala Asn Glu Leu Ala Arg Ala His Arg Leu Leu Gly Arg Gly Glu
                405                 410                 415

Ala Lys Thr Gly Asn Lys Asn Pro Thr Asn His Gly
    420                 425

<210> SEQ ID NO 40
<211> LENGTH: 1284
<212> TYPE: DNA
<213> ORGANISM: Artificial
<220> FEATURE:
<223> OTHER INFORMATION: mutated and/or codon-optimized sequence

<400> SEQUENCE: 40
atgggagaag agcgctctct gcgcgatcgc ctggaagagg tagtccaagg catcgtagag      60
ggtcgcatcc gcctgcatga agcagaccgc ctgctgggaa atgcaaatgc agcagcgttg     120
gctcgccgcc tggcactgga acgcatgctt ggagttggct tgtccagcat ggatcgacg     180 attttggact tcgaagagct tgttggccgt aatattgaaa accgatcgg tgccgtgcag     240 atccccctcg gtgtcgcggg cccgctcgcg gtccacggcg agtatgctcg cggtgacttc     300
tacattccac ttgctaccac tgaaggcgca cttgtggcat cagtgaatcg cggcgcaaag     360
```

-continued

```
gctgtgacgc tctctggcgg tgcacgcgcc cgcgtacttc gagatggcat ggcccgagca      420
ccggtgtttt ggactcctgg tgtggaagaa gcagcgcgac tcgcggaatg ggtgcaagag      480
catatggaag aagtccgtcg tgaagcagag tccacgacgc gtcacggacg tctcctcgaa      540
atccagccgt tcatcgctgg caacatcgtt tggcttcgct tcgtctattc taccggcgac      600
gccatgggca tgaacatggc aaccattgca accgataagg cggcagagtg gatcctgcgc      660
aattacccgg gagaagcgaa actcatcgca atctccggca acctctgcac agacaagaag      720
cctgctctct tgaacgctat tctgggccgc ggtaaaaccg tggtcgcgga ggcaactatt      780
aagcgcgaca tcgcattgcg cgtgcttaaa gcagctcccg aggacatcga tactgtgaac      840
cgtgtgaaaa atcttttggg cagcgctcgc gccggttcac cttcgtttaa cgcacactat      900
gctaacatca ttgcagcaat cttcatcgcg acaggacagg atgtggcgca ggtagtggag      960
tccagcatgg gatacacctg gaccgaagtt cgcaatggag accttttacat ttccgtgacg    1020 ctgcccctcct tggaactggg caccgttggc ggtggtaccc gcctgcccac acagcgcgag    1080
gcactcgccc tcctgggagc agcaggcggt ggtaacccac cgggtgccaa tgcgaagaag    1140
ttggcagagg ttacagccgc agccgtgctg gccggcgaac tcaatttgtt ggccgctctt    1200
gcagcgaatg aactcgcccg cgcgcaccgt ttgctgggtc gtggcgaagc gaagactggt    1260
aataaaaatc caaccaacca cggt                                            1284
```

<210> SEQ ID NO 41
<211> LENGTH: 352
<212> TYPE: PRT
<213> ORGANISM: Artificial
<220> FEATURE:
<223> OTHER INFORMATION: mutated and/or codon-optimized sequence

<400> SEQUENCE: 41

```
Met Ala Ser Glu Lys Glu Ile Arg Arg Glu Arg Phe Leu Asn Val Phe
1               5                   10                  15

Pro Lys Leu Val Glu Glu Leu Asn Ala Ser Leu Leu Ala Tyr Gly Met
                20                  25                  30

Pro Lys Glu Ala Cys Asp Trp Tyr Ala His Ser Leu Asn Tyr Asn Thr
            35                  40                  45

Pro Gly Gly Lys Leu Asn Arg Gly Leu Ser Val Val Asp Thr Tyr Ala
        50                  55                  60

Ile Leu Ser Asn Lys Thr Val Glu Gln Leu Gly Gln Glu Glu Tyr Glu
65                  70                  75                  80

Lys Val Ala Ile Leu Gly Trp Cys Ile Glu Leu Leu Gln Ala Tyr Phe
                85                  90                  95

Leu Val Ala Asp Asp Met Met Asp Lys Ser Ile Thr Arg Arg Gly Gln
                100                 105                 110

Pro Cys Trp Tyr Lys Val Pro Glu Val Gly Glu Ile Ala Ile Asn Asp
            115                 120                 125

Ala Phe Met Leu Glu Ala Ala Ile Tyr Lys Leu Leu Lys Ser His Phe
        130                 135                 140

Arg Asn Glu Lys Tyr Tyr Ile Asp Ile Thr Glu Leu Phe His Glu Val
145                 150                 155                 160

Thr Phe Gln Thr Glu Leu Gly Gln Leu Met Asp Leu Ile Thr Ala Pro
                165                 170                 175

Glu Asp Lys Val Asp Leu Ser Lys Phe Ser Leu Lys Lys His Ser Phe
            180                 185                 190
```

```
Ile Val Thr Phe Gly Thr Ala Tyr Tyr Ser Phe Tyr Leu Pro Val Ala
        195                 200                 205

Leu Ala Met Tyr Val Ala Gly Ile Thr Asp Glu Lys Asp Leu Lys Gln
    210                 215                 220

Ala Arg Asp Val Leu Ile Pro Leu Gly Glu Tyr Phe Gln Ile Gln Asp
225                 230                 235                 240

Asp Tyr Leu Asp Cys Phe Gly Thr Pro Glu Gln Ile Gly Lys Ile Gly
                245                 250                 255

Thr Asp Ile Gln Asp Asn Lys Cys Ser Trp Val Ile Asn Lys Ala Leu
            260                 265                 270

Glu Leu Ala Ser Ala Glu Gln Arg Lys Thr Leu Asp Glu Asn Tyr Gly
        275                 280                 285

Lys Lys Asp Ser Val Ala Glu Ala Lys Cys Lys Lys Ile Phe Asn Asp
    290                 295                 300

Leu Lys Ile Glu Gln Leu Tyr His Glu Tyr Glu Ser Ile Ala Lys
305                 310                 315                 320

Asp Leu Lys Ala Lys Ile Ser Gln Val Asp Glu Ser Arg Gly Phe Lys
                325                 330                 335

Ala Asp Val Leu Thr Ala Phe Leu Asn Lys Val Tyr Lys Arg Ser Lys
            340                 345                 350
```

<210> SEQ ID NO 42
<211> LENGTH: 1056
<212> TYPE: DNA
<213> ORGANISM: Artificial
<220> FEATURE:
<223> OTHER INFORMATION: mutated and/or codon-optimized sequence

<400> SEQUENCE: 42

```
atggcgtcgg aaaaagaaat ccgccgcgag cgcttcctga atgtgtttcc aaagctggtc      60
gaggaattga acgcttcgct gcttgcgtat ggcatgccga agaggcgtg cgattggtac     120
gcacattccc tgaactataa cacccaggc ggtaaactca accgcggtct gtccgttgta     180
gatacatatg ccattcttag caacaagacc gtagaacagt gggacaaga ggaatatgaa     240
aaggtggcta tcttgggctg tgtatcgaa ctgttgcaag cctacttcct ggtcgccgat     300
gatatgatgg ataagtccat cacgacgt ggacagccat gttggtacaa ggtccctgaa     360
gtcggcgaaa tcgctatcaa cgacgcattc atgctcgagg cagcaattta caaactttg      420
aaaagccatt ccgaaacga gaagtattac atcgacatta ccgagctctt ccatgaagtc     480
accttccaga ccgaactcgg ccaattgatg gatctgatta ccgccccga ggacaaggtc     540
gatctttcca aattcagcct gaagaaacat tccttcatcg taacctttgg tacagcatac     600
tattcattct atcttcctgt ggcactcgca atgtacgtag ccggtatcac ggatgaaaag     660
gatctgaaac aagcacgcga cgtactcatt cccctgggtg agtactttca gattcaagat     720
gactacctcg attgcttcgg cacgcctgaa caaatcggca aaatcggtac tgacatccag     780
gataataaat gctcctgggt gatcaataag gccctcgagt tggcgtcagc cgagcagcgc     840
aagactctgg acgaaaatta cggtaaaaa gattcagttg ccgaggcaaa gtgcaaaaag     900
atctttaacg atcttaagat tgaacagctt taccacgaat acgaagaaag cattgctaag     960
gatctgaaag ctaagatttc tcaggtcgat gaatcacgcg gattcaaggc cgatgtgctc    1020
actgctttcc tgaacaaggt ctacaagcgc tcaaaa                               1056
```

<210> SEQ ID NO 43
<211> LENGTH: 296

<212> TYPE: PRT
<213> ORGANISM: Abies grandis

<400> SEQUENCE: 43

```
Met Phe Asp Phe Asn Lys Tyr Met Asp Ser Lys Ala Met Thr Val Asn
1               5                   10                  15

Glu Ala Leu Asn Lys Ala Ile Pro Leu Arg Tyr Pro Gln Lys Ile Tyr
            20                  25                  30

Glu Ser Met Arg Tyr Ser Leu Leu Ala Gly Gly Lys Arg Val Arg Pro
        35                  40                  45

Val Leu Cys Ile Ala Ala Cys Glu Leu Val Gly Gly Thr Glu Glu Leu
    50                  55                  60

Ala Ile Pro Thr Ala Cys Ala Ile Glu Met Ile His Thr Met Ser Leu
65                  70                  75                  80

Met His Asp Asp Leu Pro Cys Ile Asp Asn Asp Leu Arg Arg Gly
                85                  90                  95

Lys Pro Thr Asn His Lys Ile Phe Gly Glu Asp Thr Ala Val Thr Ala
                100                 105                 110

Gly Asn Ala Leu His Ser Tyr Ala Phe Glu His Ile Ala Val Ser Thr
            115                 120                 125

Ser Lys Thr Val Gly Ala Asp Arg Ile Leu Arg Met Val Ser Glu Leu
        130                 135                 140

Gly Arg Ala Thr Gly Ser Glu Gly Val Met Gly Gln Met Val Asp
145                 150                 155                 160

Ile Ala Ser Glu Gly Asp Pro Ser Ile Asp Leu Gln Thr Leu Glu Trp
                165                 170                 175

Ile His Ile His Lys Thr Ala Met Leu Leu Glu Cys Ser Val Val Cys
            180                 185                 190

Gly Ala Ile Ile Gly Gly Ala Ser Glu Ile Val Ile Glu Arg Ala Arg
        195                 200                 205

Arg Tyr Ala Arg Cys Val Gly Leu Leu Phe Gln Val Val Asp Asp Ile
    210                 215                 220

Leu Asp Val Thr Lys Ser Ser Asp Glu Leu Gly Lys Thr Ala Gly Lys
225                 230                 235                 240

Asp Leu Ile Ser Asp Lys Ala Thr Tyr Pro Lys Leu Met Gly Leu Glu
                245                 250                 255

Lys Ala Lys Glu Phe Ser Asp Glu Leu Leu Asn Arg Ala Lys Gly Glu
            260                 265                 270

Leu Ser Cys Phe Asp Pro Val Lys Ala Ala Pro Leu Leu Gly Leu Ala
        275                 280                 285

Asp Tyr Val Ala Phe Arg Gln Asn
    290                 295
```

<210> SEQ ID NO 44
<211> LENGTH: 888
<212> TYPE: DNA
<213> ORGANISM: Artificial
<220> FEATURE:
<223> OTHER INFORMATION: mutated and/or codon-optimized sequence

<400> SEQUENCE: 44

```
atgttcgact tcaacaaata catggacagc aaggcaatga ccgtgaacga ggcgctgaat      60
aaagctattc ctttgcgtta tccgcagaag atctacgaat ccatgcgata ctctttgttg     120
gcaggtggta agcgagtgcg ccccgtgctt tgcattgcgg cttgcgagct ggtcggtggt     180
actgaggaac tggcgatccc aaccgcttgt gctatcgaga tgattcacac gatgtccctt     240
```

-continued

```
atgcacgatg acctgccctg tatcgacaac gatgatttgc gccgaggcaa gccaacaaat    300
cataagatct tcggcgagga caccgccgtc actgccggca atgctctgca ctcgtatgcc    360
ttcgagcaca ttgccgtgtc tacttccaaa acggtgggtg cagatcgcat tctgcgcatg    420
gtatccgagt tgggtcgcgc aactggctcg gagggcgtca tgggtggtca aatggtcgac    480
atcgcatctg aaggcgatcc atcgatcgac ctgcagacat ggaatggat ccacatccac      540 aagactgcga tgcttttgga atgttccgtg gtgtgcggag ctattattgg cggagcatct    600
gagatcgtga tcgagcgcgc tcgccgttat gctcgttgcg tgggtttgct gtttcaggtc    660
gtggacgaca ttctcgatgt caccaaatcc tccgatgagt tgggtaaaac tgccggcaaa    720
gacttgattt ctgacaaggc gacctacccc aagcttatgg gtctcgaaaa agccaaggag    780
ttctcagatg aactcctcaa ccgcgcaaag ggagaactct catgctttga tccagtgaag    840
gcagccccat tgcttggttt ggctgattac gtggccttcc gccagaat                 888
```

<210> SEQ ID NO 45
<211> LENGTH: 297
<212> TYPE: PRT
<213> ORGANISM: Picea abies

<400> SEQUENCE: 45

```
Met Glu Phe Asp Phe Asp Lys Tyr Met His Ser Lys Ala Ile Ala Val
1               5                   10                  15

Asn Glu Ala Leu Asp Lys Val Ile Pro Pro Arg Tyr Pro Gln Lys Ile
                20                  25                  30

Tyr Glu Ser Met Arg Tyr Ser Leu Leu Ala Gly Gly Lys Arg Val Arg
            35                  40                  45

Pro Ile Leu Cys Ile Ala Ala Cys Glu Leu Met Gly Gly Thr Glu Glu
        50                  55                  60

Leu Ala Met Pro Thr Ala Cys Ala Ile Glu Met Ile His Thr Met Ser
65                  70                  75                  80

Leu Ile His Asp Asp Leu Pro Tyr Ile Asp Asn Asp Leu Arg Arg
                85                  90                  95

Gly Lys Pro Thr Asn His Lys Val Phe Gly Glu Asp Thr Ala Ile Ile
                100                 105                 110

Ala Gly Asp Ala Leu Leu Ser Leu Ala Phe Glu His Val Ala Val Ser
            115                 120                 125

Thr Ser Arg Thr Leu Gly Thr Asp Ile Ile Leu Arg Leu Leu Ser Glu
130                 135                 140

Ile Gly Arg Ala Thr Gly Ser Glu Gly Val Met Gly Gly Gln Val Val
145                 150                 155                 160

Asp Ile Glu Ser Glu Gly Asp Pro Ser Ile Asp Leu Glu Thr Leu Glu
                165                 170                 175

Trp Val His Ile His Lys Thr Ala Val Leu Leu Glu Cys Ser Val Val
            180                 185                 190

Cys Gly Ala Ile Met Gly Gly Ala Ser Glu Asp Ile Glu Arg Ala
        195                 200                 205

Arg Arg Tyr Ala Arg Cys Val Gly Leu Leu Phe Gln Val Val Asp Asp
    210                 215                 220

Ile Leu Asp Val Ser Gln Ser Ser Glu Glu Leu Gly Lys Thr Ala Gly
225                 230                 235                 240

Lys Asp Leu Ile Ser Asp Lys Ala Thr Tyr Pro Lys Leu Met Gly Leu
                245                 250                 255
```

Glu Lys Ala Lys Glu Phe Ala Asp Glu Leu Leu Asn Arg Gly Lys Gln
            260                 265                 270

Glu Leu Ser Cys Phe Asp Pro Thr Lys Ala Ala Pro Leu Phe Ala Leu
        275                 280                 285

Ala Asp Tyr Ile Ala Ser Arg Gln Asn
        290                 295

<210> SEQ ID NO 46
<211> LENGTH: 891
<212> TYPE: DNA
<213> ORGANISM: Artificial
<220> FEATURE:
<223> OTHER INFORMATION: mutated and/or codon-optimized sequence

<400> SEQUENCE: 46
atggaatttg atttcgataa gtacatgcac agcaaagcaa ttgccgtcaa cgaggctctc      60
gataaagtta tcccacctcg ttacccacag aaaatctacg aaagcatgcg ctattccctg     120
ctggcaggcg gcaaacgcgt acgcccaatc tctgcatcg cggcctgcga acttatgggc      180
ggcaccgagg agctcgctat gccaaccgca tgcgcgattg agatgatcca ccatgagc      240
cttattcacg atgatctgcc atatatcgac aacgacgatt tgcgccgtgg aaagcctacc     300
aaccacaaag tcttcggaga ggacaccgcc atcattgctg gcgacgctct gctgtccctg     360
gcttttgagc acgttgcagt cagcacctcc cgcacgctcg gcacggatat tatcctgcgc     420
ctcctcagcg aaatcggtcg cgctaccggt tccgaaggtg tgatgggcgg tcaggtggtg     480
gatatcgaat ctgaaggcga tcccagcatc gaccttgaaa cgctggaatg ggtccatatc     540
cataagaccg cggttctgct ggaatgctct gttgtttgcg gtgcaatcat gggcggcgca     600
tcagaggatg acatcgagcg cgcacgtcgc tacgctcgtt gcgtaggctt gttgtttcaa     660
gtcgtggacg atatcctcga tgtatcccag tcttccgaag agctgggtaa gactgcgggc     720
aaggatctga tcagcgataa agccaccta ccaaaactta tgggtcttga aaagcgaag     780
gaattcgctg acgaactgct gaaccgcggc aagcaggagc tgtcctgctt tgatccaacc     840
aaagccgcac cgctcttcgc tctggcagat tacattgcga gccgtcaaa c               891

<210> SEQ ID NO 47
<211> LENGTH: 355
<212> TYPE: PRT
<213> ORGANISM: Artificial
<220> FEATURE:
<223> OTHER INFORMATION: mutated and/or codon-optimized sequence

<400> SEQUENCE: 47

Met Thr Pro Asp Val Thr Asn Asp Ala Ser Gln Glu Thr Val Asp Leu
1               5                   10                  15

Val Arg Arg Thr Ser Ala Asp Leu Leu Arg Arg Val Glu Ala Arg Ile
            20                  25                  30

Gln Ser Leu Leu Ser Ala Gly His Asp Thr Trp Ala Ala Val Asp Glu
        35                  40                  45

Arg Ala Val Val Pro Ile Asp Ala Leu Ala Glu Leu Met Ala Ser Gly
    50                  55                  60

Gly Lys Arg Ile Arg Pro Ala Phe Cys Ile Ala Gly His Leu Ala Ala
65                  70                  75                  80

Gly Gly Asp Pro Asp Asp Ser Gly Val Val Ala Ala Gly Ala Ala Leu
                85                  90                  95

Glu Met Leu His Ala Ser Leu Leu Val His Asp Asp Ile Leu Asp Asp
            100                 105                 110

Ser Ser Gln Arg Arg Gly Leu Pro Thr Val His Ala Lys His Thr Ala
        115                 120                 125

Leu His Gln Asp Leu Gly Trp Gln Gly Glu Ser Arg Arg Phe Gly Glu
    130                 135                 140

Gly Val Gly Leu Leu Val Gly Gly Leu Ala Leu Thr Tyr Ala Asp Glu
145                 150                 155                 160

Leu Met Cys Glu Ala Pro Ala Thr Ala Ile Ala Glu Trp Asn Lys Leu
                165                 170                 175

Arg Ser Glu Val Leu Ile Gly Gln Tyr Met Asp Val Val Ala Ala Ala
            180                 185                 190

Glu Phe Ser Val Asp Pro Arg Leu Ser Arg Leu Ile Ala Val Ile Lys
        195                 200                 205

Ser Gly Arg Tyr Thr Ile His Arg Pro Leu Val Ile Gly Ala Asn Val
    210                 215                 220

Ala Gly Arg Thr Asp Leu Asp Ala Ala Phe Ala Glu Tyr Gly Glu Ala
225                 230                 235                 240

Val Gly Glu Ala Phe Gln Leu Arg Asp Asp Leu Leu Asp Ala Phe Gly
                245                 250                 255

Asp Ser Ala Ala Thr Gly Lys Pro Ala Gly Leu Asp Phe Thr Gln His
            260                 265                 270

Lys Met Thr Leu Leu Leu Gly Trp Ala Met Gln Arg Asp Glu Ser Ile
        275                 280                 285

Arg Ala Leu Ile Thr Glu Pro Gly His Ser Ala Asp Asp Val Arg Arg
    290                 295                 300

His Leu Leu Asp Thr Lys Val Pro Asp Asp Val Glu Gln His Ile Ala
305                 310                 315                 320

Gly Leu Val Glu Arg Gly Cys Lys Ala Ile Thr Asp Ala Pro Ile Ala
                325                 330                 335

Pro Val Trp Arg Glu Glu Leu Met Glu Met Ala Asn Arg Val Ala Tyr
            340                 345                 350

Arg Asp Ala
        355

<210> SEQ ID NO 48
<211> LENGTH: 1065
<212> TYPE: DNA
<213> ORGANISM: Artificial
<220> FEATURE:
<223> OTHER INFORMATION: mutated and/or codon-optimized sequence

<400> SEQUENCE: 48
atgaccccag acgtgaccaa cgatgcctca caagaaaccg tcgatctggt tcgccgaacc      60
tctgcggatc tcctccgccg cgttgaagct cgcattcagt cccttctctc cgcgggccac     120
gatacctggg ctgccgtcga tgagcgagcc gttgttccaa ttgatgccct cgcagagctc     180
atggcttccg gtggaaaacg catccgcccg gcattctgca ttgccggcca cttggccgcc     240
ggtggagatc cagacgattc cggcgtcgtc gcggctggcg ccgcgctcga gatgcttcac     300
gcatcccttc tggtgcacga cgatatcctg gatgattcct ctcagcgccg cggcctccca     360
accgtccacg caaagcacac ggccctgcat caggatttgg gatggcaagg agagtcacgt     420
cgctttggag agggtgtggg actcttggtt ggtggccttg cacttaccta cgccgacgaa     480
ttgatgtgcg aagcgccagc aacagccatt gccgagtgga acaagctgcg atccgaagtg     540
cttatcggcc agtacatgga tgtggtcgca gctgcggagt ttagcgtgga cccacgcctt     600

-continued

```
tctcgcttga tcgctgtcat taaatcgggc cgctacacta ttcaccgtcc actggtcatt    660
ggtgctaacg tcgcgggccg caccgacttg gacgctgcgt tcgctgaata cggtgaagct    720
gtgggcgagg ctttccaact gcgcgatgac ctcctcgatg catttggtga tagcgccgca    780
accggtaagc cagcaggtct tgactttacc caacataaga tgaccctctt gttgggctgg    840
gcaatgcaac gcgacgagtc cattcgagcc ctcattaccg agcccggcca ctcggccgat    900
gacgttcgtc gccaccctgct tgacaccaag gtgccagacg atgttgagca gcacattgcc    960
ggtttggtgg agcgaggatg caaagctatc acagacgcac caattgcgcc cgtgtggcgc    1020
gaagaactta tggaaatggc gaatcgcgtt gcatatcgcg atgct    1065
```

```
<210> SEQ ID NO 49
<211> LENGTH: 415
<212> TYPE: PRT
<213> ORGANISM: Solanum lycopersicum

<400> SEQUENCE: 49
```

| | | | | | | | | | | | | | | |
|---|---|---|---|---|---|---|---|---|---|---|---|---|---|---|
| Met | Ile | Phe | Ser | Lys | Gly | Leu | Ala | Gln | Ile | Ser | Arg | Asn | Arg | Phe | Ser |
| 1 | | | | 5 | | | | | 10 | | | | | 15 | |
| Arg | Cys | Arg | Trp | Leu | Phe | Ser | Leu | Arg | Pro | Ile | Pro | Gln | Leu | His | Gln |
| | | | 20 | | | | | 25 | | | | | 30 | | |
| Ser | Asn | His | Ile | His | Asp | Pro | Pro | Lys | Val | Leu | Gly | Cys | Arg | Val | Ile |
| | | | 35 | | | | | 40 | | | | | 45 | | |
| His | Ser | Trp | Val | Ser | Asn | Ala | Leu | Ser | Gly | Ile | Gly | Gln | Gln | Ile | His |
| | 50 | | | | | 55 | | | | | 60 | | | | |
| Gln | Gln | Ser | Thr | Ala | Val | Ala | Glu | Glu | Val | Asp | Pro | Phe | Ser | Leu |
| 65 | | | | | 70 | | | | | 75 | | | | | 80 |
| Val | Ala | Asp | Glu | Leu | Ser | Leu | Leu | Thr | Asn | Arg | Leu | Arg | Ser | Met | Val |
| | | | | 85 | | | | | 90 | | | | | 95 | |
| Val | Ala | Glu | Val | Pro | Lys | Leu | Ala | Ser | Ala | Ala | Glu | Tyr | Phe | Phe | Lys |
| | | | 100 | | | | | 105 | | | | | 110 | | |
| Leu | Gly | Val | Glu | Gly | Lys | Arg | Phe | Arg | Pro | Thr | Val | Leu | Leu | Leu | Met |
| | | | 115 | | | | | 120 | | | | | 125 | | |
| Ala | Thr | Ala | Leu | Asn | Val | Gln | Ile | Pro | Arg | Ser | Ala | Pro | Gln | Val | Asp |
| | 130 | | | | | 135 | | | | | 140 | | | | |
| Val | Asp | Ser | Phe | Ser | Gly | Asp | Leu | Arg | Thr | Arg | Gln | Gln | Cys | Ile | Ala |
| 145 | | | | | 150 | | | | | 155 | | | | | 160 |
| Glu | Ile | Thr | Glu | Met | Ile | His | Val | Ala | Ser | Leu | Leu | His | Asp | Asp | Val |
| | | | | 165 | | | | | 170 | | | | | 175 | |
| Leu | Asp | Asp | Ala | Asp | Thr | Arg | Arg | Gly | Ile | Gly | Ser | Leu | Asn | Phe | Val |
| | | | 180 | | | | | 185 | | | | | 190 | | |
| Met | Gly | Asn | Lys | Leu | Ala | Val | Leu | Ala | Gly | Asp | Phe | Leu | Leu | Ser | Arg |
| | | | 195 | | | | | 200 | | | | | 205 | | |
| Ala | Cys | Val | Ala | Leu | Ala | Ser | Leu | Lys | Asn | Thr | Glu | Val | Val | Cys | Leu |
| | 210 | | | | | 215 | | | | | 220 | | | | |
| Leu | Ala | Thr | Val | Val | Glu | His | Leu | Val | Thr | Gly | Glu | Thr | Met | Gln | Met |
| 225 | | | | | 230 | | | | | 235 | | | | | 240 |
| Thr | Thr | Ser | Ser | Asp | Glu | Arg | Cys | Ser | Met | Glu | Tyr | Tyr | Met | Gln | Lys |
| | | | | 245 | | | | | 250 | | | | | 255 | |
| Thr | Tyr | Tyr | Lys | Thr | Ala | Ser | Leu | Ile | Ser | Asn | Ser | Cys | Lys | Ala | Ile |
| | | | 260 | | | | | 265 | | | | | 270 | | |
| Ala | Leu | Leu | Ala | Gly | His | Ser | Ala | Glu | Val | Ser | Val | Leu | Ala | Phe | Asp |
| | | | 275 | | | | | 280 | | | | | 285 | | |
| Tyr | Gly | Lys | Asn | Leu | Gly | Leu | Ala | Phe | Gln | Leu | Ile | Asp | Asp | Val | Leu |

```
                290                 295                 300
Asp Phe Thr Gly Thr Ser Ala Thr Leu Gly Lys Gly Ser Leu Ser Asp
305                 310                 315                 320

Ile Arg His Gly Ile Val Thr Ala Pro Ile Leu Tyr Ala Met Glu Glu
                325                 330                 335

Phe Pro Gln Leu Arg Thr Leu Val Asp Arg Gly Phe Asp Asp Pro Val
            340                 345                 350

Asn Val Glu Ile Ala Leu Asp Tyr Leu Gly Lys Ser Arg Gly Ile Gln
        355                 360                 365

Arg Thr Arg Glu Leu Ala Arg Lys His Ala Ser Leu Ala Ser Ala Ala
    370                 375                 380

Ile Asp Ser Leu Pro Glu Ser Asp Asp Glu Glu Val Gln Arg Ser Arg
385                 390                 395                 400

Arg Ala Leu Val Glu Leu Thr His Arg Val Ile Thr Arg Thr Lys
                405                 410                 415

<210> SEQ ID NO 50
<211> LENGTH: 1245
<212> TYPE: DNA
<213> ORGANISM: Artificial
<220> FEATURE:
<223> OTHER INFORMATION: mutated and/or codon-optimized sequence

<400> SEQUENCE: 50
atgattttca gcaaaggatt ggcgcaaatt tctcgcaacc gttttttcacg ctgccgttgg      60 ctgttttcgc tgcgaccaat ccctcagctc caccagagca atcatattca tgatccaccc     120
aaggttcttg gttgccgagt aatccacagc tgggtttcca atgcgctgtc cggtatcggc     180
cagcagatcc accagcagtc taccgcagtg gcggaggaac aagtggatcc tttctccctc     240
gtggctgatg aactctccct cctgaccaat cgattgcgct atggtcgt cgccgaagtc       300 cccaaattgg cttccgcggc ggagtacttt ttcaagttgg gcgtggaggg aaaacgcttc     360
cgaccaaccg tcttgttgct catggctact gcgctgaatg tccagatccc ccgctccgca     420
ccgcaagttg atgtggatag cttctcaggc gatcttcgta cccgacagca gtgtatcgcc     480
gagattaccg agatgatcca cgttgcttca ttgctccatg atgacgtgct tgatgatgct     540
gatacccgtc gaggcatcgg ctcactgaat ttcgttatgg caataagct tgctgttctc      600 gctggtgatt ttttgctgtc ccgcgcgtgc gtggcattgg cctctctgaa aaacaccgag     660
gtggtttgcc ttcttgcaac agttgttgag catcttgtaa ccggtgagac catgcagatg     720
accacctcgt ccgatgaacg atgcagcatg gagtactaca tgcaaaagac ctactataaa     780
acggcgtccc tgatctcgaa ctcttgtaaa gctattgcgc tcctggctgg ccactctgcg     840
gaagtttcgg tgttggcatt tgattacggt aaaaatctcg gcttggcttt ccaattgatc     900
gatgatgttc ttgatttcac tggaacttcc gcaaccttgg gcaaaggttc cctgtccgat     960
attcgccacg gcatcgtcac cgccccaatc ttgtatgcga tggaagagtt ccctcagctc    1020
cgtaccctcg ttgatcgtgg cttcgatgat ccggtaaacg tggaaattgc cctcgactac    1080
ttgggtaagt ctcgcggcat ccaacgcaca cgcgagcttg cacgtaaaca cgcgtctctc    1140
gcgagcgcgg cgatcgactc cctgccggaa tccgatgatg aagaggtgca gcgcagccgc    1200
cgtgcgcttg ttgaattgac tcaccgcgtt atcacccgta ctaag                    1245

<210> SEQ ID NO 51
<211> LENGTH: 420
<212> TYPE: PRT
```

<213> ORGANISM: Catharanthus roseus

<400> SEQUENCE: 51

```
Met Leu Phe Ser Arg Gly Leu Tyr Arg Ile Ala Arg Thr Ser Leu Asn
1               5                   10                  15
Arg Ser Arg Leu Leu Tyr Pro Leu Gln Ser Gln Ser Pro Glu Leu Leu
            20                  25                  30
Gln Ser Phe Gln Phe Arg Ser Pro Ile Gly Ser Ser Gln Lys Val Ser
        35                  40                  45
Gly Phe Arg Val Ile Tyr Ser Trp Val Ser Ser Ala Leu Ala Asn Val
50                  55                  60
Gly Gln Gln Val Gln Arg Gln Ser Asn Ser Val Ala Glu Glu Pro Leu
65                  70                  75                  80
Asp Pro Phe Ser Leu Val Ala Asp Glu Leu Ser Ile Leu Ala Asn Arg
                85                  90                  95
Leu Arg Ser Met Val Val Ala Glu Val Pro Lys Leu Ala Ser Ala Ala
            100                 105                 110
Glu Tyr Phe Phe Lys Leu Gly Val Glu Gly Lys Arg Phe Arg Pro Thr
        115                 120                 125
Val Leu Leu Leu Met Ala Thr Ala Ile Asp Ala Pro Ile Ser Arg Thr
130                 135                 140
Pro Pro Asp Thr Ser Leu Asp Thr Leu Ser Thr Glu Leu Arg Leu Arg
145                 150                 155                 160
Gln Gln Thr Ile Ala Glu Ile Thr Lys Met Ile His Val Ala Ser Leu
                165                 170                 175
Leu His Asp Asp Val Leu Asp Asp Ala Glu Thr Arg Arg Gly Ile Gly
            180                 185                 190
Ser Leu Asn Phe Val Met Gly Asn Lys Leu Ala Val Leu Ala Gly Asp
        195                 200                 205
Phe Leu Leu Ser Arg Ala Cys Val Ala Leu Ala Ser Leu Lys Asn Thr
210                 215                 220
Glu Val Val Ser Leu Leu Ala Thr Val Glu His Leu Val Thr Gly
225                 230                 235                 240
Glu Thr Met Gln Met Thr Thr Thr Ser Asp Gln Arg Cys Ser Met Glu
                245                 250                 255
Tyr Tyr Met Gln Lys Thr Tyr Tyr Met Thr Ala Ser Leu Ile Ser Asn
            260                 265                 270
Ser Cys Lys Ala Ile Ala Leu Leu Ala Gly Gln Thr Ser Glu Val Ala
        275                 280                 285
Met Leu Ala Tyr Glu Tyr Gly Lys Asn Leu Gly Leu Ala Phe Gln Leu
290                 295                 300
Ile Asp Asp Val Leu Asp Phe Thr Gly Thr Ser Ala Ser Leu Gly Lys
305                 310                 315                 320
Gly Ser Leu Ser Asp Ile Arg His Gly Ile Val Thr Ala Pro Ile Leu
                325                 330                 335
Phe Ala Ile Glu Glu Phe Pro Glu Leu Arg Ala Val Val Asp Glu Gly
            340                 345                 350
Phe Glu Asn Pro Tyr Asn Val Asp Leu Ala Leu His Tyr Leu Gly Lys
        355                 360                 365
Ser Arg Gly Ile Gln Arg Thr Arg Glu Leu Ala Ile Lys His Ala Asn
370                 375                 380
Leu Ala Ser Asp Ala Ile Asp Ser Leu Pro Val Thr Asp Asp Glu His
385                 390                 395                 400
```

```
Val Leu Arg Ser Arg Arg Ala Leu Val Glu Leu Thr Gln Arg Val Ile
            405                 410                 415

Thr Arg Arg Lys
        420

<210> SEQ ID NO 52
<211> LENGTH: 1260
<212> TYPE: DNA
<213> ORGANISM: Artificial
<220> FEATURE:
<223> OTHER INFORMATION: mutated and/or codon-optimized sequence

<400> SEQUENCE: 52
atgctgtttt cacgcggcct ctatcgcatc gcgcgaacct ccctgaaccg tagccgcctc      60
ttgtacccat tgcaatcaca aagccccgag ttgctccagt cgtttcagtt ccgctcgcct     120
attggatcat cccaaaaggt atccggattc cgtgttatct actcctgggt gtcctcggca     180
ttggccaacg tcggccagca ggtacaacga caaagcaact ccgtagcgga ggagcccctg     240
gatccatttt cactggttgc cgatgaactt tccattctcg ctaaccgtct ccgctcaatg     300
gtcgtcgctg aagtgcctaa gctcgcttcc gcagcagagt acttcttcaa gttgggtgtg     360
gagggcaagc gtttccgacc caccgtcctt ctgttgatgg cgaccgctat cgacgcaccc     420
atctctcgca caccacctga tacctcgttg ataccccttt ctactgagct tcgcctgcgc     480
caacagacca ttgccgagat caccaaaatg attcacgttg cttcgctcct ccacgatgat     540
gtgctcgatg acgctgagac ccgccgagga attggttcac ttaattttgt aatgggtaac     600
aagcttgctg tgctcgcagg tgatttcctg ctctcacgcg catgtgtggc cctggcttca     660
ctgaaaaata ccgaggtggt ttcgttgctg gccactgttg tagagcacct cgtcactggc     720
gagactatgc aaatgacaac cacgtcggac cagcgctgca gcatggagta ttatatgcag     780
aaaacttatt acatgaccgc gtctctgatt cgaactcct gcaaggccat tgcgttgctc     840
gccggacaaa cctcggaggt cgccatgctt gcatatgaat acgtaaaaa cctgggattg     900 gccttccagc tcatcgacga tgtgctggat ttcactggaa caagcgctag cctgggtaag     960
ggttccttga gcgatatccg ccatggcatc gtaacggccc caattctctt cgcgattgaa    1020
gagttccctg agttgcgtgc tgtagttgat gaaggctttg agaacccata taacgtagac    1080
cttgcttttg cattacctcg gtaaatctcg tggtattcaac gtaccgcgca actggcgatt    1140
aaacacgcca atcttgcatc agatgcgatc gattctttgc cggttaccga tgacgaacac    1200
gtgctgcgct ctcgtcgcgc acttgtggaa cttacccagc gtgtgatcac gcgtcgcaaa    1260

<210> SEQ ID NO 53
<211> LENGTH: 367
<212> TYPE: PRT
<213> ORGANISM: C. glutamicum

<400> SEQUENCE: 53

Met Ser Thr Phe Asp Ala His Asp Leu Asp Leu Asp Thr Phe Pro Glu
1               5                   10                  15

Val Val Arg Asp Arg Leu Thr Gln Phe Leu Asp Ala Gln Ala Thr Thr
            20                  25                  30

Ile Ala Gly Ile Gly Asp Pro Val Thr Glu Ala Val Ser His Leu Arg
        35                  40                  45

Ser Phe Val Leu Asn Gly Gly Lys Arg Ile Arg Pro Leu Tyr Ala Trp
    50                  55                  60

Ala Gly Phe Leu Ala Ala Gln Gly Leu Glu Asn Ser Gly Glu Lys Ile
```

```
                65                  70                  75                  80
        Glu Ala Val Leu Asp Ala Ala Ser Ser Leu Glu Phe Ile Gln Ala Tyr
                        85                  90                  95

Phe Leu Ile His Asp Asp Pro Ala Ile Asp Ser Ser Asp Thr Arg Arg
                       100                 105                 110

Gly Ala Pro Thr Val His Arg Ala Val Glu Ala Asn His Arg Ala His
                       115                 120                 125

Asn Leu Glu Gly Asp Ser Glu His Phe Gly Ser Val Ser Ile Leu
                       130                 135                 140

Ala Gly Asp Met Ala Leu Val Trp Ala Glu Asp Met Leu Gln Asp Ser
        145                 150                 155                 160

Gly Leu Ser Ala Glu Ala Leu Ala Arg Thr Arg Asp Ala Trp Arg Gly
                       165                 170                 175

Met Arg Thr Glu Val Ile Gly Gly Gln Leu Leu Asp Ile Tyr Leu Glu
                       180                 185                 190

Ala His Ala Asn Glu Ala Val Glu Leu Ala Asp Ser Val Asn Arg Phe
                       195                 200                 205

Lys Thr Ala Ala Tyr Thr Ile Ala Arg Pro Leu His Leu Gly Ala Ser
                       210                 215                 220

Ile Ala Gly Gly Ser Gln Glu Leu Ile Asp Ala Leu Leu His Tyr Gly
        225                 230                 235                 240

His Asp Ile Gly Ile Ala Phe Gln Leu Arg Asp Asp Leu Leu Gly Val
                       245                 250                 255

Phe Gly Asp Pro Lys Val Thr Gly Lys Pro Ala Gly Asp Asp Ile Arg
                       260                 265                 270

Glu Gly Lys Arg Thr Val Leu Leu Ala Leu Ala Leu Gln Arg Ala Asp
                       275                 280                 285

Lys Asn Ser Pro Glu Ala Ala Ala Ile Arg Ala Gly Ile Gly Lys
                       290                 295                 300

Val Ser Thr Pro Glu Asp Ile Ala Val Ile Ala Lys His Ile Arg Ala
        305                 310                 315                 320

Thr Gly Ala Glu Glu Val Glu Gln Arg Ile Thr Gln Leu Thr Glu
                       325                 330                 335

Ser Gly Leu Ala His Leu Asp Asp Val Glu Ile Pro Asp Glu Val Arg
                       340                 345                 350

Thr Gln Leu Arg Ala Leu Ala Ile Arg Ser Thr Glu Arg Arg Met
                       355                 360                 365

<210> SEQ ID NO 54
<211> LENGTH: 1101
<212> TYPE: DNA
<213> ORGANISM: Artificial
<220> FEATURE:
<223> OTHER INFORMATION: mutated and/or codon-optimized sequence

<400> SEQUENCE: 54
atgtctacat tcgatgctca tgacttggac ctggatacct ccctgaagt tgtgcgcgac      60 cgcctgacgc agtttctcga tgcacaggca acgacgattg cgggtatcgg agaccccgtt    120
accgaggccg tatctcactt gcgttcgttt gtcctcaacg gaggtaagcg tatccgcccc    180
ctttatgcct gggccggctt tttggccgca caaggcctgg agaatagcgg cgaaaagatt    240
gaggcggtgt ggatgcagc gagcagcttg gaattcatcc aagcttattt tcttattcac    300
gatgacccag caattgattc ctccgacacc cgtcgcggcg cacctaccgt ccaccgcgct    360
gtggaagcca accaccgcgc gcacaacttg gagggagaca gcgaacactt cggtgagtcg    420
```

-continued

```
gtttccatcc ttgcaggtga tatggccctg gtttgggcag aggacatgct tcaggattct    480
ggcctttccg cagaagcgtt ggctcgtacc cgtgacgcct ggcgcggcat gcgcaccgag    540
gtcatcggtg ccagctgct ggacatctat ctggaagctc atgctaatga agccgtcgaa     600
ctggcagaca cgtcaaccg ttttaagact gccgcatata ctattgcccg ccctcttcat     660
cttggtgcct caatcgctgg cggctcccag gaattgatcg atgcactgct ccactacgga    720
cacgatatcg gtatcgcatt ccagctccga gatgatctgc ttggtgtttt tggtgacccg    780
aaggtaacag gaaaaccagc cggcgatgac atccgtgaag gcaaacgcac agtgcttctc    840
gcattggcgt tgcagcgcgc agacaagaac agccctgagg cagctgccgc aatccgcgcg    900
ggcatcggca aggtgtccac cccggaagat attgctgtca tcgctaaaca tattcgtgcg    960
acaggcgcgg aagaagaagt agagcaacgc atcactcaac tgactgaatc aggcttggcg   1020
catttggatg atgtggaaat tcctgacgag gtgcgtaccc aactgcgcgc gctcgcaatc   1080
cgctccacgg agcgccgaat g                                             1101
```

<210> SEQ ID NO 55
<211> LENGTH: 296
<212> TYPE: PRT
<213> ORGANISM: Artificial
<220> FEATURE:
<223> OTHER INFORMATION: mutated and/or codon-optimized sequence

<400> SEQUENCE: 55

```
Met Thr Asn Lys Leu Thr Ser Phe Leu Ala Asp Arg Lys Lys Thr Ile
1               5                   10                  15

Glu Asn Gln Leu Ser Val Tyr Thr Glu Lys Leu Asp Met Pro Asp Ser
            20                  25                  30

Leu Lys Lys Ser Met Leu Tyr Ser Leu Gln Ala Gly Gly Lys Arg Leu
        35                  40                  45

Arg Pro Leu Ile Val Leu Ala Val Leu Asn Ala Tyr Gly Lys Ser Glu
    50                  55                  60

Lys Asp Gly Ile Pro Val Gly Cys Ala Val Glu Met Ile His Thr Tyr
65                  70                  75                  80

Phe Leu Ile His Asp Asp Leu Pro Cys Met Asp Asp Asp Asp Leu Arg
                85                  90                  95

Arg Gly Lys Pro Thr Asn His Lys Val Phe Gly Glu Ala Thr Ala Val
            100                 105                 110

Leu Ala Gly Asp Gly Leu Leu Thr Glu Ser Phe Lys Leu Ile Thr Ser
        115                 120                 125

His Val Ser Asp Glu Val Ser Ala Glu Lys Arg Leu Arg Leu Val Asn
    130                 135                 140

Glu Leu Ile Ser Ala Ala Gly Thr Glu Gly Met Val Gly Gly Gln Val
145                 150                 155                 160

Ala Asp Met Glu Ala Glu Asn Arg Gln Val Thr Leu Glu Glu Leu Glu
                165                 170                 175

Ser Ile His Glu Arg Lys Thr Ala Lys Leu Leu Gly Phe Cys Val Ile
            180                 185                 190

Ala Gly Ala Ile Leu Ala Asp Ala Pro Glu Glu Asp Ile Glu Thr Leu
        195                 200                 205

Arg Thr Phe Ser Ser His Ile Gly Ile Gly Phe Gln Ile Arg Asp Asp
    210                 215                 220

Ile Leu Asp Leu Glu Gly Ser Glu Glu Lys Ile Gly Lys Arg Val Gly
225                 230                 235                 240
```

```
Ser Asp Thr Thr Asn Asp Lys Ser Thr Tyr Pro Ser Leu Leu Ser Leu
            245                 250                 255

Glu Gly Ala Lys His Lys Leu Asp Val His Ile Lys Glu Ala Lys Arg
        260                 265                 270

Leu Ile Gly Gly Leu Ser Leu Gln Lys Asp Leu Leu Tyr Glu Leu Cys
        275                 280                 285

Asp Leu Ile Ala Ala Arg Asp His
        290                 295

<210> SEQ ID NO 56
<211> LENGTH: 888
<212> TYPE: DNA
<213> ORGANISM: Artificial
<220> FEATURE:
<223> OTHER INFORMATION: mutated and/or codon-optimized sequence

<400> SEQUENCE: 56
atgactaata agctgacgtc cttcctcgca gaccgtaaaa agactatcga aaatcaattg      60
tctgtgtaca cagaaaagct cgatatgcct gattccctca gaagtctat gctttactcc     120
cttcaggcag gtggcaagcg tttgcgcccc ctcatcgtgc ttgcggttct caacgcctac     180
ggtaagtcag agaaagatgg tatcccggtt ggatgcgccg tggaaatgat ccacacctat     240
tttcttatcc acgacgatct tccgtgtatg gacgatgacg accttcgccg tggtaagcca     300
actaaccaca aggttttttgg tgaggcaact gcggttcttg caggtgatgg tctgcttacc     360
gaatccttta aacttatcac ttcccatgtt tctgatgaag tgtctgcaga aaaacgtctg     420
cgcctggtga acgaactcat cagcgccgcg ggcaccgaag gtatggtagg aggacaagtg     480
gctgatatgg aagccgagaa ccgtcaggtt acgcttgaag aactcgagtc tattcacgaa     540
cgcaagaccg ccaagctctt gggcttctgt gttattgctg gagccatcct tgcagatgca     600
cctgaagagg atattgaaac attgcgtacc ttttcatccc acatcggcat cggttttcag     660
atccgagacg acattcttga tctcgagggc tccgaagaaa agattggtaa acgcgtgggc     720
tccgacacca ccaatgacaa gtctacttac ccgtctcttc ttagccttga aggcgcaaag     780
cataagttgg acgttcatat taaggaggcg aagcgtttga ttggtggtct gagcctccag     840
aaagacttgc tctacgagct gtgcgatctc atcgcagcac gcgatcac                  888

<210> SEQ ID NO 57
<211> LENGTH: 396
<212> TYPE: PRT
<213> ORGANISM: S. cerevisiae S288c

<400> SEQUENCE: 57

Met Thr Val Tyr Thr Ala Ser Val Thr Ala Pro Val Asn Ile Ala Thr
1               5                   10                  15

Leu Lys Tyr Trp Gly Lys Arg Asp Thr Lys Leu Asn Leu Pro Thr Asn
            20                  25                  30

Ser Ser Ile Ser Val Thr Leu Ser Gln Asp Asp Leu Arg Thr Leu Thr
        35                  40                  45

Ser Ala Ala Thr Ala Pro Glu Phe Glu Arg Asp Thr Leu Trp Leu Asn
    50                  55                  60

Gly Glu Pro His Ser Ile Asp Asn Glu Arg Thr Gln Asn Cys Leu Arg
65                  70                  75                  80

Asp Leu Arg Gln Leu Arg Lys Glu Met Glu Ser Lys Asp Ala Ser Leu
            85                  90                  95
```

```
Pro Thr Leu Ser Gln Trp Lys Leu His Ile Val Ser Glu Asn Asn Phe
            100                 105                 110
Pro Thr Ala Ala Gly Leu Ala Ser Ser Ala Ala Gly Phe Ala Ala Leu
        115                 120                 125
Val Ser Ala Ile Ala Lys Leu Tyr Gln Leu Pro Gln Ser Thr Ser Glu
    130                 135                 140
Ile Ser Arg Ile Ala Arg Lys Gly Ser Gly Ser Ala Cys Arg Ser Leu
145                 150                 155                 160
Phe Gly Gly Tyr Val Ala Trp Glu Met Gly Lys Ala Glu Asp Gly His
                165                 170                 175
Asp Ser Met Ala Val Gln Ile Ala Asp Ser Ser Asp Trp Pro Gln Met
            180                 185                 190
Lys Ala Cys Val Leu Val Val Ser Asp Ile Lys Lys Asp Val Ser Ser
        195                 200                 205
Thr Gln Gly Met Gln Leu Thr Val Ala Thr Ser Glu Leu Phe Lys Glu
    210                 215                 220
Arg Ile Glu His Val Val Pro Lys Arg Phe Glu Val Met Arg Lys Ala
225                 230                 235                 240
Ile Val Glu Lys Asp Phe Ala Thr Phe Ala Lys Glu Thr Met Met Asp
                245                 250                 255
Ser Asn Ser Phe His Ala Thr Cys Leu Asp Ser Phe Pro Pro Ile Phe
            260                 265                 270
Tyr Met Asn Asp Thr Ser Lys Arg Ile Ile Ser Trp Cys His Thr Ile
        275                 280                 285
Asn Gln Phe Tyr Gly Glu Thr Ile Val Ala Tyr Thr Phe Asp Ala Gly
    290                 295                 300
Pro Asn Ala Val Leu Tyr Tyr Leu Ala Glu Asn Glu Ser Lys Leu Phe
305                 310                 315                 320
Ala Phe Ile Tyr Lys Leu Phe Gly Ser Val Pro Gly Trp Asp Lys Lys
                325                 330                 335
Phe Thr Thr Glu Gln Leu Glu Ala Phe Asn His Gln Phe Glu Ser Ser
            340                 345                 350
Asn Phe Thr Ala Arg Glu Leu Asp Leu Glu Leu Gln Lys Asp Val Ala
        355                 360                 365
Arg Val Ile Leu Thr Gln Val Gly Ser Gly Pro Gln Glu Thr Asn Glu
    370                 375                 380
Ser Leu Ile Asp Ala Lys Thr Gly Leu Pro Lys Glu
385                 390                 395

<210> SEQ ID NO 58
<211> LENGTH: 1188
<212> TYPE: DNA
<213> ORGANISM: Artificial
<220> FEATURE:
<223> OTHER INFORMATION: mutated and/or codon-optimized sequence

<400> SEQUENCE: 58
atgaccgttt acaccgcctc agtcaccgca ccagttaaca ttgcaaccct taaatactgg      60
ggcaagcgcg atactaagct taaccttcct accaactcat cgatctcggt gaccctgtct     120
caggatgatc tgcgaacgct tacttctgcg gcaacagcac agaattcga gcagatacg      180 ctctggctga atggcgaacc gcattccatt gacaacgagc gcacccagaa ctgcttgcgt    240
gatcttcgcc aactccgtaa ggagatggaa agcaaagatg caagcctccc aaccctctct    300
caatggaaac ttcacatcgt ctctgaaaac aacttcccta cggcggctgg cctggcgtcc    360
```

```
tcggcagctg gcttcgctgc attggtttcc gccattgcaa agctttatca gcttccgcaa    420
tcgacctccg agattagccg catcgcccgc aagggttcag gttcggcatg tcgctctctc    480
tttggaggct acgtggcctg ggaaatggga aaggccgaag atggtcacga ttccatggcg    540
gtgcaaatcg ccgatagctc agattggcct caaatgaagg cctgtgtgtt ggtggtatcc    600
gacatcaaaa aagacgtttc ctcgactcaa ggaatgcaac ttacggtagc tacgagcgaa    660
ctgtttaagg agcgcattga gcatgtggtg cccaaacgct tgaagtcat  gcgtaaggca    720 atcgtggaga aggacttcgc gaccttcgcg aaggaaacta tgatggatag caacagcttc    780
cacgctacgt gtctggattc gttccctccg attttctata tgaatgacac gtctaaacgc    840
atcatttcct ggtgtcacac gatcaaccaa ttctacggcg aaactatcgt agcatacact    900
tttgacgcag gaccgaacgc cgttctctac tacctcgccg aaaacgagtc aaaattgttc    960
gccttcatct acaaactctt tggatccgtc cctggttggg acaagaagtt cacgactgaa   1020
cagttggaag cattcaacca tcagtttgaa agctctaact tcacagcccg tgagctggac   1080
ctcgaactgc agaaagatgt ggcacgcgtc attcttaccc aagtgggctc cggaccccaa   1140
gagacgaatg agtctctgat tgacgccaaa acgggtctcc ccaaagaa               1188
```

<210> SEQ ID NO 59
<211> LENGTH: 650
<212> TYPE: PRT
<213> ORGANISM: Yarrowia lipolytica CLIB 122 / E 150

<400> SEQUENCE: 59

```
Met Ser Ala Asn Glu Asn Ile Ser Arg Phe Asp Ala Pro Val Gly Lys
1               5                   10                  15

Glu His Pro Ala Tyr Glu Leu Phe His Asn His Thr Arg Ser Phe Val
            20                  25                  30

Tyr Gly Leu Gln Pro Arg Ala Cys Gln Gly Met Leu Asp Phe Asp Phe
        35                  40                  45

Ile Cys Lys Arg Glu Asn Pro Ser Val Ala Gly Val Ile Tyr Pro Phe
    50                  55                  60

Gly Gly Gln Phe Val Thr Lys Met Tyr Trp Gly Thr Lys Glu Thr Leu
65                  70                  75                  80

Leu Pro Val Tyr Gln Gln Val Glu Lys Ala Ala Ala Lys His Pro Glu
                85                  90                  95

Val Asp Val Val Asn Phe Ala Ser Ser Arg Ser Val Tyr Ser Ser
            100                 105                 110

Thr Met Glu Leu Leu Glu Tyr Pro Gln Phe Arg Thr Ile Ala Ile Ile
        115                 120                 125

Ala Glu Gly Val Pro Glu Arg Arg Ala Arg Glu Ile Leu His Lys Ala
    130                 135                 140

Gln Lys Lys Gly Val Thr Ile Ile Gly Pro Ala Thr Val Gly Gly Ile
145                 150                 155                 160

Lys Pro Gly Cys Phe Lys Val Gly Asn Thr Gly Met Met Asp Asn
                165                 170                 175

Ile Val Ala Ser Lys Leu Tyr Arg Pro Gly Ser Val Ala Tyr Val Ser
            180                 185                 190

Lys Ser Gly Gly Met Ser Asn Glu Leu Asn Asn Ile Ser His Thr
        195                 200                 205

Thr Asp Gly Val Tyr Glu Gly Ile Ala Ile Gly Gly Asp Arg Tyr Pro
    210                 215                 220

Gly Thr Thr Phe Ile Asp His Ile Leu Arg Tyr Glu Ala Asp Pro Lys
```

-continued

```
                225                 230                 235                 240
            Cys Lys Ile Ile Val Leu Leu Gly Glu Val Gly Val Glu Glu Tyr
                            245                 250                 255
            Arg Val Ile Glu Ala Val Lys Asn Gly Gln Ile Lys Lys Pro Ile Val
                            260                 265                 270
            Ala Trp Ala Ile Gly Thr Cys Ala Ser Met Phe Lys Thr Glu Val Gln
                        275                 280                 285
            Phe Gly His Ala Gly Ser Met Ala Asn Ser Asp Leu Glu Thr Ala Lys
                    290                 295                 300
            Ala Lys Asn Ala Ala Met Lys Ser Ala Gly Phe Tyr Val Pro Asp Thr
            305                 310                 315                 320
            Phe Glu Asp Met Pro Glu Val Leu Ala Glu Leu Tyr Glu Lys Met Val
                            325                 330                 335
            Ala Lys Gly Glu Leu Ser Arg Ile Ser Glu Pro Glu Val Pro Lys Ile
                            340                 345                 350
            Pro Ile Asp Tyr Ser Trp Ala Gln Glu Leu Gly Leu Ile Arg Lys Pro
                        355                 360                 365
            Ala Ala Phe Ile Ser Thr Ile Ser Asp Asp Arg Gly Gln Glu Leu Leu
                    370                 375                 380
            Tyr Ala Gly Met Pro Ile Ser Glu Val Phe Lys Glu Asp Ile Gly Ile
            385                 390                 395                 400
            Gly Gly Val Met Ser Leu Leu Trp Phe Arg Arg Arg Leu Pro Asp Tyr
                            405                 410                 415
            Ala Ser Lys Phe Leu Glu Met Val Leu Met Leu Thr Ala Asp His Gly
                        420                 425                 430
            Pro Ala Val Ser Gly Ala Met Asn Thr Ile Ile Thr Thr Arg Ala Gly
                    435                 440                 445
            Lys Asp Leu Ile Ser Ser Leu Val Ala Gly Leu Leu Thr Ile Gly Thr
            450                 455                 460
            Arg Phe Gly Gly Ala Leu Asp Gly Ala Ala Thr Glu Phe Thr Thr Ala
            465                 470                 475                 480
            Tyr Asp Lys Gly Leu Ser Pro Arg Gln Phe Val Asp Thr Met Arg Lys
                        485                 490                 495
            Gln Asn Lys Leu Ile Pro Gly Ile Gly His Arg Val Lys Ser Arg Asn
                    500                 505                 510
            Asn Pro Asp Phe Arg Val Glu Leu Val Lys Asp Phe Val Lys Lys Asn
                515                 520                 525
            Phe Pro Ser Thr Gln Leu Leu Asp Tyr Ala Leu Ala Val Glu Glu Val
            530                 535                 540
            Thr Thr Ser Lys Lys Asp Asn Leu Ile Leu Asn Val Asp Gly Ala Ile
            545                 550                 555                 560
            Ala Val Ser Phe Val Asp Leu Met Arg Ser Cys Gly Ala Phe Thr Val
                            565                 570                 575
            Glu Glu Thr Glu Asp Tyr Leu Lys Asn Gly Val Leu Asn Gly Leu Phe
                        580                 585                 590
            Val Leu Gly Arg Ser Ile Gly Leu Ile Ala His His Leu Asp Gln Lys
                    595                 600                 605
            Arg Leu Lys Thr Gly Leu Tyr Arg His Pro Trp Asp Asp Ile Thr Tyr
                610                 615                 620
            Leu Val Gly Gln Glu Ala Ile Gln Lys Arg Val Glu Ile Ser Ala
            625                 630                 635                 640
            Gly Asp Val Ser Lys Ala Lys Thr Arg Ser
                            645                 650
```

<210> SEQ ID NO 60
<211> LENGTH: 1950
<212> TYPE: DNA
<213> ORGANISM: Artificial
<220> FEATURE:
<223> OTHER INFORMATION: mutated and/or codon-optimized sequence

<400> SEQUENCE: 60

| | | | | | |
|---|---|---|---|---|---|
| atgtctgcaa | atgaaaacat | ttcccgcttt | gatgcacctg | tgggtaagga | gcatccagcc | 60 |
| tatgagctgt | tccataacca | cacccgctcc | ttcgtctacg | gtctccagcc | tcgcgcgtgc | 120 |
| cagggtatgc | tcgactttga | tttcatttgt | aagcgcgaga | accctcggt | tgccggtgtt | 180 |
| atctacccctt | tcggcggtca | gttcgtgact | aagatgtact | ggggtaccaa | ggagaccctg | 240 |
| ctcccggtgt | accagcaagt | tgaaaaagca | gcagcgaaac | atcccgaagt | cgacgtcgtc | 300 |
| gtgaacttcg | cgtcgtcccg | cagcgtctac | agctccacaa | tggaactttt | ggaataccca | 360 |
| caattccgca | ccatcgctat | catcgcgag | ggcgtcccag | aacgccgtgc | gcgcgaaatc | 420 |
| ctgcacaagg | ctcagaaaaa | gggcgtgacg | attatcggac | cggcaaccgt | cggcggcatt | 480 |
| aagcccggtt | gctttaaagt | tggtaatacg | gtggcatga | tggacaacat | cgtggcgtcc | 540 |
| aagctgtacc | gcccaggttc | cgttgcttac | gtctccaagt | ccggtggtat | gtcaaatgag | 600 |
| cttaataaca | tcatttccca | cacgaccgat | ggcgtgtacg | agggaatcgc | aattggtggc | 660 |
| gaccgctacc | cgggcacaac | ttttattgat | cacatcttgc | gttacgaagc | ggatccaaag | 720 |
| tgcaagatca | ttgtgctctt | gggcgaagta | ggtggcgtgg | aagagtaccg | cgttatcgag | 780 |
| gcggttaaaa | acggtcaaat | taagaagcca | atcgtagcgt | gggcaatcgg | cacctgcgcc | 840 |
| tccatgttta | agacggaagt | acagtttggc | catgctggct | caatggctaa | ctcagacctc | 900 |
| gagacggcta | aagcaaaaaa | tgcggcaatg | aaatcagcag | gctttttacgt | gccggatacc | 960 |
| ttcgaggata | tgcccgaagt | cttggccgag | ctctacagaa | gatggtggc | gaaaggcgag | 1020 |
| ctcagccgca | tctccgaacc | ggaggttcct | aagatcccga | tcgactatag | ctgggcgcag | 1080 |
| gaacttggtt | tgatccgcaa | gccagccgca | ttcatctcta | ccatctcaga | cgaccgcggc | 1140 |
| caagagctcc | tttacgcggg | catgcccatc | tcagaggtct | tcaaggagga | catcggcatc | 1200 |
| ggtggcgtta | tgtccctgct | gtggtttcgt | cgccgtctgc | ctgattatgc | atcgaaattc | 1260 |
| cttgaaatgg | tgcttatgct | gacggccgac | cacggacctg | ccgtttccgg | tgcgatgaat | 1320 |
| acgatcatca | ccactcgagc | gggtaaggac | ctcattttcct | cccttgttgc | cggccttctt | 1380 |
| acaattggta | cccgcttcgg | cggagcattg | gacggcgcgg | ccacagagtt | tactaccgcc | 1440 |
| tacgataagg | gcttgtcgcc | ccgccaattt | gtcgatacaa | tgcgcaagca | aaacaagctc | 1500 |
| atcccaggca | tcggccaccg | agtgaagtcc | cgtaataacc | ccgatttccg | tgtggaactg | 1560 |
| gttaaggact | ttgtgaagaa | gaatttcccg | tccacccagc | tgttggatta | cgcgctcgcc | 1620 |
| gttgaggagg | tgaccacatc | taaaaaggat | aacttgatcc | tcaacgttga | tggtgcgatt | 1680 |
| gcggtttcgt | tcgtcgatct | tatgcgctcg | tgtggtgctt | ttaccgttga | agaaacagaa | 1740 |
| gattatctga | aaatggcgt | tttgaacggt | ttgtttgtcc | tcggtcgttc | cattggcctg | 1800 |
| attgcgcacc | acctggacca | gaaacgtctt | aaaaccggtc | tttaccgcca | tccttgggat | 1860 |
| gacattacgt | acctcgttgg | ccaagaggca | attcagaaga | agcgtgtgga | gatctctgca | 1920 |
| ggcgacgttt | caaaggcgaa | gactcgaagc | | | | 1950 |

<210> SEQ ID NO 61

<211> LENGTH: 652
<212> TYPE: PRT
<213> ORGANISM: Artificial
<220> FEATURE:
<223> OTHER INFORMATION: mutated and/or codon-optimized sequence

<400> SEQUENCE: 61

Met Ser Gln Thr His Lys His Ala Ile Pro Ala Asn Ile Ala Asp Arg
1               5                   10                  15

Cys Leu Ile Asn Pro Glu Gln Tyr Glu Thr Lys Tyr Lys Gln Ser Ile
                20                  25                  30

Asn Asp Pro Asp Thr Phe Trp Gly Glu Gln Gly Lys Ile Leu Asp Trp
            35                  40                  45

Ile Thr Pro Tyr Gln Lys Val Lys Asn Thr Ser Phe Ala Pro Gly Asn
50                  55                  60

Val Ser Ile Lys Trp Tyr Glu Asp Gly Thr Leu Asn Leu Ala Ala Asn
65                  70                  75                  80

Cys Leu Asp Arg His Leu Gln Glu Asn Gly Asp Arg Thr Ala Ile Ile
                85                  90                  95

Trp Glu Gly Asp Asp Thr Ser Gln Ser Lys His Ile Ser Tyr Arg Glu
            100                 105                 110

Leu His Arg Asp Val Cys Arg Phe Ala Asn Thr Leu Leu Asp Leu Gly
        115                 120                 125

Ile Lys Lys Gly Asp Val Val Ala Ile Tyr Met Pro Met Val Pro Glu
130                 135                 140

Ala Ala Val Ala Met Leu Ala Cys Ala Arg Ile Gly Ala Val His Ser
145                 150                 155                 160

Val Ile Phe Gly Gly Phe Ser Pro Glu Ala Val Ala Gly Arg Ile Ile
                165                 170                 175

Asp Ser Ser Ser Arg Leu Val Ile Thr Ala Asp Glu Gly Val Arg Ala
            180                 185                 190

Gly Arg Ser Ile Pro Leu Lys Lys Asn Val Asp Asp Ala Leu Lys Asn
        195                 200                 205

Pro Asn Val Thr Ser Val Glu His Val Ile Val Leu Lys Arg Thr Gly
210                 215                 220

Ser Asp Ile Asp Trp Gln Glu Gly Arg Asp Leu Trp Trp Arg Asp Leu
225                 230                 235                 240

Ile Glu Lys Ala Ser Pro Glu His Gln Pro Glu Ala Met Asn Ala Glu
                245                 250                 255

Asp Pro Leu Phe Ile Leu Tyr Thr Ser Gly Ser Thr Gly Lys Pro Lys
            260                 265                 270

Gly Val Leu His Thr Thr Gly Gly Tyr Leu Val Tyr Ala Ala Thr Thr
        275                 280                 285

Phe Lys Tyr Val Phe Asp Tyr His Pro Gly Asp Ile Tyr Trp Cys Thr
290                 295                 300

Ala Asp Val Gly Trp Val Thr Gly His Ser Tyr Leu Leu Tyr Gly Pro
305                 310                 315                 320

Leu Ala Cys Gly Ala Thr Thr Leu Met Phe Glu Gly Val Pro Asn Trp
                325                 330                 335

Pro Thr Pro Ala Arg Met Cys Gln Val Val Asp Lys His Gln Val Asn
            340                 345                 350

Ile Leu Tyr Thr Ala Pro Thr Ala Ile Arg Ala Leu Met Ala Glu Gly
        355                 360                 365

Asp Lys Ala Ile Glu Gly Thr Asp Arg Ser Ser Leu Arg Ile Leu Gly
370                 375                 380

Ser Val Gly Glu Pro Ile Asn Pro Glu Ala Trp Glu Trp Tyr Trp Lys
385                 390                 395                 400

Lys Ile Gly Lys Glu Lys Cys Pro Val Val Asp Thr Trp Trp Gln Thr
            405                 410                 415

Glu Thr Gly Gly Phe Met Ile Thr Pro Leu Pro Gly Ala Ile Glu Leu
        420                 425                 430

Lys Ala Gly Ser Ala Thr Arg Pro Phe Phe Gly Val Gln Pro Ala Leu
    435                 440                 445

Val Asp Asn Glu Gly His Pro Gln Glu Gly Ala Thr Glu Gly Asn Leu
450                 455                 460

Val Ile Thr Asp Ser Trp Pro Gly Gln Ala Arg Thr Leu Phe Gly Asp
465                 470                 475                 480

His Glu Arg Phe Glu Gln Thr Tyr Phe Ser Thr Phe Lys Asn Met Tyr
                485                 490                 495

Phe Ser Gly Asp Gly Ala Arg Arg Asp Glu Asp Gly Tyr Tyr Trp Ile
            500                 505                 510

Thr Gly Arg Val Asp Asp Val Leu Asn Val Ser Gly His Arg Leu Gly
        515                 520                 525

Thr Ala Glu Ile Glu Ser Ala Leu Val Ala His Pro Lys Ile Ala Glu
530                 535                 540

Ala Ala Val Val Gly Ile Pro His Ala Ile Lys Gly Gln Ala Ile Tyr
545                 550                 555                 560

Ala Tyr Val Thr Leu Asn His Gly Glu Glu Pro Ser Pro Glu Leu Tyr
                565                 570                 575

Ala Glu Val Arg Asn Trp Val Arg Lys Glu Ile Gly Pro Leu Ala Thr
            580                 585                 590

Pro Asp Val Leu His Trp Thr Asp Ser Leu Pro Lys Thr Arg Ser Gly
        595                 600                 605

Lys Ile Met Arg Arg Ile Leu Arg Lys Ile Ala Ala Gly Asp Thr Ser
610                 615                 620

Asn Leu Gly Asp Thr Ser Thr Leu Ala Asp Pro Gly Val Val Glu Lys
625                 630                 635                 640

Pro Leu Glu Glu Lys Gln Ala Ile Ala Met Pro Ser
                645                 650

<210> SEQ ID NO 62
<211> LENGTH: 1956
<212> TYPE: DNA
<213> ORGANISM: Artificial
<220> FEATURE:
<223> OTHER INFORMATION: mutated and/or codon-optimized sequence

<400> SEQUENCE: 62
atgtctcaga ctcacaaaca cgctatccct gctaacattg ccgaccgctg tcttattaac      60
cctgagcaat atgaaactaa atacaagcaa tcgattaacg acccagatac cttttgggga     120
gagcagggca aaatcctcga ctggatcacc ccataccaaa aggtaaaaaa cacctcattt     180
gccccaggta acgtgtccat caagtggtac gaagatggta ctttgaacct ggcggccaac     240
tgccttgacc gacacctgca agagaacggt gaccgcaccg caatcatctg ggagggcgac     300
gacacctcac aatccaaaca catctcatat cgtgaacttc atcgcgacgt tgccgtttc      360 gcaaacacgt tgctcgatct gggcatcaag aagggtgatg ttgtggcaat ctacatgccg     420
atggttccag aagcagcagt cgcgatgctt gcatgcgcac gatcggcgc ggttcactca      480 gtgatcttcg gcggattttc ccccgaagcc gttgctggcc gtattatcga tagctcttcc     540

-continued

```
cgcctggtga tcactgctga cgagggtgtg cgcgcaggtc gttccattcc gttgaagaag    600
aacgtcgatg atgccttgaa gaatcccaat gtgacctccg tggaacacgt tatcgtgttg    660
aaacgcactg gctcagacat cgactggcag gaaggccgag atttgtggtg cgagacctc    720
atcgaaaagg cgtccccgga acatcaacct gaggcaatga acgcggaaga tccgttgttt    780
attttgtaca cctcgggaag cacgggtaag ccaaaaggtg tgctccatac caccggcggt    840
tatctcgtgt acgcagcgac tactttcaaa tatgttttcg actatcaccc cggagatatc    900
tactggtgca cagcagacgt tggttgggtt accggacatt cctacctgct gtacggtcct    960
ctggcatgcg cgcaactac gttgatgttt gaaggtgtgc ctaactggcc tactccagcg    1020
cgcatgtgtc aagtcgtgga caagcaccag gtaaacatcc tctatacagc acctaccgcc    1080
atccgagccc tcatggctga aggcgataag gccattgagg gtacagatcg ttcctccttg    1140
cgtatcctcg gctcagtggg cgaaccaatc aaccctgaag catgggaatg gtactggaag    1200
aagattggaa aggagaagtg tccagttgtg gatacctggt ggcagacaga gactggtggt    1260
ttcatgatta cccctctccc gggagcgatt gagttgaaag ccggttccgc gacccgccca    1320
ttcttcggag tacagccagc gcttgtggac aacgaaggac acccacagga aggcgccacc    1380
gaaggcaacc tggtcatcac ggacagctgg ccaggtcagg cacgtaccct gttcggcgac    1440
catgagcgct tcgagcaaac gtacttctct accttcaaga acatgtattt ctccggtgac    1500
ggtgcccgtc gcgatgaaga tggctactac tggattacag gccgcgttga tgacgttctc    1560
aacgttagcg acaccgtttt gggtaccgca gaaatcgaat ccgctctggt agcacacccg    1620
aaaatcgctg aagcagccgt ggtgggtatc ccgcacgcga tcaagggtca agctatctac    1680
gcatacgtca cgcttaatca cggagaagaa ccatcgcccg agttgtacgc cgaggtgcgc    1740
aattgggtcc gaaaagaaat tggcccactg gcaaccccg atgtgctcca ttggactgat    1800
agcctgccca agactcgttc tggtaaaatt atgcgccgca tcctgcgcaa gattgcagct    1860
ggagacacct ccaatttggg cgatacctcc actttggccg atccaggagt ggtggagaaa    1920
ccgctcgaag aaaaacaggc aatcgctatg ccttcc                               1956
```

<210> SEQ ID NO 63
<211> LENGTH: 500
<212> TYPE: PRT
<213> ORGANISM: S. cerevisiae S288c

<400> SEQUENCE: 63

```
Met Thr Lys Leu His Phe Asp Thr Ala Glu Pro Val Lys Ile Thr Leu
1               5                   10                  15

Pro Asn Gly Leu Thr Tyr Glu Gln Pro Thr Gly Leu Phe Ile Asn Asn
                20                  25                  30

Lys Phe Met Lys Ala Gln Asp Gly Lys Thr Tyr Pro Val Glu Asp Pro
            35                  40                  45

Ser Thr Glu Asn Thr Val Cys Glu Val Ser Ser Ala Thr Thr Glu Asp
        50                  55                  60

Val Glu Tyr Ala Ile Glu Cys Ala Asp Arg Ala Phe His Asp Thr Glu
65                  70                  75                  80

Trp Ala Thr Gln Asp Pro Arg Glu Arg Gly Arg Leu Leu Ser Lys Leu
                85                  90                  95

Ala Asp Glu Leu Glu Ser Gln Ile Asp Leu Val Ser Ser Ile Glu Ala
            100                 105                 110

Leu Asp Asn Gly Lys Thr Leu Ala Leu Ala Arg Gly Asp Val Thr Ile
```

```
            115                 120                 125
Ala Ile Asn Cys Leu Arg Asp Ala Ala Tyr Ala Asp Lys Val Asn
    130                 135                 140

Gly Arg Thr Ile Asn Thr Gly Asp Gly Tyr Met Asn Phe Thr Thr Leu
145                 150                 155                 160

Glu Pro Ile Gly Val Cys Gly Gln Ile Ile Pro Trp Asn Phe Pro Ile
                165                 170                 175

Met Met Leu Ala Trp Lys Ile Ala Pro Ala Leu Ala Met Gly Asn Val
            180                 185                 190

Cys Ile Leu Lys Pro Ala Ala Val Thr Pro Leu Asn Ala Leu Tyr Phe
        195                 200                 205

Ala Ser Leu Cys Lys Lys Val Gly Ile Pro Ala Gly Val Val Asn Ile
    210                 215                 220

Val Pro Gly Pro Gly Arg Thr Val Gly Ala Ala Leu Thr Asn Asp Pro
225                 230                 235                 240

Arg Ile Arg Lys Leu Ala Phe Thr Gly Ser Thr Glu Val Gly Lys Ser
                245                 250                 255

Val Ala Val Asp Ser Ser Glu Ser Asn Leu Lys Lys Ile Thr Leu Glu
            260                 265                 270

Leu Gly Gly Lys Ser Ala His Leu Val Phe Asp Asp Ala Asn Ile Lys
        275                 280                 285

Lys Thr Leu Pro Asn Leu Val Asn Gly Ile Phe Lys Asn Ala Gly Gln
    290                 295                 300

Ile Cys Ser Ser Gly Ser Arg Ile Tyr Val Gln Glu Gly Ile Tyr Asp
305                 310                 315                 320

Glu Leu Leu Ala Ala Phe Lys Ala Tyr Leu Glu Thr Glu Ile Lys Val
                325                 330                 335

Gly Asn Pro Phe Asp Lys Ala Asn Phe Gln Gly Ala Ile Thr Asn Arg
            340                 345                 350

Gln Gln Phe Asp Thr Ile Met Asn Tyr Ile Asp Ile Gly Lys Lys Glu
        355                 360                 365

Gly Ala Lys Ile Leu Thr Gly Gly Glu Lys Val Gly Asp Lys Gly Tyr
    370                 375                 380

Phe Ile Arg Pro Thr Val Phe Tyr Asp Val Asn Glu Asp Met Arg Ile
385                 390                 395                 400

Val Lys Glu Glu Ile Phe Gly Pro Val Val Thr Val Ala Lys Phe Lys
                405                 410                 415

Thr Leu Glu Glu Gly Val Glu Met Ala Asn Ser Ser Glu Phe Gly Leu
            420                 425                 430

Gly Ser Gly Ile Glu Thr Glu Ser Leu Ser Thr Gly Leu Lys Val Ala
        435                 440                 445

Lys Met Leu Lys Ala Gly Thr Val Trp Ile Asn Thr Tyr Asn Asp Phe
    450                 455                 460

Asp Ser Arg Val Pro Phe Gly Val Lys Gln Ser Gly Tyr Gly Arg
465                 470                 475                 480

Glu Met Gly Glu Glu Val Tyr His Ala Tyr Thr Glu Val Lys Ala Val
                485                 490                 495

Arg Ile Lys Leu
            500

<210> SEQ ID NO 64
<211> LENGTH: 1500
<212> TYPE: DNA
<213> ORGANISM: Artificial
```

<220> FEATURE:
<223> OTHER INFORMATION: mutated and/or codon-optimized sequence

<400> SEQUENCE: 64

```
atgaccaagc ttcacttcga caccgcagaa ccggttaaga tcaccctgcc aaacggcctc      60
acttatgaac agcccaccgg cctgttcatc aacaacaaat tcatgaaggc gcaggatggc     120
aagacctacc cggtcgagga cccatcgacg gagaatactg tttgtgaagt gtcctcggcg     180
acgactgaag atgtcgagta tgcaatcgag tgcgctgatc gagcattcca tgatactgaa     240
tgggcgacac aagatcctcg tgagcgtggt cgtctgctct ccaagcttgc ggacgagctt     300
gaatcccaaa ttgatctggt gtcttctatt gaagctctcg ataatggaaa accctcgct     360
ctggcccgcg gtgacgtgac catcgctatt aactgcctgc gcgacgcggc agcttacgca     420
gataaggtca atggccgcac cattaacaca ggcgatggtt atatgaattt acaaccttg     480
gagcctattg gagtgtgcgg ccagattatc ccatggaact cccccatcat gatgctcgct     540
tggaagattg cccccagccct tgcaatggga acgtttgca ttctgaaacc ggccgcagtg     600
acgcccctga atgctctgta tttcgcatct ctgtgtaaga aggtaggtat ccccgctggc     660
gtcgttaaca ttgttcctgg tccaggtcgt actgtaggag cggcgctcac caacgatccg     720
cgcatccgta aactggcgtt caccggatcg acggaagtgg gtaagtccgt cgcagtcgac     780
tcttccgaat ctaatctcaa gaagattacg ctcgaactcg gcggcaaatc tgcacacctc     840
gtcttcgatg atgctaatat caagaaaacc ttgccgaacc tcgtcaacgg tattttcaag     900
aatgcgggcc aaatctgctc ctccggcagc cgtatctacg ttcaggaagg tatttacgac     960
gagctgctcg cagccttcaa ggcgtatctg gagacggaaa ttaaggtggg caacccattt    1020
gataaagcca acttcagggg cgctattact aatcgccagc agtttgacac cattatgaac    1080
tacattgata ttggtaagaa ggaaggcgct aagattctca ctggaggaga aaaggttggt    1140
gacaaaggat actttatccg tcccactgta ttctacgatg tgaacgaaga catgcgcatt    1200
gtgaaggaag aaattttcgg tccagttgtt acagtggcaa agttcaaaac cctcgaggaa    1260
ggtgttgaga tggctaatag cagcgagttc ggcctgggat caggcattga cacagaatcc    1320
ctttcgaccg gcctgaaggt ggccaagatg ttgaaggctg gcacagtttg gatcaatacc    1380
tataatgatt ttgactcccg tgttccgttt ggcggcgtga acaatccgg ttacggccgc    1440
gaaatgggcg aggaggtgta ccacgcatac accgaagtga aggcagttcg aatcaaattg    1500
```

<210> SEQ ID NO 65
<211> LENGTH: 348
<212> TYPE: PRT
<213> ORGANISM: S. cerevisiae S288c

<400> SEQUENCE: 65

```
Met Ser Ile Pro Glu Thr Gln Lys Ala Ile Ile Phe Tyr Glu Ser Asn
1               5                   10                  15

Gly Lys Leu Glu His Lys Asp Ile Pro Val Pro Lys Pro Lys Pro Asn
            20                  25                  30

Glu Leu Leu Ile Asn Val Lys Tyr Ser Gly Val Cys His Thr Asp Leu
        35                  40                  45

His Ala Trp His Gly Asp Trp Pro Leu Pro Thr Lys Leu Pro Leu Val
    50                  55                  60

Gly Gly His Glu Gly Ala Gly Val Val Val Gly Met Gly Glu Asn Val
65                  70                  75                  80

Lys Gly Trp Lys Ile Gly Asp Tyr Ala Gly Ile Lys Trp Leu Asn Gly
```

```
                   85                  90                  95
        Ser Cys Met Ala Cys Glu Tyr Cys Glu Leu Gly Asn Glu Ser Asn Cys
                        100                 105                 110

Pro His Ala Asp Leu Ser Gly Tyr Thr His Asp Gly Ser Phe Gln Glu
                    115                 120                 125

Tyr Ala Thr Ala Asp Ala Val Gln Ala Ala His Ile Pro Gln Gly Thr
                130                 135                 140

Asp Leu Ala Glu Val Ala Pro Ile Leu Cys Ala Gly Ile Thr Val Tyr
        145                 150                 155                 160

Lys Ala Leu Lys Ser Ala Asn Leu Arg Ala Gly His Trp Ala Ala Ile
                        165                 170                 175

Ser Gly Ala Ala Gly Gly Leu Gly Ser Leu Ala Val Gln Tyr Ala Lys
                    180                 185                 190

Ala Met Gly Tyr Arg Val Leu Gly Ile Asp Gly Gly Pro Gly Lys Glu
                195                 200                 205

Glu Leu Phe Thr Ser Leu Gly Gly Glu Val Phe Ile Asp Phe Thr Lys
            210                 215                 220

Glu Lys Asp Ile Val Ser Ala Val Lys Ala Thr Asn Gly Gly Ala
        225                 230                 235                 240

His Gly Ile Ile Asn Val Ser Val Ser Glu Ala Ala Ile Glu Ala Ser
                        245                 250                 255

Thr Arg Tyr Cys Arg Ala Asn Gly Thr Val Val Leu Val Gly Leu Pro
                    260                 265                 270

Ala Gly Ala Lys Cys Ser Ser Asp Val Phe Asn His Val Val Lys Ser
                275                 280                 285

Ile Ser Ile Val Gly Ser Tyr Val Gly Asn Arg Ala Asp Thr Arg Glu
            290                 295                 300

Ala Leu Asp Phe Phe Ala Arg Gly Leu Val Lys Ser Pro Ile Lys Val
        305                 310                 315                 320

Val Gly Leu Ser Ser Leu Pro Glu Ile Tyr Glu Lys Met Glu Lys Gly
                        325                 330                 335

Gln Ile Ala Gly Arg Tyr Val Val Asp Thr Ser Lys
                    340                 345

<210> SEQ ID NO 66
<211> LENGTH: 1044
<212> TYPE: DNA
<213> ORGANISM: Artificial
<220> FEATURE:
<223> OTHER INFORMATION: mutated and/or codon-optimized sequence

<400> SEQUENCE: 66
atgtccatcc cggaaaccca gaaagccatt atcttttacg agagcaacgg caagctcgaa      60
cataaggata ttccagtgcc aaaaccgaag ccaaacgagc tcctgatcaa cgttaagtac     120
tccggagtgt gccacacgga tctgcacgct tggcatggcg attggcccct ccctactaag     180
ctgccactgg tcggcggaca cgaaggcgct ggtgtggtgg tgggaatggg tgagaacgtt     240
aaaggctgga agattggcga ctacgctggc atcaaatggc tgaatggttc ctgcatggct     300
tgtgaatact gtgagcttgg taatgaaagc aactgcccgc acgccgattt gagcggatac     360
acacatgatg gctccttcca ggagtacgct accgccgacg ctgtgcaagc agcgcacatt     420
ccacaaggca ccgacctcgc tgaagttgct ccaatcctgt gtgctggcat caccgtatac     480
aaggctctca atccgcaaa cctgcgcgcg ggccactggg cagcgatttc aggcgctgcc     540
ggcggtctcg gttccttggc tgtgcaatac gcaaaggcta tgggataccg agtactggga     600
```

```
attgacggcg gaccaggaaa agaggaactt ttcacgtccc tcggcggcga ggtcttcatc    660
gattttacca agagaagga catcgtctcc gctgtcgtga aggcaactaa cggcggcgct    720
cacggtatca tcaacgtgtc tgtttcggag gcggctatcg aggctagcac ccgatactgc    780
cgtgcaaatg gcacgtcgt gttggttggc ctgccagcgg gcgcaaagtg ctcttctgat    840
gtcttcaacc atgttgttaa gtccatttcg attgtgggct catacgttgg caatcgcgct    900
gacactcgtg aggcgttgga cttcttcgcg cgcggcctcg taaagtcgcc tatcaaggtt    960
gtcggtttga gcagcctgcc cgaaatctac gaaaaaatgg aaaagggtca aattgccggc   1020
cgatatgtcg tcgataccct ctaaa                                         1044
```

<210> SEQ ID NO 67
<211> LENGTH: 497
<212> TYPE: PRT
<213> ORGANISM: Yarrowia lipolytica CLIB 122 / E 150

<400> SEQUENCE: 67

```
Met Ser Ala Lys Ser Ile His Glu Ala Asp Gly Lys Ala Leu Leu Ala
1               5                   10                  15

His Phe Leu Ser Lys Ala Pro Val Trp Ala Glu Gln Gln Pro Ile Asn
            20                  25                  30

Thr Phe Glu Met Gly Thr Pro Lys Leu Ala Ser Leu Thr Phe Glu Asp
        35                  40                  45

Gly Val Ala Pro Glu Gln Ile Phe Ala Ala Glu Lys Thr Tyr Pro
    50                  55                  60

Trp Leu Leu Glu Ser Gly Ala Lys Phe Val Ala Lys Pro Asp Gln Leu
65                  70                  75                  80

Ile Lys Arg Arg Gly Lys Ala Gly Leu Leu Val Leu Asn Lys Ser Trp
                85                  90                  95

Glu Glu Cys Lys Pro Trp Ile Ala Glu Arg Ala Ala Lys Pro Ile Asn
            100                 105                 110

Val Glu Gly Ile Asp Gly Val Leu Arg Thr Phe Leu Val Glu Pro Phe
        115                 120                 125

Val Pro His Asp Gln Lys His Glu Tyr Tyr Ile Asn Ile His Ser Val
    130                 135                 140

Arg Glu Gly Asp Trp Ile Leu Phe Tyr His Glu Gly Gly Val Asp Val
145                 150                 155                 160

Gly Asp Val Asp Ala Lys Ala Ala Lys Ile Leu Ile Pro Val Asp Ile
                165                 170                 175

Glu Asn Glu Tyr Pro Ser Asn Ala Thr Leu Thr Lys Glu Leu Leu Ala
            180                 185                 190

His Val Pro Glu Asp Gln His Gln Thr Leu Leu Asp Phe Ile Asn Arg
        195                 200                 205

Leu Tyr Ala Val Tyr Val Asp Leu Gln Phe Thr Tyr Leu Glu Ile Asn
    210                 215                 220

Pro Leu Val Val Ile Pro Thr Ala Gln Gly Val Glu Val His Tyr Leu
225                 230                 235                 240

Asp Leu Ala Gly Lys Leu Asp Gln Thr Ala Glu Phe Glu Cys Gly Pro
                245                 250                 255

Lys Trp Ala Ala Ala Arg Ser Pro Ala Ala Leu Gly Gln Val Val Thr
            260                 265                 270

Ile Asp Ala Gly Ser Thr Lys Val Ser Ile Asp Ala Gly Pro Ala Met
        275                 280                 285
```

| | | | | | | | | | | | |
|---|---|---|---|---|---|---|---|---|---|---|---|
| Val | Phe | Pro | Ala | Pro | Phe | Gly | Arg | Glu | Leu | Ser | Lys | Glu | Glu | Ala | Tyr |
| | | 290 | | | | 295 | | | | 300 | |
| Ile | Ala | Glu | Leu | Asp | Ser | Lys | Thr | Gly | Ala | Ser | Leu | Lys | Leu | Thr | Val |
| 305 | | | | | 310 | | | | | 315 | | | | | 320 |
| Leu | Asn | Ala | Lys | Gly | Arg | Ile | Trp | Thr | Leu | Val | Ala | Gly | Gly | Ala |
| | | | | 325 | | | | | 330 | | | | | 335 |
| Ser | Val | Val | Tyr | Ala | Asp | Ala | Ile | Ala | Ser | Ala | Gly | Phe | Ala | Asp | Glu |
| | | | | 340 | | | | | 345 | | | | | 350 |
| Leu | Ala | Asn | Tyr | Gly | Glu | Tyr | Ser | Gly | Ala | Pro | Asn | Glu | Thr | Gln | Thr |
| | | | | 355 | | | | | 360 | | | | | 365 |
| Tyr | Glu | Tyr | Ala | Lys | Thr | Val | Leu | Asp | Leu | Met | Thr | Arg | Gly | Asp | Ala |
| | 370 | | | | | 375 | | | | | 380 |
| His | Pro | Glu | Gly | Lys | Val | Leu | Phe | Ile | Gly | Gly | Ile | Ala | Asn | Phe |
| 385 | | | | | 390 | | | | | 395 | | | | | 400 |
| Thr | Gln | Val | Gly | Ser | Thr | Phe | Lys | Gly | Ile | Ile | Arg | Ala | Phe | Arg | Asp |
| | | | | 405 | | | | | 410 | | | | | 415 |
| Tyr | Gln | Ser | Ser | Leu | His | Asn | His | Lys | Val | Lys | Ile | Tyr | Val | Arg | Arg |
| | | | | 420 | | | | | 425 | | | | | 430 |
| Gly | Gly | Pro | Asn | Trp | Gln | Glu | Gly | Leu | Arg | Leu | Ile | Lys | Ser | Ala | Gly |
| | | | | 435 | | | | | 440 | | | | | 445 |
| Asp | Glu | Leu | Asn | Leu | Pro | Met | Glu | Ile | Tyr | Gly | Pro | Asp | Met | His | Val |
| | 450 | | | | | 455 | | | | | 460 |
| Ser | Gly | Ile | Val | Pro | Leu | Ala | Leu | Leu | Gly | Lys | Arg | Pro | Lys | Asn | Val |
| 465 | | | | | 470 | | | | | 475 | | | | | 480 |
| Lys | Pro | Phe | Gly | Thr | Gly | Pro | Ser | Thr | Glu | Ala | Ser | Thr | Pro | Leu | Gly |
| | | | | 485 | | | | | 490 | | | | | 495 |
| Val |

<210> SEQ ID NO 68
<211> LENGTH: 1491
<212> TYPE: DNA
<213> ORGANISM: Artificial
<220> FEATURE:
<223> OTHER INFORMATION: mutated and/or codon-optimized sequence

<400> SEQUENCE: 68

```
atgagcgcca agagcatcca cgaggctgat ggcaaagcac tccttgccca cttcttgtcc      60
aaagcaccag tctgggcaga gcaacagccc atcaataact tgagatgggt acccccaaa     120
ctggcaagcc tgactttcga ggatggtgta gcgcctgagc aaatcttcgc cgctgcagaa     180
aaaacctacc cgtggctgct tgaatcaggt gctaagttcg tcgccaagcc tgatcagctg     240
attaagcgac gtggtaaggc gggcttgctt gtgcttaaca atcctgggaa gaatgtaag      300
ccctggattg ccgagcgcgc agcgaagcct attaatgtag agggaatcga cggcgtgttg     360
cgtacctttc tcgttgaacc atttgtcccc catgatcaga agcatgaata ttacatcaac     420
atccatagcg tccgcgaagg tgattggatc ctgtttttac cacgaaggtgg tgtcgacgtg     480
ggcgacgttg atgctaaggc agcaaaaatc ctgatcccgg ttgatattga aaacgagtac     540
ccatcaaatg caaccctcac caaggagctt ttggctcatg tgcctgaaga tcagcaccaa     600
accttgctcg atttcatcaa ccgcctctac gcggtatacg tagatctgca attcacctac     660
ttggaaatta cccgctcgt ggtgattcct acggctcagg gagtcgaggt gcactatctc     720
gatttggcag gtaagttgga ccagaccgca gaattcgaat gtggacctaa atgggcggcc     780
gctcgttccc ccgcggcctt gggacaggtc gttacgatcg acgcgggtag caccaaggtc     840
```

-continued

```
tcgattgacg ctggtccagc catggtgttc ccagccccgt ttggccgcga actgagcaaa      900
gaagaagcat acatcgcgga actggattct aagacgggtg cctctctcaa gcttactgtc      960
ttgaacgcaa agggccgcat ctggacccct gtcgcaggtg gaggagcaag cgtggtctac     1020
gcagacgcga tcgcctccgc tggatttgct gatgaactgg ctaattacgg agagtactcg     1080
ggtgcaccga acgagaccca gacttatgaa tatgccaaga ccgtcctcga tctcatgacc     1140
cgtggagacg cgcacccaga gggaaaggtg ctgttcatcg gcggaggcat cgccaacttc     1200
acccaggtag gctccacttt caaaggtatt atccgcgcct tccgtgacta ccaatcatcc     1260
cttcacaatc acaaggttaa gatctacgtc cgccgcggtg gtccaaactg gcaggaaggt     1320
ctgcgactta tcaaatctgc aggcgacgag ctgaatctcc caatggagat ttacggccca     1380
gatatgcacg tcagcggcat cgtgcccctc gctctgttgg gtaaacgccc taagaatgtg     1440
aagccattcg gaaccggccc ttccactgag gcatcgactc cactgggtgt g              1491
```

<210> SEQ ID NO 69
<211> LENGTH: 887
<212> TYPE: PRT
<213> ORGANISM: E. coli (strain K12)

<400> SEQUENCE: 69

```
Met Ser Glu Arg Phe Pro Asn Asp Val Asp Pro Ile Glu Thr Arg Asp
1               5                  10                  15

Trp Leu Gln Ala Ile Glu Ser Val Ile Arg Glu Gly Val Glu Arg
            20                  25                  30

Ala Gln Tyr Leu Ile Asp Gln Leu Leu Ala Glu Ala Arg Lys Gly Gly
        35                  40                  45

Val Asn Val Ala Ala Gly Thr Gly Ile Ser Asn Tyr Ile Asn Thr Ile
    50                  55                  60

Pro Val Glu Glu Gln Pro Glu Tyr Pro Gly Asn Leu Glu Leu Glu Arg
65                  70                  75                  80

Arg Ile Arg Ser Ala Ile Arg Trp Asn Ala Ile Met Thr Val Leu Arg
                85                  90                  95

Ala Ser Lys Lys Asp Leu Glu Leu Gly Gly His Met Ala Ser Phe Gln
            100                 105                 110

Ser Ser Ala Thr Ile Tyr Asp Val Cys Phe Asn His Phe Phe Arg Ala
        115                 120                 125

Arg Asn Glu Gln Asp Gly Gly Asp Leu Val Tyr Phe Gln Gly His Ile
    130                 135                 140

Ser Pro Gly Val Tyr Ala Arg Ala Phe Leu Glu Gly Arg Leu Thr Gln
145                 150                 155                 160

Glu Gln Leu Asp Asn Phe Arg Gln Glu Val His Gly Asn Gly Leu Ser
                165                 170                 175

Ser Tyr Pro His Pro Lys Leu Met Pro Glu Phe Trp Gln Phe Pro Thr
            180                 185                 190

Val Ser Met Gly Leu Gly Pro Ile Gly Ala Ile Tyr Gln Ala Lys Phe
        195                 200                 205

Leu Lys Tyr Leu Glu His Arg Gly Leu Lys Asp Thr Ser Lys Gln Thr
    210                 215                 220

Val Tyr Ala Phe Leu Gly Asp Gly Glu Met Asp Glu Pro Glu Ser Lys
225                 230                 235                 240

Gly Ala Ile Thr Ile Ala Thr Arg Glu Lys Leu Asp Asn Leu Val Phe
                245                 250                 255

Val Ile Asn Cys Asn Leu Gln Arg Leu Asp Gly Pro Val Thr Gly Asn
```

```
                260                 265                 270
Gly Lys Ile Ile Asn Glu Leu Glu Gly Ile Phe Glu Gly Ala Gly Trp
            275                 280                 285

Asn Val Ile Lys Val Met Trp Gly Ser Arg Trp Asp Glu Leu Leu Arg
290                 295                 300

Lys Asp Thr Ser Gly Lys Leu Ile Gln Leu Met Asn Glu Thr Val Asp
305                 310                 315                 320

Gly Asp Tyr Gln Thr Phe Lys Ser Lys Asp Gly Ala Tyr Val Arg Glu
                325                 330                 335

His Phe Phe Gly Lys Tyr Pro Glu Thr Ala Ala Leu Val Ala Asp Trp
            340                 345                 350

Thr Asp Glu Gln Ile Trp Ala Leu Asn Arg Gly Gly His Asp Pro Lys
        355                 360                 365

Lys Ile Tyr Ala Ala Phe Lys Lys Ala Gln Glu Thr Lys Gly Lys Ala
    370                 375                 380

Thr Val Ile Leu Ala His Thr Ile Lys Gly Tyr Gly Met Gly Asp Ala
385                 390                 395                 400

Ala Glu Gly Lys Asn Ile Ala His Gln Val Lys Lys Met Asn Met Asp
                405                 410                 415

Gly Val Arg His Ile Arg Asp Arg Phe Asn Val Pro Val Ser Asp Ala
            420                 425                 430

Asp Ile Glu Lys Leu Pro Tyr Ile Thr Phe Pro Glu Gly Ser Glu Glu
        435                 440                 445

His Thr Tyr Leu His Ala Gln Arg Gln Lys Leu His Gly Tyr Leu Pro
    450                 455                 460

Ser Arg Gln Pro Asn Phe Thr Glu Lys Leu Glu Leu Pro Ser Leu Gln
465                 470                 475                 480

Asp Phe Gly Ala Leu Leu Glu Glu Gln Ser Lys Glu Ile Ser Thr Thr
                485                 490                 495

Ile Ala Phe Val Arg Ala Leu Asn Val Met Leu Lys Asn Lys Ser Ile
            500                 505                 510

Lys Asp Arg Leu Val Pro Ile Ile Ala Asp Glu Ala Arg Thr Phe Gly
        515                 520                 525

Met Glu Gly Leu Phe Arg Gln Ile Gly Ile Tyr Ser Pro Asn Gly Gln
    530                 535                 540

Gln Tyr Thr Pro Gln Asp Arg Glu Gln Val Ala Tyr Lys Glu Asp
545                 550                 555                 560

Glu Lys Gly Gln Ile Leu Gln Glu Gly Ile Asn Glu Leu Gly Ala Gly
                565                 570                 575

Cys Ser Trp Leu Ala Ala Ala Thr Ser Tyr Ser Thr Asn Asn Leu Pro
            580                 585                 590

Met Ile Pro Phe Tyr Ile Tyr Tyr Ser Met Phe Gly Phe Gln Arg Ile
        595                 600                 605

Gly Asp Leu Cys Trp Ala Ala Gly Asp Gln Gln Ala Arg Gly Phe Leu
    610                 615                 620

Ile Gly Gly Thr Ser Gly Arg Thr Thr Leu Asn Gly Glu Gly Leu Gln
625                 630                 635                 640

His Glu Asp Gly His Ser His Ile Gln Ser Leu Thr Ile Pro Asn Cys
                645                 650                 655

Ile Ser Tyr Asp Pro Ala Tyr Ala Tyr Glu Val Ala Val Ile Met His
            660                 665                 670

Asp Gly Leu Glu Arg Met Tyr Gly Glu Lys Gln Glu Asn Val Tyr Tyr
        675                 680                 685
```

```
Tyr Ile Thr Thr Leu Asn Glu Asn Tyr His Met Pro Ala Met Pro Glu
        690                 695                 700
Gly Ala Glu Glu Gly Ile Arg Lys Gly Ile Tyr Lys Leu Glu Thr Ile
705                 710                 715                 720
Glu Gly Ser Lys Gly Lys Val Gln Leu Leu Gly Ser Gly Ser Ile Leu
                725                 730                 735
Arg His Val Arg Glu Ala Ala Glu Ile Leu Ala Lys Asp Tyr Gly Val
            740                 745                 750
Gly Ser Asp Val Tyr Ser Val Thr Ser Phe Thr Glu Leu Ala Arg Asp
        755                 760                 765
Gly Gln Asp Cys Glu Arg Trp Asn Met Leu His Pro Leu Glu Thr Pro
770                 775                 780
Arg Val Pro Tyr Ile Ala Gln Val Met Asn Asp Ala Pro Ala Val Ala
785                 790                 795                 800
Ser Thr Asp Tyr Met Lys Leu Phe Ala Glu Gln Val Arg Thr Tyr Val
                805                 810                 815
Pro Ala Asp Asp Tyr Arg Val Leu Gly Thr Asp Gly Phe Gly Arg Ser
            820                 825                 830
Asp Ser Arg Glu Asn Leu Arg His His Phe Glu Val Ala Ser Tyr
        835                 840                 845
Val Val Val Ala Ala Leu Gly Glu Leu Ala Lys Arg Gly Glu Ile Asp
        850                 855                 860
Lys Lys Val Val Ala Asp Ala Ile Ala Lys Phe Asn Ile Asp Ala Asp
865                 870                 875                 880
Lys Val Asn Pro Arg Leu Ala
                885

<210> SEQ ID NO 70
<211> LENGTH: 2661
<212> TYPE: DNA
<213> ORGANISM: Artificial
<220> FEATURE:
<223> OTHER INFORMATION: mutated and/or codon-optimized sequence

<400> SEQUENCE: 70
atgagcgagc gcttccccaa tgacgttgat cccattgaga cccgcgattg gttgcaggcg        60
atcgagtcgg tcatccgtga ggagggagtc gaacgagccc agtatttgat cgatcaactg       120
cttgcagaag cccgcaaggg aggcgtgaat gtcgcggctg gtaccggcat tagcaattac       180
atcaacacca tcccagtcga ggagcaacca gagtaccctg gtaatcttga actcgaacgc       240
cgtattcgca gcgccattcg ctggaacgca attatgaccg ttctgcgcgc gtcaaagaaa       300
gacctcgaac tgggaggtca tatggcatcc tttcaatcct cagccaccat ctacgacgtt       360
tgctttaacc acttcttccg cgcgcgtaat gaacaagatg gcggagacct ggtttatttt       420
cagggtcata tctcgccggg cgtctacgca cgcgccttcc tggaaggacg cctgacgcaa       480
gaacagctcg acaatttccg acaagaagtg cacggcaacg actgtcctc ttacccgcat       540 ccaaaactga tgcctgagtt ctggcaattt ccaacggtgt ccatgggtct cggcccaatc       600
ggtgcaatct accaggcaaa gtttctgaag tacctggagc accgcggcct caaagatacg       660
tccaagcaaa ccgtctacgc gtttctgggt gacggagaaa tggatgagcc tgaatccaag       720
ggcgctatta cgattgccac tcgcgaaaag ctcgacaacc tggtcttcgt catcaattgc       780
aacctgcaac gattgacgg tccggttacg ggcaatggca agatcattaa tgagctcgaa       840
ggcatcttcg agggcgctgg ctggaacgtg attaaggtga tgtgggttc tcgctgggac       900
```

```
gaactgctgc gcaaagacac cagcggcaag ctgattcagc tgatgaacga gaccgtggat    960
ggtgattacc agaccttcaa gtccaaggat ggagcctacg tccgtgagca ctttttttgga  1020
aaatatcctg aaacggcagc attggtggca gattggaccg acgagcagat ctgggcgctg  1080
aatcgcggtg gccatgaccc taagaaaatc tacgcggcct tcaagaaggc acaagaaacc  1140
aagggcaaag ccactgtcat cttggcgcat accatcaaag gctacggtat gggcgatgcc  1200
gctgagggca aaacatcgc tcatcaagtt aagaagatga acatggatgg tgtccgccac  1260
atccgcgatc gctttaacgt ccccgtctct gacgcagata ttgagaagct gccatacatc  1320
accttcccag aaggctccga ggaacatacc tatctccacg cacagcgcca gaagctccat  1380
ggttaccttc cgtcgcgtca gccaaatttc accgaaaaat tggaattgcc ctcattgcaa  1440
gattttggcg cgctcttgga ggaacagtct aaagagatct ctacaaccat cgcgtttgtg  1500
cgtgccctca acgtcatgtt gaagaacaag tctatcaagg atcgattggt gcccattatc  1560
gctgatgaag cccgcacctt cggtatggag ggtttgtttc gccagattgg catctactct  1620
cccaatggcc agcaatacac cccacaggat cgcgaacaag ttgcctacta taggaagac   1680
gagaaaggcc agatccttca agaaggcatc aacgaacttg gcgcgggatg cagctggctc  1740
gccgctgcca caagctactc aactaacaac ctcccgatga tccctttcta tatctactat  1800
tcgatgttcg gcttccaacg cattggcgac ttgtgctggg cggcaggcga tcaacaagcc  1860
cgcggctttc tgattggcgg tacttcgggt cgcactacgc tcaacggcga aggtctccag  1920
catgaggatg gtcattcgca catccaatca ctcaccattc caaactgtat ttcctatgac  1980
cccgcatacg cttacgaggt tgcggtcatc atgcacgatg gtctggaacg tatgtacggc  2040
gagaagcagg aaaatgtgta ttactacatc accaccctga atgaaaatta ccatatgcct  2100
gccatgcctg agggtgcgga agaggaat  tcgtaagggta tctacaagct ggaaacaatt  2160
gaaggatcca agggtaaggt acagcttctg ggatctggct ccattcttcg tcatgtgcgc  2220
gaagcagcgg aaatcctcgc aaaagattac ggcgtaggca gcgacgttta ctccgttacg  2280
agcttcactg aactggcccg cgacggccag gactgtgagc gttggaacat gctgcatccc  2340
cttgaaaccc cacgcgtgcc gtatatcgca caagtaatga atgacgcccc tgccgtcgcc  2400
tcgactgact atatgaagct cttcgccgaa caggtccgca cgtacgttcc agcagatgat  2460
taccgcgttc tgggcaccga cggctttggc cgctccgatt cacgcgagaa cctgcgacac  2520
cacttcgagg tcgacgcttc ctacgtggta gtagctgcgc tcggagaact ggcaaagcgt  2580
ggcgagatcg acaaaaaggt agttgctgat gctatcgcta agttcaacat tgacgccgac  2640
aaggtcaatc cccgcttggc a                                             2661
```

<210> SEQ ID NO 71
<211> LENGTH: 120
<212> TYPE: PRT
<213> ORGANISM: S. cerevisiae S288c

<400> SEQUENCE: 71

Met Pro Lys Val Tyr Ser Tyr Gln Glu Val Ala Glu His Asn Gly Pro
1               5                   10                  15

Glu Asn Phe Trp Ile Ile Ile Asp Asp Lys Val Tyr Asp Val Ser Gln
            20                  25                  30

Phe Lys Asp Glu His Pro Gly Gly Asp Glu Ile Ile Met Asp Leu Gly
        35                  40                  45

Gly Gln Asp Ala Thr Glu Ser Phe Val Asp Ile Gly His Ser Asp Glu

```
                        50                  55                  60
Ala Leu Arg Leu Leu Lys Gly Leu Tyr Ile Gly Asp Val Asp Lys Thr
 65                  70                  75                  80

Ser Glu Arg Val Ser Val Glu Lys Val Ser Thr Ser Glu Asn Gln Ser
                    85                  90                  95

Lys Gly Ser Gly Thr Leu Val Val Ile Leu Ala Ile Leu Met Leu Gly
                100                 105                 110

Val Ala Tyr Tyr Leu Leu Asn Glu
            115                 120

<210> SEQ ID NO 72
<211> LENGTH: 360
<212> TYPE: DNA
<213> ORGANISM: Artificial
<220> FEATURE:
<223> OTHER INFORMATION: mutated and/or codon-optimized sequence

<400> SEQUENCE: 72
atgccaaagg tctattctta tcaggaagtc gcagaacaca acggcccaga aaacttctgg     60
atcattatcg atgataaggt ttacgatgtg tcgcagttca agacgaaaca cccaggtgga    120
gatgaaatta ttatggatct tggcggacaa gatgcgacgg aaagctttgt tgatatcggt    180
cactcagacg aagccttgcg cctcctcaag ggcctttaca tcggtgacgt agataaaacc    240
tcggagcgcg tttccgtcga gaaagtttcc acctcagaga accaatccaa aggctccggt    300
accctcgtgg tgatcctcgc tattctgatg ttgggtgtcg cctattatct tctgaatgag    360

<210> SEQ ID NO 73
<211> LENGTH: 485
<212> TYPE: PRT
<213> ORGANISM: Emericella nidulans ATCC 38163

<400> SEQUENCE: 73

Met Ser Ala Lys Ser Ile Phe Glu Ala Asp Gly Lys Ala Ile Leu Asn
  1               5                  10                  15

Tyr His Leu Thr Arg Ala Pro Val Ile Lys Pro Thr Pro Leu Pro Pro
                 20                  25                  30

Ser Asn Thr His Asn Pro Pro Lys Leu Ala Ser Leu Tyr Phe Pro
             35                  40                  45

Asp Asp Leu Ser Val Lys Asp Val Leu Asp Gln Ala Glu Val Thr Tyr
 50                  55                  60

Pro Trp Leu Leu Thr Pro Gly Ser Lys Phe Val Ala Lys Pro Asp Gln
 65                  70                  75                  80

Leu Ile Lys Arg Arg Gly Lys Ser Gly Leu Leu Ala Leu Asn Lys Thr
                 85                  90                  95

Trp Ala Glu Ala Arg Glu Trp Ile Glu Ala Arg Ala Thr Lys Glu Gln
                100                 105                 110

Gln Val Glu Thr Val Val Gly Val Leu Arg His Phe Leu Val Glu Pro
            115                 120                 125

Phe Val Pro His Pro Gln Glu Thr Glu Tyr Tyr Ile Asn Ile His Ser
130                 135                 140

Val Arg Glu Gly Asp Trp Ile Leu Phe Thr His Glu Gly Gly Val Asp
145                 150                 155                 160

Val Gly Asp Val Asp Ala Lys Ala Glu Lys Leu Leu Ile Pro Val Asn
                165                 170                 175

Leu Lys Asn Tyr Pro Ser Asn Glu Glu Ile Ala Ser Ala Leu Leu Ser
                180                 185                 190
```

Lys Val Pro Lys Gly Ile His Asn Val Leu Val Asp Phe Ile Ser Arg
            195                 200                 205

Leu Tyr Ala Val Tyr Val Asp Cys Gln Phe Thr Tyr Leu Glu Ile Asn
            210                 215                 220

Pro Leu Val Val Ile Pro Asn Ala Asp Ala Thr Ser Ala Asp Val His
225                 230                 235                 240

Phe Leu Asp Leu Ala Ala Lys Leu Asp Gln Thr Ala Glu Phe Glu Cys
            245                 250                 255

Gly Thr Lys Trp Ala Val Ala Arg Ser Pro Ala Asn Leu Gly Leu Ala
            260                 265                 270

Ala Leu Pro Thr Ser Asp Lys Val Asn Ile Asp Ala Gly Pro Pro Met
            275                 280                 285

Glu Phe Pro Ala Pro Phe Gly Arg Glu Leu Ser Lys Glu Lys Phe
            290                 295                 300

Ile Ser Asp Met Asp Ala Lys Thr Gly Ala Ser Leu Lys Leu Thr Val
305                 310                 315                 320

Leu Asn Pro Asn Gly Arg Val Trp Thr Leu Val Ala Gly Gly Gly Ala
            325                 330                 335

Ser Val Val Tyr Ala Asp Ala Ile Ala Ser Ala Gly Phe Val Ser Glu
            340                 345                 350

Leu Ala Asn Tyr Gly Glu Tyr Ser Gly Ala Pro Thr Glu Thr Gln Thr
            355                 360                 365

Phe Asn Tyr Ala Arg Thr Ile Leu Asp Leu Met Leu Arg Ser Pro Ile
            370                 375                 380

His Pro Asp Gly Lys Val Leu Phe Ile Gly Gly Ile Ala Asn Phe
385                 390                 395                 400

Thr Asn Val Ala Ser Thr Phe Lys Gly Val Ile Arg Ala Leu Arg Glu
            405                 410                 415

Val Ala Pro Val Leu Asn Glu His Lys Val Gln Ile Trp Val Arg Arg
            420                 425                 430

Ala Gly Pro Asn Tyr Gln Glu Gly Leu Lys Asn Ile Lys Ala Val Gly
            435                 440                 445

Glu Glu Leu Gly Leu Asn Met His Val Tyr Gly Pro Glu Met His Val
            450                 455                 460

Ser Gly Ile Val Pro Leu Ala Leu Gln Gly Lys Gln Thr Asp Ile Lys
465                 470                 475                 480

Glu Phe Gly Thr Ala
            485

<210> SEQ ID NO 74
<211> LENGTH: 1455
<212> TYPE: DNA
<213> ORGANISM: Artificial
<220> FEATURE:
<223> OTHER INFORMATION: mutated and/or codon-optimized sequence

<400> SEQUENCE: 74
atgtcggcca agtcgatctt cgaagcagac ggaaaagcaa ttttgaatta ccacctgacc     60
cgcgcaccag tgatcaaacc aaccctctg ccaccttcca acactcataa cccccctccg     120
aaattggctt ctctctactt cccggacgac ttgtccgtga aggacgttct cgatcaagca     180
gaagttacat atccgtggct tcttacccca ggctccaaat tgtggccaa acctgatcag     240 ttgatcaaac gtcgcggcaa atccggcctt ctggcgttga caagacatg ggccgaagca     300 cgtgagtgga ttgaagctcg agcaactaag gaacaacagg tggaaactgt agtgggagtt     360

-continued

```
ctccgtcact tcctggttga accttttgtg cctcaccctc aggagacgga gtactacatt      420
aacatccact ccgtgcgcga gggtgactgg atcctcttta cccacgaggg cggtgtcgat      480
gtcggcgatg tcgacgccaa agcagagaag ctgttgatcc cggtgaatct caagaactac      540
ccctccaacg aggagatcgc atctgcattg ttgtccaagg tccctaaggg aatccataac      600
gtccttgtgg actttatctc ccgtctgtac gcggtctatg ttgattgtca atttacgtac      660
ctcgaaatca acccattggt cgtgattccc aacgcggacg caacttccgc tgatgttcat      720
tttcttgatc tcgctgcgaa gctggatcag acagccgaat cgaatgcgg taccaagtgg       780 gccgtcgctc gttctcccgc caacttgggc ctcgcagcct tgcctacgag cgataaggtg      840
aacattgacg cgggacctcc gatggaattt cctgcccct tggtcgcga gctgtcaaaa        900 gaagaaaaat ttatttccga catggatgct aagaccggag cgagccttaa gctcaccgtc      960
cttaatccga acggccgcgt gtggaccctc gtcgccggcg gaggtgcctc tgtggtatac     1020
gcagacgcga ttgcttctgc aggcttcgtg tccgaattgg ctaactacgg tgagtactcg     1080
ggcgcaccga ccgaaaccca aaccttcaac tacgcccgca ccatcttgga tctgatgctg     1140
cgctccccaa ttcacccgga cggtaaggtg ctttttcattg gcggtggaat tgccaacttc    1200
acaaacgttg cgagcaccct caaaggagtg atccgtgctc tgcgtgaagt ggcaccagtt     1260
ttgaacgaac acaaagtgca gatctgggtg cgccgcgcag gtccaaatta ccaagaaggt     1320
ctgaaaaata tcaaagcggt tggtgaggaa ctcggactta acatgcatgt ctacggccca     1380
gaaatgcacg tcagcggcat tgtaccgctg gcactgcaag gcaagcaaac cgatattaaa     1440
gaattcggca ccgcg                                                      1455
```

<210> SEQ ID NO 75
<211> LENGTH: 630
<212> TYPE: PRT
<213> ORGANISM: E. coli (strain K12)

<400> SEQUENCE: 75

```
Met Ala Ile Glu Ile Lys Val Pro Asp Ile Gly Ala Asp Glu Val Glu
1               5                   10                  15

Ile Thr Glu Ile Leu Val Lys Val Gly Asp Lys Val Glu Ala Glu Gln
            20                  25                  30

Ser Leu Ile Thr Val Glu Gly Asp Lys Ala Ser Met Glu Val Pro Ser
        35                  40                  45

Pro Gln Ala Gly Ile Val Lys Glu Ile Lys Val Ser Val Gly Asp Lys
    50                  55                  60

Thr Gln Thr Gly Ala Leu Ile Met Ile Phe Asp Ser Ala Asp Gly Ala
65                  70                  75                  80

Ala Asp Ala Ala Pro Ala Gln Ala Glu Lys Lys Glu Ala Ala Pro
                85                  90                  95

Ala Ala Ala Pro Ala Ala Ala Ala Lys Asp Val Asn Val Pro Asp
            100                 105                 110

Ile Gly Ser Asp Glu Val Glu Val Thr Glu Ile Leu Val Lys Val Gly
        115                 120                 125

Asp Lys Val Glu Ala Glu Gln Ser Leu Ile Thr Val Glu Gly Asp Lys
    130                 135                 140

Ala Ser Met Glu Val Pro Ala Pro Phe Ala Gly Thr Val Lys Glu Ile
145                 150                 155                 160

Lys Val Asn Val Gly Asp Lys Val Ser Thr Gly Ser Leu Ile Met Val
                165                 170                 175
```

```
Phe Glu Val Ala Gly Glu Ala Gly Ala Ala Pro Ala Ala Lys Gln
            180                 185                 190

Glu Ala Ala Pro Ala Ala Pro Ala Pro Ala Ala Gly Val Lys Glu
        195                 200                 205

Val Asn Val Pro Asp Ile Gly Gly Asp Glu Val Glu Val Thr Glu Val
210                 215                 220

Met Val Lys Val Gly Asp Lys Val Ala Ala Glu Gln Ser Leu Ile Thr
225                 230                 235                 240

Val Glu Gly Asp Lys Ala Ser Met Glu Val Pro Ala Pro Phe Ala Gly
                245                 250                 255

Val Val Lys Glu Leu Lys Val Asn Val Gly Asp Lys Val Lys Thr Gly
            260                 265                 270

Ser Leu Ile Met Ile Phe Glu Val Glu Gly Ala Ala Pro Ala Ala Ala
            275                 280                 285

Pro Ala Lys Gln Glu Ala Ala Pro Ala Pro Ala Ala Lys Ala Glu
        290                 295                 300

Ala Pro Ala Ala Ala Pro Ala Ala Lys Ala Glu Gly Lys Ser Glu Phe
305                 310                 315                 320

Ala Glu Asn Asp Ala Tyr Val His Ala Thr Pro Leu Ile Arg Arg Leu
                325                 330                 335

Ala Arg Glu Phe Gly Val Asn Leu Ala Lys Val Lys Gly Thr Gly Arg
            340                 345                 350

Lys Gly Arg Ile Leu Arg Glu Asp Val Gln Ala Tyr Val Lys Glu Ala
        355                 360                 365

Ile Lys Arg Ala Glu Ala Ala Pro Ala Ala Thr Gly Gly Gly Ile Pro
370                 375                 380

Gly Met Leu Pro Trp Pro Lys Val Asp Phe Ser Lys Phe Gly Glu Ile
385                 390                 395                 400

Glu Glu Val Glu Leu Gly Arg Ile Gln Lys Ile Ser Gly Ala Asn Leu
                405                 410                 415

Ser Arg Asn Trp Val Met Ile Pro His Val Thr His Phe Asp Lys Thr
            420                 425                 430

Asp Ile Thr Glu Leu Glu Ala Phe Arg Lys Gln Gln Asn Glu Glu Ala
        435                 440                 445

Ala Lys Arg Lys Leu Asp Val Lys Ile Thr Pro Val Val Phe Ile Met
450                 455                 460

Lys Ala Val Ala Ala Ala Leu Glu Gln Met Pro Arg Phe Asn Ser Ser
465                 470                 475                 480

Leu Ser Glu Asp Gly Gln Arg Leu Thr Leu Lys Lys Tyr Ile Asn Ile
                485                 490                 495

Gly Val Ala Val Asp Thr Pro Asn Gly Leu Val Val Pro Val Phe Lys
            500                 505                 510

Asp Val Asn Lys Lys Gly Ile Ile Glu Leu Ser Arg Glu Leu Met Thr
        515                 520                 525

Ile Ser Lys Lys Ala Arg Asp Gly Lys Leu Thr Ala Gly Glu Met Gln
530                 535                 540

Gly Gly Cys Phe Thr Ile Ser Ser Ile Gly Gly Leu Gly Thr Thr His
545                 550                 555                 560

Phe Ala Pro Ile Val Asn Ala Pro Glu Val Ala Ile Leu Gly Val Ser
                565                 570                 575

Lys Ser Ala Met Glu Pro Val Trp Asn Gly Lys Glu Phe Val Pro Arg
            580                 585                 590
```

```
Leu Met Leu Pro Ile Ser Leu Ser Phe Asp His Arg Val Ile Asp Gly
        595                 600                 605

Ala Asp Gly Ala Arg Phe Ile Thr Ile Ile Asn Asn Thr Leu Ser Asp
        610                 615                 620

Ile Arg Arg Leu Val Met
625             630

<210> SEQ ID NO 76
<211> LENGTH: 1890
<212> TYPE: DNA
<213> ORGANISM: Artificial
<220> FEATURE:
<223> OTHER INFORMATION: mutated and/or codon-optimized sequence

<400> SEQUENCE: 76
```

| | | | | | |
|---|---|---|---|---|---|
| atggccatcg | aaatcaaggt | gccagacatc | ggtgccgatg | aagtcgaaat | caccgagatt | 60 |
| ctcgtcaaag | tcggcgataa | agtggaagca | gaacagtcct | tgatcaccgt | agagggtgat | 120 |
| aaggctagca | tggaagttcc | tagcccgcag | gctggcattg | tgaaggaaat | taaggtttca | 180 |
| gttggtgaca | aaactcaaac | gggagcccct | tattatgatc | tcgactcggc | agacggagct | 240 |
| gccgatgcgg | cgccggccca | agccgaagaa | aagaaagaag | cggctccagc | agcagcaccc | 300 |
| gccgctgccg | cagctaagga | tgttaacgtg | cctgatatcg | gctctgacga | agtggaagtc | 360 |
| accgaaatct | tggtcaaggt | gggtgataag | gtggaagcag | aacagtcttt | gattacggtt | 420 |
| gaaggagata | aggctagcat | ggaagtgcca | gcacccttcg | cgggcaccgt | taaggaaatc | 480 |
| aaagtgaatg | tcggcgataa | ggtatctacc | ggctctctca | ttatggtttt | cgaagtcgcg | 540 |
| ggtgaagcag | gagccgccgc | accagccgca | agcaagagg | cagcaccagc | ggcagcacct | 600 |
| gctccggctg | caggcgtgaa | ggaggtaaac | gtccctgata | ttggtggcga | tgaagttgag | 660 |
| gtgaccgagg | tgatggtgaa | agttggagat | aaggttgcag | ctgaacaatc | cttgattact | 720 |
| gtggagggtg | ataaggcgtc | tatggaagtt | cccgctccat | tgccggcgt | cgtcaaggag | 780 |
| cttaaggtga | acgttggaga | caaggtgaag | accggaagcc | tcatcatgat | tttcgaagtt | 840 |
| gagggtgcag | cccctgccgc | agctccagcc | aagcaagagg | cagccgctcc | cgcgccagcg | 900 |
| gcgaaagctg | aggctcctgc | agcggccccc | gccgctaaag | ccgaaggcaa | atccgaattc | 960 |
| gctgagaatg | acgcttatgt | acacgcaaca | cctctgatcc | gtcgcctggc | acgcgaattt | 1020 |
| ggagtcaacc | tcgcaaaggt | caagggcaca | ggccgcaagg | tcgaatcct | tcgcgaagac | 1080 |
| gttcaagcat | atgttaagga | agccatcaag | cgcgcggaag | cggcaccggc | agccaccggt | 1140 |
| ggtggaatcc | ccggcatgtt | gccctggccc | aaagtggact | tctcgaagtt | tggcgagatt | 1200 |
| gaggaagtgg | agctgggtcg | catccagaaa | atttccggcg | caaacctgtc | cgcaactgg | 1260 |
| gtcatgatt | ctcacgtgac | ccatttcgat | aaaaccgata | ttaccgagtt | ggaagcgttt | 1320 |
| cgtaaacaac | aaaacgaaga | agcggctaag | cgtaagctcg | acgttaaaat | taccccccgtt | 1380 |
| gtctttatca | tgaaggcggt | agctgctgct | ctcgaacaaa | tgccgcgctt | caactcttcc | 1440 |
| cttagcgagg | acggacaacg | ccttacattg | aagaagtaca | tcaatatcgg | cgttgctgtc | 1500 |
| gatactccca | acggcctcgt | ggtcccagtg | tttaaggatg | ttaacaagaa | gggtatcatt | 1560 |
| gagctcagcc | gtgagctgat | gacgatcagc | aagaaggcac | gcgatggtaa | gctgaccgcg | 1620 |
| ggagaaatgc | aaggtggctg | cttcactatc | tcgtctatcg | gaggccttgg | aacaacgcac | 1680 |
| ttcgcgccga | tcgtcaacgc | accagaggtg | gcgatcctgg | gcgtttccaa | atctgcgatg | 1740 |
| gagcctgtct | ggaatggcaa | agagttcgta | cctcgactta | tgcttccaat | ttccctgagc | 1800 |

```
ttcgaccatc gcgtgatcga tggagcagat ggtgcacgct tcattaccat tatcaataac    1860
acgctgtcgg acatccgacg attggttatg                                     1890
```

<210> SEQ ID NO 77
<211> LENGTH: 352
<212> TYPE: PRT
<213> ORGANISM: Artificial
<220> FEATURE:
<223> OTHER INFORMATION: mutated and/or codon-optimized sequence

<400> SEQUENCE: 77

```
Met Ala Ser Glu Lys Glu Ile Arg Arg Glu Arg Phe Leu Asn Val Phe
1               5                   10                  15

Pro Lys Leu Val Glu Glu Leu Asn Ala Ser Leu Leu Ala Tyr Gly Met
            20                  25                  30

Pro Lys Glu Ala Cys Asp Trp Tyr Ala His Ser Leu Asn Tyr Asn Thr
        35                  40                  45

Pro Gly Gly Lys Leu Asn Arg Gly Leu Ser Val Val Asp Thr Tyr Ala
    50                  55                  60

Ile Leu Ser Asn Lys Thr Val Glu Gln Leu Gly Gln Glu Glu Tyr Glu
65                  70                  75                  80

Lys Val Ala Ile Leu Gly Trp Cys Ile Glu Leu Leu Gln Ala Tyr Trp
                85                  90                  95

Leu Val Ala Asp Asp Met Met Asp Lys Ser Ile Thr Arg Arg Gly Gln
            100                 105                 110

Pro Cys Trp Tyr Lys Val Pro Glu Val Gly Glu Ile Ala Ile Trp Asp
        115                 120                 125

Ala Phe Met Leu Glu Ala Ala Ile Tyr Lys Leu Leu Lys Ser His Phe
    130                 135                 140

Arg Asn Glu Lys Tyr Tyr Ile Asp Ile Thr Glu Leu Phe His Glu Val
145                 150                 155                 160

Thr Phe Gln Thr Glu Leu Gly Gln Leu Met Asp Leu Ile Thr Ala Pro
                165                 170                 175

Glu Asp Lys Val Asp Leu Ser Lys Phe Ser Leu Lys Lys His Ser Phe
            180                 185                 190

Ile Val Thr Phe Lys Thr Ala Tyr Tyr Ser Phe Tyr Leu Pro Val Ala
        195                 200                 205

Leu Ala Met Tyr Val Ala Gly Ile Thr Asp Glu Lys Asp Leu Lys Gln
    210                 215                 220

Ala Arg Asp Val Leu Ile Pro Leu Gly Glu Tyr Phe Gln Ile Gln Asp
225                 230                 235                 240

Asp Tyr Leu Asp Cys Phe Gly Thr Pro Glu Gln Ile Gly Lys Ile Gly
                245                 250                 255

Thr Asp Ile Gln Asp Asn Lys Cys Ser Trp Val Ile Asn Lys Ala Leu
            260                 265                 270

Glu Leu Ala Ser Ala Glu Gln Arg Lys Thr Leu Asp Glu Asn Tyr Gly
        275                 280                 285

Lys Lys Asp Ser Val Ala Glu Ala Lys Cys Lys Lys Ile Phe Asn Asp
    290                 295                 300

Leu Lys Ile Glu Gln Leu Tyr His Glu Tyr Glu Glu Ser Ile Ala Lys
305                 310                 315                 320

Asp Leu Lys Ala Lys Ile Ser Gln Val Asp Glu Ser Arg Gly Phe Lys
                325                 330                 335

Ala Asp Val Leu Thr Ala Phe Leu Asn Lys Val Tyr Lys Arg Ser Lys
            340                 345                 350
```

<210> SEQ ID NO 78
<211> LENGTH: 1056
<212> TYPE: DNA
<213> ORGANISM: Artificial
<220> FEATURE:
<223> OTHER INFORMATION: mutated and/or codon-optimized sequence

<400> SEQUENCE: 78

```
atggcatccg agaaggaaat ccgtcgtgaa cgattcctga cgtattccc aaagctcgtc      60
gaagagctta atgcttcctt gcttgcgtac ggaatgccga aggaagcgtg cgactggtat    120
gcgcattctc tcaactataa cacacctggc ggtaagctga atcgcggtct cagcgtggtg    180
gacacgtacg caatcctcag caataagacc gtggaacagc tgggacagga ggagtacgag    240
aaagttgcta tccttggatg gtgtatcgaa ctgctgcaag cctattggtt ggtagctgat    300
gacatgatgg ataagagcat cactcgacgt ggtcaaccat gctggtacaa ggtgccggag    360
gttggcgaaa tcgcgatctg ggatgcgttc atgttggagg ccgcaattta taagcttctc    420
aagtcccact ttcgtaacga aaagtactat attgacatca gaactcttt tcatgaagtg     480
accttccaaa ccgagctcgg ccaactcatg gatttgatca ccgccccga agataaggtg     540
gacctttcga agttctccct caagaagcac tcgttcattg ttaccttcaa gacagcatac    600
tactcatttt acctgccagt cgccctcgca atgtacgtgg cgggcatcac tgatgaaaag    660
gatctgaagc aggcccgcga cgtccttatc cctcttggag agtacttcca gatccaggac    720
gattacttgg attgttttgg cacccccagag cagattggta aaatcggtac tgatatccaa    780
gacaacaaat gttcctgggt aattaacaag gctctcgagt tggcttccgc ggaacaacgc    840
aagactcttg acgaaaatta cggtaagaaa gattcagtcg ctgaagccaa gtgcaagaaa    900
atctttaacg atcttaaaat cgaacagttg taccacgagt atgaagagtc tatcgctaaa    960
gacctgaaag ctaaaatttc ccaggtcgat gagtcacgcg gcttcaaagc ggatgtgctc   1020
accgccttcc ttaacaaggt gtataagcgc tccaaa                              1056
```

<210> SEQ ID NO 79
<211> LENGTH: 299
<212> TYPE: PRT
<213> ORGANISM: Artificial
<220> FEATURE:
<223> OTHER INFORMATION: mutated and/or codon-optimized sequence

<400> SEQUENCE: 79

Met Asp Phe Pro Gln Gln Leu Glu Ala Cys Val Lys Gln Ala Asn Gln
1               5                   10                  15

Ala Leu Ser Arg Phe Ile Ala Pro Leu Pro Phe Gln Asn Thr Pro Val
            20                  25                  30

Val Glu Thr Met Gln Tyr Gly Ala Leu Leu Gly Gly Lys Arg Leu Arg
        35                  40                  45

Pro Phe Leu Val Tyr Ala Thr Gly His Met Phe Gly Val Ser Thr Asn
    50                  55                  60

Thr Leu Asp Ala Pro Ala Ala Val Glu Cys Ile His Ala Tyr Phe
65                  70                  75                  80

Leu Ile His Asp Asp Leu Pro Ala Met Asp Asp Asp Leu Arg Arg
                85                  90                  95

Gly Leu Pro Thr Cys His Val Lys Phe Gly Glu Ala Asn Ala Ile Leu
            100                 105                 110

Ala Gly Asp Ala Leu Gln Thr Leu Ala Phe Ser Ile Leu Ser Asp Ala

|  |  |  | 115 |  |  |  | 120 |  |  |  | 125 |  |
| --- | --- | --- | --- | --- | --- | --- | --- | --- | --- | --- | --- | --- |

Asp Met Pro Glu Val Ser Asp Arg Asp Arg Ile Ser Met Ile Ser Glu
130 135 140

Leu Ala Ser Ala Ser Gly Ile Ala Gly Met Cys Gly Gly Gln Ala Leu
145 150 155 160

Asp Leu Asp Ala Glu Gly Lys His Val Pro Leu Asp Ala Leu Glu Arg
165 170 175

Ile His Arg His Lys Thr Gly Ala Leu Ile Arg Ala Ala Val Arg Leu
180 185 190

Gly Ala Leu Ser Ala Gly Asp Lys Gly Arg Arg Ala Leu Pro Val Leu
195 200 205

Asp Lys Tyr Ala Glu Ser Ile Gly Leu Ala Phe Gln Val Gln Asp Asp
210 215 220

Ile Leu Asp Val Val Gly Asp Thr Ala Thr Leu Gly Lys Arg Gln Gly
225 230 235 240

Ala Asp Gln Gln Leu Gly Lys Ser Thr Tyr Pro Ala Leu Leu Gly Leu
245 250 255

Glu Gln Ala Arg Lys Lys Ala Arg Asp Leu Ile Asp Asp Ala Arg Gln
260 265 270

Ser Leu Lys Gln Leu Ala Glu Gln Ser Leu Asp Thr Ser Ala Leu Glu
275 280 285

Ala Leu Ala Asp Tyr Ile Ile Gln Arg Asn Lys
290 295

<210> SEQ ID NO 80
<211> LENGTH: 897
<212> TYPE: DNA
<213> ORGANISM: Artificial
<220> FEATURE:
<223> OTHER INFORMATION: mutated and/or codon-optimized sequence

<400> SEQUENCE: 80

```
atggacttcc cgcagcagct cgaggcctgc gttaagcagg ccaatcaggc gttgtcacgt    60
ttcatcgctc ccctgccttt ccagaacaca ccagtagtgg aaaccatgca atacggcgcc   120
ctgctgggtg aaaacgcttt gcgcccattc ttggtgtacg caaccggcca catgttcggc   180
gtctctacta acacccttga tgcacctgca gcggccgtgg agtgtatcca cgcctacttc   240
ttgatccacg acgatttgcc ggctatggat gatgatgatc tccgacgagg cctccctacc   300
tgccatgtaa aattcggcga agcgaatgcg atcttggcag gtgatgcgct gcagacactt   360
gccttttcga ttctgagcga cgcggatatg ccggaagtct ccgaccgaga ccgcatctcc   420
atgatcagcg agttggcttc tgcctccggt atcgcgggca tgtgcggagg tcaggctctt   480
gaccttgacg cagagggcaa gcacgttccc ttggacgctt tggagcgtat ccaccgccat   540
aagaccggcg ccttgatccg cgccgcggtc cgcttgggcg cgctgtctgc gggcgataag   600
ggacgccgcg cactcccagt gctcgataag tacgccgaat ccattggcct tgcttttcag   660
gtgcaggatg acatccttga tgtagtcggc gataccgcaa ctctcggcaa acgccagggc   720
gcggaccaac aattgggtaa gtcaacctac ccagctctgc tgggcttgga gcaagcacga   780
aagaaagccc gcgacctgat cgacgatgcc cgccaatctc ttaaacaact ggccgaacaa   840
tctctcgata ccagcgcact cgaggcactc gcagattaca tcatccaacg taataag      897
```

<210> SEQ ID NO 81
<211> LENGTH: 474
<212> TYPE: PRT

```
<213> ORGANISM: Artificial
<220> FEATURE:
<223> OTHER INFORMATION: mutated and/or codon-optimized sequence

<400> SEQUENCE: 81

Met Ser Thr Glu Ile Lys Thr Gln Val Val Leu Gly Ala Gly Pro
1               5                   10                  15

Ala Gly Tyr Ser Ala Ala Phe Arg Cys Ala Asp Leu Gly Leu Glu Thr
            20                  25                  30

Val Ile Val Glu Arg Tyr Asn Thr Leu Gly Gly Val Cys Leu Asn Val
            35                  40                  45

Gly Cys Ile Pro Ser Lys Ala Leu Leu His Val Ala Lys Val Ile Glu
50                  55                  60

Glu Ala Lys Ala Leu Ala Glu His Gly Ile Val Phe Gly Glu Pro Lys
65                  70                  75                  80

Thr Asp Ile Asp Lys Ile Arg Thr Trp Lys Glu Lys Val Ile Asn Gln
                85                  90                  95

Leu Thr Gly Gly Leu Ala Gly Met Ala Lys Gly Arg Lys Val Lys Val
            100                 105                 110

Val Asn Gly Leu Gly Lys Phe Thr Gly Ala Asn Thr Leu Glu Val Glu
        115                 120                 125

Gly Glu Asn Gly Lys Thr Val Ile Asn Phe Asp Asn Ala Ile Ile Ala
130                 135                 140

Ala Gly Ser Arg Pro Ile Gln Leu Pro Phe Ile Pro His Glu Asp Pro
145                 150                 155                 160

Arg Ile Trp Asp Ser Thr Asp Ala Leu Glu Leu Lys Glu Val Pro Glu
                165                 170                 175

Arg Leu Leu Val Met Gly Gly Gly Ile Ile Ala Leu Glu Met Ala Thr
            180                 185                 190

Val Tyr His Ala Leu Gly Ser Gln Ile Asp Val Val Arg Lys His
        195                 200                 205

Gln Val Ile Arg Ala Ala Asp Lys Asp Ile Val Lys Val Phe Thr Lys
    210                 215                 220

Arg Ile Ser Lys Lys Phe Asn Leu Met Leu Glu Thr Lys Val Thr Ala
225                 230                 235                 240

Val Glu Ala Lys Glu Asp Gly Ile Tyr Val Thr Met Glu Gly Lys Lys
                245                 250                 255

Ala Pro Ala Glu Pro Gln Arg Tyr Asp Ala Val Leu Val Ala Ile Gly
            260                 265                 270

Arg Val Pro Asn Gly Lys Asn Leu Asp Ala Gly Lys Ala Gly Val Glu
        275                 280                 285

Val Asp Asp Arg Gly Phe Ile Arg Val Asp Lys Gln Leu Arg Thr Asn
    290                 295                 300

Val Pro His Ile Phe Ala Ile Gly Asp Ile Val Gly Gln Pro Met Leu
305                 310                 315                 320

Ala His Lys Gly Val His Glu Gly His Val Ala Ala Glu Val Ile Ala
                325                 330                 335

Gly Lys Lys His Tyr Phe Asp Pro Lys Val Ile Pro Ser Ile Ala Tyr
            340                 345                 350

Thr Glu Pro Glu Val Ala Trp Val Gly Leu Thr Glu Lys Glu Ala Lys
        355                 360                 365

Glu Lys Gly Ile Ser Tyr Glu Thr Ala Thr Phe Pro Trp Ala Ala Ser
    370                 375                 380

Gly Arg Ala Ile Ala Ser Asp Cys Ala Asp Gly Met Thr Lys Leu Ile
```

```
                385                 390                 395                 400
            Phe Asp Lys Glu Ser His Arg Val Ile Gly Gly Ala Ile Val Gly Thr
                        405                 410                 415

Asn Gly Gly Glu Leu Leu Gly Glu Ile Gly Leu Ala Ile Glu Met Gly
                    420                 425                 430

Cys Asp Ala Glu Asp Ile Ala Leu Thr Ile His Ala His Pro Thr Leu
                        435                 440                 445

His Glu Ser Val Gly Leu Ala Ala Glu Val Phe Glu Gly Ser Ile Thr
                    450                 455                 460

Asp Leu Pro Asn Pro Lys Ala Lys Lys Lys
            465                 470

<210> SEQ ID NO 82
<211> LENGTH: 1422
<212> TYPE: DNA
<213> ORGANISM: Artificial
<220> FEATURE:
<223> OTHER INFORMATION: mutated and/or codon-optimized sequence

<400> SEQUENCE: 82
atgtcgactg agatcaagac ccaagtcgta gtcctgggcg caggccctgc cggatactcc      60
gccgcgttcc gctgcgcgga cctcggtctt gaaaccgtga ttgtcgaacg ttacaacaca     120
ctgggcggtg tatgccttaa cgtgggctgc atcccctcca aagcactgtt gcacgttgcg     180
aaggtgattg aagaggcaaa ggcgctcgcg aacacggca tcgtcttcgg cgaacctaag      240
actgacatcg ataaaattcg aacttggaag gaaaagtga ttaaccagct taccggagga     300
ctggcaggta tggcaaaggg ccgaaaagtc aaagtggtga atggtttggg taagttcacc     360
ggcgccaaca ccctggaagt ggagggcgaa acggcaaaa cggtcattaa tttcgacaac     420
gcaattattg cagcaggttc gcgccctatc cagctgccct tcattccaca tgaggacccc     480
cgtatctggg atagcacaga cgcactgaa ctcaaggaag tcccagaacg tctgctggtg     540
atgggtggcg gtattatcgc actcgaaatg gccacagtct accacgcgtt gggttctcag     600
atcgatgtgg ttgtacgcaa gcaccaagtg atccgcgccg cggacaaaga tatcgttaag     660
gtatttacca agcgcatttc aaagaagttc aacttgatgc tcgaaaccaa ggttaccgct     720
gttgaagcta aggaagacgg aatctacgtg accatggaag aaagaaggc tcccgcagag     780
ccacagcgct acgatgcagt gcttgttgca attggacgcg tgcctaacgg caaaaatctc     840
gatgccggta agctggcgt agaggtagat gaccgtggtt ttatccgcgt tgataagcaa     900
ttgcgaacga atgtgccaca catttttgct atcggtgaca ttgtgggtca accgatgctt     960
gcccacaagg gcgtccacga aggccacgtg gccgccgagg ttatcgccgg taagaaacac    1020
tactttgatc aaaagtttat cccgtccatt gcctacactg aaccggaagt ggcatgggtg    1080
ggcttgaccg aaaagaagc aaaagaaaag gcattagct atgaaacagc aacctttccg    1140
tgggccgcat ccggccgcgc cattgcgagc gactgcgcgg acggcatgac taaattgatt    1200
tttgacaagg aaagccatcg cgtgatcgga ggtgcaatcg tgggtaccaa cggtggcgag    1260
ttgttgggtg agatcggcct cgctatcgaa atgggctgcg acgccgaaga tatcgctctg    1320
accattcacg cacacccaac cctgcatgaa tctgttggcc tggctgcgga ggtcttcgag    1380
ggctccatca ccgatctccc aaatccaaaa gcaaagaaaa aa                      1422

<210> SEQ ID NO 83
<211> LENGTH: 474
<212> TYPE: PRT
```

-continued

<213> ORGANISM: E. coli ATCC 9637

<400> SEQUENCE: 83

```
Met Ser Thr Glu Ile Lys Thr Gln Val Val Leu Gly Ala Gly Pro
1               5                  10                  15

Ala Gly Tyr Ser Ala Ala Phe Arg Cys Ala Asp Leu Gly Leu Glu Thr
            20                  25                  30

Val Ile Val Glu Arg Tyr Asn Thr Leu Gly Gly Val Cys Leu Asn Val
        35                  40                  45

Gly Cys Ile Pro Ser Lys Ala Leu Leu His Val Ala Lys Val Ile Glu
    50                  55                  60

Glu Ala Lys Ala Leu Ala Glu His Gly Ile Val Phe Gly Glu Pro Lys
65                  70                  75                  80

Thr Asp Ile Asp Lys Ile Arg Thr Trp Lys Glu Lys Val Ile Asn Gln
                85                  90                  95

Leu Thr Gly Gly Leu Ala Gly Met Ala Lys Gly Arg Lys Val Lys Val
            100                 105                 110

Val Asn Gly Leu Gly Lys Phe Thr Gly Ala Asn Thr Leu Glu Val Glu
        115                 120                 125

Gly Glu Asn Gly Lys Thr Val Ile Asn Phe Asp Asn Ala Ile Ile Ala
    130                 135                 140

Ala Gly Ser Arg Pro Ile Gln Leu Pro Phe Ile Pro His Glu Asp Pro
145                 150                 155                 160

Arg Ile Trp Asp Ser Thr Asp Ala Leu Glu Leu Lys Glu Val Pro Glu
                165                 170                 175

Arg Leu Leu Val Met Gly Gly Gly Ile Ile Gly Leu Glu Met Gly Thr
            180                 185                 190

Val Tyr His Ala Leu Gly Ser Gln Ile Asp Val Val Glu Met Phe Asp
        195                 200                 205

Gln Val Ile Pro Ala Ala Asp Lys Asp Ile Val Lys Val Phe Thr Lys
    210                 215                 220

Arg Ile Ser Lys Lys Phe Asn Leu Met Leu Glu Thr Lys Val Thr Ala
225                 230                 235                 240

Val Glu Ala Lys Glu Asp Gly Ile Tyr Val Thr Met Glu Gly Lys Lys
                245                 250                 255

Ala Pro Ala Glu Pro Gln Arg Tyr Asp Ala Val Leu Val Ala Ile Gly
            260                 265                 270

Arg Val Pro Asn Gly Lys Asn Leu Asp Ala Gly Lys Ala Gly Val Glu
        275                 280                 285

Val Asp Asp Arg Gly Phe Ile Arg Val Asp Lys Gln Leu Arg Thr Asn
    290                 295                 300

Val Pro His Ile Phe Ala Ile Gly Asp Ile Val Gly Gln Pro Met Leu
305                 310                 315                 320

Ala His Lys Gly Val His Glu Gly His Val Ala Ala Glu Val Ile Ala
                325                 330                 335

Gly Lys Lys His Tyr Phe Asp Pro Lys Val Ile Pro Ser Ile Ala Tyr
            340                 345                 350

Thr Glu Pro Glu Val Ala Trp Val Gly Leu Thr Glu Lys Glu Ala Lys
        355                 360                 365

Glu Lys Gly Ile Ser Tyr Glu Thr Ala Thr Phe Pro Trp Ala Ala Ser
    370                 375                 380

Gly Arg Ala Ile Ala Ser Asp Cys Ala Asp Gly Met Thr Lys Leu Ile
385                 390                 395                 400
```

```
    Phe Asp Lys Glu Ser His Arg Val Ile Gly Gly Ala Ile Val Gly Thr
                    405                 410                 415

Asn Gly Gly Glu Leu Leu Gly Glu Ile Gly Leu Ala Ile Glu Met Gly
                420                 425                 430

Cys Asp Ala Glu Asp Ile Ala Leu Thr Ile His Ala His Pro Thr Leu
            435                 440                 445

His Glu Ser Val Gly Leu Ala Ala Glu Val Phe Glu Gly Ser Ile Thr
        450                 455                 460

Asp Leu Pro Asn Pro Lys Ala Lys Lys Lys
    465                 470

<210> SEQ ID NO 84
<211> LENGTH: 1422
<212> TYPE: DNA
<213> ORGANISM: Artificial
<220> FEATURE:
<223> OTHER INFORMATION: mutated and/or codon-optimized sequence

<400> SEQUENCE: 84
atgtcaactg agattaaaac tcaggtggtc gttctgggcg ccggaccagc tggctattca      60
gcagcgtttc gctgcgcaga tctgggcctg agacagtaa tcgttgagcg ttataacacc     120
cttggcggtg tctgcctgaa cgtcggatgc atcccttcta aggccctgct gcacgtggca     180
aaagtcatcg aagaagcgaa ggctcttgcc gaacacggca tcgtgtttgg agaaccaaag     240
actgacatcg acaagatccg cacatggaaa gagaaggtga tcaaccaact caccggtggt     300
ttggccggta tggcaaaggg tcgcaaagtt aaggtagtca atggccttgg caaatttacc     360
ggcgcaaaca ctcttgaagt ggaaggtgag aacggaaaga ctgtgatcaa cttcgacaac     420
gcaatcatcg cagccggctc gcgtcctatt caactgccgt tcatcccaca cgaagatccg     480
cgtatctggg atagcaccga tgcgctggag ctgaaagaag taccggaacg attgctcgtc     540
atgggtggag gtatcatcgg cttggagatg ggaaccgtat accacgcact ggctccccag     600
atcgacgttg tcgaaatgtt cgatcaggtg attccagcag cagataagga tatcgtgaag     660
gtgttcacca gcgcatttc aaagaagttc aatctgatgt ggaaaccaa ggttacggca     720
gtggaagcaa aggaggatgg tatctacgtg actatggagg taaaaaagc accagcggaa     780
ccccagcgat acgacgcagt tctcgtcgct atcggacgcg tcccaaatgg taagaatctg     840
gacgctggca agcaggcgt cgaagtggat gaccgtggct catccgcgt agataaacag     900
ttgcgcacaa atgttccaca catctttgca attggagaca tcgtaggcca gcccatgctg     960
gcccacaaag tgtccatga aggtcacgtg gcggctgagg ttatcgcagg caagaagcac    1020
tacttcgatc aaaggtgat ccccagcatt gcctatacgg agccagaggt agcttgggtt    1080
ggtttgaccg aaaagagagc aaaggagaag ggtatctcgt atgaaacagc aacctttcca    1140
tgggccgcgt ccggacgtgc tatcgcaagc gactgcgcag atggcatgac caagctgatc    1200
ttcgacaaag aatcccaccg cgtgatcggt ggtgctattg ttggcactaa cggcggcgaa    1260
ctcttgggcg aaatcggctt ggcaattgaa atgggctgcg atgctgagga catcgctttg    1320
accatccacg cacacccgac cctgcatgag tctgtgggac tggcagccga agtgttcgaa    1380
ggctcaatca ccgacctccc taatcccaag gctaagaaga aa                       1422

<210> SEQ ID NO 85
<211> LENGTH: 299
<212> TYPE: PRT
<213> ORGANISM: Artificial
<220> FEATURE:
```

<223> OTHER INFORMATION: mutated and/or codon-optimized sequence

<400> SEQUENCE: 85

| | | | | | | | | | | | | | | |
|---|---|---|---|---|---|---|---|---|---|---|---|---|---|---|
| Met | Asp | Phe | Pro | Gln | Leu | Glu | Ala | Cys | Val | Lys | Gln | Ala | Asn | Gln |
| 1 | | | | 5 | | | | 10 | | | | | | 15 |
| Ala | Leu | Ser | Arg | Phe | Ile | Ala | Pro | Leu | Pro | Phe | Gln | Asn | Thr | Pro | Val |
| | | | 20 | | | | | 25 | | | | | 30 | | |
| Val | Glu | Thr | Met | Gln | Tyr | Gly | Ala | Leu | Leu | Gly | Gly | Lys | Arg | Leu | Arg |
| | | 35 | | | | | 40 | | | | | 45 | | | |
| Pro | Phe | Leu | Val | Tyr | Ala | Thr | Gly | His | Met | Phe | Gly | Val | Ser | Thr | Asn |
| | 50 | | | | | 55 | | | | | 60 | | | | |
| Thr | Leu | Asp | Ala | Pro | Ala | Ala | Ala | Val | Glu | Cys | Ile | His | Ala | Tyr | Phe |
| 65 | | | | | 70 | | | | | 75 | | | | | 80 |
| Leu | Ile | His | Asp | Asp | Leu | Pro | Ala | Met | Asp | Asp | Asp | Leu | Arg | Arg |
| | | | | 85 | | | | | 90 | | | | | 95 |
| Gly | Leu | Pro | Thr | Cys | His | Val | Lys | Phe | Gly | Glu | Ala | Asn | Ala | Ile | Leu |
| | | | 100 | | | | | 105 | | | | | 110 | | |
| Ala | Gly | Asp | Ala | Leu | Gln | Thr | Leu | Ala | Phe | Ser | Ile | Leu | Ser | Asp | Ala |
| | | | 115 | | | | | 120 | | | | | 125 | | |
| Asp | Met | Pro | Glu | Val | Ser | Asp | Arg | Asp | Arg | Ile | Ser | Met | Ile | Ser | Glu |
| | 130 | | | | | 135 | | | | | 140 | | | | |
| Leu | Ala | Ser | Ala | Ser | Gly | Ile | Ala | Gly | Met | Cys | Gly | Gly | Gln | Ala | Leu |
| 145 | | | | | 150 | | | | | 155 | | | | | 160 |
| Asp | Leu | Asp | Ala | Glu | Gly | Lys | His | Val | Pro | Leu | Asp | Ala | Leu | Glu | Arg |
| | | | | 165 | | | | | 170 | | | | | 175 | |
| Ile | His | Arg | His | Lys | Thr | Gly | Ala | Leu | Ile | Arg | Ala | Ala | Val | Arg | Leu |
| | | | | 180 | | | | | 185 | | | | | 190 | |
| Gly | Ala | Leu | Ser | Ala | Gly | Asp | Lys | Gly | Arg | Arg | Ala | Leu | Pro | Val | Leu |
| | | | 195 | | | | | 200 | | | | | 205 | | |
| Asp | Lys | Tyr | Ala | Glu | Ser | Ile | Gly | Leu | Ala | Phe | Gln | Val | Gln | Asp | Asp |
| | 210 | | | | | 215 | | | | | 220 | | | | |
| Ile | Leu | Asp | Val | Val | Gly | Asp | Thr | Ala | Thr | Leu | Gly | Lys | Arg | Gln | Gly |
| 225 | | | | | 230 | | | | | 235 | | | | | 240 |
| Ala | Asp | Gln | Gln | Leu | Gly | Lys | Ser | Thr | Tyr | Pro | Ala | Leu | Leu | Gly | Leu |
| | | | | 245 | | | | | 250 | | | | | 255 | |
| Glu | Gln | Ala | Arg | Lys | Lys | Ala | Arg | Asp | Leu | Ile | Asp | Asp | Ala | Arg | Gln |
| | | | | 260 | | | | | 265 | | | | | 270 | |
| Ser | Leu | Lys | Gln | Leu | Ala | Glu | Gln | Ser | Leu | Asp | Thr | Ser | Ala | Leu | Glu |
| | | | 275 | | | | | 280 | | | | | 285 | | |
| Ala | Leu | Ala | Asp | Tyr | Ile | Ile | Gln | Arg | Asn | Lys |
| | | | 290 | | | | | 295 | | |

<210> SEQ ID NO 86
<211> LENGTH: 897
<212> TYPE: DNA
<213> ORGANISM: Artificial
<220> FEATURE:
<223> OTHER INFORMATION: mutated and/or codon-optimized sequence

<400> SEQUENCE: 86

```
atggacttcc cgcaacagct tgaagcgtgt gtgaaacagg ccaaccaagc ccttcacgg      60 ttcattgccc cgcttccgtt ccaaaatacg ccggttgtag agacgatgca atacggcgcc    120
ctgcttggtg gtaaacggtt acgccctttc ctcgtgtacg caacaggaca tatgtttggt    180
gtcagcacaa atacactgga cgctccagcg gcggctgtgg aatgtatcca tgcatacttt    240
```

```
ttaattcacg atgacttgcc tgcaatggac gatgacgact taagacgtgg gctcccgacg    300
tgccacgtaa aatttggcga agctaacgcc attctggcgg gagacgcgct tcaaacgctc    360
gcctttagca tcctgtccga tgctgatatg ccggaggtat cggatcgcga tcgcattagt    420
atgatctcag aattggccag cgcttcaggg attgccggca tgtgtggcgg gcaggcgtta    480
gacttggacg cggagggcaa acacgtccct ttagatgcgc ttgagagaat acatagacat    540
aagacagggg cgcttatcag agcagctgta agacttggcg cgctgtctgc gggcgataaa    600
ggaagacggg ccctgccggt tttagataag tatgcagaat cgatcggact ggcgttccaa    660
gtgcaggacg acatccttga tgtcgttggt gataccgcga cacttgggaa agacagggc    720 gcggatcaac agcttggcaa atccacctat ccggcttttgc tcgggctgga gcaagcgcga    780
aaaaaagcta gagacttaat tgatgatgcc cgccagagct taaagcaact cgcggagcaa    840
tcgctggata catcagcact ggaagctctg gctgactata ttatccaacg taacaag      897

<210> SEQ ID NO 87
<211> LENGTH: 897
<212> TYPE: DNA
<213> ORGANISM: Artificial
<220> FEATURE:
<223> OTHER INFORMATION: mutated and/or codon-optimized sequence

<400> SEQUENCE: 87
atggatttcc cacaacaatt ggaggcctgc gttaagcagg cgaaccaagc tctttcgcga     60
ttcatcgcgc cactcccgtt tcaaaacacg ccagtggtcg aaactatgca atacggcgct    120
ttgcttggtg gaaagcgttt gcgcccctttc cttgtttacg caaccggtca catgtttggt    180
gtctctacta acacacttga tgcccccgcg gcggccgtgg agtgtatcca cgcttacttc    240
ctcattcacg atgacctccc tgcgatggac gatgatgacc tgcgtcgtgg cctgcccacc    300
tgtcacgtga aatttggtga agctaacgcc atcctggctg gcgacgcact gcagacccctt    360 gccttctcca ttctgagcga cgcagacatg cctgaagtct ccgaccgtga tcgcatctcg    420
atgatttccg agctcgcgtc cgccagcggc attgccggta tgtgcggtgg tcaggccctt    480
gacctggatg ctgaaggcaa acacgtgccg cttgatgctc tcgaacgcat ccaccgacac    540
aagaccggcg cgctgattcg tgctgccgtg cgcctcggcg ctttgtccgc aggtgacaaa    600
ggacgccgcg ctctcccagt attggataaa tatgccgaat ccattggtct cgccttccaa    660
gtgcaagacg atatcctcga cgtggtgggc gataccgcga cccttggaaa gcgtcaaggt    720
gcggaccagc agctgggaaa gtccacttat cccgcactcc tcggtttgga gcaggcacgc    780
aagaaggccc gcgacctgat tgatgacgcg cgtcaatcac tgaaacaact cgcagagcaa    840
tccctggata catctgccct ggaggccctg gcagactaca tcatccaacg taacaag      897

<210> SEQ ID NO 88
<211> LENGTH: 897
<212> TYPE: DNA
<213> ORGANISM: Artificial
<220> FEATURE:
<223> OTHER INFORMATION: mutated and/or codon-optimized sequence

<400> SEQUENCE: 88
atggactttc cacaacagct ggaagcatgc gtgaagcagg ctaaccaggc tctatcaaga     60
ttcatcgcgc ccttaccttt ccaaaatacg cctgttgtgg aaactatgca gtatggggca    120
ttattgggtg gtaaaaggtt aaggccgttt ttagtgtatg ctacggggca catgttcggt    180
gtcagtacaa atacacttga cgcacctgca gcggctgttg aatgtattca tgcttatttt    240
```

```
ttaatccatg atgatttacc tgcaatggat gatgatgatt tgcgtagagg cctaccaaca    300
tgtcatgtga aatttggtga agcaaatgct attctagctg gggacgcttt gcaaacttta    360
gcgttcagca tcttgtccga tgcagatatg cctgaagtta gcgatagaga tagaattagt    420
atgatctcag aattagcatc cgcttctgga atcgctggca tgtgtggtgg ccaagcgctg    480
gatttggatg ctgaaggaaa acacgtaccg ttggatgcct tggaaagaat tcataggcat    540
aaaacgggtg cattgattcg tgctgctgtg cgtcttggtg ctctgtctgc gggagacaag    600
ggtagaaggg cgttgccagt tttggataaa tatgctgaaa gcattgggtt agcgtttcaa    660
gttcaagatg acatcttgga tgtggttgga gacacagcca ctttaggtaa agacaaggca    720
gcagaccagc aattaggcaa atctacttac cctgcattgt tgggtttaga gcaggctcgt    780
aagaaggcta gagacttgat agacgatgct agacagtcat tgaagcaatt ggccgaacag    840
agccttgata cgagcgccct tgaagcctta gctgattaca ttatccaaag aaataaa      897

<210> SEQ ID NO 89
<211> LENGTH: 897
<212> TYPE: DNA
<213> ORGANISM: Artificial
<220> FEATURE:
<223> OTHER INFORMATION: mutated and/or codon-optimized sequence

<400> SEQUENCE: 89
atggactttc tcagcaact ggaggcctgc gtgaagcagg ctaaccaggc actgagccgg     60
tttatcgccc cccttccctt tcaaaacact cctgtcgtcg agacgatgca atacggtgct   120
cttctcggtg gtaagcgact ccgacccttc ctcgtttacg ctacaggcca tatgtttgga   180
gtctccacca ataccctcga cgccccagct gccgccgtcg aatgcatcca tgcttacttc   240
ctgatccacg acgacctgcc cgctatggac gacgatgacc tgcgacgagg actccccact   300
tgtcatgtca aattcggcga ggctaacgcc attctggctg gagacgccct ccagactctc   360
gctttctcta tcctctccga cgctgacatg cctgaagtct ctgatcgaga ccggatttcc   420
atgatttccg agctgcctc ggcctccggc attgccggaa tgtgtggtgg tcaggctctc   480
gacctggacg ctgagggcaa gcatgtgccc ctcgacgccc ttgagcggat tcatcggcac   540
aagacgggcg ctctcatccg agctgccgtt cggctcggag ctctgtctgc cggagacaag   600
ggtcgacggg ctctcccccgt ccttgataag tacgctgagt ccattggcct ggcctttcaa   660
gttcaggatg atattctcga cgtcgtcggt gatacggcca cccttggcaa gcgacaaggt   720
gctgaccagc agctgggcaa gtcgacctac cctgccctgc tcggactcga acaggcccga   780
aagaaggcac gtgatctgat cgacgacgca cgacagagcc tgaaacaact ggccgagcag   840
tctcttgaca cctccgccct ggaggctctc gccgactaca ttattcagcg aaacaag      897

<210> SEQ ID NO 90
<211> LENGTH: 1056
<212> TYPE: DNA
<213> ORGANISM: Artificial
<220> FEATURE:
<223> OTHER INFORMATION: mutated and/or codon-optimized sequence

<400> SEQUENCE: 90
atggcatctg agaaggagat cagaagagaa cgcttttaa acgtgtttcc gaaactggta     60
gaagagttaa atgcgagcct gcttgcgtac ggcatgccaa aggaagcatg tgattggtat   120
gcacacagct taaattataa tacaccggga ggtaagctta acagagggct ttctgtagtg   180
```

```
gacacgtatg ctatattaag taataaaaca gtggaacaac ttggccaaga agaatatgaa      240
aaggtggcca tcctggggtg gtgcattgag cttttacaag catattggct tgtggcggat      300
gatatgatgg acaagtcaat tacacgtcgt ggtcagccgt gctggtataa ggtaccggaa      360
gttggggaaa tagctatctg ggacgcattt atgcttgaag ctgctattta taaacttctt      420
aaaagccatt tccgtaatga aaagtattac attgacatta ccgaactttt tcatgaggta      480
acatttcaaa ccgaactggg gcagcttatg gacttgatta cagcaccgga ggacaaagtt      540
gatctgtcga aattctcact taaaaaacat tcttttattg taacgttcaa gactgcgtat      600
tattcatttt atctgccggt cgcgcttgca atgtatgtag ccggcattac agatgaaaag      660
gacttaaaac aggctcggga tgttctgatt ccattggggg aatatttcca aattcaggat      720
gactatctgg actgttttgg tacccccgaa cagattggta aaatcggcac agatatccaa      780
gataataaat gctcctgggt tatcaataaa gcactgaaac tggctagcgc tgaacaaaga      840
aagactttgg atgaaaacta cggcaagaaa gatagcgtcg ctgaagctaa gtgcaaaaaa      900
atttttaacg acttaaaaat cgagcaactg taccacgaat atgaagaaag tattgctaaa      960
gatctcaaag ctaaaataag ccaggtggat gaatctcgcg ggttcaaagc agatgtattg     1020
acagcgtttc ttaataaagt gtataaacga tccaaa                               1056

<210> SEQ ID NO 91
<211> LENGTH: 1056
<212> TYPE: DNA
<213> ORGANISM: Artificial
<220> FEATURE:
<223> OTHER INFORMATION: mutated and/or codon-optimized sequence

<400> SEQUENCE: 91
atggctagcg aaaaggagat ccgaagagag agattcctca acgtgttccc taaacttgtg       60
gaggagctca acgcttcgct cctcgcttac ggtatgccca aggaggcctg tgattggtat      120
gcacactccc ttaactacaa cacgcctggt ggtaagctca accgaggtct ttctgttgtc      180
gataccttat caattctttc caacaagacc gtcgagcaac tgggtcagga ggagtacgag      240
aaagtggcaa ttcttggctg gtgcattgaa ctcctccaag cttactggct ggtggctgat      300
gacatgatgg acaagagcat caccccgacga ggtcagccct gctggtacaa ggtgccagag      360
gttggagaga tcgccatttg ggacgcattt atgctggagg ctgccattta caagctcctt      420
aagtctcact ttcgaaacga gaagtactac atcgacatta ctgagctctt tcacgaagtg      480
acttttcaga ctgagctggg tcagcttatg gatctcatta ccgctcccga ggataaagtg      540
gatctgtcga agttttccct caagaagcat tcgtttattg tcaccttcaa gacagcatac      600
tactcttttt acctgcccgt cgccctcgca atgtacgtcg caggaattac cgatgagaaa      660
gacctcaagc aggcacgtga cgtcctcatc cccctcggcg agtactttca gattcaggat      720
gactatctcg actgcttcgg tacccccaga caaatcggaa agattggaac tgacatccag      780
gacaataagt gctcttgggt tattaacaag gcccttgagc tggcttccgc cgagcaacga      840
aagacccttg acgagaatta cggcaagaag gatagcgtgg ccgaggccaa gtgcaagaag      900
atcttcaacg acctcaagat cgagcagctc taccacgagt acgaggagtc gattgctaag      960
gaccttaagg ctaagattag ccaggtggac gagtcccggg gattcaaggc tgacgtcctg     1020
accgcctttc tcaacaaggt ctacaagcga tccaag                               1056

<210> SEQ ID NO 92
<211> LENGTH: 603
```

<212> TYPE: PRT
<213> ORGANISM: Perilla setoyensis

<400> SEQUENCE: 92

```
Met Cys Ser Ile Ser Gln Lys Val Val Ile Gly Leu Asn Lys Ala Ala
1               5                   10                  15

Ala Asn Asn Cys Leu Gln Asn Leu Asp Arg Arg Gly Phe Lys Thr Arg
            20                  25                  30

Arg Val Ser Ser Ser Glu Ala Ala Ser Cys Leu Arg Ala Ser Ser Ser
        35                  40                  45

Leu Gln Leu Asp Val Lys Pro Val Glu Glu Gly Arg Arg Ser Gly Asn
    50                  55                  60

Tyr Gln Pro Ser Ile Trp Asp Phe Asn Tyr Val Gln Ser Leu Asn Thr
65                  70                  75                  80

Pro Tyr Lys Glu Glu Arg Tyr Leu Thr Arg His Ala Glu Leu Ile Val
                85                  90                  95

Gln Val Lys Pro Leu Leu Glu Lys Lys Met Glu Ala Thr Gln Gln Leu
            100                 105                 110

Glu Leu Ile Asp Asp Leu Asn Asn Leu Gly Leu Ser Tyr Phe Phe Gln
        115                 120                 125

Asp Arg Ile Lys Gln Ile Leu Ser Phe Ile Tyr Asp Glu Asn Gln Cys
    130                 135                 140

Phe His Ser Asn Ile Asn Asp Gln Ala Glu Lys Arg Asp Leu Tyr Phe
145                 150                 155                 160

Thr Ala Leu Gly Phe Arg Leu Leu Arg Gln His Gly Phe Asn Val Ser
                165                 170                 175

Gln Glu Val Phe Asp Cys Phe Lys Asn Asp Lys Gly Ser Asp Phe Lys
            180                 185                 190

Ala Ser Leu Ser Gly Asn Thr Lys Gly Leu Leu Gln Leu Tyr Glu Ala
        195                 200                 205

Ser Phe Leu Val Arg Glu Gly Glu Asp Thr Leu Glu Leu Ala Arg Gln
    210                 215                 220

Phe Ala Thr Lys Phe Leu Arg Arg Lys Leu Asp Glu Ile Asp Asp Asn
225                 230                 235                 240

His Leu Leu Ser Arg Ile His His Ser Leu Glu Ile Pro Leu His Trp
                245                 250                 255

Arg Ile Gln Arg Leu Glu Ala Arg Trp Phe Leu Asp Ala Tyr Ala Thr
            260                 265                 270

Arg His Asp Met Asn Pro Ile Ile Leu Glu Leu Ala Lys Leu Asp Phe
        275                 280                 285

Asn Ile Ile Gln Ala Thr His Gln Glu Glu Leu Lys Asp Val Ser Arg
    290                 295                 300

Trp Trp Gln Asn Thr Arg Leu Ala Glu Lys Leu Pro Phe Val Arg Asp
305                 310                 315                 320

Arg Leu Val Glu Ser Tyr Phe Trp Ala Ile Ala Leu Phe Glu Pro His
                325                 330                 335

Gln Tyr Gly Tyr Gln Arg Arg Val Ala Ala Lys Ile Ile Thr Leu Ala
            340                 345                 350

Thr Ser Ile Asp Asp Val Tyr Asp Ile Tyr Gly Thr Leu Asp Glu Leu
        355                 360                 365

Gln Leu Phe Thr Asp Asn Phe Arg Arg Trp Asp Thr Glu Ser Leu Gly
    370                 375                 380

Gly Leu Pro Tyr Ser Met Gln Leu Phe Tyr Met Val Ile His Asn Phe
385                 390                 395                 400
```

```
Val Ser Glu Leu Ala Tyr Glu Ile Leu Lys Glu Lys Gly Phe Ile Ala
                405                 410                 415
Ile Pro Tyr Leu Gln Arg Ser Trp Val Asp Leu Ala Glu Ser Phe Leu
            420                 425                 430
Lys Glu Ala Asn Trp Tyr Tyr Ser Gly Tyr Thr Pro Ser Leu Glu Glu
        435                 440                 445
Tyr Ile Asp Asn Gly Ser Ile Ser Ile Gly Ala Val Ala Val Leu Ser
    450                 455                 460
Gln Val Tyr Phe Thr Leu Ala Asn Ser Ile Glu Lys Pro Lys Ile Glu
465                 470                 475                 480
Ser Met Tyr Lys Tyr His His Ile Leu Arg Leu Ser Gly Leu Leu Val
                485                 490                 495
Arg Leu His Asp Asp Leu Gly Thr Ser Leu Phe Glu Lys Lys Arg Gly
            500                 505                 510
Asp Val Pro Lys Ala Val Glu Ile Cys Met Lys Glu Arg Asn Asp Thr
        515                 520                 525
Glu Glu Glu Ala Glu Glu His Val Lys Tyr Leu Ile Arg Glu Ala Trp
    530                 535                 540
Lys Glu Met Asn Thr Ala Thr Ala Ala Gly Cys Pro Phe Met Asp
545                 550                 555                 560
Glu Leu Asn Val Ala Ala Ala Asn Leu Gly Arg Ala Ala Gln Phe Val
                565                 570                 575
Tyr Leu Asp Gly Asp Gly His Gly Val Gln His Ser Lys Ile His Gln
            580                 585                 590
Gln Met Gly Gly Leu Met Phe Lys Pro Tyr Val
        595                 600

<210> SEQ ID NO 93
<211> LENGTH: 1809
<212> TYPE: DNA
<213> ORGANISM: Artificial
<220> FEATURE:
<223> OTHER INFORMATION: mutated and/or codon-optimized sequence

<400> SEQUENCE: 93
atgtgcagca tctctcaaaa ggtcgttatt ggattgaata aggcagcggc caataactgc      60
ctccaaaacc ttgatcgccg aggttttaaa cacgccgtg tttcatcctc cgaagcggct     120
tcttgcctcc gagcctcaag ctcgctgcag cttgatgtca agccggtgga ggaaggccga     180
cgttccggta actatcagcc atcaatctgg gattttaatt atgtccagtc cctcaacacc     240
ccctacaaag aggaacgtta ccttacccga cacgcggaac tcatcgttca ggtcaagccg     300
cttctcgaaa aaagatgga ggctactcag cagttggagc tcatcgatga ccttaacaac     360
ctcggtctga gctactttt ccaagaccgc atcaagcaga ttctctcatt catctatgat     420
gaaaatcagt gtttccactc caatatcaat gatcaagctg aaaagcgaga cctgtacttt     480
accgcccttg gatttcgtct ccttcgccag cacggcttta acgtgtctca ggaggtgttc     540
gattgcttca aaaacgataa aggctccgat tttaaagcgt ccctgtctgg aaacaccaag     600
ggcctcctcc agctctacga agcctccttc ttggtccgtg agggtgaaga caccctcgaa     660
ctggcccgtc agttcgcgac caagttcctg cgccgcaagc ttgacgaaat cgacgacaac     720
catctgctct cacgaattca ccactcactc gaaatcccgt tgcactggcg catccagcgt     780
ctggaggcgc gctggtttct ggacgcgtac gctacacgcc acgatatgaa tcccattatc     840
ttggagctcg caaaactgga ctttaatatt attcaagcaa cccaccaaga agagctcaag     900
```

```
gacgtgagcc gttggtggca gaatacgcgc ctggccgaaa agctcccgtt tgtgcgcgat    960
cgacttgtcg agtcatactt ttgggccatc gcactctttg agccacatca atatggatac   1020
cagcgccgtg ttgctgccaa gattatcacc ctcgcgacat ccatcgatga cgtgtacgac   1080
atctacggca ctctcgacga gctccaactt tttaccgata acttccgtcg ctgggacacg   1140
gaatccttgg gcggtcttcc ttactcgatg cagttgttct acatggtgat tcacaacttt   1200
gtctctgagt tggcctatga aatcctgaaa gaaaaaggtt ttatcgccat ccctacctc    1260 caacgctcct gggttgattt ggcagaatcc tttttgaaag aggcaaactg gtactactct   1320
ggttatacac cctccctcga agaatacatc gacaacggct ccatctcaat ggcgcagta    1380 gctgtgttgt cccaagttta tttcactttg gcaaattcta tcgaaaagcc aaagattgaa   1440
tctatgtaca agtaccacca tattttgcgt ctgtcgggtt tgttggtgcg cctgcacgat   1500
gacttgggaa cttccttgtt cgagaagaag cgcggcgatg ttcctaaggc ggtcgaaatt   1560
tgcatgaaag aacgcaacga tacggaggag gaagcagaag aacacgttaa gtacttgatt   1620
cgcgaagcct ggaaggagat gaacactgct acggcagctg caggatgtcc ttttatggat   1680
gagctcaacg tggctgctgc caatctgggt cgcgcagccc agttcgtgta cctcgacgga   1740
gacggtcatg gcgtgcagca ctccaaaatc catcaacaga tgggtggcct tatgtttaaa   1800
ccgtatgtg                                                           1809

<210> SEQ ID NO 94
<211> LENGTH: 1809
<212> TYPE: DNA
<213> ORGANISM: Artificial
<220> FEATURE:
<223> OTHER INFORMATION: mutated and/or codon-optimized sequence

<400> SEQUENCE: 94
atgtgctcta tttcccaaaa agtagttatt ggccttaaca aggcggctgc taacaactgc     60
ttacaaaatc ttgacagacg tggtttcaaa actcgtagag tttcatcttc cgaggccgct    120
agctgcctgc gggcctctag ctcttttgcag ctggacgtta accagtgga agaggggcgc    180 agatcgggga actatcagcc atcgatctgg gactttaatt acgtacaatc actgaatact    240
ccttacaaag aagaacggta tctgacacgg cacgcagaac tgattgtcca agtgaaacca    300
ctgctggaaa agaagatgga agccacccaa caactggaac tcatcgacga cctgaacaac    360
ttgggactgt cctactttt tcaggacaga attaaacaaa ttctttcatt tatatacgac    420
gaaaatcaat gctttcattc taatatcaac gatcaagccg aaaaacggga cctttacttc    480
acggctttag gttttcgtct gcttagacag catggcttca atgtgagtca agaagtattc    540
gactgcttta aaaacgataa gggatcgac tttaaagctt cattatcagg taacaccaaa    600
ggcttgcttc aattgtatga agcgagtttt ttagtccgag aaggggaaga tactcttgaa    660
ttagcccgac agttcgcgac taaattcctg cgtagaaaac tggatgaaat cgacgataac    720
catcttttaa gccgcattca tcattccttg gaaattccgt acattggcg cattcagcgg    780 ttggaagcac gctggttcct tgacgcttat gctacgcgtc atgacatgaa tccaatcatc    840
ctcgaactcg cgaaacttga ctttaatatt attcaagcta cacatcaaga gaacttaaa    900 gacgtatcta gatggtggca gaacacacgt ctggccgaga acttccgtt gtccgggac     960 agattagtgg aatcttatt ctgggctatt gctcttttg aacctcatca atatgggtac   1020
caacgtcgag ttgctgctaa gattattaca ttggcaacaa gcattgatga tgtttacgat  1080
```

```
atttacggga ctttggatga attacaactt tttacggata attttcggag atgggataca   1140
gagtccctgg gtgggcttcc gtattctatg cagctgtttt atatggttat ccataatttc   1200
gtgagcgaac ttgcgtatga aattctgaaa gaaaaaggct ttatagccat tccttatctt   1260
cagagaagtt gggttgacct ggccgagtcc tttctcaaag aggcgaactg gtactattcc   1320
ggctataccc ctagcctgga agaatacatc gataacgggt ctatcagcat aggcgcagtc   1380
gcagtgcttt cacaggttta ttttacgttg gctaacagta ttgaaaaacc taagatagag   1440
agcatgtata aatatcacca tatcttgcgc ttatctggtt tgttagtccg cttacatgat   1500
gaccttggaa caagtctgtt cgagaagaag cggggcgatg taccgaaggc ggttgagatt   1560
tgcatgaaag aacggaatga cacagaagaa gaagcagaag aacatgttaa atacctgatc   1620
cgcgaagctt ggaaagaaat gaacacagct acagcagctg ccgggtgtcc gtttatggat   1680
gaattgaatg tcgcggcggc aaatctgggt cgggcagccc agtttgtata tttggatggg   1740
gacggccatg gcgtccagca tagtaaaatt catcaacaga tgggaggctt gatgttcaaa   1800
ccttacgtc                                                            1809

<210> SEQ ID NO 95
<211> LENGTH: 1809
<212> TYPE: DNA
<213> ORGANISM: Artificial
<220> FEATURE:
<223> OTHER INFORMATION: mutated and/or codon-optimized sequence

<400> SEQUENCE: 95
atgtgttcaa tatcacaaaa agtcgtaatt gggttgaaca aggccgctgc caataactgt     60
ttgcagaatt tggataggag gggtttcaaa acaagaaggg tcagctcttc cgaggcggca    120
tcatgcttaa gagcttccag tagcttgcaa ctagatgtta aaccagtcga ggagggtaga    180
aggtcaggga actaccaacc aagtatctgg gatttcaatt atgtccaatc attgaatact    240
ccctataagg aggagcgtta cttaactaga catgcggaac tgattgtcca agtgaaacct    300
ttgttagaaa agaagatgga agctactcaa cagctggaat taattgacga tctaaataat    360
ttaggtttgt cttatttttt ccaagatagg atcaagcaaa tattgtcatt tatctatgac    420
gagaatcaat gtttccactc taacattaac gaccaggcag aaaagaggga cctgtatttt    480
accgcattgg gttttaggct tctacgtcag catggtttta atgtttctca agaagttttt    540
gattgcttta aaaatgacaa aggtagcgat tttaaggcta gcttatctgg caacaccaaa    600
ggtttgttgc aactatacga agcttctttt ctggtgagag aagggggaga tactctagaa    660
ctagctagac aattcgctac caaatttctg aggagaaaat tggatgaaat tgatgataac    720
catctattaa gcagaataca ccattctcta gagattccat tgcattggag aatccaacgt    780
ttggaagcca ggtggttctt ggatgcttat gcaacacgtc atgatatgaa cccaattatt    840
ttggagcttg ccaaacttga ttttaacata attcaggcta cccatcaaga gaacttaag     900
gatgtttcca gatggtggca gaacactcgt ttggctgaaa agcttccatt tgtaagagat    960
agactagtcg aatcatactt tgggcaatc gccttatttg aaccacatca gtacggttac   1020
caacgtagag tcgccgctaa ataataact ttggccactt ctatagatga tgtttatgat   1080
atttacggga cattagatga attgcaactt ttcaccgaca atttcagaag atgggatacc   1140
gaaagcctag gcggtctacc ttatagtatg caattgttct atatggttat tcataatttt   1200
gtttcagaat tggcttacga aatactgaaa gaaaaaggtt tcattgccat tccttattta   1260
caaaggagtt gggtggactt agcagaaagc tttctgaaag aggcgaattg gtattattca   1320
```

```
ggttatactc cgtctctgga ggagtatatt gataacggca gcatctctat tggtgcagtg    1380
gcagtattga gccaagtcta ctttaccttac gctaacagca ttgaaaaacc aaaaattgag    1440
tccatgtata ataccatca catcttaaga ctttctggat tgttagtacg tttacacgac    1500
gatctgggca ccagtttgtt cgaaaaaaaa aggggcgacg tccctaaggc agtagaaatt    1560
tgtatgaaag aaaggaacga tacagaagaa gaagctgaag agcatgtgaa atatctgatt    1620
agagaggcgt ggaaggaaat gaacacagct acagctgctg cagggtgtcc attcatggat    1680
gaattaaacg tagctgcagc caatctgggt cgtgccgctc agttcgttta tttagacggt    1740
gatggtcatg gggttcagca ttccaagata caccaacaaa tgggggggttt aatgtttaag    1800 ccttatgta                                                             1809
```

<210> SEQ ID NO 96  
<211> LENGTH: 1809  
<212> TYPE: DNA  
<213> ORGANISM: Artificial  
<220> FEATURE:  
<223> OTHER INFORMATION: mutated and/or codon-optimized sequence

<400> SEQUENCE: 96

```
atgtgttcca tctcgcagaa agttgtgatc ggcctgaaca aggctgccgc taacaactgt      60
ctccagaacc tggatcgacg aggtttcaag acaagacggg tgtcttcttc cgaggctgct     120
tcctgcctgc gagcatctag ctcccttcag cttgacgtca agcctgtcga ggagggtcga     180
cggtctggca actaccaacc ctccatttgg gacttcaatt acgtgcaatc gctgaacact     240
ccttacaagg aggagcgata cctcacccga cacgccgagc tcattgttca ggtcaagccc     300
ctccttgaga agaagatgga ggcaacccag cagctggagc tgattgatga cctgaacaac     360
ctgggcctct cctacttctt tcaggaccgg attaagcaaa ttctgtcctt tatttacgac     420
gagaaccaat gttttcattc taacatcaac gaccaggctg aaaagcgaga tctttacttc     480
accgccctcg gattccgtct cctccgacag cacggcttta acgtttcgca agaggtcttt     540 gattgctttta agaatgataa aggctccgac ttcaaggctt ctcttcctgg taacaccaag     600
ggtctgctgc aactgtacga agcttccttt cttgttagag agggcgagga taccctggag     660
ctggcccggc agtttgctac caagttcctg cgacgaaagc tggatgagat tgacgacaac     720
caccttctgt cccgaatcca ccactcgctt gagatccccc tccactggcg aatccagcga     780
ctggaagcta atggtttct ggatgcctac gctactcgac acgacatgaa tcctattatc     840
ctggagctgg ccaagcttga cttcaacatc atccaggcca cccaccagga ggaactgaaa     900
gacgtctctc gatggtggca gaacacccga cttgccgaaa agctcccctt tgtgcgagac     960
cgactggtcg agagctactt tgggctatt gccctctttg agcccaccac gtacggttac     1020
cagcgaagag tcgctgctaa aatcatcacc ctggccacta gcatcgacga cgtttacgac    1080
atttacggaa ccctcgatga gctgcaactg tttaccgata ctttcggcg ttgggacaca    1140 gaaagccttg gaggtctgcc ctactctatg cagctcttct atatggtgat ccacaacttt    1200
gtgtctgagc tggcttatga gatccttaag gaaaagggct tcatcgccat cccttacctt    1260
cagcgatcct gggtcgatct tgccgagtct ttcctcaagg aggccaactg gtatactctc    1320
ggctacaccc catctctgga ggagtatatt gataacggtt ctatttctat cggcgccgtg    1380
gctgtccttt cccaagtcta tttcacactg gctaattcca tcgagaagcc caagattgaa    1440
tctatgtaca aataccatca catcctgcga ctgagcggtc ttctggtgcg gcttcatgac    1500
```

```
gatcttggca cttctctgtt cgagaagaaa cgaggagatg tgcctaaggc tgtcgagatt    1560
tgtatgaaag agcgtaacga caccgaggag gaggccgagg agcacgtgaa gtacctgatt    1620
cgagaggcat ggaaagaaat gaacaccgct actgccgccg ctggttgccc ctttatggat    1680
gagctgaacg ttgcagccgc caaccttggc cgagcagccc agttcgtcta cctggacggc    1740
gacggccacg gcgtccagca ttctaaaatt caccagcaga tgggtggcct gatgttcaag    1800
ccctatgtc                                                            1809
```

<210> SEQ ID NO 97
<211> LENGTH: 591
<212> TYPE: PRT
<213> ORGANISM: Vitis vinifera (Grape)

<400> SEQUENCE: 97

```
Met Ser Arg Phe Val Thr Met Pro Ser His Val Leu Pro Ser Ser Phe
1               5                   10                  15

Val Ala Pro Ser Leu Gln Val Ser Ser Ser Pro Cys Ser Trp Arg Thr
            20                  25                  30

Arg Pro Ser Pro Cys Thr Ser Cys His Leu Ser Pro Ser Ser Ser Ser
        35                  40                  45

Lys Pro Leu Leu Gly Ser His Asp Tyr Ser Leu Leu Lys Ser Leu Thr
    50                  55                  60

Leu Ser Pro His Ala Val Asn Ser Glu Ala Asp Ser Ser Thr Arg Arg
65                  70                  75                  80

Met Lys Glu Val Lys Glu Arg Thr Trp Glu Ala Phe Tyr Arg Ala Trp
                85                  90                  95

Asp Ser Arg Ala Ala Met Glu Met Val Asp Thr Val Glu Arg Leu Gly
            100                 105                 110

Leu Ser Tyr His Phe Glu Asp Glu Ile Asn Ala Leu Leu Gln Arg Phe
        115                 120                 125

Cys Asp Trp Asn Ala Ser Glu Asp Leu Phe Thr Thr Ala Leu Arg Phe
    130                 135                 140

Arg Leu Leu Arg Gln Asn Gly Phe Pro Thr His Ser Asp Val Phe Gly
145                 150                 155                 160

Lys Phe Met Asp Lys Asn Gly Lys Phe Lys Glu Ser Leu Thr Glu Asp
                165                 170                 175

Ile Trp Gly Met Leu Ser Leu His Glu Ala Ser His Leu Gly Ala Lys
            180                 185                 190

Asn Glu Glu Val Leu Ala Glu Ala Lys Glu Phe Thr Arg Ile His Leu
        195                 200                 205

Ile Gln Ser Met Pro His Met Glu Pro His Phe Ser Ser His Val Gly
    210                 215                 220

Arg Ala Leu Glu Leu Pro Arg His Leu Arg Met Val Arg Leu Glu Ala
225                 230                 235                 240

Arg Asn Tyr Ile Gly Glu Tyr Ser Arg Glu Ser Asn Pro Asn Leu Ala
                245                 250                 255

Phe Leu Glu Leu Ala Lys Leu Asp Phe Asp Met Val Gln Ser Leu His
            260                 265                 270

Gln Lys Glu Leu Ala Glu Ile Val Arg Trp Trp Lys Gln Leu Gly Leu
        275                 280                 285

Val Asp Lys Leu Asp Phe Ala Arg Asp Arg Pro Met Glu Cys Phe Leu
    290                 295                 300

Trp Thr Val Gly Ile Phe Pro Asp Pro Arg His Ser Ser Cys Arg Ile
305                 310                 315                 320
```

Glu Leu Thr Lys Ala Ile Ala Ile Leu Leu Val Ile Asp Asp Ile Tyr
            325                 330                 335

Asp Ser Tyr Gly Ser Leu Asp Glu Leu Ala Leu Phe Thr Asp Ala Val
            340                 345                 350

Lys Arg Trp Asp Leu Gly Ala Met Asp Gln Leu Pro Glu Tyr Met Lys
            355                 360                 365

Ile Cys Tyr Met Ala Leu Tyr Asn Thr Thr Asn Asp Ile Ala Tyr Arg
            370                 375                 380

Ile Leu Lys Glu His Gly Trp Ser Val Ile Glu Asp Leu Lys Arg Thr
385                 390                 395                 400

Trp Met Asp Ile Phe Gly Ala Phe Leu Ala Glu Ala Tyr Cys Phe Lys
                405                 410                 415

Gly Gly His Val Pro Ser Leu Glu Glu Tyr Leu Thr Asn Ala Val Thr
            420                 425                 430

Thr Gly Gly Thr Tyr Met Ala Leu Val His Ala Phe Phe Leu Met Gly
            435                 440                 445

Gln Gly Val Thr Arg Glu Asn Met Ala Met Leu Lys Pro Tyr Pro Asn
        450                 455                 460

Ile Phe Ser Cys Ser Gly Lys Ile Leu Arg Leu Trp Asp Asp Leu Gly
465                 470                 475                 480

Thr Ala Arg Glu Glu Gln Glu Arg Gly Asp Asn Ala Ser Ser Ile Glu
                485                 490                 495

Cys Tyr Lys Arg Glu Arg Glu Met Asp Thr Val Leu Glu Asp Glu Ala
            500                 505                 510

Cys Arg Lys His Ile Arg Gln Met Ile Gln Ser Leu Trp Val Glu Leu
            515                 520                 525

Asn Gly Glu Leu Val Ala Ser Ser Ala Leu Pro Leu Ser Ile Ile Lys
        530                 535                 540

Ala Ala Phe Asn Leu Ser Arg Thr Ala Gln Val Ile Tyr Gln His Gly
545                 550                 555                 560

Asp Asp Asn Lys Thr Ser Ser Val Glu Asp His Val Gln Ala Leu Leu
                565                 570                 575

Phe Arg Pro Val Ser Ser Asn Gly His Ala Gln Ile Thr Met His
            580                 585                 590

<210> SEQ ID NO 98
<211> LENGTH: 1773
<212> TYPE: DNA
<213> ORGANISM: Artificial
<220> FEATURE:
<223> OTHER INFORMATION: mutated and/or codon-optimized sequence

<400> SEQUENCE: 98
atgtctcgct tcgttacaat gccatctcat gtattaccta gttcattcgt tgcgcctagc      60
ctgcaggtgt cgtctagccc cgtgttcttg agaactcggc cgtccccttg cacttcatgc     120
catttatcac cgagctcttc atcaaaacct ctcttaggat ctcacgatta ttcacttttg     180
aaatccttaa cgttatctcc acacgccgta aactcggaag cagattcatc cacacggcgc     240
atgaaagagg tgaaagaaag aacgtgggaa gccttttatc gagcatggga tagtagagct     300
gccatggaga tggtggacac agtcgagcgc cttggacttt cctatcactt tgaagatgaa     360
attaatgcgc tgcttcaaag attttgcgac tggaacgcgt cagaggattt gtttacaacc     420
gccttaagat ttagactgct tcggcagaat gggtttccta ctcactccga tgtgtttgga     480
aagtttatgg acaagaacgg aaaatttaag gagagtctga cggaagatat ttggggtatg     540

```
ctttcgcttc atgaagcttc acatcttggg gcaaaaaacg aggaagtcct tgctgaagca      600
aaagagttta ctcgaataca tcttattcag tctatgccgc atatggagcc tcatttctcg      660
tcacacgtag gtcgggcact tgaactccct cgtcatctcc ggatggtgcg tctcgaagct      720
cgtaattata tcggggaata ttcacgtgaa agcaacccga acctcgcatt ccttgaattg      780
gccaaattgg atttcgatat ggtacaatca ttgcatcaaa agagctggc ggaaattgtt       840 cgatggtgga acaattagg attagtcgac aaattagatt ttgctcgcga tcggccgatg       900
gagtgttttc tctggaccgt tggtatcttc ccggatcctc ggcattccag ctgtcgtatt      960
gaattgacga agctattgc gattctgttg gtcattgacg atatttatga ttcatatgga      1020
agcttggatg aactggcttt atttactgat gctgttaaaa gatgggatct gggtgcgatg     1080
gatcaacttc cggagtatat gaaaatctgc tacatggctc tgtacaacac aacaaacgat     1140
atagcataca gaatattaaa agagcacggc tggagcgtaa ttgaagattt aaaacgcaca     1200
tggatggaca tctttgggc gttttttggca gaagcatact gtttcaaagg tggacatgtt     1260
ccgagccttg aggaatactt aacaaacgca gtcacgactg gcggcaccta tggcccctt     1320 gttcacgcgt tctttcttat gggacaaggc gtgactcgtg aaaatatggc catgcttaaa     1380
ccgtatccta atatcttctc atgtagcggt aaaattcttc gactttggga tgacttgggt     1440
acagctcgag aagaacaaga gcgcgggat aatgcgagct ccattgaatg ctacaaaaga     1500
gaaagagaaa tggatacggt actggaagat gaagcatgta gaaaacatat cagacagatg     1560
atccaatcac tgtgggtgga acttaacggc gagctggtgg ccagcagcgc tctgccgttg     1620
tcaattataa agccgcgtt taacctttcc cgtacagctc aagttatcta tcagcacggt     1680
gatgataaca aaacatcatc agttgaagac catgtccaag ccctttttgtt tcgtccggta     1740 tcttcaaatg gtcatgctca aatcacgatg cat                                  1773
```

<210> SEQ ID NO 99
<211> LENGTH: 1773
<212> TYPE: DNA
<213> ORGANISM: Artificial
<220> FEATURE:
<223> OTHER INFORMATION: mutated and/or codon-optimized sequence

<400> SEQUENCE: 99

```
atgtcccgtt ttgtcactat gccatcgcac gtcttgccta gcagcttcgt agcgccatct       60
ctgcaagtgt cttcatcccc atgctcgtgg cgcacccgcc cttccccatg cacctcttgt      120
cacttgtcac catcctcttc ttcaaaacca cttttgggca gccacgatta ctccctgctt      180
aagagcctga cccttctcc acacgccgtg aattccgaag cggattcttc cacccgccga      240
atgaaggaag tcaaggagcg cacatgggaa gctttctatc gagcctggga ttcacgtgct      300
gctatggaga tggttgacac cgtggaacgt ctgggtcttt cataccactt tgaggacgaa      360
attaatgcgc tcttgcagcg cttttgtgat tggaacgctt ccgaagatct gttcacaacc      420
gccttgcgtt tccgccttct cgccagaaac ggttttccta cccattctga cgtctttggc      480
aaattcatgg ataagaacgg aaaattcaag gaaagcttga ctgaggatat ctggggaatg      540
ctgtcattgc atgaggcatc gcacttgggc gcaaaaaacg aggaggtcct cgcggaagca      600
aaggagttca cccgcatcca tctgatccaa tcaatgccgc atatggaacc tcacttctcc      660
tcccacgtcg gacgcgctct ggaactccct cgcatcttc gcatggtgcg actcgaagct      720
cgcaattata tcggcgagta ctcccgcgag agcaacccga atcttgcatt cttggaactc      780
```

```
gcgaagttgg attttgacat ggtgcagtca ctccaccaaa aggaactcgc ggagatcgtt      840
cgctggtgga acagctggg tctcgtggac aagttggatt tcgcgcgcga ccgacctatg      900
gaatgcttcc tctggaccgt gggcatcttt cctgatcctc gacattcctc ttgtcgcatc     960
gaattgacta aagcaatcgc catcctcctg gttatcgacg atatttatga ctcatatggc    1020
agcctcgacg aattggcact gttcacagac gcagtcaaac gctgggattt gggagcgatg    1080
gatcagttgc ccgaatatat gaagatctgc tatatggcac tttacaacac cacaaacgat    1140
atcgcgtacc gcatccttaa agaacatggt tggtccgtta tcgaagactt gaagcgcacc    1200
tggatggaca tcttcggtgc gttcctcgcg gaggcatact gtttcaaagg cggtcacgta    1260
ccctctctcg aggaatacct caccaatgca gtcaccactg gaggcactta tatggccctg    1320
gtccacgctt ttttcctcat gggtcagggc gtgacccgcg aaaatatggc catgcttaag    1380
ccatacccaa acattttctc atgttccgga aaaattctgc gcctttggga cgatcttggt    1440
accgctcgcg aggagcaaga acgcggagac aacgcttctt ccatcgagtg ctataaacga    1500
gagcgcgaaa tggacaccgt gctcgaagac gaagcatgtc gcaagcatat ccgccaaatg    1560
atccagtcac tttgggtgga gcttaacggt gagctcgtgg catcttcggc tcttccactg    1620
tccattatta aggcggcgtt caacctgtct cgcacggcac aagtcatcta ccaacacgga    1680
gacgataaca agacttcgtc tgtggaggac catgtacagg ccttgctgtt tcgtcccgtt    1740
tcttcaaacg gccacgctca atcaccatg cac                                  1773

<210> SEQ ID NO 100
<211> LENGTH: 1773
<212> TYPE: DNA
<213> ORGANISM: Artificial
<220> FEATURE:
<223> OTHER INFORMATION: mutated and/or codon-optimized sequence

<400> SEQUENCE: 100
atgagtagat tgttactat gccctcacat gtcctaccat cttcttttgt agcccccttcc      60 ttgcaagtca gctcaagtcc gtgtagttgg agaactaggc cgagcccatg tacttcatgt     120
catttaagtc cgtcctcaag cagcaaacca ttgctgggat cccatgacta ttctttgcta     180
aaatccttga cgttgtctcc tcacgcagtt aactcagagg cagattcatc tacaaggaga    240
atgaaagaag tgaaagaaag aacttgggaa gcgttctaca gagcatggga ttcaagggca    300
gcaatggaaa tggtcgatac ggtggaaaga ttaggcttgt cataccattt tgaagacgaa    360
ataaatgctt tgcttcaaag gttctgtgac tggaatgcat ctgaggatct ttttacgacc    420
gcactaagat ttagactgtt gagacagaac ggcttcccaa cgcatagcga tgtgtttggt    480
aagttcatgg ataagaatgg gaaatttaag gagtccttaa ccgaagacat ctggggaatg    540
ttatccttgc atgaagcttc ccaccttggt gccaaaaacg aggaagtctt ggccgaagct    600
aaagaattca ccagaattca cctaatacaa tccatgcccc atatggaacc acatttctcc    660
tctcatgtgg ggagagcctt agagttgccg agacacttaa ggatggttag actagaagct    720
aggaactata tcggggaata ttcaagagaa agtaatccga atttggcgtt tttggagctt    780
gctaagttgg attttgatat ggttcaatcc ctgcaccaaa agaactagc cgaaatagtt    840 aggtggtgga agcaattagg tctggttgat aaactggact tgctagaga tagaccaatg    900 gagtgctttc tttggacggt aggtatcttc cctgacccaa ggcacagctc ttgtagaatt    960
gaacttacta aggcaatcgc catcctattg gtaattgatg atatctacga tagttatggt    1020
agtctggacg aattggcctt atttactgac gcagtaaaga gatgggatct aggtgctatg    1080
```

```
gatcagctgc ctgagtatat gaaaatctgt tacatggccc tttataacac cactaatgat   1140
atcgcatata gaatcttgaa ggagcacggt tggtcagtga ttgaagattt aaaaaggact   1200
tggatggata ttttggagc ttttcttgct gaagcttatt gctttaaagg tggtcatgtc    1260
ccctcattag aagaatacct gaccaatgcc gtgactactg gtggtaccta catggcttta   1320
gtgcatgcct tttttcttat gggtcaaggc gttactcgtg aaaacatggc aatgctgaaa   1380
ccatatccca atatattcag ctgctcaggt aagattttac gtttatggga cgatcttggt   1440
actgcaagag aagaacaaga aaggggggac aatgcatcca gcattgaatg ctataaaaga   1500
gaacgtgaaa tggacacagt gttagaagat gaagcttgca gaaaacatat aagacaaatg   1560
attcaatctt tatgggttga actaaacggg gagctagtgg cgtcaagtgc gcttccctta   1620
agtatcatca aggcagcttt taacctaagt agaaccgcac aagttattta ccagcacggc   1680
gatgataaca aaacctcctc agttgaagac cacgttcaag ctctattatt ccgtccagtt   1740
tcaagtaacg acatgccca aattacaatg cat                                 1773

<210> SEQ ID NO 101
<211> LENGTH: 1773
<212> TYPE: DNA
<213> ORGANISM: Artificial
<220> FEATURE:
<223> OTHER INFORMATION: mutated and/or codon-optimized sequence

<400> SEQUENCE: 101
atgtcgcgat tcgttaccat gccctccac gtgcttccat cgtccttcgt tgctccatct     60
ctccaggttt cgtcgtctcc ctgttcttgg agaactcgac cttccccctg tacttcttgt    120
catctgtccc ccagctcgtc gtccaaacct ctgctgggta gccacgatta cagcctcctg    180
aagtctctca cccttctctcc tcacgctgtt aactccgagg ccgattcctc cacccgacgg   240
atgaaagagg tgaaggagcg aacttgggaa gccttctacc gagctgggga ctcccgggcc    300
gcaatggaga tggtcgacac tgtcgaaaga ctgggtctgt cttaccactt tgaggatgag    360
atcaacgctc tcctccagag attctgtgat tggaacgcct cggaggacct gttcacgacc    420
gctctccgat tccgactcct gagacagaac ggcttcccca cacattcgga cgtcttcggc   480
aagttcatgg acaagaacgg aaagttcaag gagtcgctca cggaagacat ctggggaatg    540 cttttctctcc atgaggcctc gcacctgggc gctaagaatg aggaggtcct cgccgaggcc   600
aaggagttta cccgaatcca ccttatccag agcatgcctc acatggagcc tcactttttcc   660 tcccacgtcg gtcgagccct tgagctgccc cgacatcttc gaatggtccg actgagggct    720
cgtaactaca ttggcgagta ctctagagag tccaaccca acctggcctt cctcgaactc     780
gccaagctgg atttcgacat ggtccagtcg ctgcaccaga aggagctcgc cgagattgtc    840
cgatggtgga agcaactcgg ccttgtcgac aaactggatt cgctcgaga tcgacccatg    900 gagtgcttcc tgtggaccgt tggtattttc cccgacccc gtcactcttc ctgccgaatc    960
gagctgacca aggccatcgc cattctgctc gttattgatg acatttacga ctcctacgga   1020
agccttgacg agctcgcact cttcaccgac gccgtgaagc gatgggatct gggtgccatg   1080
gatcaactgc ccgagtacat gaagatctgc tacatggccc tttacaacac aaccaacgac   1140
atcgcttacc gaatccttaa ggagcacgga tggtctgtta ttgaggacct caagcgaacg   1200
tggatggata tcttcggagc cttttctggct gaggcctact gtttcaaggg aggccatgtc   1260
ccttcgctcg aagagtatct gaccaacgct gtcaccaccg gtggtactta catggctctg   1320
```

-continued

```
gtccacgcat tcttcctgat gggtcaagga gtcacaagag agaatatggc tatgcttaag    1380
ccctatccca acatttttc ttgctctgga aagattctcc ggctctggga tgacctcggc     1440
```

```
gtccacgcat tcttcctgat gggtcaagga gtcacaagag agaatatggc tatgcttaag    1380
ccctatccca acattttttc ttgctctgga aagattctcc ggctctggga tgacctcggc    1440
actgctcgag aggagcagga gcgaggcgat aacgcttcct cgattgagtg ctacaagcga    1500
gagcgagaga tggataccgt ccttgaggac gaggcttgcc gtaagcatat tcgtcaaatg    1560
attcagtcgc tctgggttga gctgaacgga gaactggttg catcgtccgc cctccctctg    1620
tcgatcatca aagccgcttt caacctctcg agaactgctc aggtgattta ccagcacgga    1680
gatgacaaca agaccagctc tgtcgaagac cacgtccagg ctctgctttt cagacctgtg    1740
tcctcgaacg gtcacgctca aattaccatg cac                                 1773
```

<210> SEQ ID NO 102
<211> LENGTH: 501
<212> TYPE: PRT
<213> ORGANISM: Phaseolus angularis (Azuki bean) (Vigna angularis)

<400> SEQUENCE: 102

```
Met Glu Thr Asn Ser Thr Leu Phe Phe Thr Phe Thr Val Leu Leu Ile
1               5                   10                  15

Thr Ile Ile Thr Phe Leu Lys Ala Leu Lys Ser Leu Phe Thr Pro Asn
            20                  25                  30

Lys Ser Lys Ser Asn Leu Pro Pro Gly Pro Lys Gly Leu Pro Leu Val
        35                  40                  45

Gly Asn Leu Leu Gln Leu Gly Ala Lys Pro His Gln Thr Leu Ala Thr
    50                  55                  60

Leu Ala Asn Ile His Gly Ser Ile Met Ser Leu Lys Leu Gly Gln Glu
65                  70                  75                  80

Thr Thr Ile Val Met Ser Ser Ala Glu Ala Ala Lys Gly Val Leu Gln
                85                  90                  95

Ile His Asp His Phe Leu Ser Asn Arg Lys Ile Pro Asp Ala Met Arg
            100                 105                 110

Gly Ser Ser His Asp His Phe Ser Leu Pro Phe Met Pro Val Ser Gln
        115                 120                 125

Gln Trp Arg Glu Leu Arg Lys Leu Cys Asn Glu Leu Leu Phe Ser Asn
    130                 135                 140

Lys Asn Leu Asp Ala Thr Gln Gly Leu Arg Ser Lys Lys Val Arg Glu
145                 150                 155                 160

Leu Tyr Ser Asp Ile His Arg Ser Ser Leu Lys Gly Glu Pro Val Asn
                165                 170                 175

Ile Gly Arg Leu Ala Phe Lys Thr Thr Ile Asn Gln Leu Ser Asn Thr
            180                 185                 190

Ile Tyr Ser Glu Asp Phe Leu Gln Ser Ala Glu Lys Ala Gly Glu Met
        195                 200                 205

Lys Glu Leu Val Thr Asn Ile Met Lys Glu Val Gly Arg Pro Asn Leu
    210                 215                 220

Ala Asp Cys Phe Pro Val Leu Lys Met Ile Asp Pro His Gly Ile Arg
225                 230                 235                 240

Arg Arg Thr Gly Ser Tyr Phe Ser Lys Leu Leu Asn Ile Phe Lys Ser
                245                 250                 255

Leu Ile His Lys Arg Leu Glu Leu Arg Lys Asp Ala Ala Gly Tyr Cys
            260                 265                 270

Thr Lys Lys Asp Met Leu Asp Ala Met Leu Asn Asp Ala Gln His Lys
        275                 280                 285

Met Asp Ile Val Lys Ile Gln Arg Leu Ser Leu Asp Leu Phe Val Ala
```

```
                290                 295                 300
Gly Thr Asp Thr Val Thr Ser Thr Val Glu Trp Ala Met Ala Glu Leu
305                 310                 315                 320

Leu His Asn Pro His Val Met Ser Lys Ala Lys Glu Glu Leu Glu Arg
                325                 330                 335

Ile Ile Gly Lys Asp Asn Leu Val Glu Glu Ser Asp Ile Ala Lys Leu
                340                 345                 350

Pro Tyr Leu Gln Ala Ile Val Lys Glu Thr Phe Arg Leu His Pro Ala
                355                 360                 365

Val Pro Leu Leu Leu Pro Arg Lys Ala Glu Val Glu Phe Glu Met His
            370                 375                 380

Gly Tyr Thr Ile Pro Lys Gly Ala Gln Val Leu Ile Asn Val Trp Ala
385                 390                 395                 400

Ile Gly Arg Asp Pro Asn Leu Trp Glu Lys Pro Arg Leu Phe Trp Pro
                405                 410                 415

Glu Arg Phe Leu Glu Ser Glu Ile Asp Phe Lys Gly Arg Ser Phe Glu
                420                 425                 430

Leu Thr Pro Phe Gly Gly Gly Arg Arg Ile Cys Pro Gly Leu Pro Leu
                435                 440                 445

Ala Ile Arg Leu Val Phe Leu Met Leu Gly Leu Phe Ile Asn Ser Phe
            450                 455                 460

Asp Trp Glu Leu Gln Asp Ile Gln Pro Glu Asp Met Asn Met Asp Glu
465                 470                 475                 480

Asn Phe Gly Leu Thr Leu Glu Lys Ala Gln Pro Val Leu Ala Ile Pro
                485                 490                 495

Ile Ile Pro Lys His
                500

<210> SEQ ID NO 103
<211> LENGTH: 1503
<212> TYPE: DNA
<213> ORGANISM: Artificial
<220> FEATURE:
<223> OTHER INFORMATION: mutated and/or codon-optimized sequence

<400> SEQUENCE: 103
atggagacta actctaccct tttctttaca ttcaccgtcc tcctgatcac aatcattacg     60
ttcctgaagg cgttgaaatc tttgtttacc cctaacaagt caaaatctaa cctcccaccc    120
ggtcccaagg gccttccttt ggttggcaac ctgcttcagt gggcgcgaa gccgcaccag     180 accctcgcaa ccctcgcaaa catccacgga tccatcatgt ccctcaaatt gggtcaagag    240
acaaccatcg tgatgtcttc cgctgaggcc gcaagggag ttctgcagat tcatgatcat    300
ttcctctcaa accgcaaaat ccccgacgca atgcgcggct cctcccacga ccacttctcc    360
cttcctttca tgcctgtttc ccaacagtgg cgagaattgc gaaagctttg caacgaactc    420
ctgttctcca caagaaacct ggacgctaca caaggcctgc gctccaaaaa ggttcgagaa    480
ctgtacagcg atattcaccg cagctcgctg aagggcgagc ccgtgaacat cggtcgtctg    540
gcttttaaaa cgaccatcaa ccaactttct aacaccatct actcggaaga cttcttgcaa    600
tccgccgaga agcgggcga atgaaggaa ctcgttacca atattatgaa ggaggttggc     660
cgcccgaacc ttgccgactg cttccccgtt ctgaaaatga tcgaccccca cggcatccgc    720
cgtcgaaccg gctcttactt cagcaagctg cttaatatct tcaaatccct gatccacaag    780
cgtctggaac ttcgtaaaga tgctgcgggc tactgtacta aaaaggatat gcttgacgcg    840
```

| | |
|---|---|
| atgctgaacg acgcccaaca caaaatggac atcgttaaga tccagcgtct ctctcttgat | 900 |
| ttgttcgttg caggaacgga taccgtcacc tccactgtcg agtgggctat ggctgaactg | 960 |
| cttcacaacc cccacgttat gtcaaaggct aaagaggaac tcgaacgcat tatcggtaag | 1020 |
| gataatctgg tggaggagtc agacatcgcc aagttgcctt acttgcaggc tatcgtgaag | 1080 |
| gagaccttcc gtctccaccc agcagtcccc cttttgctgc cacgcaaagc cgaggttgaa | 1140 |
| tttgaaatgc acggttacac aatccccaaa ggcgcccagg tcctgatcaa tgtctgggcc | 1200 |
| attggtcgcg acccgaactt gtgggaaaag ccacgcctgt tttggcccga gcgatttctt | 1260 |
| gaatccgaga tcgacttcaa gggccgatcg ttcgagctca cccgttcgg cggcggccgt | 1320 |
| cgcatctgcc ctggactccc attggcgatc cgacttgttt ttctgatgct cggcctgttt | 1380 |
| attaactctt tcgattggga acttcaggac attcagccgg aagacatgaa tatggacgaa | 1440 |
| aacttcggtc tgactcttga aaaggcccag ccagttctcg caattccaat cattccaaaa | 1500 |
| cac | 1503 |

<210> SEQ ID NO 104
<211> LENGTH: 1503
<212> TYPE: DNA
<213> ORGANISM: Artificial
<220> FEATURE:
<223> OTHER INFORMATION: mutated and/or codon-optimized sequence

<400> SEQUENCE: 104

| | |
|---|---|
| atggaaacca acagtacttt attctttaca tttacagtcc ttcttatcac tatcataaca | 60 |
| tttctcaagg cgctcaaaag tttattcacg ccgaataaat caaatcaaa tcttccgcct | 120 |
| ggaccaaaag gactcccgct ggttggaaat cttttgcaac tcggggcaaa acctcatcag | 180 |
| acattagcta cgcttgctaa cattcacgga agcattatgt ctctgaagtt aggtcaagaa | 240 |
| acaacaattg tcatgtcttc ggcggaggcg gctaaaggcg ttttgcagat ccacgatcat | 300 |
| tttctgagca accggaaaat tcctgacgcc atgcgtggta gctcacatga tcatttctca | 360 |
| ttaccgttca tgccagtaag ccaacaatgg cgcgagctga aaaactgtg taatgagtta | 420 |
| ttattttcaa ataaaaactt ggatgcaacg caggggctga aagcaaaaa agttcgtgaa | 480 |
| ctgtattcag atatacatcg ctcgtctctt aaaggcgaac cggtcaacat cgggagactt | 540 |
| gcttttaaaa caacaattaa ccaattgagc aatacgatct actcggagga cttccttcaa | 600 |
| agcgcggaaa agcaggtga atgaaggaa ctggtcacaa acatcatgaa ggaagtggga | 660 |
| cgtccgaatc tggctgactg ttttccggtg ctgaaaatga ttgatcctca cggaattcgc | 720 |
| cgccggacag gttcatattt ctcaaaactt ctgaatatat tcaaaagctt aattcataaa | 780 |
| cgcttagagt tgcgcaaaga tgctgcaggc tattgcacga agaaagatat gctggatgcg | 840 |
| atgctgaacg atgctcaaca taaaatggat atcgtgaaaa tccagcggct ctcactcgac | 900 |
| ttatttgttg ctggcacaga taccgtcacc tcgaccgtcg agtgggccat ggcagagttg | 960 |
| ctgcataatc cacacgtaat gtccaaagct aaagaagaac tggaaagaat cattggcaag | 1020 |
| gataacctcg ttgaagaaag cgacatcgcg aaacttcctt acttacaggc gattgtaaag | 1080 |
| gagacgttta actgcatcc agcagtacct ctgcttcttc cgcgcaaagc tgaagtagaa | 1140 |
| tttgaaatgc atggatatac gatcccgaaa ggggcacagg tactcatcaa tgtgtgggcg | 1200 |
| attggcagag atccaaattt gtgggaaaaa cctcgttgt tttggcctga aagattcctg | 1260 |
| gagtcagaaa ttgacttcaa gggcagatcc ttcgaactca cgccgtttgg cggggccgg | 1320 |
| cgtatttgcc ctggcctgcc gttagccatt agattggttt tcttgatgtt aggcttattc | 1380 |

| | |
|---|---|
| atcaatagct tcgattggga gctccaggat attcaaccgg aagacatgaa tatggacgaa | 1440 |
| aactttggct taacactgga gaaagcacag ccggtactgg ccattccgat catcccgaaa | 1500 |
| cat | 1503 |

<210> SEQ ID NO 105
<211> LENGTH: 1503
<212> TYPE: DNA
<213> ORGANISM: Artificial
<220> FEATURE:
<223> OTHER INFORMATION: mutated and/or codon-optimized sequence

<400> SEQUENCE: 105

| | |
|---|---|
| atggaaacta acagcacttt atttttaca ttcacagtct tacttattac gataattacg | 60 |
| ttcctgaaag ctctgaaatc actatttact ccaaataaaa gtaagtctaa cttgccccct | 120 |
| ggcccaaagg gtttgccact tgttggaaat ctattgcaat taggtgcaaa acctcatcaa | 180 |
| acactggcta ctttggctaa tacatggg tccattatga gcctaaagtt gggccaagag | 240 |
| acaactatag tgatgtcttc tgctgaagca gccaagggtg tcttgcaaat acatgatcat | 300 |
| ttcctgagca atagaaagat tcctgacgct atgaggggaa caagccacga tcatttctca | 360 |
| ttgccattca tgcctgtatc ccagcaatgg agagaattaa gaaaattatg taatgaactg | 420 |
| ttattttcta caagaatct ggatgcaaca cagggcttaa gatcaaagaa agttagggaa | 480 |
| ttatattcag atatccatcg tagttcttta aaaggcgaac cagtcaacat cggcagactg | 540 |
| gcatttaaaa ccaccattaa ccagttgtct aataccattt atagcgaaga tttcttacaa | 600 |
| tctgccgaaa aagctggcga gatgaaagaa ttggttacta atatcatgaa ggaagttggt | 660 |
| aggccgaacc ttgcagactg ctttcctgtc ttgaagatga tagatccaca tggcattaga | 720 |
| agaagaacgg gttcttattt ttctaagttg cttaatattt tcaaatcatt gatccacaag | 780 |
| aggtggagt tgagaaaaga tgcggcagga tattgtacga aaaaagacat gctggatgca | 840 |
| atgcttaacg atgctcagca taagatggat atagttaaga tccaaagatt atctttggat | 900 |
| ttgttcgtcg ccggtactga tactgttacc tccactgtag aatgggccat ggcagaattg | 960 |
| cttcataacc cgcatgtcat gtcaaaagct aaagaagaat tggaaagaat tattggcaag | 1020 |
| gataatctgg tagaggaaag tgacatagct aaacttccat acttgcaagc cattgttaag | 1080 |
| gagactttta gattgcatcc agcagtgcct cttcttttgc caagaaaggc tgaagtggaa | 1140 |
| tttgaaatgc acggctacac aattccaaaa ggagctcaag tgttgatcaa tgtatgggcc | 1200 |
| attggtcgtg acccaaatct atgggaaaaa ccacgtttat tctggccaga gatttttg | 1260 |
| gaatcagaaa ttgacttcaa gggcaggtca ttcgagttga ccccattcgg cggtggtaga | 1320 |
| aggatatgtc ctggcttacc acttgccatc cgtttagtat ttttgatgct gggctattc | 1380 |
| attaactctt ttgactggga gcttcaagat attcagcccg aggatatgaa catggatgag | 1440 |
| aatttcgggc tgacacttga aaaagcgcaa cctgtattag ctattccgat aattccaaaa | 1500 |
| cat | 1503 |

<210> SEQ ID NO 106
<211> LENGTH: 1503
<212> TYPE: DNA
<213> ORGANISM: Artificial
<220> FEATURE:
<223> OTHER INFORMATION: mutated and/or codon-optimized sequence

<400> SEQUENCE: 106

```
atggagacca actcgactct gttctttact tttactgttc tcctgatcac cattatcacc      60
ttcctcaagg cactgaagtc gctgttcacc cccaataagt cgaagagcaa cctccccccc     120
ggtcctaagg gcctccctct ggtgggaaac ctcctccagc tcggcgccaa acctcatcag     180
actctggcta ccctggccaa cattcacggc agcatcatgt cgctcaagct tggtcaggag     240
actactatcg tcatgtcgtc ggccgaggct gctaagggcg tccttcagat ccacgatcac     300
ttcctgtcta accgaaagat ccccgacgct atgagaggat cttctcacga ccatttctct     360
ctcccttttca tgccagtctc gcagcagtgg cgagagcttc gaaagctctg taacgagctt     420
ctcttctcta ataagaacct tgatgctact cagggtctca gatctaagaa ggttcgagag     480
ctgtattcgg acattcatcg atcttctctg aagggtgagc ccgtcaacat tggtagactg     540
gctttcaaga caacaattaa tcagctctct aacacaattt acagcgagga cttcctccag     600
tcggctgaga aggccggtga aatgaaggaa ctcgtcacca acatcatgaa ggaagtgggc     660
cggcccaacc ttgctgattg cttccccgtt ctcaagatga ttgaccccca tggaatccgg     720
cgacggaccg gctcctattt ttccaagctc ctgaacattt tcaagtccct catccacaag     780
cgactcgaac tccgaaaaga cgccgccggt tactgtacca aaaagacat gcttgacgct     840
atgctcaacg acgcacagca caagatggat attgtcaaga ttcagcgact gtccctcgac     900
ctgttcgtgg ctggaaccga caccgttaca tctacagtcg aatgggctat ggccgaactg     960
ctgcataacc ctcacgtgat gagcaaggct aaggaggagc ttgagcgaat catcggaaag    1020
gacaacctcg tggaggagtc ggacatcgcc aagctgcctt accttcaagc cattgttaag    1080
gagacctttc gactgcaccc agctgttcca ctgctgctcc caagaaaagc tgaggtcgag    1140
ttcgaaatgc acggatatac aatccccaag ggagctcagg ttcttatcaa cgtctgggct    1200
attgacgag accccaacct ctgggagaag cctcgactct tttggcctga gcgattcctc    1260
gagagcgaga ttgactttaa gggtagatct ttcgaactga ccccctttgg tggcggacga    1320
cggatctgcc ccggtctgcc cctcgctatt cgactggttt tcctcatgct ggcctcttc    1380
atcaatagct ttgactggga gcttcaagac attcagcctg aagacatgaa catggacgag    1440
aacttcggcc tgaccctgga aaggcccag cccgtcctgg caatccccat catccccaag    1500
cac                                                                 1503
```

<210> SEQ ID NO 107
<211> LENGTH: 495
<212> TYPE: PRT
<213> ORGANISM: Swertia mussotii (Felwort)

<400> SEQUENCE: 107

```
Met Asp Phe Asp Phe Leu Thr Ile Ala Ile Gly Phe Leu Phe Thr Ile
1               5                   10                  15

Thr Leu Tyr Gln Ala Leu Asn Phe Phe Ser Arg Lys Ser Lys Asn Leu
            20                  25                  30

Pro Pro Gly Pro Ser Pro Leu Pro Leu Ile Gly Asn Leu His Leu Leu
        35                  40                  45

Gly Asp Gln Pro His Lys Ser Leu Ala Lys Leu Ala Lys Lys His Gly
    50                  55                  60

Pro Ile Met Gly Leu Gln Leu Gly Gln Val Thr Ile Val Val Thr
65                  70                  75                  80

Ser Ser Gly Met Ala Lys Glu Val Leu Gln Lys Gln Asp Leu Ala Phe
                85                  90                  95

Ser Ser Arg Ser Ile Pro Asn Ala Ile His Ala His Asp Gln Tyr Lys
```

```
                    100                 105                 110
Tyr Ser Val Ile Trp Leu Pro Val Ala Ser Arg Trp Arg Gly Leu Arg
            115                 120                 125

Lys Ala Leu Asn Ser Asn Met Phe Ser Gly Asn Arg Leu Asp Ala Asn
    130                 135                 140

Gln His Leu Arg Ser Arg Lys Val Gln Glu Leu Ile Ala Tyr Cys Arg
145                 150                 155                 160

Lys Ser Ser Gln Thr Gly Asp Ala Ile Asp Val Gly Arg Ala Ala Phe
                165                 170                 175

Arg Thr Ser Leu Asn Leu Leu Ser Asn Thr Met Phe Ser Lys Asp Leu
            180                 185                 190

Thr Asp Pro Tyr Ser Asp Ser Ala Lys Glu Phe Lys Asp Leu Val Trp
        195                 200                 205

Asn Val Met Val Glu Ala Gly Lys Pro Asn Leu Val Asp Tyr Phe Pro
    210                 215                 220

Leu Leu Asp Lys Val Asp Pro Gln Gly Ile Arg Lys Arg Met Thr Ile
225                 230                 235                 240

His Phe Gly Lys Ile Leu Glu Leu Phe Gly Gly Leu Ile Asp Glu Arg
                245                 250                 255

Leu Gln Gln Lys Lys Ala Lys Gly Val Asn Asp Asp Val Leu Asp Val
            260                 265                 270

Leu Leu Thr Thr Ser Glu Glu Ser Pro Glu Glu Ile Asp Arg Thr His
        275                 280                 285

Ile Gln Arg Met Cys Leu Asp Leu Phe Val Ala Gly Thr Asp Thr Thr
    290                 295                 300

Ser Ser Thr Leu Glu Trp Ala Met Ser Glu Met Leu Lys Asn Pro Glu
305                 310                 315                 320

Lys Met Lys Ala Ala Gln Ala Glu Leu Ala Gln Val Ile Gly Lys Gly
                325                 330                 335

Lys Ala Val Glu Glu Ala Asp Leu Ala Arg Leu Pro Tyr Leu Arg Cys
            340                 345                 350

Ala Ile Lys Glu Thr Leu Arg Ile His Pro Pro Val Pro Leu Leu Ile
        355                 360                 365

Pro Arg Arg Thr Glu Gln Glu Val Glu Val Cys Gly Tyr Thr Val Pro
    370                 375                 380

Lys Asn Ser Gln Val Leu Val Asn Val Trp Ala Ile Ser Arg Asp Asp
385                 390                 395                 400

Ala Ile Trp Lys Asp Pro Leu Ser Phe Lys Pro Glu Arg Phe Leu Glu
                405                 410                 415

Ser Glu Leu Glu Met Arg Gly Lys Asp Phe Glu Leu Ile Pro Phe Gly
            420                 425                 430

Ala Gly Arg Arg Ile Cys Pro Gly Leu Pro Leu Ala Val Arg Met Val
        435                 440                 445

Pro Val Met Leu Gly Ser Leu Leu Asn Ser Phe Asp Trp Lys Leu Glu
    450                 455                 460

Gly Gly Ile Ala Pro Lys Asp Leu Asp Met Glu Glu Lys Phe Gly Ile
465                 470                 475                 480

Thr Leu Gln Lys Ala His Pro Leu Arg Ala Val Ala Thr Pro Leu
                485                 490                 495

<210> SEQ ID NO 108
<211> LENGTH: 1485
<212> TYPE: DNA
<213> ORGANISM: Artificial
```

<220> FEATURE:
<223> OTHER INFORMATION: mutated and/or codon-optimized sequence

<400> SEQUENCE: 108

```
atggatttcg atttccttac gattgccatt ggatttcttt ttacaattac cttgtatcag      60
gctctgaatt ttttcagtcg taaatcgaaa aaccttccgc caggaccatc accgctgcct     120
ttgataggga atcttcattt gttaggtgac cagcctcata atcgttggc caagcttgcg      180
aagaaacatg gtcctattat gggcttacaa ttgggccaag tgacgactat tgttgttacg     240
tctagcggca tggccaagga agttcttcaa agcaggatt tagcttttc atcccgttct       300
attccaaatg cgatacatgc acatgatcag tacaagtact cagtgatttg gcttcctgtg     360
gcatcacggt ggcgtgggct gcgcaaagct ttgaattcca acatgttttc cggaaacaga     420
ctggatgcga accaacatct gcggtctcgc aaagtgcagg aattaattgc ctattgcaga     480
aaatcaagcc aaactggtga cgcaattgac gtagggcgag ccgcctttcg aacatctctt     540
aacctcctgt ctaacacgat gttttctaaa gacctcactg atccttactc cgattccgcg     600
aaagaattca aggatttggt ctggaacgtg atggttgagg cgggaaaacc taacttggtg     660
gattattttc cgctccttga taaagtggac ccgcaaggaa ttcggaagcg catgacgatc     720
cattttggta aaattctcga gcttttggc ggattaattg atgaacgtct tcagcaaaaa      780
aaggcgaagg gagtgaacga cgacgttctt gacgtgcttc tgacgacctc tgaggaatcc     840
ccagaagaga ttgatcggac tcatattcag cgtatgtgcc tggatttgtt tgtggccggt     900
acggacacta cctcctccac gctcgaatgg gcaatgtcgg aaatgttaaa aaatcctgag     960
aaaatgaaag cggctcaagc agaactggcc caagtcatcg gcaaaggcaa agccgtagaa    1020
gaagccgatc ttgctcgctt gccgtattta cggtgcgcaa ttaaagaaac cctgagaatc    1080
catccgcctg tcccgctttt aatccctcga agaacagaac aagaggtcga agtctgtgga    1140
tataccgtgc ctaaaaattc acaagtgctc gtaaacgtct gggcgattag tcgtgacgac    1200
gcgatatgga aagacccgct tagttttaaa ccggaacggt tcctcgagag cgagttagaa    1260
atgcggggta aggatttcga gctgattcct ttcgggcgg gtagaagaat ctgccctggc     1320
ctgccgctgg cggtgcggat ggttccagtt atgcttggtt ctctgcttaa ttcattcgat    1380
tggaaactgg agggtggaat cgcgccgaag gacctggata tggaggagaa atttggaatt    1440
actttacaga aggcgcatcc tcttcgcgca gttgccacgc ctctc                    1485
```

<210> SEQ ID NO 109
<211> LENGTH: 1485
<212> TYPE: DNA
<213> ORGANISM: Artificial
<220> FEATURE:
<223> OTHER INFORMATION: mutated and/or codon-optimized sequence

<400> SEQUENCE: 109

```
atggatttg atttttaac cattgcaatt ggtttttat tcaccattac gttgtatcaa        60
gcgttaaatt ttttttctag gaagtccaaa aaccttccgc caggtccttc tccactgcca    120
ctaatcggca acctacatct tttgggtgat cagcctcaca atcattggc aaaattggcg     180
aagaaacacg gccgattat gggtctacaa ctgggtcaag taacgaccat agttgtaaca    240
tctagtggca tggctaaaga agtacttcaa agcaagatt tagcttttc ctcaagatct     300
ataccaaacg caatacatgc ccatgatcaa tacaagtaca gtgttatatg gctgccagtt    360
gcttccagat ggcgtgggct acgtaaagcg ctaaattcta acatgttctc tggcaataga    420
```

```
ttggacgcca accagcattt aagatctaga aaagtgcaag aattaattgc atactgtaga      480
aaatctagtc aaacagggga tgccatagat gtagggcgtg ctgcgtttag aaccagcttg      540
aatttattgt ctaacactat gttttcaaaa gacttgaccg atccctacag cgactccgca      600
aaggaattta agatttagt ttggaacgtt atggtagagg ctggaaaacc gaatttggtg       660
gattattttc ccttgttgga taaggtcgac ccccagggta ttagaaagag aatgacaatt      720
cacttcggaa agatattgga actgtttggt ggattgatag acgaacgttt acaacaaaag     780
aaagccaaag gtgtgaatga tgatgtgctt gatgttttgc taactacaag cgaggaaagt      840
ccggaagaaa tagataggac ccatatccaa aggatgtgtt tggacttgtt tgttgccgga     900
actgatacca ctagttcaac attagaatgg gctatgtctg agatgttgaa aaatcctgag     960
aaaatgaaag ctgcacaggc agagttggcg caagtgatag gtaaaggtaa agctgtagag     1020
gaagcggatt tggctagatt accctatttg aggtgtgcta tcaaggaaac tcttaggatt     1080
catcctccag taccactatt aattccacgt agaaccgaac aggaagtgga agtgtgtgga     1140
tataccgtac gaagaactc tcaagtgctg gtaaatgtgt gggccatttc tagagatgat      1200
gctatatgga aagacccatt atcttttaaa cccgagaggt ttctggaaag cgagttggaa     1260
atgagaggca aagactttga attgatccca tttggggcgg ggagaagaat ctgtcctgga     1320
ttgccgttgg cagtgagaat ggttccagtt atgctgggtt ctctgttgaa cagtttcgat     1380
tggaagttag agggagggat agcccctaaa gatctggaca tggaagaaaa gtttggcatt     1440
actcttcaaa aagcccatcc actaagggcc gtagctacac cgctg                     1485
```

<210> SEQ ID NO 110
<211> LENGTH: 1485
<212> TYPE: DNA
<213> ORGANISM: Artificial
<220> FEATURE:
<223> OTHER INFORMATION: mutated and/or codon-optimized sequence

<400> SEQUENCE: 110

```
atggatttcg atttcctgac cattgcaatc ggctttcttt ttaccattac tctttaccag       60
gctcttaact tcttctctcg aaagtctaag aaccteccte ctggaccttc ccccctgccc      120
ctgatcggaa accttcacct cctcggcgac cagccccaca gtccctggc taagcttgct       180 aaaaagcacg gccccatcat gggtcttcag ctgggacagg ttacaactat tgttgttacc      240
agctccggaa tggctaagga ggtgctccag aaacaggacc ttgccttctc ctcgagatcc      300
atccccaacg ccatccatgc cacgatcag tacaagtact ctgttatttg gctccctgtg       360
gcctctcgtt ggcgaggtct ccgaaaagct ctgaattcca acatgttcag cggtaaccgt      420
ctggacgcaa atcagcatct ccggtctaga aaggttcagg agctgattgc ttactgtcga     480
aagtcttcgc agacaggtga cgctatcgat gtgggtagag cagccttccg aacttcgctg      540
aacctcctct cgaataccat gttctctaag gatcttaccg atccatacag cgattctgcc     600
aaggagttta aggacctggt ttggaacgtc atggtcgagg caggtaagcc taacctggtt     660
gattactttc ccctgcttga taaagtggac cctcagggaa ttcgaaagag aatgaccatt      720
cattttggta agatcctcga gctgttcggt ggccttatcg acgagcgact ccagcagaaa     780
aaggccaagg gtgttaacga cgacgttctc gacgtgctgc tgacgacatc tgaggagtcc     840
cccgaggaaa ttgaccgaac ccatatccaa agaatgtgtc tggacctctt tgtcgctggt     900
actgacacca cttcctccac actggagtgg gcaatgtcgg aaatgctcaa gaaccctgag     960
aagatgaagg ctgcccaggc cgagcttgcc caggtcatcg gcaagggtaa ggccgtggaa    1020
```

```
gaggccgacc tcgctcgact gccctacctt cgatgtgcta tcaaggagac gctgagaatc    1080
cacccccctg tgcccctcct catccccgt  cgaaccgagc aggaagttga ggtctgtggc    1140
tacaccgtcc caaagaactc ccaggttctc gttaacgtgt gggctatttc cagagatgac    1200
gccatctgga aggaccctct gtcttttaag cctgagcgat tcctggagtc cgagctggag    1260
atgcggggaa aggactttga actgatcccc tttggagctg acgacgaat  ctgccccggt    1320 ctcccctgg  ccgtccgaat ggtccccgtc atgcttggat cgctcctcaa ctcgtttgac    1380
tggaagcttg aaggcggaat tgctcccaag gaccttgata tggaagagaa gttcggtatc    1440
actctgcaga aagcacaccc cctccgggca gtcgccactc tctg                     1485
```

<210> SEQ ID NO 111
<211> LENGTH: 864
<212> TYPE: DNA
<213> ORGANISM: Artificial
<220> FEATURE:
<223> OTHER INFORMATION: mutated and/or codon-optimized sequence

<400> SEQUENCE: 111

```
atgacagcag ataacaattc catgcctcac ggtgctgtgt cttcatacgc gaaactggtg      60
cagaaccaaa cacctgagga tattctcgag gaattccccg aaatcatccc tctccagcag     120
cgcccgaaca cccgctcctc tgaaacctct aatgacgaat ccggcgagac atgtttctcc     180
ggccacgacg aagagcaaat taagctgatg aacgaaaatt gcatcgtgtt ggactgggat     240
gacaacgcca ttggagccgg taccaaaaag gtgtgccatc tgatggagaa cattgaaaag     300
ggactgctcc atcgagcttt ctcagtgttc attttcaatg aacagggtga gctcctgctg     360
caacagcgcg caacggaaaa gattaccttc cccgacctct ggactaacac ctgctgctca     420
cacccattgt gtatcgatga cgaacttggc ttgaagggca agcttgatga taagattaag     480
ggcgcaatca cggccgctgt tcgtaaactc gatcacgaac ttggaattcc tgaagacgaa     540
accaagactc gcggcaaatt tcacttcttg aatcgtatcc actatatggc gccttccaac     600
gagccttggg gcgagcacga gatcgactat attttgttct acaagatcaa tgcaaaggag     660
aacctgactg tgaacccgaa tgtgaatgaa gtgcgtgact tcaagtgggt ctcaccgaac     720
gatctgaaga ccatgtttgc cgatccatcc tacaaattca ccccgtggtt caaaattatc     780
tgtgaaaact atctgttcaa ttggtgggaa caactcgacg atttgtccga ggtcgagaac     840
gatcgtcaaa tccaccgtat gctt                                            864
```

<210> SEQ ID NO 112
<211> LENGTH: 1485
<212> TYPE: DNA
<213> ORGANISM: Artificial
<220> FEATURE:
<223> OTHER INFORMATION: mutated and/or codon-optimized sequence

<400> SEQUENCE: 112

```
atggattttg atttcttgac aatcgcaatt ggtttcctgt tcaccattac cttgtaccaa      60
gcgctcaact tctttagccg caaatccaag aacctcccac caggtccgag ccccctcccg     120
cttattggca acctgcactt gctgggagat cagccgcaca atcattggc  gaagctcgct     180 aagaagcacg gtccaattat gggtctgcag ttgggccaag ttacaactat cgtcgtgacc     240
tcgtccggaa tggcaaagga ggttttgcaa aaacaagatt tggctttctc gtcccgctcc     300
atccccaacg ctatccacgc acacgaccag tacaagtaca gcgtgatttg gctgcccgtt     360
```

```
gctagccgct ggcgcggatt gcgcaaggca ctgaattcca acatgttctc tggcaaccgc    420
ttggacgcca accaacacct tcgatcccgc aaagtgcaag aactgatcgc ttactgtcgc    480
aaaagctctc agaccggcga tgccattgac gtaggccgcg cggcatttcg aacctcgctc    540
aaccttctct cgaacacgat gttttcaaaa gaccttaccg acccatattc agattccgcc    600
aaggagttca aggaccttgt ttggaacgtg atggtcgaag ccggcaagcc gaatcttgtc    660
gattactttc cgttgctcga taaggtggat ccccagggaa tccgcaagcg tatgaccatc    720
cacttcggaa aaatcctgga gctgttcggt ggcctgatcg acgagcgcct tcaacagaag    780
aaggccaagg gagttaatga cgacgtgctg gatgtgcttc tcaccacctc tgaagagtcc    840
cctgaggaga tcgatcgtac acacatccag cgcatgtgtc ttgatttgtt cgtggctgga    900
acagatacca caagctcaac cttggagtgg gcaatgtcgg agatgcttaa gaacccggaa    960
aagatgaagg ctgcacaggc ggaactggcc caggtaatcg gcaagggtaa ggcagtagaa   1020
gaggctgacc tcgcacgact cccatatctc cgttgtgcta tcaaggagac cctgcgtatt   1080
cacccgccgg tccctcttct tattcctcgc cgcaccgagc aggaggttga agtgtgtggt   1140
tacactgtgc ccaaaaactc ccaagtgctg gtcaacgttt gggcgatctc gcgcgatgac   1200
gccatctgga aagacccttt gtccttcaag ccagagcgtt ttttggaatc cgagctggag   1260
atgcgtggaa aggattttga attgatcccg ttcggtgccg gtcgtcgcat ctgcccgggt   1320
cttccccttg cagtacgcat ggtcccggta atgctgggct cgctcctgaa ctcttttgat   1380
tggaaacttg agggcggtat cgctccaaag gacttggata tggaagaaaa gttcggaatt   1440
actttgcaaa aagcacaccc gttgcgcgca gtcgcaaccc ctctg                   1485
```